United States Patent
He et al.

(10) Patent No.: US 11,680,059 B2
(45) Date of Patent: Jun. 20, 2023

(54) ORGANIC MIXTURE AND APPLICATION THEREOF IN ORGANIC ELECTRONIC DEVICES

(71) Applicant: GUANGZHOU CHINARAY OPTOELECTRONIC MATERIALS LTD., Guangdong (CN)

(72) Inventors: Ruifeng He, Guangdong (CN); Jiahui Tan, Guangdong (CN); Weijie Lin, Guangdong (CN); Junyou Pan, Guangdong (CN)

(73) Assignee: GUANGZHOU CHINARAY OPTOELECTRONIC MATERIALS LTD., Guangdong (CN)

( * ) Notice: Subject to any disclaimer, the term of this patent is extended or adjusted under 35 U.S.C. 154(b) by 361 days.

(21) Appl. No.: 16/955,551

(22) PCT Filed: Dec. 20, 2018

(86) PCT No.: PCT/CN2018/122489
§ 371 (c)(1),
(2) Date: Jun. 18, 2020

(87) PCT Pub. No.: WO2019/120263
PCT Pub. Date: Jun. 27, 2019

(65) Prior Publication Data
US 2020/0317646 A1 Oct. 8, 2020

(30) Foreign Application Priority Data

Dec. 21, 2017 (CN) .......................... 201711396126.5

(51) Int. Cl.
| | |
|---|---|
| *H01L 51/00* | (2006.01) |
| *C07D 403/14* | (2006.01) |
| *C07C 211/54* | (2006.01) |
| *C07D 239/74* | (2006.01) |
| *C07D 251/24* | (2006.01) |
| *C07D 403/04* | (2006.01) |
| *H01L 51/50* | (2006.01) |

(52) U.S. Cl.
CPC .......... *C07D 403/14* (2013.01); *C07C 211/54* (2013.01); *C07D 239/74* (2013.01); *C07D 251/24* (2013.01); *C07D 403/04* (2013.01); *H01L 51/0059* (2013.01); *H01L 51/0067* (2013.01); *H01L 51/0072* (2013.01); *H01L 51/5004* (2013.01); *H01L 51/5016* (2013.01); *H01L 2251/552* (2013.01)

(58) Field of Classification Search
None
See application file for complete search history.

(56) References Cited

U.S. PATENT DOCUMENTS

| | | | |
|---|---|---|---|
| 6,824,895 B1 | 11/2004 | Sowinski et al. | |
| 6,830,828 B2 | 12/2004 | Thompson et al. | |
| 6,835,469 B2 | 12/2004 | Kwong et al. | |
| 6,892,692 B2 | 5/2005 | Barrett | |
| 7,029,766 B2 | 4/2006 | Huo et al. | |
| 9,169,282 B2 | 10/2015 | Stoessel et al. | |
| 2001/0041512 A1 | 11/2001 | Kato et al. | |
| 2001/0053462 A1 | 12/2001 | Mishima | |
| 2002/0027140 A1 | 3/2002 | George | |
| 2002/0156450 A1 | 10/2002 | Drevik et al. | |
| 2005/0258742 A1 | 11/2005 | Tsai et al. | |
| 2007/0087219 A1 | 4/2007 | Ren et al. | |
| 2007/0252517 A1 | 11/2007 | Owczarczyk et al. | |
| 2008/0027220 A1 | 1/2008 | Stossel et al. | |
| 2009/0061681 A1 | 3/2009 | McMunigal et al. | |
| 2009/0134784 A1 | 5/2009 | Lin et al. | |
| 2012/0004407 A1 | 1/2012 | Stoessel et al. | |
| 2012/0217869 A1 | 8/2012 | Adachi et al. | |
| 2013/0256645 A1* | 10/2013 | Min ................... | H01L 51/0054 546/281.1 |

(Continued)

FOREIGN PATENT DOCUMENTS

| | | |
|---|---|---|
| CN | 102282150 A | 12/2011 |
| CN | 103483332 A | 1/2014 |
| CN | 106910831 A1 | 6/2017 |

(Continued)

OTHER PUBLICATIONS

Machine translation of KR-20160075131, translation generated on Jun. 2, 2022, 32 pages. (Year: 2022).*
Endo et al., "Thermally Activated Delayed Fluorescence from $Sn^{4+}$-Porphyrin Complexes and Their Application to Organic Light-Emitting Diodes—A Novel Mechanism for Electroluminescence", Advanced Materials, vol. 21, 2009, pp. 4802-4806.
Li et al., Highly Efficient Organic Light-Emitting Diode Based on a Hidden Thermally Activated Delayed Fluorescence Channel in a Heptazine Derivative, Advanced Materials, vol. 25, 2013, pp. 1-5.
Dias et al., "Triplet Harvesting with 100% Efficiency by Way of Thermally Activated Delayed Fluorescence in Charge Transfer OLEO Emitters", Advanced Materials, vol. 25, 2013, pp. 3707-3714.

(Continued)

*Primary Examiner* — Robert S Loewe
(74) *Attorney, Agent, or Firm* — PV IP PC; Wei Te Chung; Zhigang Ma

(57) ABSTRACT

The present invention relates to an organic mixture and an application thereof in organic electronic devices. The organic mixture comprises a spirofluorene organic compound containing a fused heterocyclic ring and an aromatic fused heterocyclic organic compound containing an electron-donating group. A combination of the two materials may be used as a host material of a phosphorescent organic light-emitting diode (OLED), which may use the energy of excitons and balance the charge transport to the greatest extent and which may effectively reduce the concentration of excitons and the operating voltage of a corresponding device, thereby effectively improving the efficiency and service life of the related electronic device in order to provide an effective solution for improving the overall performance of an organic electronic device.

20 Claims, No Drawings

(56) References Cited

U.S. PATENT DOCUMENTS

| | | | | |
|---|---|---|---|---|
| 2016/0126475 A1* | 5/2016 | Lee | ................ | H01L 51/0059<br>257/40 |
| 2017/0179395 A1* | 6/2017 | Kim | ................ | H01L 51/0074 |

FOREIGN PATENT DOCUMENTS

| | | |
|---|---|---|
| EP | 1191613 B1 | 3/2006 |
| EP | 1191614 B1 | 5/2009 |
| EP | 1191612 B1 | 9/2009 |
| JP | 2000070655 A | 3/2000 |
| KR | 20170116944 A | 10/2017 |
| KR | 20170141987 A | 12/2017 |
| TW | 201309696 A | 3/2013 |
| TW | 201309778 A | 3/2013 |
| TW | 201343874 A | 11/2013 |
| TW | 201350558 A | 12/2013 |
| WO | 2002027141 A1 | 4/2002 |
| WO | 2002027142 A1 | 4/2002 |
| WO | 2005033244 A1 | 4/2005 |
| WO | 2005019373 A3 | 5/2005 |
| WO | 2007095118 A3 | 12/2007 |
| WO | 2009118087 A1 | 10/2009 |
| WO | 2009146770 A2 | 12/2009 |
| WO | 2010015307 A1 | 2/2010 |
| WO | 2010031485 A1 | 3/2010 |
| WO | 2010054728 A1 | 5/2010 |
| WO | 2010054731 A1 | 5/2010 |
| WO | 2010086089 A1 | 8/2010 |
| WO | 2010099852 A1 | 9/2010 |
| WO | 2010102709 A1 | 9/2010 |
| WO | 2010135519 A1 | 11/2010 |
| WO | 2011110277 A1 | 9/2011 |
| WO | 2011157339 A1 | 12/2011 |
| WO | 2012007086 A1 | 1/2012 |
| WO | 2012007087 A1 | 1/2012 |
| WO | 2012007088 A1 | 1/2012 |
| WO | 2011141110 A3 | 5/2013 |
| WO | 2013094620 A1 | 6/2013 |
| WO | 2013107487 A1 | 7/2013 |
| WO | 2013133359 A1 | 9/2013 |
| WO | 2013154064 A1 | 10/2013 |
| WO | 2013174471 A1 | 11/2013 |
| WO | 2014007565 A1 | 1/2014 |
| WO | 2014008982 A1 | 1/2014 |
| WO | 2014024131 A1 | 2/2014 |
| WO | 2014031977 A1 | 2/2014 |
| WO | 2014038456 A1 | 3/2014 |
| WO | 2014112450 A1 | 7/2014 |
| WO | 2014023377 A3 | 9/2014 |
| WO | 2015034125 A1 | 3/2015 |
| WO | 2015111848 A1 | 7/2015 |
| WO | 2018095393 A1 | 5/2018 |

OTHER PUBLICATIONS

Mehes et al., "Enhanced Electroluminescence Efficiency in a Spiro-Acridine Derivative through Thermally Activated Delayed Fluorescence", Angew. Chem. Int. Ed., vol. 51, 2012, pp. 11311-11315.
Endo et al., "Efficient up-conversion of triplet excitons into a singlet state and its application for organic light emitting diodes", Applied Physics Letters, vol. 98, 2011, pp. 083302-1-083302-3.
Lee et al., "High-efficiency organic light-emitting diodes utilizing thermally activated delayed fluorescence from triazinebased donor-acceptor hybrid molecules", Applied Physics Letters, vol. 101, 2012, pp. 093306-1-093306-4.
Nakagawa et al., "Electroluminescence based on thermally activated delayed fluorescence generated by a spirobifluorene donor-acceptor structure" Chem. Commun., vol. 48, 2012, pp. 9580-9582.
Tanaka et al., "Efficient green thermally activated delayed fluorescence (TADF) from a phenoxazine-triphenyltriazine (PXZ-TRZ) derivative", Chem. Commun., vol. 48, 2012, pp. 11392-11394.
Nasu et al., "A highly luminescent spiro-anthracenone-based organic light-emitting diode exhibiting thermally activated delayed fluorescence", Chem. Commun., vol. 48, 2013, pp. 1-3.
Komino et al., "Suppression of Efficiency Roll-Off Characteristics in Thermally Activated Delayed Fluorescence Based Organic Light-Emitting Diodes Using Randomly Oriented Host Molecules", Chemistry of Materials, vol. 25, 2013, pp. 3038-3047.
Tanaka et al., "Twisted Intramolecular Charge Transfer State for Long-Wavelength Thermally Activated Delayed Fluorescence", Chemistry Materials, vol. 25, 2013, pp. 3766-3771.
Zhang et al., "Design of Efficient Thermally Activated Delayed Fluorescence Materials for Pure Blue Organic Light Emitting Diodes", Journal of the American Chemical Society, vol. 134, 2012, pp. 14706-14709.
Lee et al., "Oxadiazole- and triazole-based highly-efficient thermally activated delayed fluorescence emitters for organic light-emitting diodes", Journal of Materials Chemistry C, vol. 1, 2013, pp. 1-6.
Ishimatsu et al., "Solvent Effect on Thermally Activated Delayed Fluorescence by 1,2,3,5-Tetrakis(carbazol-9-yl)-4,6-dicyanobenzene", The Journal of Physical Chemistry A, vol. 117, 2013, pp. 5607-5612.
Goushi et al., "Organic light-emitting diodes employing efficient reverse intersystem crossing for triplet-to-singlet state conversion", Nature Photonics, vol. 6, Apr. 2012, pp. 253-258.
Uoyama et al., "Highly efficient organic light-emitting diodes from delayed fluorescence", Nature, vol. 492, Dec. 13, 2012, pp. 234-238.
Adachi et al., "High-efficiency red electrophosphorescence devices", Applied Physics Letters, vol. 78 (2001), pp. 1622-1624.
Baldo et al., "High-efficiency fluorescent organic light-emitting devices using a phosphorescent sensitizer", Nature, vol. 403, Feb. 17, 2000, pp. 750-753.
Kido et al., "Bright red lightemitting organic electroluminescent devices having a europium complex as an emitter", Appl Phys Lett, vol. 65, 1994, pp. 2124-2126.
Johnson et al., "Luminescent Iridium(I), Rhodium(I), and Platinum(II) Dithiolate Complexes", J. Am. Chem. Soc., vol. 105, 1983, pp. 1795-1802.
Kido et al., "Electroluminescence in a Terbium Complex", Chemistry Letters, 1990, pp. 657-660.
Ma et al., "Electroluminescence from triplet metal-ligand charge-transfer excited state of transition metal complexes" Synth Metals, vol. 94, 1998, pp. 245-248.
Wrighton et al., "The Nature of the Lowest Excited State in Tricarbonylchloro-1,10-phenanthrolinerhenium(I) and Related Complexes", Journal of the American Chemical Society, vol. 96, Feb. 20, 1974, pp. 998-1003.
Kipphan (Handbook of Print Media: Technologies and Production Methods), ISBN 3-540-67326-1, Chapter 1.3, pp. 40-67, Chapter 1.5, pp. 117-144, Chapter 5.5, pp. 711-730.
Bulovic et.al. "Transparent light-emitting devices", Nature, vol. 380, Mar. 7, 1996, p. 29.
Gu et al., "Transparent organic light emitting devices" Applied Physics Letters, vol. 68, No. 19, May 6, 1996, pp. 2606-2608.
Newkome et al., Dendrimers and Dendrons: Concepts, Syntheses, Applications. Wiley-VCH Verlag GmbH & Co. KGaA, (2002) pp. 1-21, 51-76, 76-102, 102-118, 191-234, 234-282, 282-309, 331-365, 366-393, 395-431, 431-455.
PCT/CN2018/122489, "International Search Report", dated Mar. 28, 2019, 2 pages.

* cited by examiner

ORGANIC MIXTURE AND APPLICATION THEREOF IN ORGANIC ELECTRONIC DEVICES

The present disclosure claims priority to Chinese Patent Application No. 201711396126.5, filed on Dec. 21, 2017, entitled "A kind of mixtures and applications thereof in electronic devices", the entire contents of which are incorporated by reference herein.

TECHNICAL FIELD

The present disclosure relates to the field of photoelectric materials, particularly to organic mixtures and applications thereof in organic electronic devices.

BACKGROUND

With the advantages of light weight, active emitting, wide viewing angle, high contrast, high emitting efficiency, low energy consumption, easy preparation for flexible and large-sized panels, etc., organic light-emitting diodes (OLEDs) are regarded as the display and lighting devices of next generation in the industry.

The main problems that need to be solved urgently are to promote the large-scale industrialization of the organic light-emitting diodes and to further improve the luminescence properties and lifetime of the organic light-emitting diodes. Among them, the development of high-performance organic photoelectric materials is the key to solving the problem.

Organic light-emitting diodes are apparatuses that convert electrical energy into light energy. To further improve the emitting efficiency of the organic light-emitting diodes, it is necessary to increase the energy conversion efficiency and reduce energy loss as much as possible. In terms of light-emitting materials, since phosphorescent emitting materials enable simultaneously emitting light using the singlet and triplet excitons, and the organic light-emitting diodes using phosphorescent emitting materials can achieve nearly 100% internal electroluminescence quantum efficiency, the phosphorescent materials, especially, red and green phosphorescent materials, have become the mainstream material system in the industry. However, the red and green phosphorescent emitting materials themselves are susceptible to the imbalance of charge transport and aggregation-caused quenching, etc., the key to obtaining high efficient and long-life light-emitting diodes is the host material.

The host material plays an important role in energy transport and exciton dispersion in the light-emitting layer. From the aspect of energy transport, the host material needs to have suitable HOMO and LUMO energy levels that can reduce the barriers for electron and hole injection, thereby reducing the operating voltage of the device; the triplet energy level of the host material need to be higher than that of the light-emitting guest material, which can prevent the energy from returning; the host material needs to have a certain charge transport balancing ability, so that the exciton recombination area is concentrated in the center of the light-emitting layer, achieving high energy utilization efficiency and device stability. From the aspect of exciton dispersion, there are suitable steric hindrance structural units in the host material structure, that can effectively prevent the close packing between molecules and play the role of exciton dispersion, thereby reducing the aggregation quenching of triplet excitons.

It is difficult to achieve the optimal results in both energy transport and exciton dispersion with a single host due to the limitations of structure and molecular weight, while using a mixture as a co-host material, each component of the mixture exerts its own performance characteristics, respectively, for example, the collocation of electron transport and hole transport materials can have a more prominent effect in energy level matching, charge balance and space effect. In the prior art, the electrons of linear structure are mostly collocated with the hole co-hosts, utilize the collocation of the n-type host of biphenyl structure and the p-type host of bicarbazole structure, the lifetime of the device thereof is more than twice that of the corresponding single host material, as described in patents WO2015034125A1, WO2015111848A1, etc. However, if the material structure can be further designed and optimized for such co-host materials, there should be a lot of room for improvement especially in exciton dispersion.

Fused heterocyclic spirofluorene compounds have a vertically crossing spatial structure, which can effectively prevent the close packing between molecules and reduce the concentration of excitons, and are expected to further improve the stability of the devices. If the fused heterocyclic spirofluorene compound is used as a structural scaffold, the electron-accepting group is appropriately introduced to make it have electron-transporting properties, and at the same time, it is combined with a hole transport host with energy level matched, it may further improve the luminescence properties and lifetime of the organic light-emitting diodes.

SUMMARY

In view of the above-mentioned shortcomings of the prior art, the object of the present disclosure is to provide an organic mixture and application thereof in organic electronic devices, the mixture comprises a spirofluorene organic compound H1 containing fused heterocyclic rings and an aromatic fused heterocyclic organic compound H2 containing electron-donating groups, aiming to solve the problems of the existing poor performance and low lifetime of the organic electronic devices.

The technical solutions of the present disclosure are as follows:

An organic mixture comprising an organic compound H1 and an organic compound H2, wherein the organic compound H1 is a compound represented by following general formula (1):

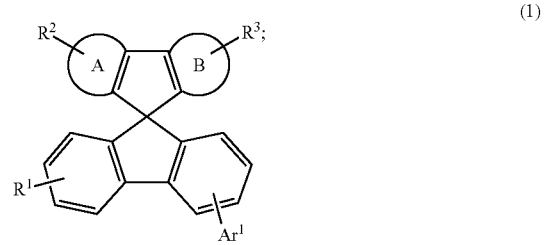

wherein,

A and B each independently represent an aromatic hydrocarbon group with 6 to 30 ring atoms or an aromatic heterocyclic group with 6 to 30 ring atoms, and at least one of A and B has more than 6 ring atoms;

$R^1$, $R^2$ and $R^3$ are substituents, each independently selected from the group consisting of H, deuterium, F, CN, alkenyl, alkynyl, nitrile group, amino group, nitro group, acyl, alkoxy group, carbonyl, sulfonyl, substituted or unsubstituted alkyl with 1 to 30 carbon atoms, substituted or unsubstituted cycloalkyl with 3 to 30 carbon atoms, and substituted or unsubstituted aromatic hydrocarbon group or aromatic heterocyclic group with 5 to 60 ring atoms, and the $R^1$, $R^2$ and $R^3$ each may substitute H on any one or more carbon atoms of the fused rings or benzene rings;

$Ar^1$ represents a substituted or unsubstituted aromatic hydrocarbon group with 5 to 100 ring atoms or aromatic heterocyclic group with 5 to 100 ring atoms, and contains at least one electron-accepting group, and the $Ar^1$ may bond to any one of the carbon atoms of the benzene ring;

the organic compound H2 is a compound represented by general formula (2):

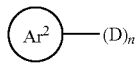

(2)

wherein, $Ar^2$ represents a substituted or unsubstituted alkyl with 1 to 30 carbon atoms, a substituted or unsubstituted cycloalkyl with 3 to 30 carbon atoms, a substituted or unsubstituted aromatic hydrocarbon group with 5 to 100 ring atoms or aromatic heterocyclic group with 5 to 100 ring atoms;

D is an electron-donating group; and n is an integer of 1-6.

A formulation comprising one organic mixture described above and an organic solvent is further provided.

An organic electronic device comprising at least one organic mixture described above is further provided.

In one of the embodiments, the light-emitting layer is prepared by one of the following methods:

(1) vacuum evaporating a source being the mixture comprising the organic compound H1 and the organic compound H2, to deposit the light-emitting layer;

(2) vacuum evaporating two separate sources being the organic compound H1 and the organic compound H2 respectively, to deposit the light-emitting layer; and;

(3) solution processing a raw material being the above-mentioned formulation to deposit the light-emitting layer.

The beneficial effects of the present disclosure are as follows:

the organic mixture of the present disclosure comprises a spirofluorene organic compound H1 containing fused heterocyclic rings and an aromatic fused heterocyclic organic compound H2 containing electron-donating groups, which can be applied to organic electronic devices. Taking an electroluminescent device for example, the organic mixture described in the present disclosure can provide a higher emitting efficiency and lifetime of the device. The possible reasons for which are as follows, but are not limited to: the spirofluorene organic compound H1 containing fused heterocyclic rings has an appropriate energy level and a vertically crossing spatial structure that can effectively prevent close packing between molecules and reduce the concentration of excitons. Using the fused heterocyclic spirofluorene as a basic skeleton and introducing an appropriate electron-accepting unit to design it into an electron-transporting molecule, and then collocating with another type of aromatic fused heterocyclic organic compound H2 containing electron-donating groups to form a mixture, which can balance electron and hole transport, thereby effectively reducing the loss of energy, in turn improving the performance and lifetime of the device.

DETAILED DESCRIPTION OF THE EMBODIMENTS

The present disclosure provides an organic mixture and application thereof in organic electronic devices, the mixture comprises a spirofluorene organic compound containing fused heterocyclic rings and an aromatic fused heterocyclic organic compound containing electron-donating groups. In order to make the purpose, technical solution and effects of the present disclosure clearer and more specific, the present disclosure will be further described in detail below. It should be understood that the specific embodiments illustrated herein are merely for the purpose of explanation, and should not be deemed to limit the disclosure.

In the present disclosure, host material, matrix material, Host or Matrix material have the same meaning and they can be used interchangeably.

In the present disclosure, metal organic clathrate, metal organic complex, and organometallic complex have the same meaning and they can be used interchangeably.

In the present disclosure, "substituted" in the expression "substituted or unsubstituted" means that the hydrogen atom in the substituent is substituted by a substituent, and "unsubstituted" represents that the hydrogen atom in the group is not substituted by a substituent. Wherein, the substituent may be selected from the following group consisting of: H, D, F, CN, alkenyl, alkynyl, nitrile group, amino group, nitro group, acyl, alkoxy, carbonyl, sulfonyl, boron-containing group, silicon-containing group, alkyl with 1-50 (in a further embodiment, 1-18; and in a still further embodiment, 1-8) carbon atoms, cycloalkyl with 3-50 (in a further embodiment, 3-10; in a further embodiment, 3-8; and in a particular embodiment, 5 or 6) ring atoms, and aromatic hydrocarbon group or aromatic heterocyclic group with 3-50 (in a further embodiment, 3-25; and in a still further embodiment, 3-18) ring atoms.

In the present disclosure, the number of "ring atoms" means the atom number of the atoms constituted the ring itself of the structural compound (such as, a monocyclic compound, a fused ring compound, a cross-linked compound, a carbocyclic compound, a heterocyclic compound) obtained by bonding atoms into rings. When the ring is substituted with a substituent, the atoms contained in the substituent are not included in the ring-constituting atoms. As for the number of "ring atoms" described below is the same unless otherwise specified. For example, the benzene ring contains 6 ring atoms, the naphthalene ring contains 10 ring atoms, and the thienyl contains 5 ring atoms.

In the present disclosure, the "aromatic hydrocarbon group" refers to a hydrocarbon group containing at least one aromatic ring, including monocyclic group and polycyclic ring system. The "heteroaromatic group" refers to a hydrocarbon group (containing heteroatoms) comprising at least one heteroaromatic ring, including monocyclic group and polycyclic ring system. Such polycyclic rings may have two or more rings wherein two carbon atoms are shared by two adjacent rings, i.e., a fused ring. At least one ring of these polycyclic rings is aromatic or heteroaromatic. For the purpose of the present disclosure, the aromatic or heteroaromatic ring systems not only include aryl or heteroaryl systems, but also have a plurality of aryl or heteroaryl groups interrupted by short non-aromatic units (<10% of non-H atoms, particularly less than 5% of non-H atoms, such as C, N or O atoms). Therefore, systems such as 9,9'-spirobifluorene, 9,9-diarylfluorene, triarylamine, diaryl ether and the like are also considered to be aromatic ring systems for the purpose of the present disclosure.

Specifically, examples of the aromatic hydrocarbon group include: benzene, naphthalene, anthracene, phenanthrene, perylene, tetracene, pyrene, benzopyrene, triphenylene, acenaphthene, fluorene, and derivatives thereof.

Specifically, examples of the aromatic heterocyclic group include: furan, benzofuran, thiophene, benzothiophene, pyrrole, pyrazole, triazole, imidazole, oxazole, oxadiazole, thiazole, tetrazole, indole, carbazole, pyrroloimidazole, pyrrolopyrrole, thienopyrrole, thienothiophene, furopyrrole, furofuran, thienofuran, benzisoxazole, benzisothiazole, benzimidazole, pyridine, pyrazine, pyridazine, pyrimidine, triazine, quinoline, isoquinoline, cinnoline, quinoxaline, phenanthridine, perimidine, quinazoline, quinazolinone, and derivatives thereof.

The present disclosure provides an organic mixture comprising an organic compound H1 and an organic compound H2, and the organic compound H1 is a compound represented by following general formula (1):

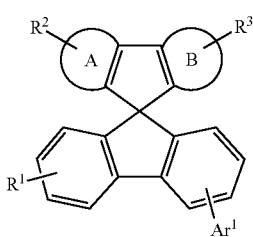
(1)

wherein,

A and B independently represent an aromatic hydrocarbon group with 6-30 ring atoms or an aromatic heterocyclic group with 6-30 ring atoms, and at least one of A and B has more than 6 ring atoms;

$R^1$, $R^2$ and $R^3$ are substituents, each independently selected from the group consisting of H, deuterium, F, CN, alkenyl, alkynyl, nitrile group, amino group, nitro group, acyl, alkoxy group, carbonyl, sulfonyl, substituted or unsubstituted alkyl with 1-30 carbon atoms, substituted or unsubstituted cycloalkyl with 3 to 30 carbon atoms, and substituted or unsubstituted aromatic hydrocarbon group or aromatic heterocyclic group with 5 to 60 ring atoms, and the $R^1$, $R^2$ and $R^3$ each may substitute H on any one or more carbon atoms of the fused rings or benzene rings;

$Ar^1$ represents a substituted or unsubstituted aromatic hydrocarbon group with 5 to 100 ring atoms or aromatic heterocyclic group with 5 to 100 ring atoms, and contains at least one electron-accepting group, and the $Ar^1$ may bond to any one of the carbon atoms of the benzene rings;

the organic compound H2 is a compound represented by general formula (2):

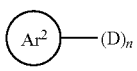
(2)

wherein, $Ar^2$ represents a substituted or unsubstituted alkyl with 1-30 carbon atoms, a substituted or unsubstituted cycloalkyl with 3 to 30 carbon atoms, a substituted or unsubstituted aromatic hydrocarbon group with 5 to 100 ring atoms or aromatic heterocyclic group with 5 to 100 ring atoms;

D is an electron-donating group; and n is an integer of 1-6.

In certain embodiments, A and B shown in general formula (1) each independently represent an aromatic hydrocarbon group with 6 to 25 ring atoms or aromatic heterocyclic group with 6 to 25 ring atoms; in a further embodiment, A and B each independently represent an aromatic hydrocarbon group with 6 to 20 ring atoms or aromatic heterocyclic group with 6 to 20 ring atoms; in a particular embodiment, A and B each independently represent an aromatic hydrocarbon group with 6 to 15 ring atoms or aromatic heterocyclic group with 6 to 15 ring atoms.

In some embodiments, A and B shown in general formula (1) may be the same or different, and selected from the group consisting of following structural groups, wherein H on the rings may be arbitrarily substituted:

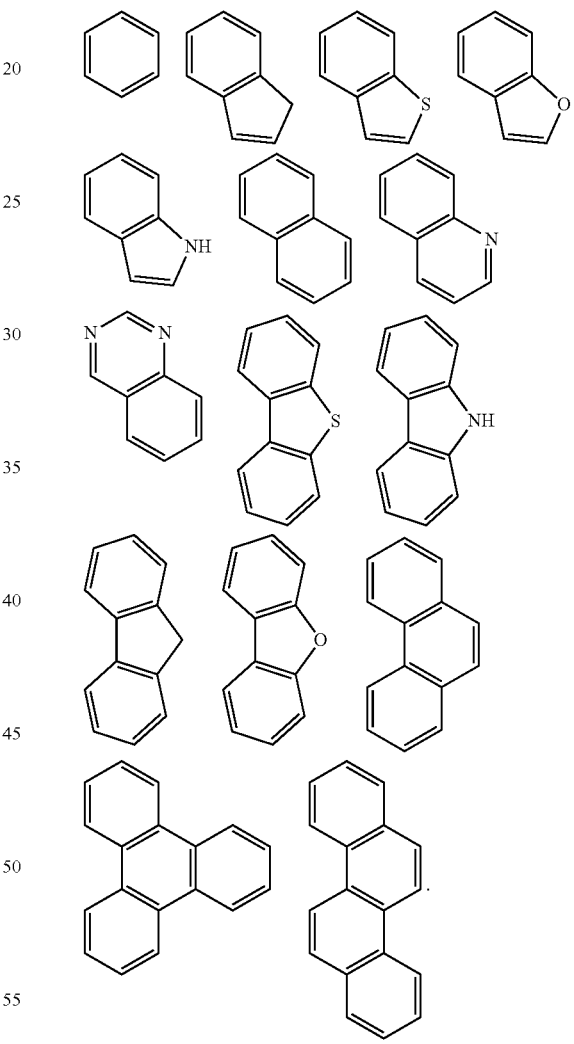

In some embodiments, at least one of A and B is

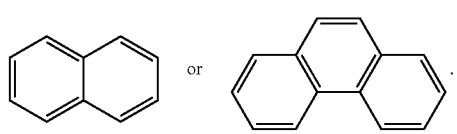

In certain embodiments, the substituents $R^1$, $R^2$ and $R^3$ are each independently selected from the group consisting of H, D, CN, nitrile group, substituted or unsubstituted alkyl with 1 to 18 carbon atoms, substituted or unsubstituted cycloalkyl with 3 to 18 carbon atoms, and substituted or unsubstituted aromatic hydrocarbon group or aromatic heterocyclic group with 5 to 30 ring atoms; in a further embodiment, $R^1$, $R^2$ and $R^3$ are each independently selected from the group consisting of H, D, substituted or unsubstituted alkyl with 1 to 12 carbon atoms, and substituted or unsubstituted aromatic hydrocarbon group or aromatic heterocyclic group with 5 to 20 ring atoms; in a particular embodiment, $R^1$, $R^2$ and $R^3$ are each independently selected from the group consisting of H, D, substituted or unsubstituted alkyl with 1 to 6 carbon atoms, and substituted or unsubstituted aromatic hydrocarbon group or aromatic heterocyclic group with 5 to 15 ring atoms.

In some embodiments, $R^1$, $R^2$ and $R^3$ are H.

In certain embodiments, $Ar^1$ shown in general formula (1) represents a substituted or unsubstituted aromatic hydrocarbon group with 5 to 80 ring atoms or aromatic heterocyclic group with 5 to 80 ring atoms; in a further embodiment, $Ar^1$ represents a substituted or unsubstituted aromatic hydrocarbon group with 5 to 60 ring atoms or aromatic heterocyclic group with 5 to 60 ring atoms; in a still further embodiment, $Ar^1$ represents a substituted or unsubstituted aromatic hydrocarbon group with 5 to 40 ring atoms or aromatic heterocyclic group with 5 to 40 ring atoms; in a particular embodiment, $Ar^1$ represents a substituted or unsubstituted aromatic hydrocarbon group with 5 to 30 ring atoms or aromatic heterocyclic group with 5 to 30 ring atoms.

In certain embodiments, $Ar^2$ shown in general formula (2) represents a substituted or unsubstituted alkyl with 1 to 20 carbon atoms, a substituted or unsubstituted cycloalkyl with 3 to 25 carbon atoms, a substituted or unsubstituted aromatic hydrocarbon group with 5 to 80 ring atoms or aromatic heterocyclic group with 5 to 80 ring atoms; in a further embodiment, $Ar^2$ represents a substituted or unsubstituted alkyl with 1 to 10 carbon atoms, a substituted or unsubstituted cycloalkyl with 3 to 15 carbon atoms, a substituted or unsubstituted aromatic hydrocarbon group with 5 to 60 ring atoms or aromatic heterocyclic group with 5 to 60 ring atoms; in a particular embodiment, $Ar^2$ represents a substituted or unsubstituted alkyl with 1 to 6 carbon atoms, a substituted or unsubstituted cycloalkyl with 3 to 10 carbon atoms, a substituted or unsubstituted aromatic hydrocarbon group with 5 to 40 ring atoms or aromatic heterocyclic group with 5 to 40 ring atoms.

In some embodiments, $Ar^1$ in general formula (1) and $Ar^2$ in general formula (2) may comprise one or more of the following structural groups:

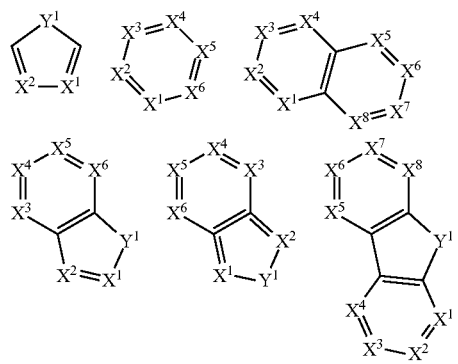

-continued

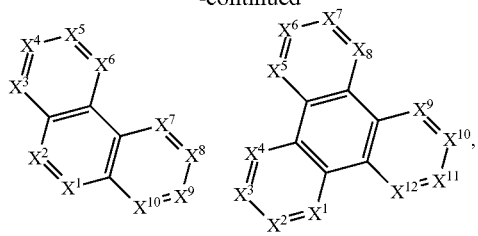

wherein, $X^1$-$X^{12}$ each independently represent $CR^4$ or N; at least one of $X^1$-$X^{12}$ is N when it is $Ar^1$.

$Y^1$ is selected from the group consisting of $N(R^4)$, $C(R^4R^5)$, $Si(R^4R^5)$, $C(=O)$, S, and O;

$R^4$ and $R^5$ each independently represent H, a substituted or unsubstituted alkyl with 1-30 carbon atoms, a substituted or unsubstituted cycloalkyl with 3 to 30 carbon atoms, a substituted or unsubstituted aromatic hydrocarbon group with 5 to 60 ring atoms or aromatic heterocyclic group with 5 to 60 ring atoms.

In some further embodiments, $Ar^1$ in general formula (1) and $Ar^2$ in general formula (2) may comprise one or more of the following structural groups, wherein H on the ring may be arbitrarily substituted:

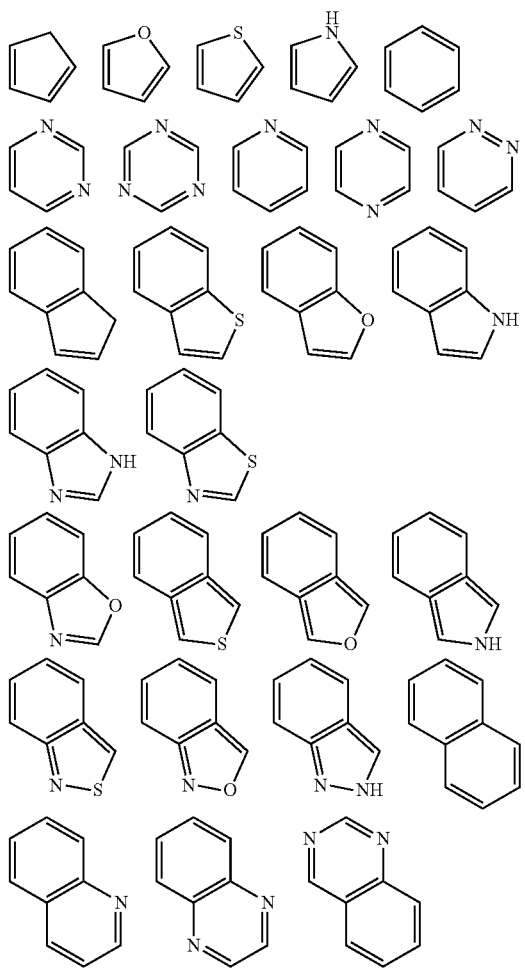

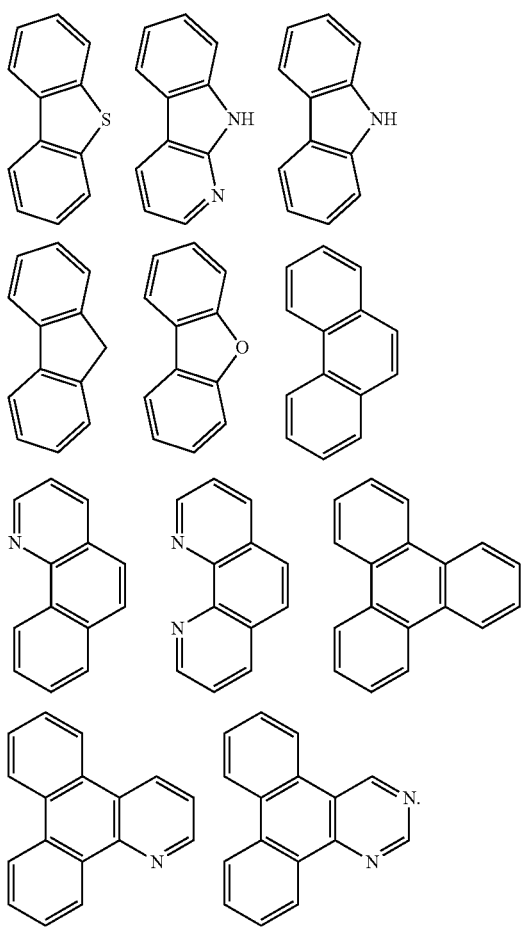

In certain embodiments, Ar¹ has a structure represented by formula (10):

$$Ar^4 — R_0 — Ar^6 \quad (10)$$

wherein, $R_0$ represents the electron-accepting group; $Ar^4$ and $Ar^6$ each independently represent a substituted or unsubstituted aromatic hydrocarbon group with 5 to 30 ring atoms or aromatic heterocyclic group with 5 to 30 ring atoms, or is absent.

In certain embodiments, $Ar^4$ and $Ar^6$ are each independently one selected from the following structural groups:

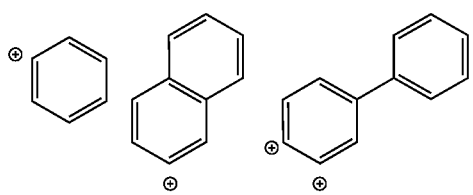

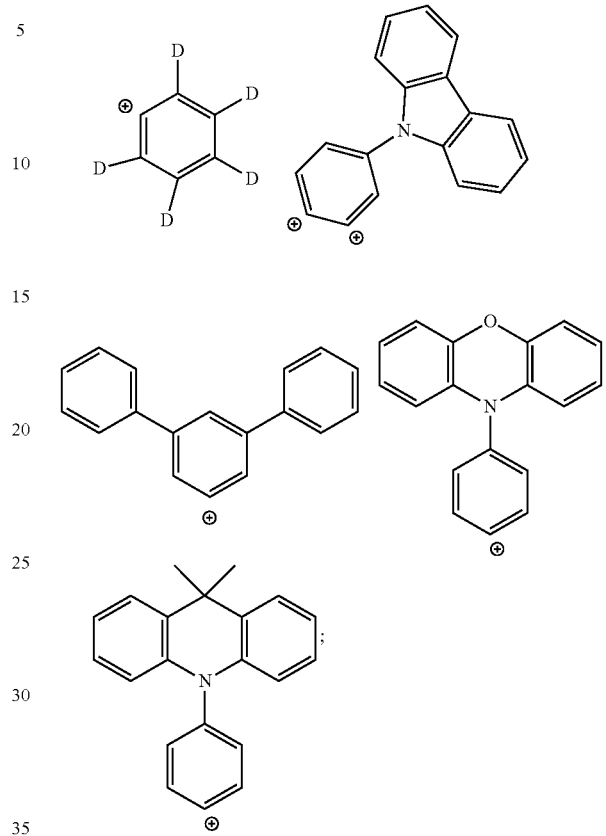

wherein, ⊕ represents the bonding sites between $Ar^4$ or $Ar^6$ and $R_0$.

In certain embodiments, $Ar^2$ is one selected from the following structural groups, wherein H on the rings may be arbitrarily substituted:

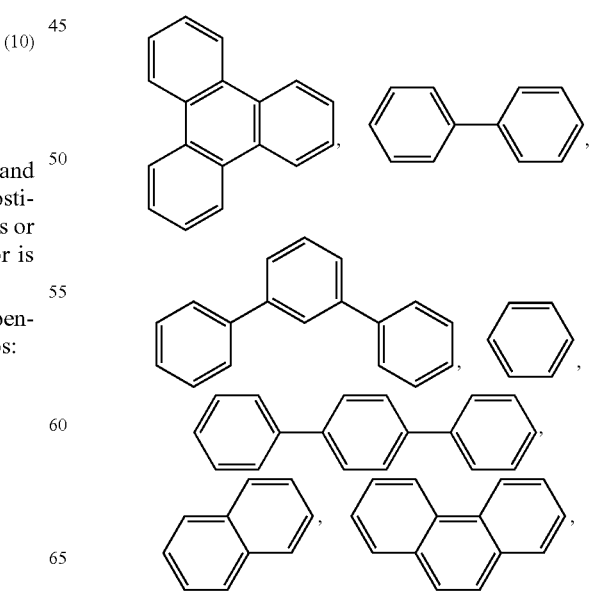

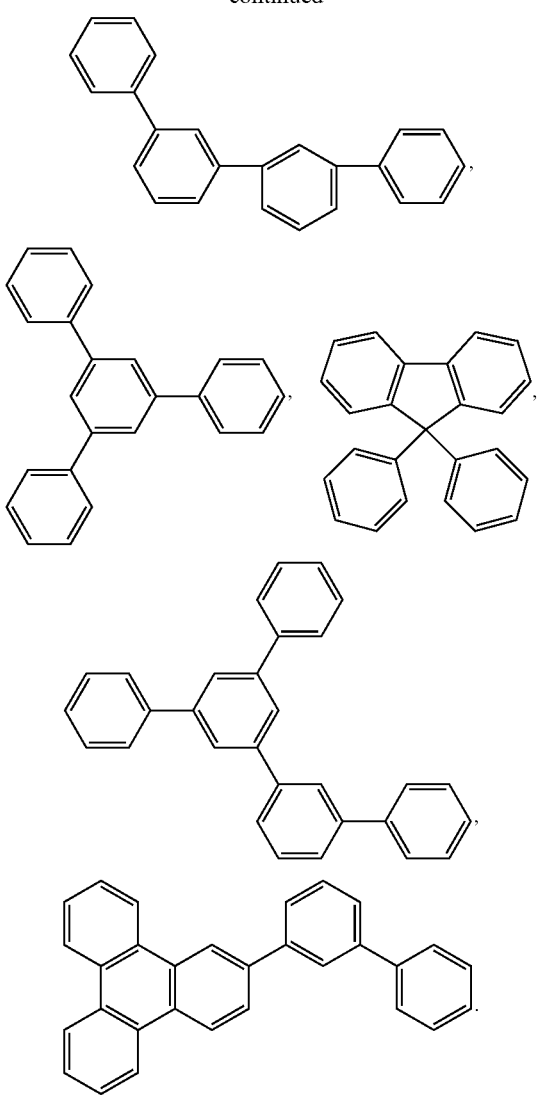

In some embodiments, the electron-accepting group $R_0$ contained in $Ar^1$ of general formula (1) may be selected from the group consisting of F, cyano group, and the following groups:

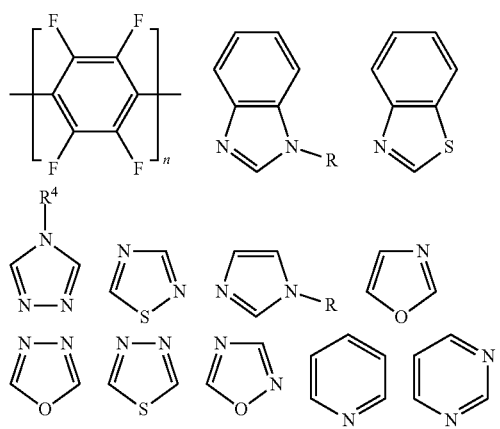

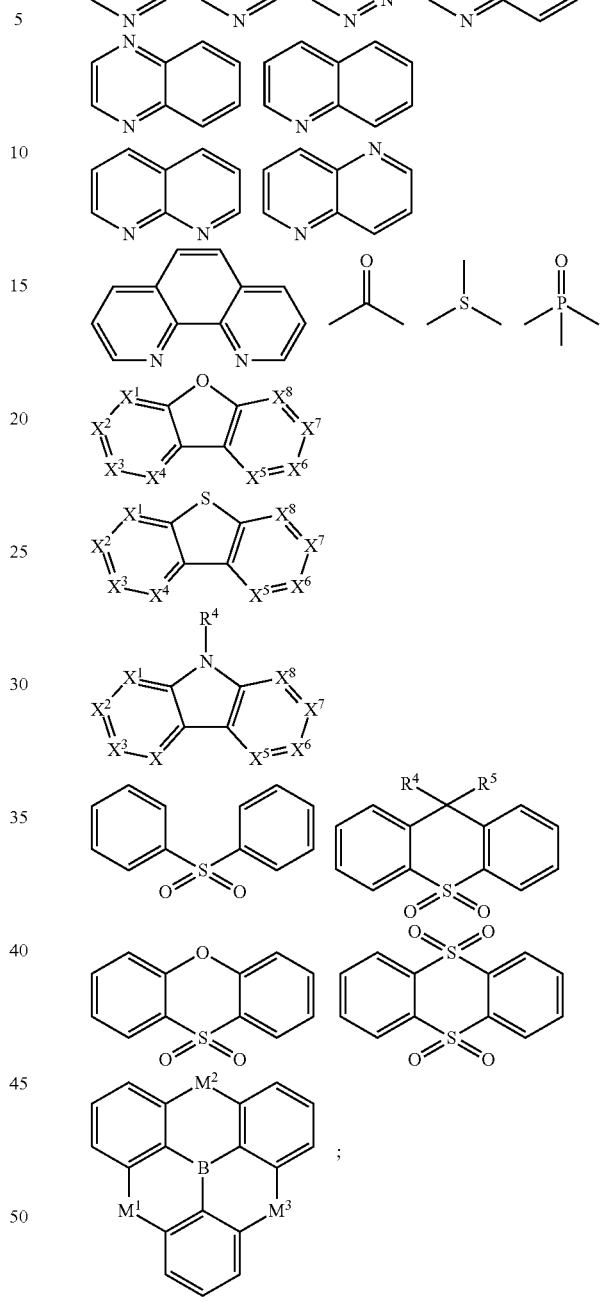

wherein, m is 1, 2 or 3; $X^1$-$X^8$ are selected from $CR^4$ or N, and at least one is N; $M^1$, $M^2$ and $M^3$ each independently represent $N(R^4)$, $C(R^4R^5)$, $Si(R^4R^5)$, O, $C=N(R^4)$, $C=C(R^4R^5)$, $P(R^4)$, $P(=O)R^4$, S, S=O, $SO_2$ or none; R, $R^4$ and $R^5$ each independently represent H, a substituted or unsubstituted alkyl with 1-30 carbon atoms, a substituted or unsubstituted cycloalkyl with 3 to 30 carbon atoms, a substituted or unsubstituted aromatic hydrocarbon group or aromatic heterocyclic group with 5 to 60 ring atoms.

In a further embodiment, the electron-accepting group $R_0$ contained in $Ar^1$ of general formula (1) may be selected from the group consisting of F, cyano group, and the following groups:

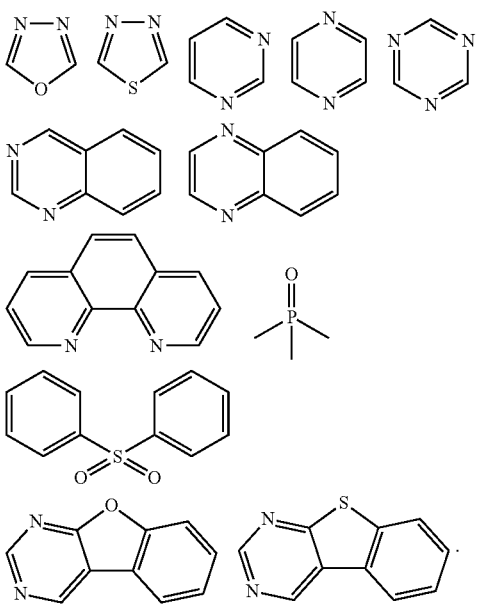

In one embodiment, Ar¹ of general formula (1) may be selected from the the following groups:

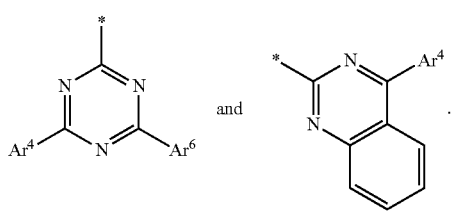

In some embodiments, the electron-donating (or electron-donor) group D in general formula (2) contains any one of the following groups, wherein H on the rings may be arbitrarily substituted:

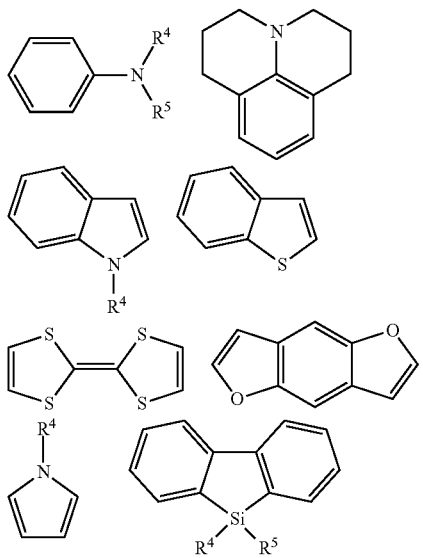

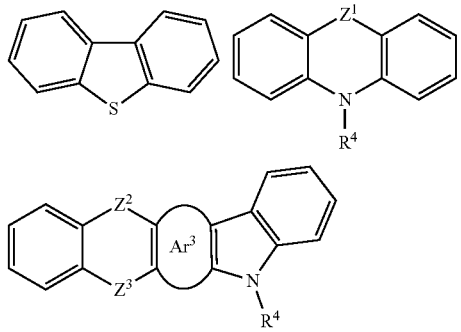

wherein, $Ar^3$ represents an aromatic hydrocarbon group with 5 to 40 ring atoms or an aromatic heterocyclic group with 5 to 40 ring atoms;

$Z^1$, $Z^2$ and $Z^3$ each independently represent a single bond, $N(R^4)$, $C(R^4R^5)$, $Si(R^4R^5)$, O, $C=N(R^4)$, $C=C(R^4R^5)$, $P(R^4)$, $P(=O)R^4$, S, S=O or $SO_2$, wherein $Z^2$ and $Z^3$ are not single bonds simultaneously.

$R^4$ and $R^5$ are defined as above.

In some further embodiments, the electron-donating (or electron-donor) group D in general formula (2) contains any one of the following groups:

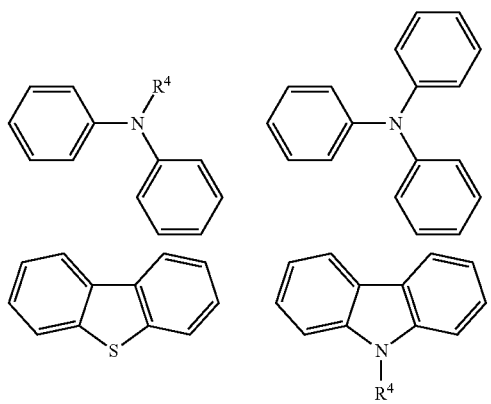

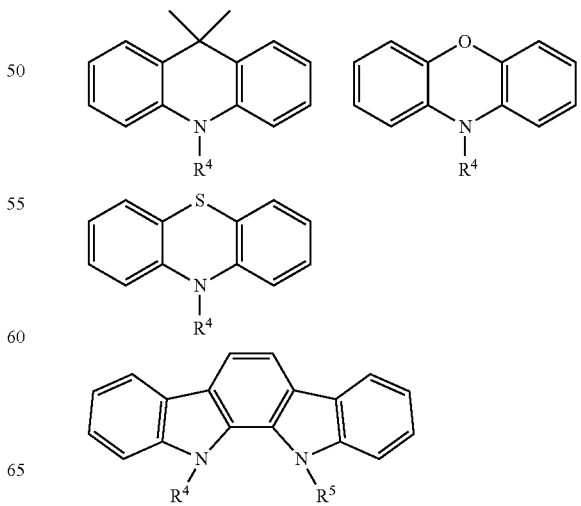

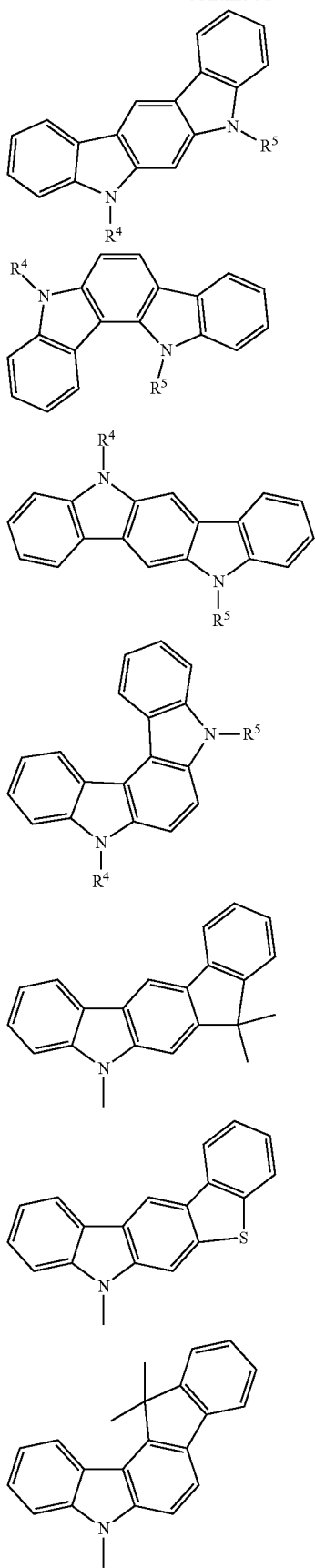
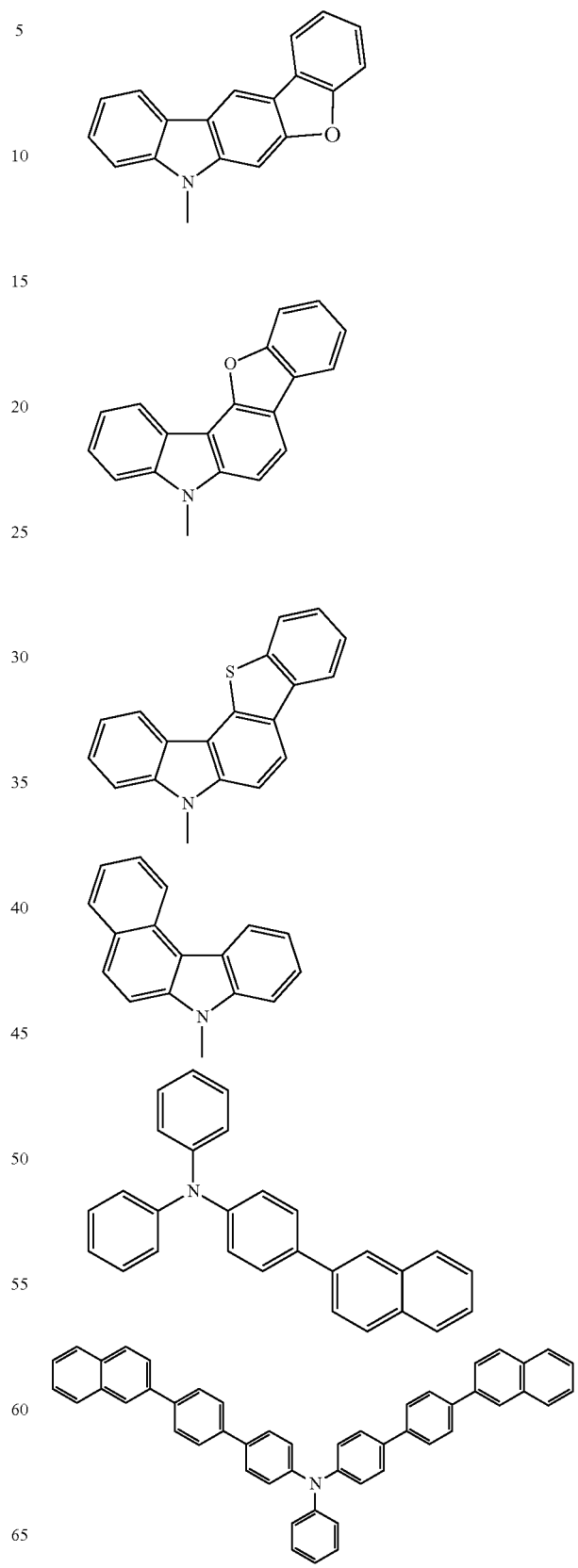

-continued

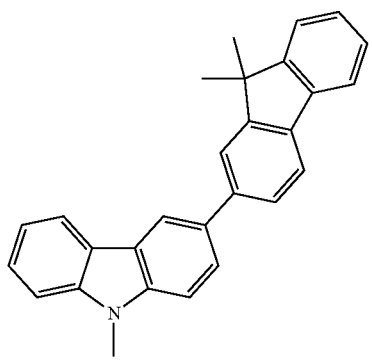 [SMILES: Cn1c2ccccc2c2cc(-c3ccc4c(c3)C(C)(C)c3ccccc3-4)ccc21]

$R^4$ and $R^5$ are defined as above.

In certain embodiments, n is an integer of 1 to 4; in a further embodiment, n is an integer of 1 to 3; in a particular embodiment, n is an integer of 1 to 2.

In certain embodiments, the organic compound H1 or H2 in the mixture of the present disclosure has a higher triplet energy level $T_1$, typically $T_1 \geq 2.2$ eV, in a further embodiment, $T_1 \geq 2.3$ eV, in a still further embodiment, $T_1 \geq 2.4$ eV, in yet another embodiment, $T_1 \geq 2.5$ eV, in a particular embodiment, $T_1 \geq 2.6$ eV.

Typically, the triplet energy level $T_1$ of the organic compound depends on the substructure having the largest conjugated system in the compound. In general, $T_1$ decreases progressively as the conjugated system increases. In certain embodiments, the substructure of general formula (1) as represented by the following general formula (1a) has the largest conjugated system.

(1a)

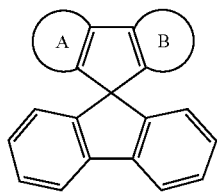

In certain embodiments, in the case where the substituents are removed from general formula (1a), the number of the ring atoms thereof is no more than 36, in a further embodiment, it is no more than 33, in a particular embodiment, it is no more than 30.

In other embodiments, in the case where the substituents are removed from general formula (1a), the organic compound of general formula (1a) has $T_1 \geq 22.2$ eV, in another embodiment, $T_1 \geq 2.3$ eV, in yet another embodiment, $T_1 \geq 2.4$ eV, in a further embodiment, $T_1 \geq 2.6$ eV, in a particular embodiment, $T_1 \geq 2.7$ eV.

In some embodiments, according to the organic mixture of the present disclosure, wherein H1 is one selected from the following structural formulas:

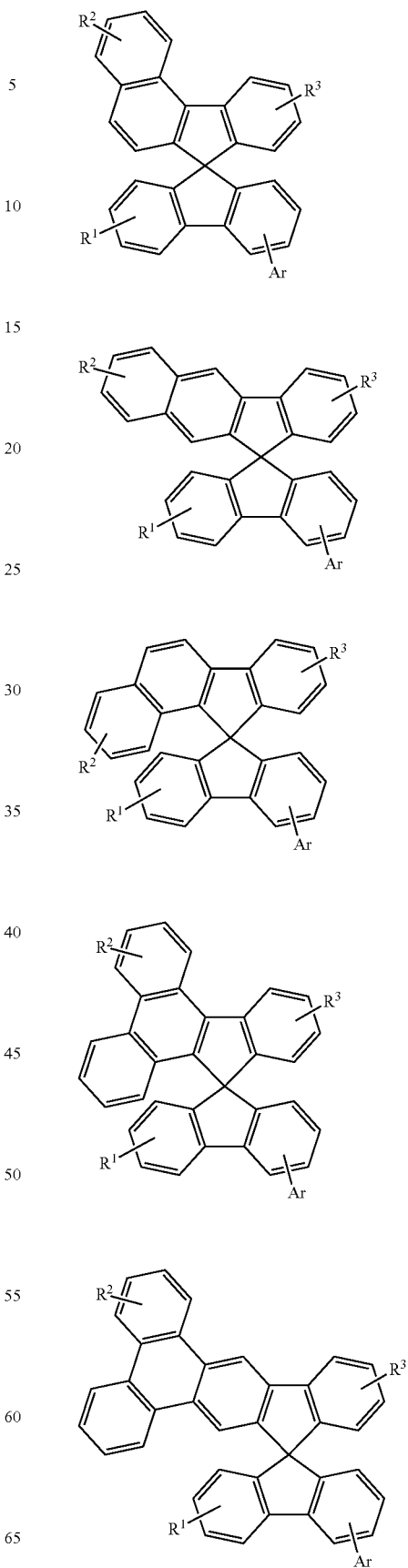

-continued
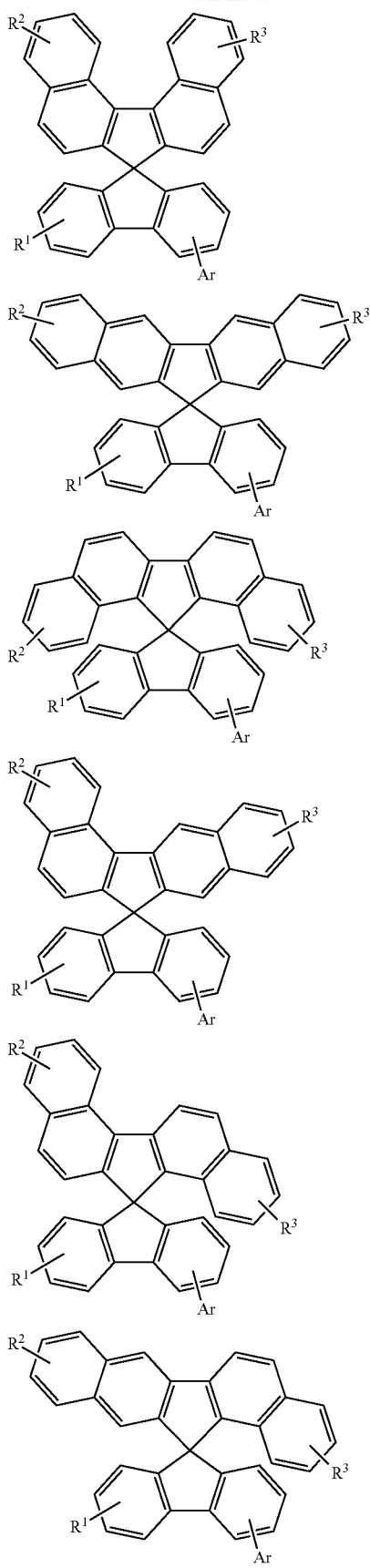
-continued
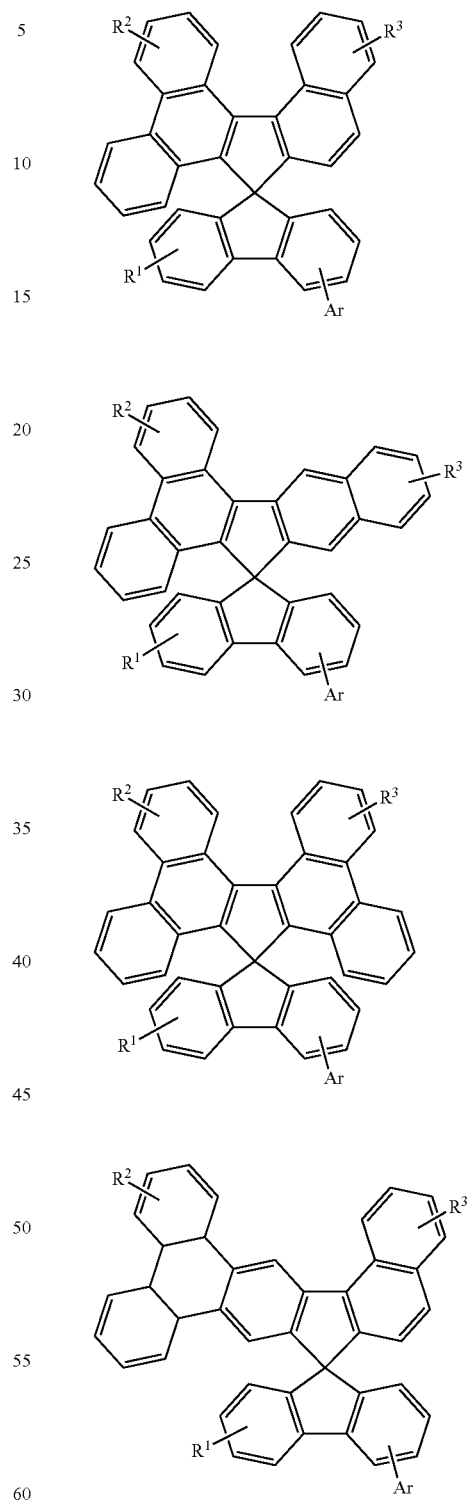
wherein, $R^1$, $R^2$, $R^3$ and $Ar^1$ are defined as described above.
In some embodiments, according to the organic mixture of the present disclosure, wherein H1 is a compound represented by following formulas:

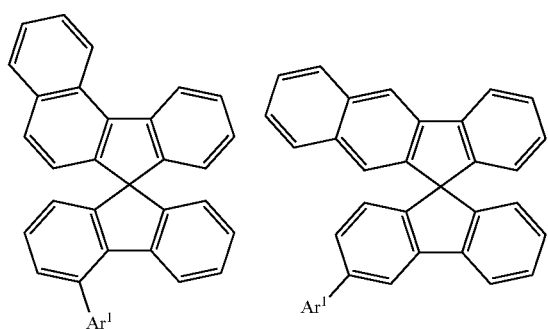
In some embodiments, according to the organic mixture of the present disclosure, wherein H2 is one selected from the following structural formulas:
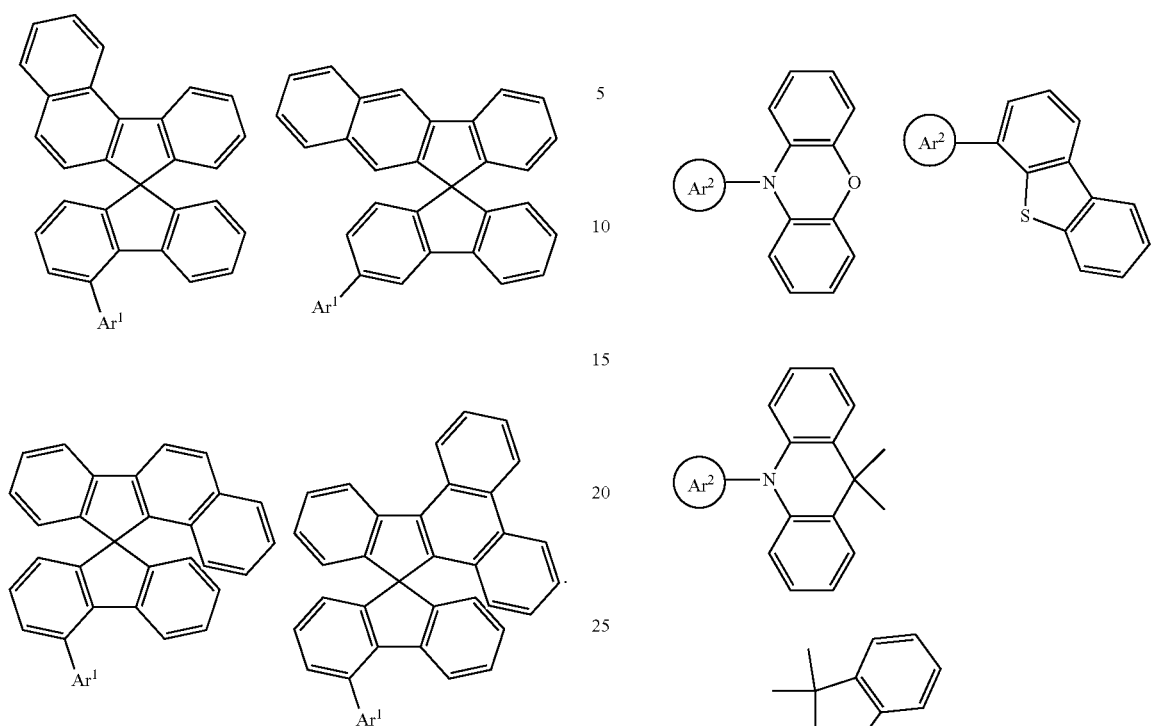
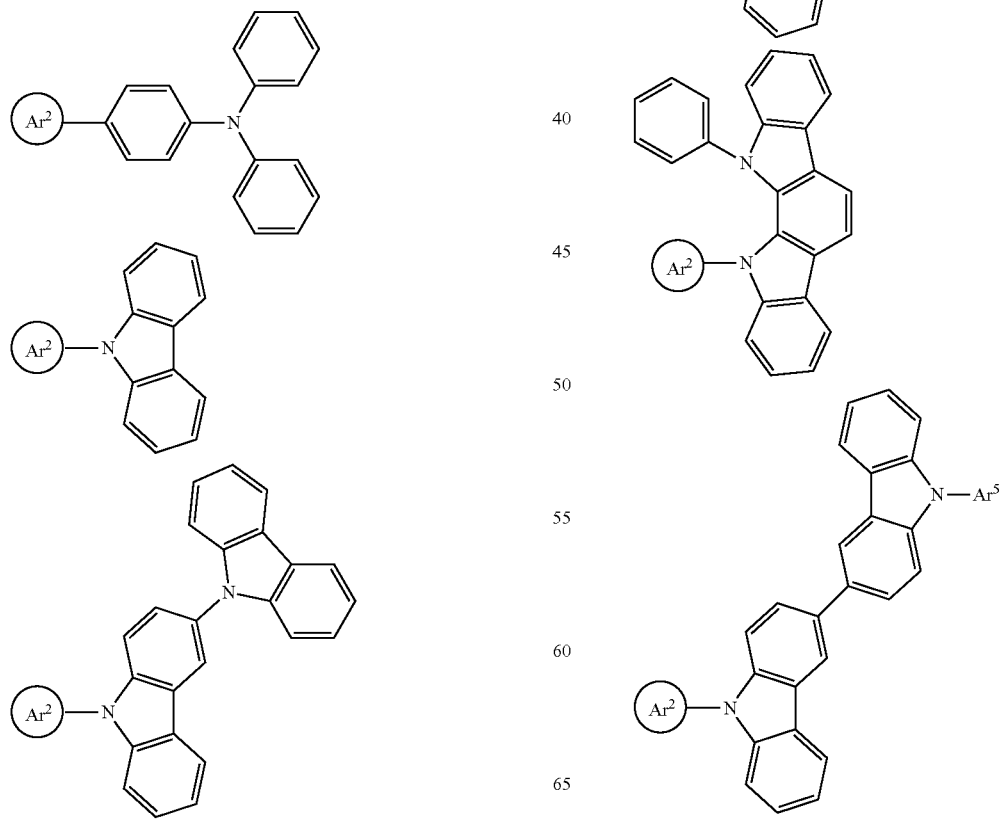

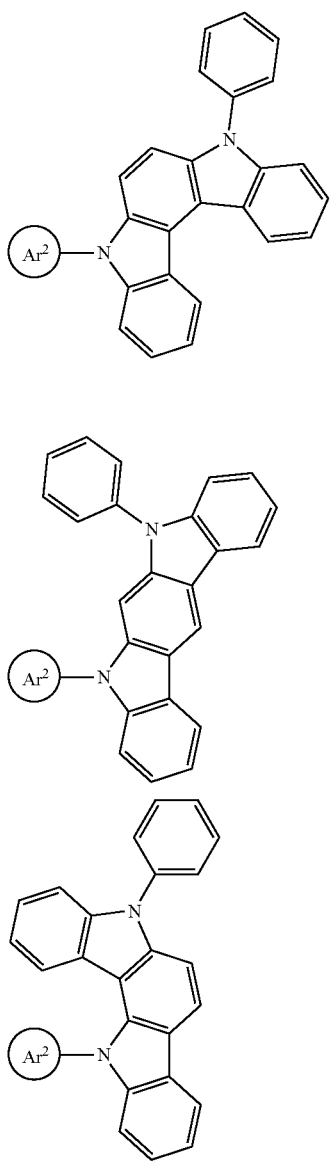

wherein, Ar² is defined as described above, and the definition of Ar⁵ refers to that of Ar².

In some further embodiments, the organic compound H2 is a compound represented by following formulas:

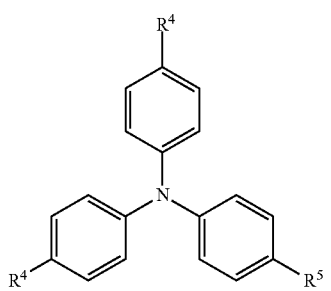

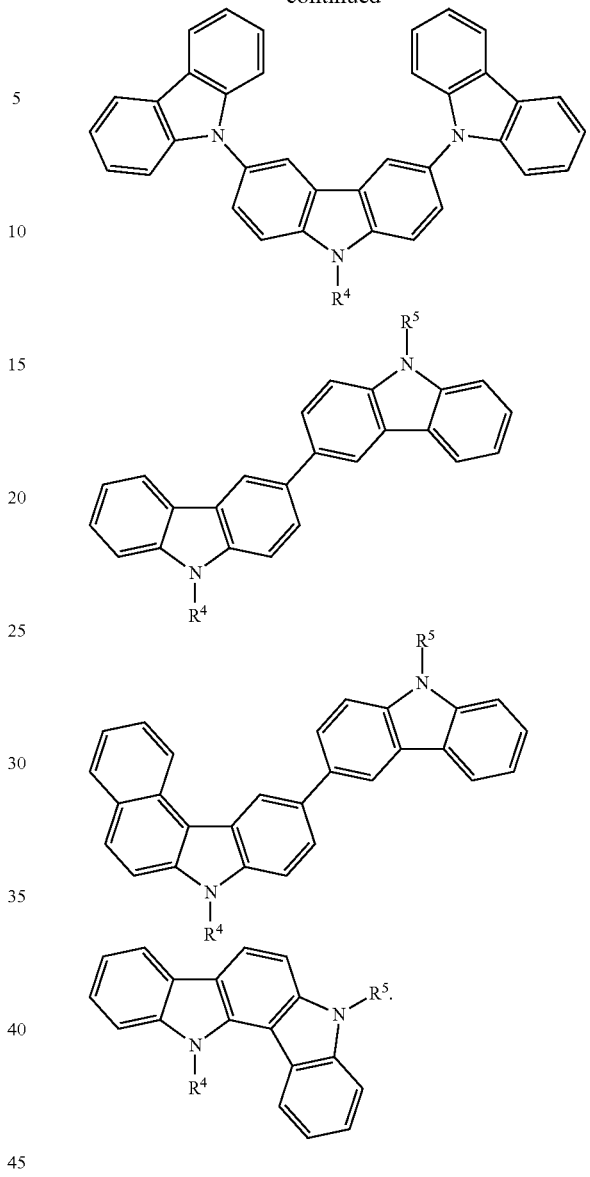

In certain embodiments, in the organic mixture, H1 and H2 form a type II heterojunction structure, that is, the highest occupied molecular orbital (HOMO) energy level of H1 is lower than the HOMO of H2, and the lowest unoccupied molecular orbital (LUMO) energy level of H1 is lower than the LUMO of H2.

In a further embodiment, in the organic mixture, min ((LUMO(H1)−HOMO(H2), LUMO(H2)−HOMO(H1))≤min(ET(H1), ET(H2))+0.1 eV, wherein, LUMO(H1), HOMO(H1) and ET(H1) are the lowest unoccupied molecular orbital energy level, the highest occupied molecular orbital energy level and the triplet energy levels of H1, respectively, and LUMO(H2), HOMO(H2) and ET(H2) are the lowest unoccupied molecular orbital energy level, highest occupied molecular orbital energy level and triplet energy levels of H2, respectively.

In one embodiment, in the organic mixture, min((LUMO(H1)−HOMO(H2), LUMO(H2)−HOMO(H1))≤min($E_T$(H1), $E_T$(H2));

In another embodiment, in the organic mixture, min ((LUMO(H1)−HOMO(H2), LUMO(H2)−HOMO(H1))≤min($E_T$(H1,$E_T$(H2))−0.05 eV;

In a further embodiment, in the organic mixture, min((LUMO(H1)−HOMO(H2), LUMO(H2)−HOMO(H1))≤min($E_T$(H1), $E_T$(H2))−0.1 eV;

In a still further embodiment, in the organic mixture, min((LUMO(H1)−HOMO(H2), LUMO(H2)−HOMO(H1))≤min($E_T$(H1), $E_T$(H2))−0.15 eV;

In a particular embodiment, in the organic mixture, min((LUMO(H1)−HOMO(H2), LUMO(H2)−HOMO(H1))≤min($E_T$(H1), $E_T$(H2))−0.2 eV;

In the present embodiment, the energy level structure of the organic material, the triplet energy level $E_T$, HOMO and LUMO play a key role. The determinations of these energy levels are described below.

The HOMO and LUMO energy levels can be measured by photoelectric effect, such as XPS (X-ray photoelectron spectroscopy) and UPS (Ultraviolet photoelectron spectroscopy), or by cyclic voltammetry (hereinafter referred to as CV). Recently, quantum chemistry method such as density functional theory (hereinafter referred to as DFT), has also become a feasible method for calculating molecular orbital energy levels.

The triplet energy level $E_T$ of organic materials can be measured by low temperature time-resolved luminescence spectroscopy, or obtained by quantum simulation calculation (e.g., by Time-dependent DFT), such as by the commercial software Gaussian 03W (Gaussian Inc.) in which the specific simulation method may refer to WO2011141110 or may be as described in the embodiments below.

It should be noted that, the absolute values of HOMO, LUMO and $E_T$ depend on the measurement method or calculation method used, even for the same method, different HOMO/LUMO value may be obtained by different evaluation methods, such as at starting point and peak point on the CV curve. Therefore, reasonable and meaningful comparisons should be made by using the same measurement method and the same evaluation method. In the description of the embodiments of the present disclosure, the values of HOMO, LUMO and E are based on the simulations of Time-dependent DFT, but this does not affect the application of other measurement or calculation methods.

A possible advantage of the organic mixture according to the present disclosure is that the excited state of the system will preferentially occupy the exciplex with the lowest energy, or to facilitate the energy transfer of the triplet excited state of H1 or H2 to the exciplex, thereby improving the concentration of the exciplex.

In one embodiment, the organic mixture according to the present disclosure may be used as a phosphorescent host material.

In the present disclosure, (HOMO-1) is defined as the second highest occupied molecular orbital energy level, and (HOMO-2) is the third highest occupied molecular orbital energy level, and so on. (LUMO+1) is defined as the second lowest unoccupied molecular orbital energy level, and (LUMO+2) is the third lowest occupied molecular orbital energy level, and so on.

In other embodiments, in the organic mixture, H1 and H2 form a type I heterojunction structure, that is, the highest occupied molecular orbital (HOMO) energy level of H1 is lower than the HOMO of H2, and the lowest unoccupied molecular orbital (LUMO) energy level of H1 is higher than the LUMO of H2.

In a particular embodiment, according to the formulation of the present disclosure, wherein H2 has thermally activated delayed fluorescent (Thermally activated delayed fluorescent, TADF) properties.

According to the principle of thermally activated delayed fluorescent TADF material (see Adachi et al., *Nature*, Vol 492, 234, (2012)), when the (S1-T1) of organic compound is small enough, the triplet excitons of the organic compound can be converted to singlet excitons via reverse internal conversion, thereby achieving high efficient light emission. In general, TADF material is obtained by linking an electron-donor group to an electron deficiency or electron acceptor group directly or via other groups, that is, having a distinct D-A structure.

In one embodiment, according to the formulation of the present disclosure, wherein H2 has a smaller (S1-T1), generally (S1-T1)≤0.30 eV, in a further embodiment, (S1-T1)≤0.25 eV, in a still further embodiment, (S1-T1)≤0.20 eV, in yet another embodiment, (S1-T1)≤0.15 eV, and in a particular embodiment, (S1-T1)≤0.10 eV.

In certain embodiments, according to the mixture of the present disclosure, wherein H2 contains at least one electron-donor group, and contains at least one electron acceptor group. In another embodiment, H2 has the structure of general formula (2), wherein $Ar^2$ contains at least one electron-donor group. Suitable TADF materials that may be used as H2 will be described in detail below.

In the mixture, when H1 and H2 form a type I or type II heterojunction structure, there are some special requirements due to stability or process considerations.

In a further embodiment, according to the mixture of the present disclosure, wherein at least one of H1 and H2 has a ((LUMO+1)−LUMO) greater than or equal to 0.1 eV, in a further embodiment, at least one of H1 and H2 has a ((LUMO+1)−LUMO) greater than or equal to 0.15 eV, in a still further embodiment, at least one of H1 and H2 has a ((LUMO+1)−LUMO) greater than or equal to 0.20 eV, in a yet further embodiment, at least one of H1 and H2 has a ((LUMO+1)−LUMO) greater than or equal to 0.25 eV, and in a particular embodiment, at least one of H1 and H2 has a ((LUMO+1)−LUMO) greater than or equal to 0.30 eV.

In another embodiment, according to the mixture of the present disclosure, wherein at least one of H1 and H2 has a (HOMO−(HOMO−1)) greater than or equal to 0.2 eV, in a further embodiment, at least one of H1 and H2 has a (HOMO−(HOMO−1)) greater than or equal to 0.25 eV, in a still further embodiment, at least one of H1 and H2 has a (HOMO−(HOMO−1)) greater than or equal to 0.30 eV, in a yet further embodiment, at least one of H1 and H2 has a (HOMO−(HOMO−1)) greater than or equal to 0.35 eV, and in a particular embodiment, at least one of H1 and H2 has a (HOMO−(HOMO−1)) greater than or equal to 0.40 eV.

In one embodiment, the molar ratio of H1 to H2 in the mixture material is from 2:8 to 8:2; in a further embodiment, it is from 3:7 to 7:3; and in a still further embodiment, it is from 4:6 to 6:4.

In one embodiment, at least one of H1 and H2 in the mixture material according to the present disclosure has a glass transition temperature $T_g$≥100° C. In another embodiment, at least one of H1 and H2 in the mixture material according to the present disclosure has a $T_g$≥120° C. In a further embodiment, at least one of H1 and H2 in the mixture material according to the present disclosure has a $T_g$≥140° C., in a still further embodiment, at least one of H1 and H2 in the mixture material according to the present disclosure has a $T_g$≥160° C., and in a particular embodiment, at least one of H1 and H2 in the mixture material according to the present disclosure has a $T_g$≥180° C.

In a further embodiment, at least one of H1 and H2 in the mixture material according to the present disclosure is partially deuterated, further 10% of H is deuterated, still further 20% of H is deuterated, even further 30% of H is deuterated, particularly 40% of H is deuterated.

In one embodiment, in the mixture material according to the present disclosure, H1 and H2 are both small molecule materials.

One object of the present disclosure is to provide a material solution for evaporated-type OLEDs.

In one embodiment, the mixture material according to the present disclosure is used for evaporated-type OLED devices. For this purpose, H1 and H2 in the mixture material according to the present disclosure has a molecular weight of ≤1000 g/mol, ≤900 g/mol in one embodiment, ≤850 g/mol in another embodiment, ≤800 g/mol in a further embodiment, ≤700 g/mol in a particular embodiment.

In one embodiment, the difference between the molecular weight of H1 and that of H2 in the mixture material does not exceed 100 Dalton; in a further embodiment, the difference between the molecular weight of H1 and that of H2 in the mixture material does not exceed 60 Dalton; and in a still further embodiment, the difference between the molecular weight of H1 and that of H2 in the mixture material does not exceed 30 Dalton.

In another embodiment, the difference between the sublimation temperature of H1 and that of H2 in the mixture material does not exceed 30 K; in a further embodiment, the difference between the sublimation temperature of H1 and that of H2 in the mixture material does not exceed 20 K; and in a still further embodiment, the difference between the sublimation temperature of H1 and that of H2 in the mixture material does not exceed 10 K.

Another object of the present disclosure is to provide a material solution for printing OLEDs.

For this purpose, at least one of (especially both of) H1 and H2 in the mixture according to the present disclosure has a molecular weight of ≥700 g/mol, at least one of (especially both of) H1 and H2 in the mixture according to the present disclosure has a molecular weight of ≥800 g/mol in one embodiment, at least one of (especially both of) H1 and H2 in the mixture according to the present disclosure has a molecular weight of ≥900 g/mol in another embodiment, at least one of (especially both of) H1 and H2 in the mixture according to the present disclosure has a molecular weight of ≥1000 g/mol in a further embodiment, at least one of (especially both of) H1 and H2 in the mixture according to the present disclosure has a molecular weight of ≥1100 g/mol in a particular embodiment.

In the co-host in the form of premix in the evaporated-type OLEDs, the two host materials are required to have similar chemical properties or physical properties, such as molecular weight and sublimation temperature. The present disclosure has been found that the two host materials with different properties may improve film-forming properties in solution-processed OLEDs, thereby improving the performance of devices. In addition to the molecular weight and sublimation temperature, the properties mentioned can also be others, such as glass transition temperature, different molecular volumes, etc. Therefore, as for printing OLEDs, embodiments of the mixture according to the present disclosure are:

1) The difference between the molecular weight of H1 and that of H2 is 120 g/mol, in a further embodiment, it is ≥140 g/mol, in a still further embodiment, it is ≥160 g/mol, and in a particular embodiment, it is ≥180 g/mol.

2) The difference between the sublimation temperature of H1 and that of H2 is ≥60 K, in a further embodiment, it is ≥70 K, in a still further embodiment, it is ≥75 K, and in a particular embodiment, it is ≥80 K.

3) The difference between the glass transition temperature of H1 and that of H2 is ≥20 K, in a further embodiment, it is ≥30 K, in a still further embodiment, it is ≥40 K, and in a particular embodiment, it is ≥45 K.

4) The difference between the molecular volume of H1 and that of H2 is ≥20%, in a further embodiment, it is ≥30%, in a still further embodiment, it is ≥40%, and in a particular embodiment, it is ≥45%.

In other embodiments, at least one of (especially both of) H1 and H2 in the mixture according to the present disclosure has a solubility in toluene at 25° C. of ≥2 mg/ml, in a further embodiment, it is ≥3 mg/ml, in a still further embodiment, it is ≥4 mg/ml, and in a particular embodiment, it is ≥5 mg/ml.

The term "small molecule" as defined herein refers to a molecule that is not a polymer, oligomer, dendrimer, or blend. In particular, there is no repetitive structure in small molecules. The small molecule has a molecular weight ≤3000 g/mole, in a further embodiment, it is ≤2000 g/mole, and in a particular embodiment, it is ≤1500 g/mole.

Polymer includes homopolymer, copolymer, and block copolymer. In addition, in the present disclosure, the polymer also includes dendrimer, and for the synthesis and application of dendrimers, see [Dendrimers and Dendrons, Wiley-VCH Verlag GmbH & Co. KGaA, 2002, Ed. George R. Newkome, Charles N. Moorefield, Fritz Vogtle.].

Conjugated polymer is a polymer whose backbone is primarily consisted of the sp2 hybrid orbital of C atoms. Famous examples are polyacetylene and poly (phenylene vinylene), the C atoms on the backbones of which may also be substituted by other non-C atoms, and which are still considered to be conjugated polymers when the sp2 hybridization on the backbones is interrupted by some natural defects. In addition, the conjugated polymer in the present disclosure also include aryl amine, aryl phosphine and other heteroaromatics, organometallic complexes, and the like in the backbone.

Specific examples of the compound represented by the general formula (1) are exemplified below, but are not limited to:

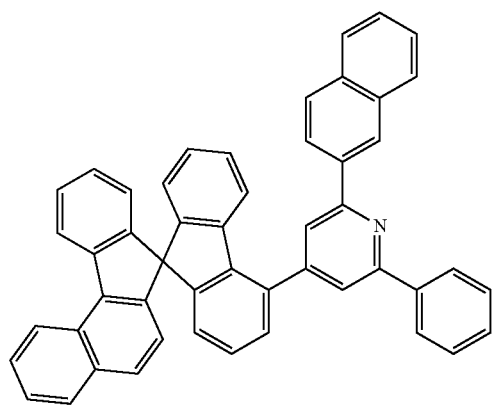

(1-1)

-continued
(1-2)
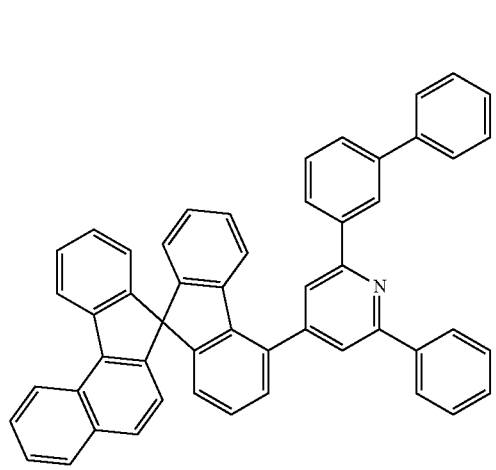
(1-3)
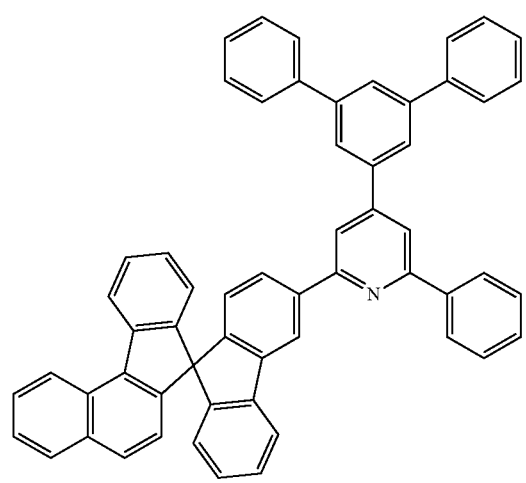
(1-4)
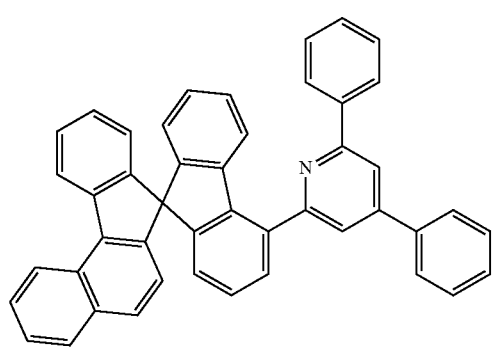
-continued
(1-5)
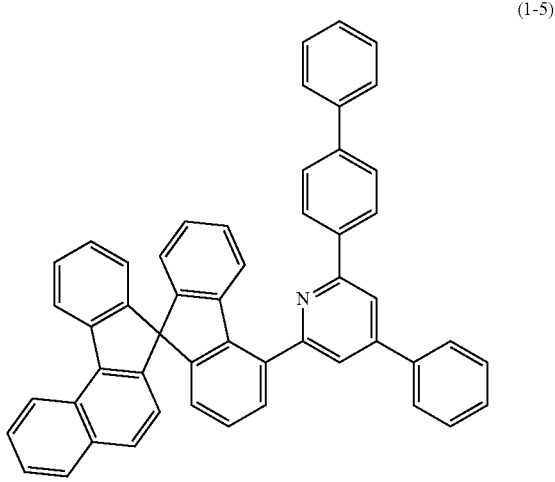
(1-6)
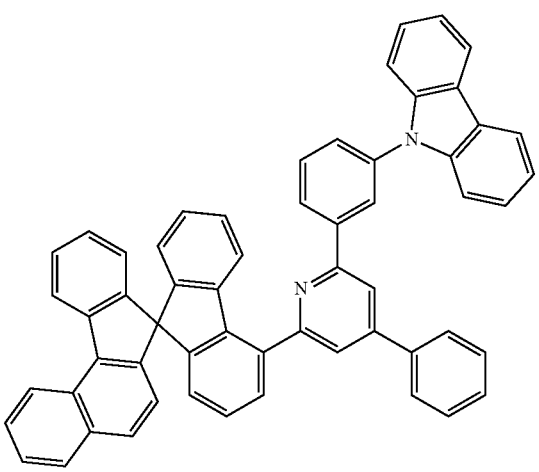
(1-7)
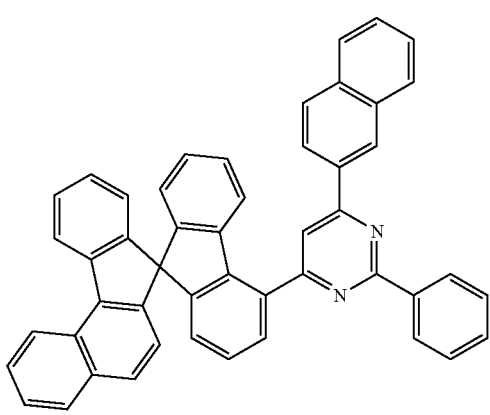

(1-8)
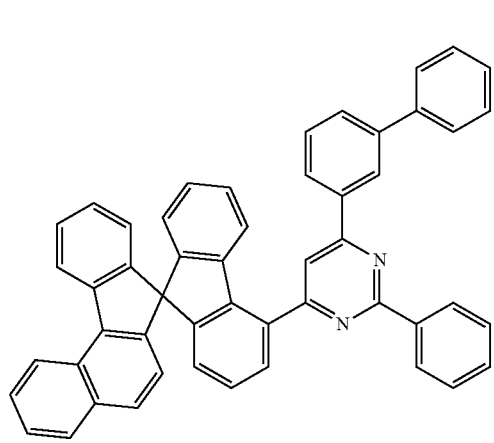
(1-9)
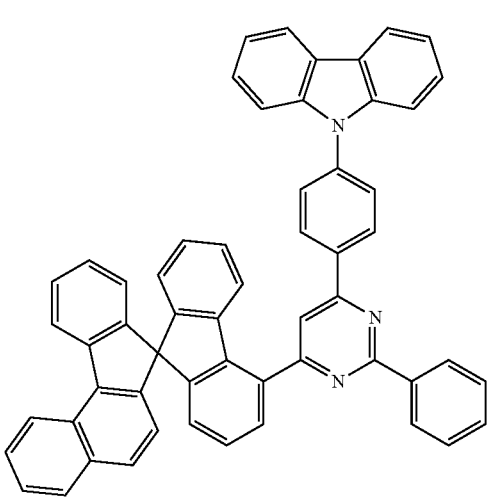
(1-10)
(1-11)
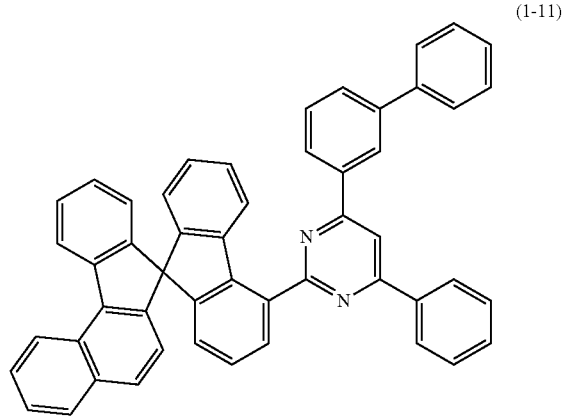
(1-12)
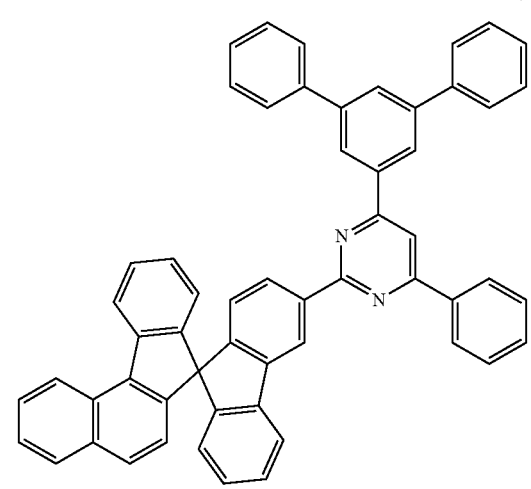
(1-13)
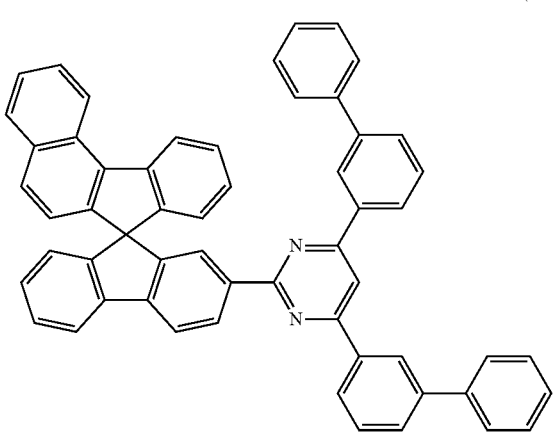

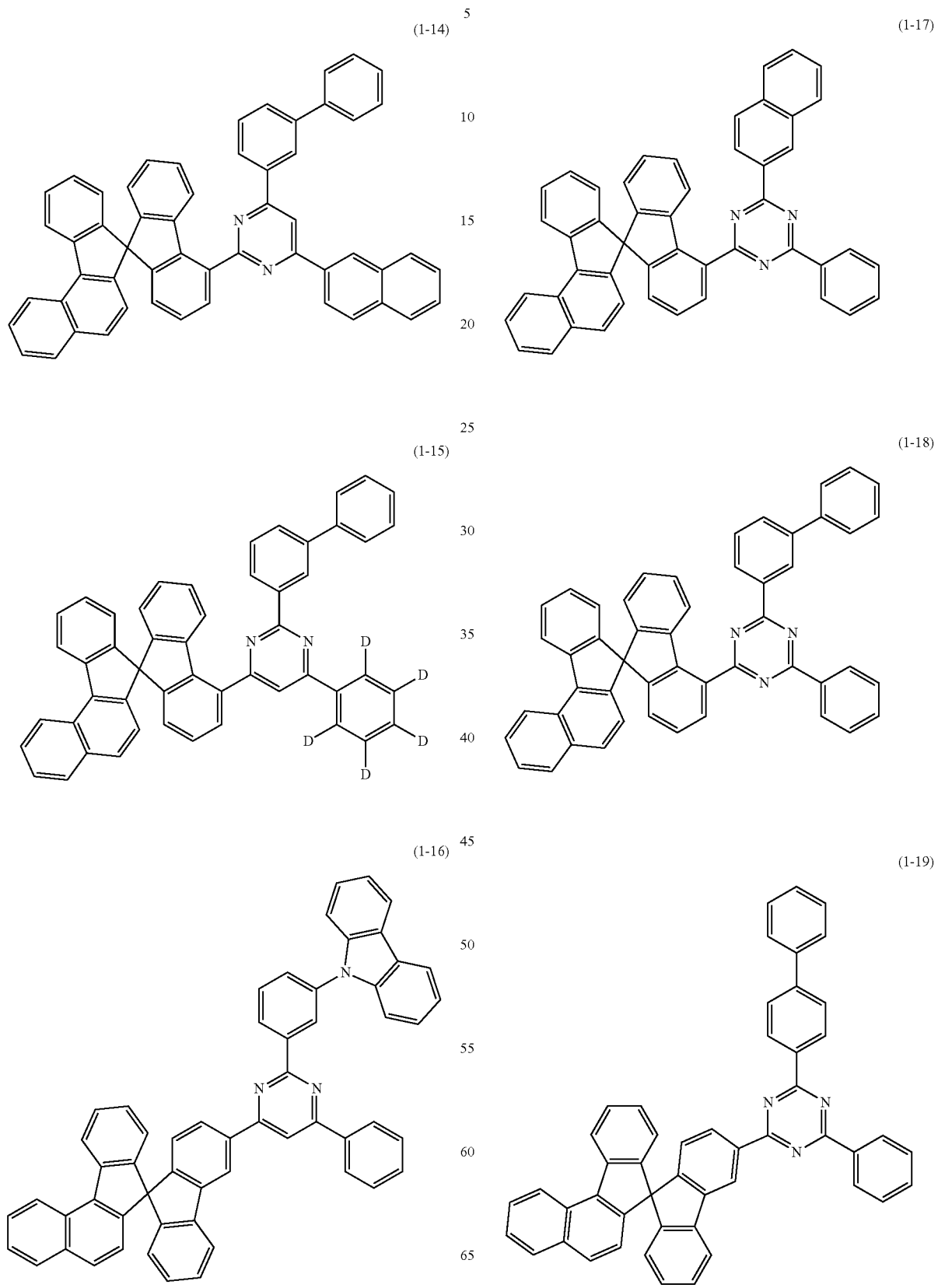

(1-20)
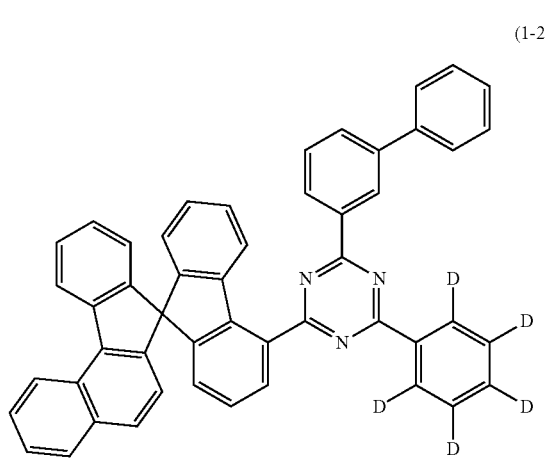
(1-21)
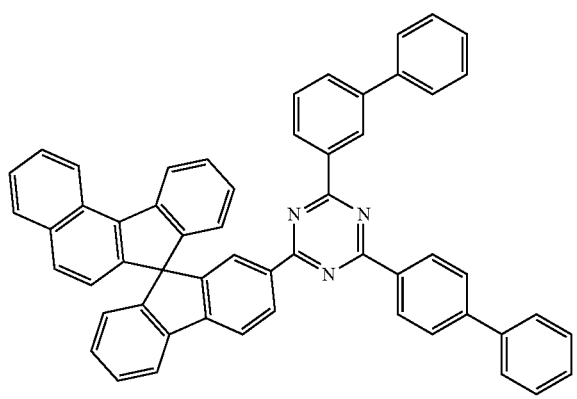
(1-22)
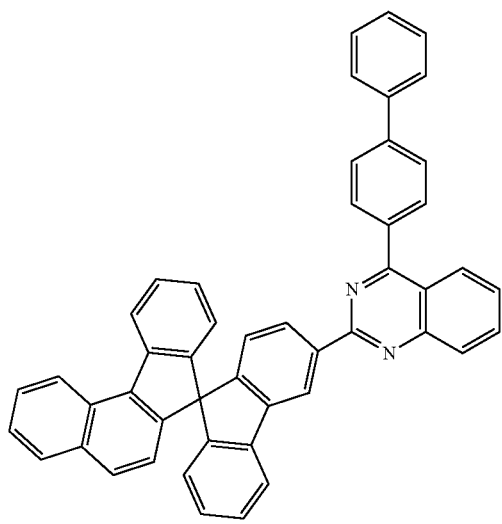
(1-23)
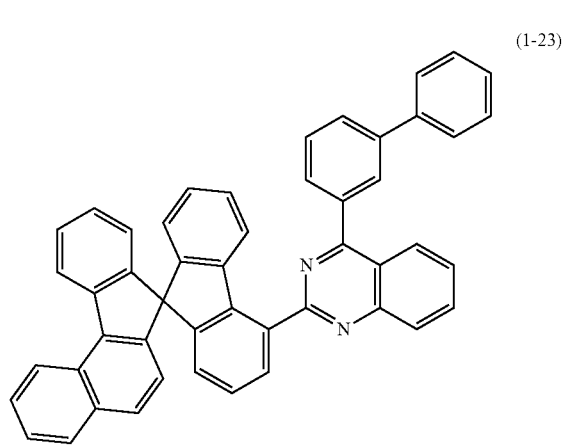
(1-24)
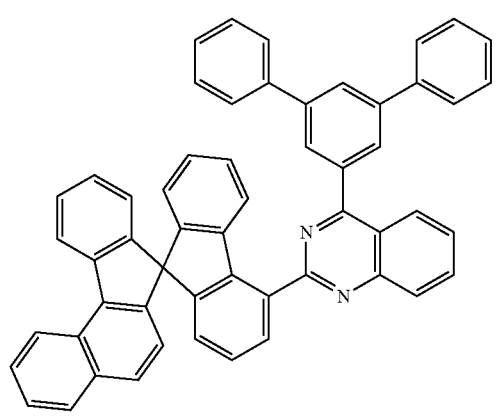
(1-25)
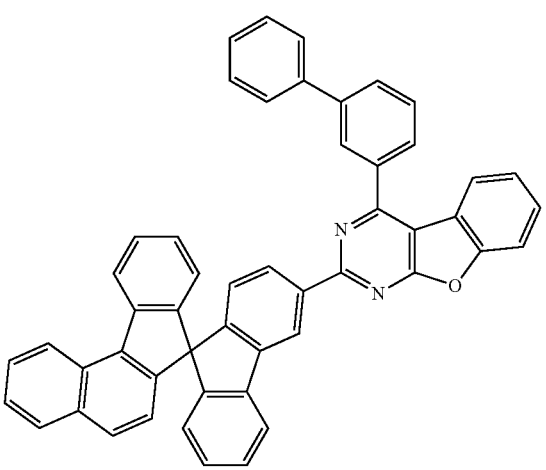

(1-26)
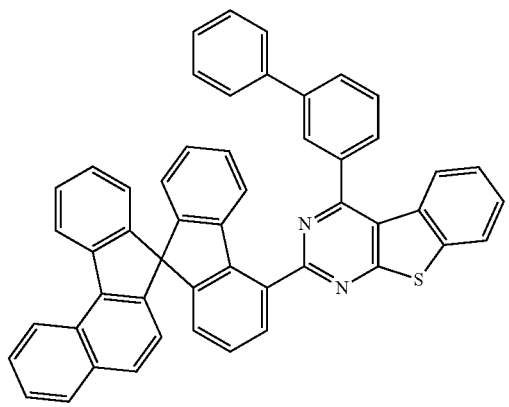
(1-27)
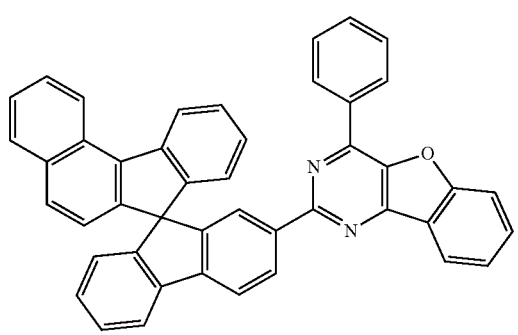
(1-30)
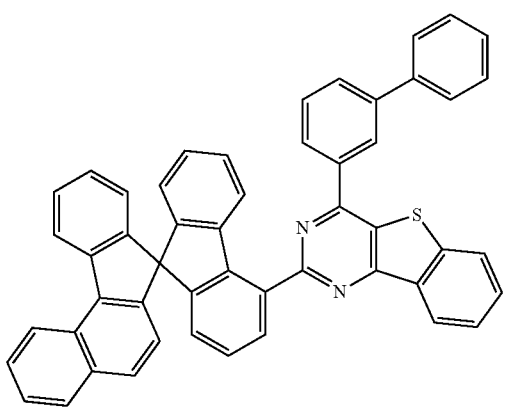
(1-31)
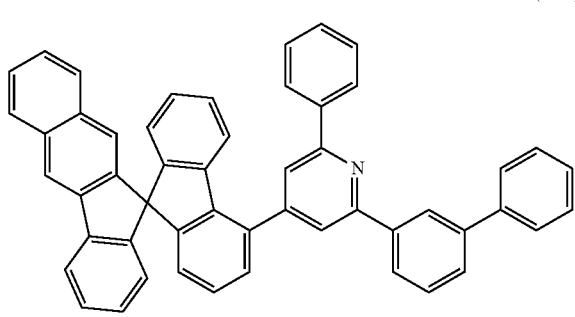
(1-28)
(1-32)
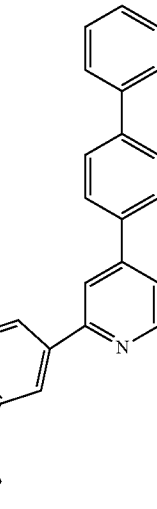
(1-29)
(1-33)
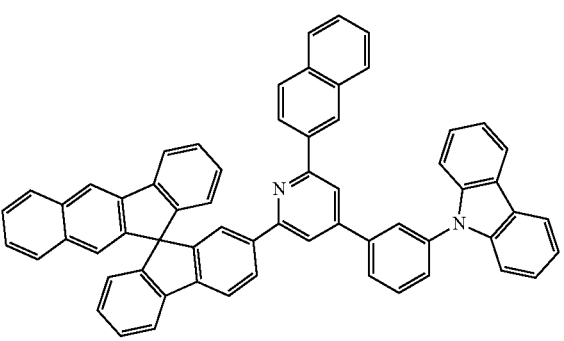

(1-34)
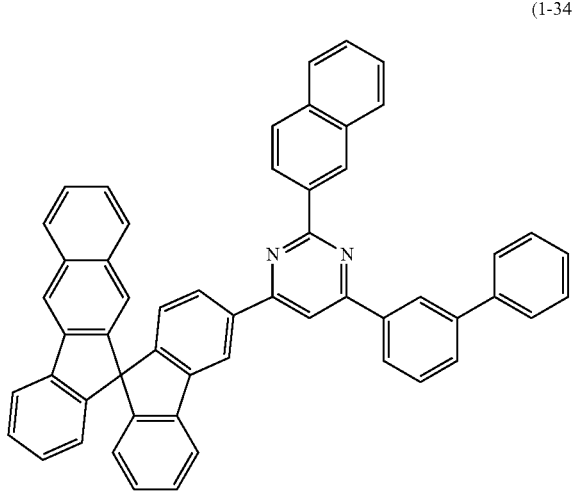
(1-35)
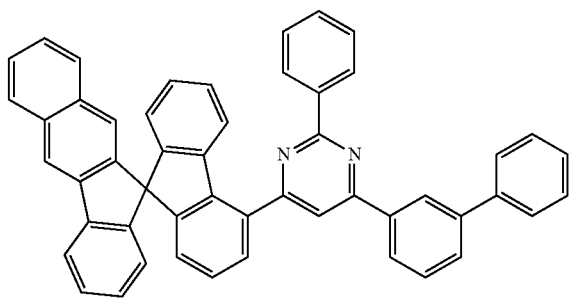
(1-36)
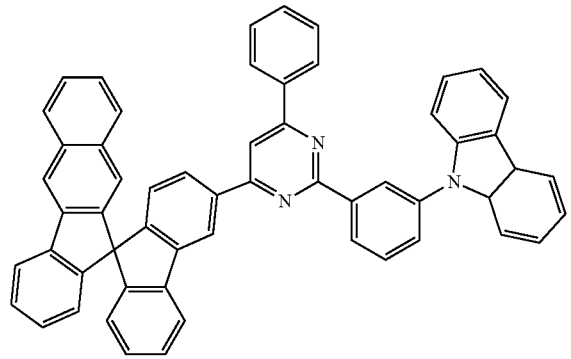
(1-37)
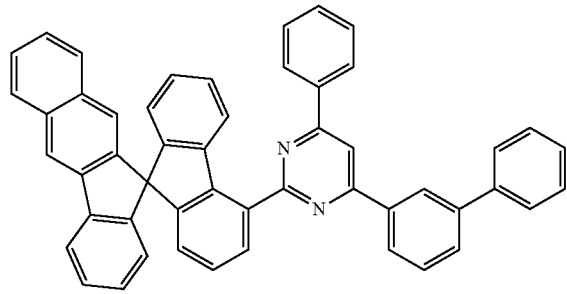
(1-38)
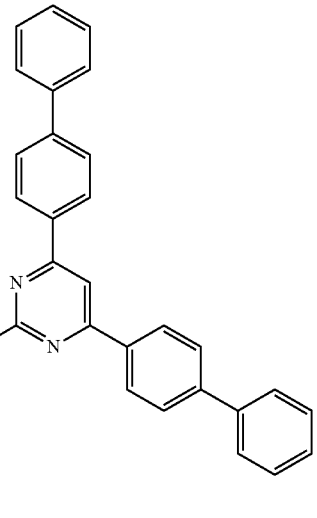
(1-39)
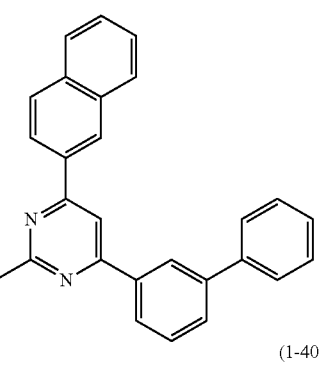
(1-40)
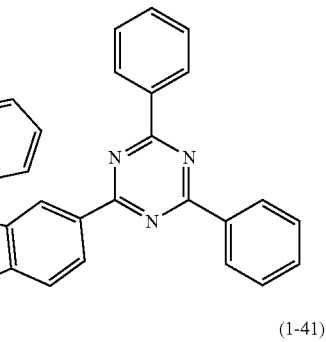
(1-41)
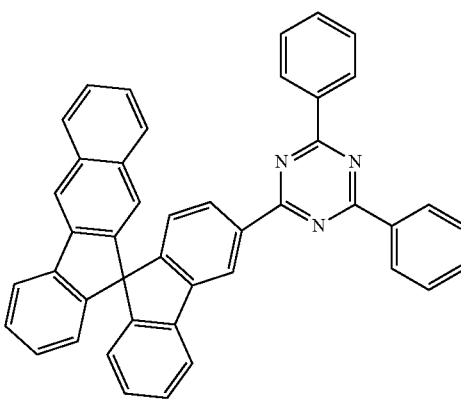

(1-42)
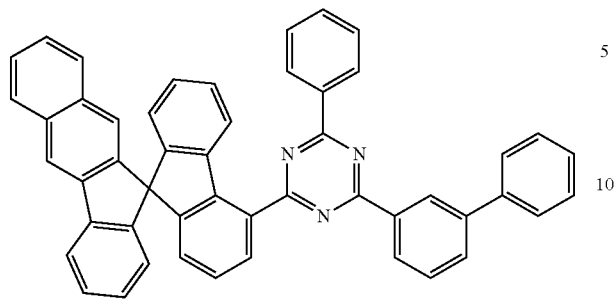
(1-43)
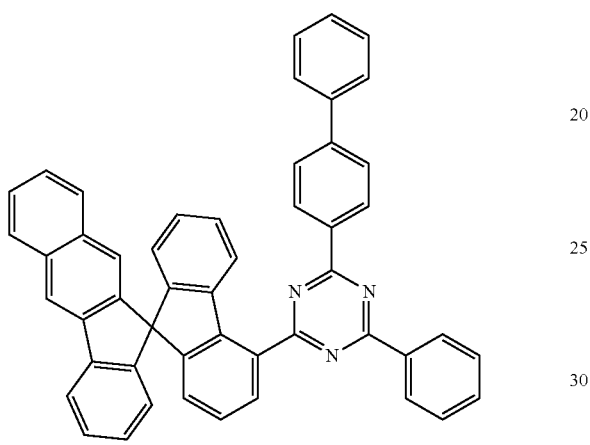
(1-44)
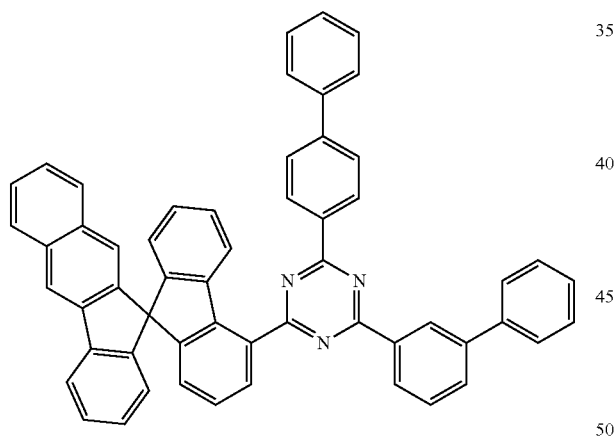
(1-45)
(1-46)
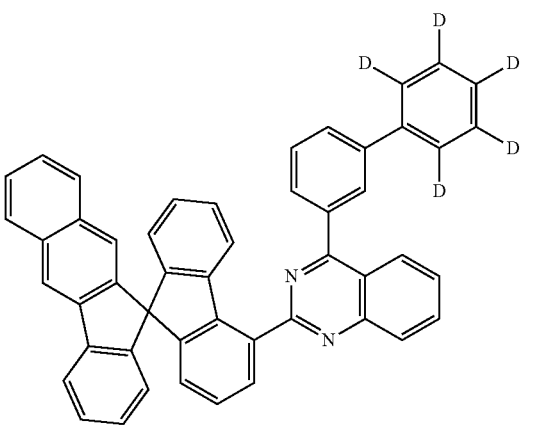
(1-47)
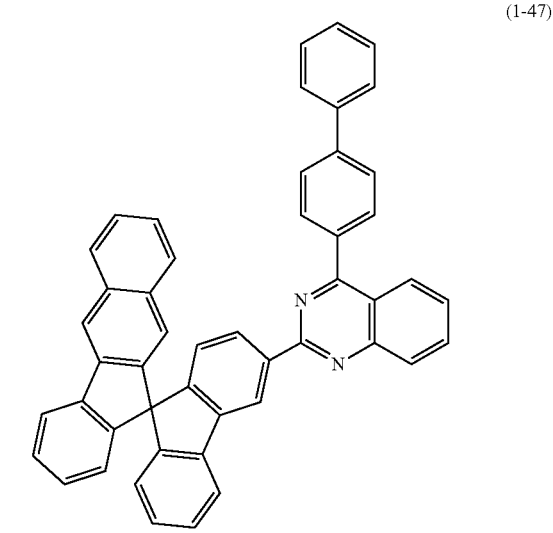
(1-48)
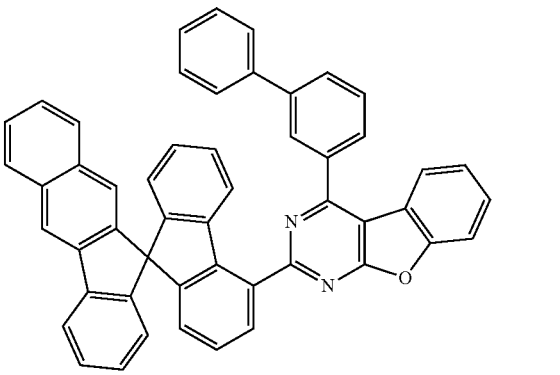

(1-49)
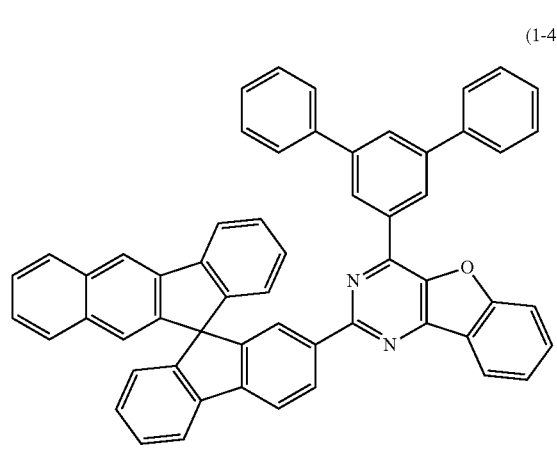
(1-50)
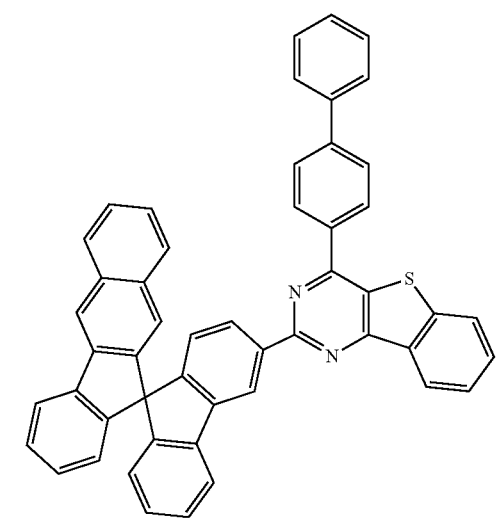
(1-52)
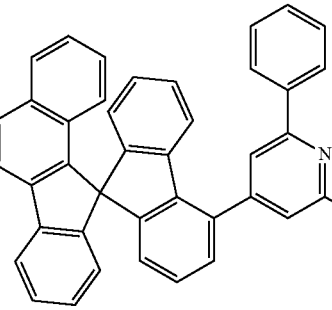
(1-53)
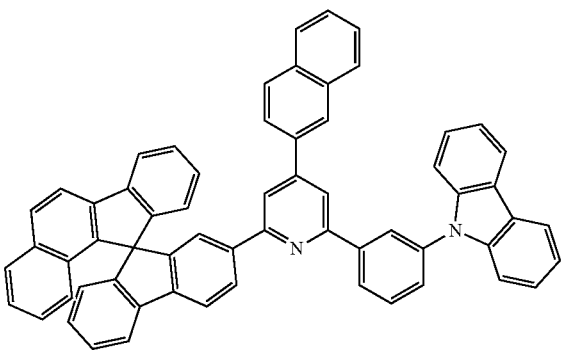
(1-54)
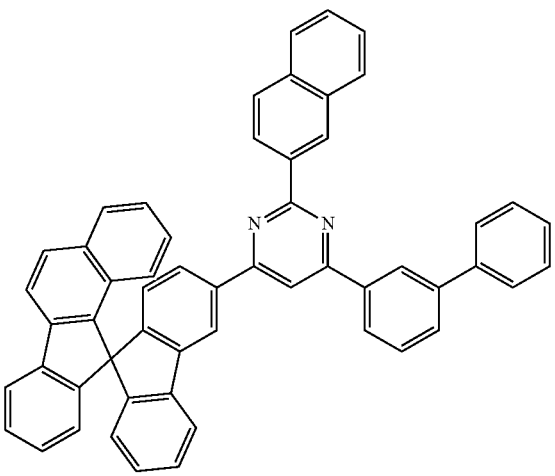
(1-55)
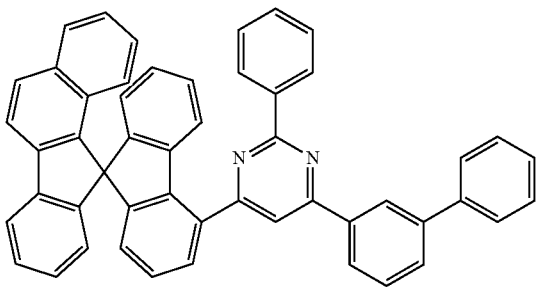
(1-51)

(1-56)
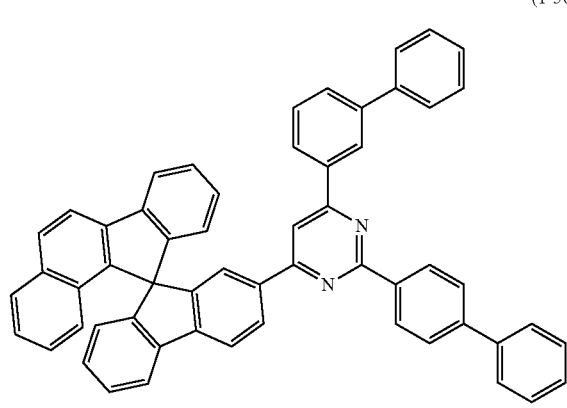
(1-57)
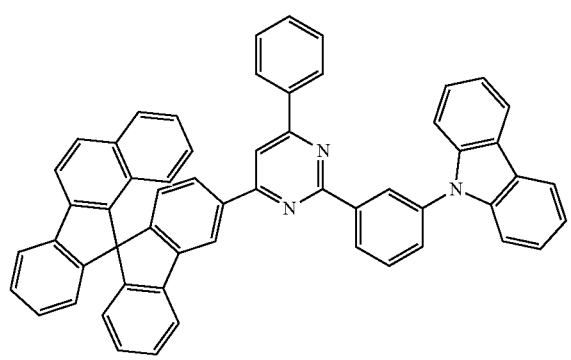
(1-58)
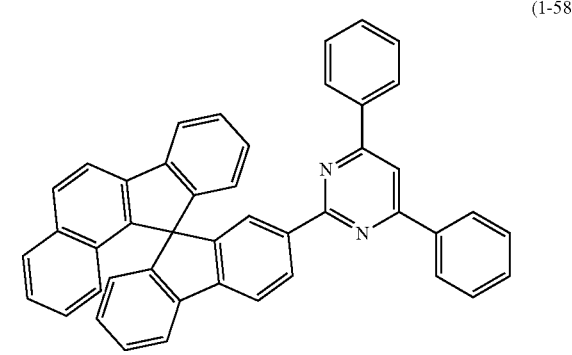
(1-59)
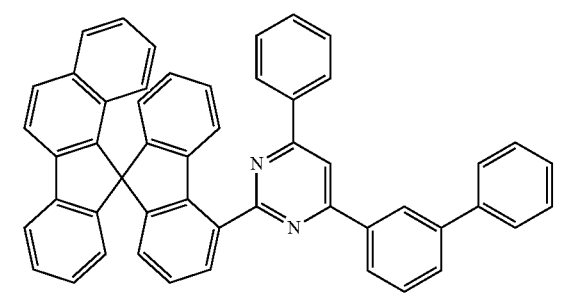
(1-60)
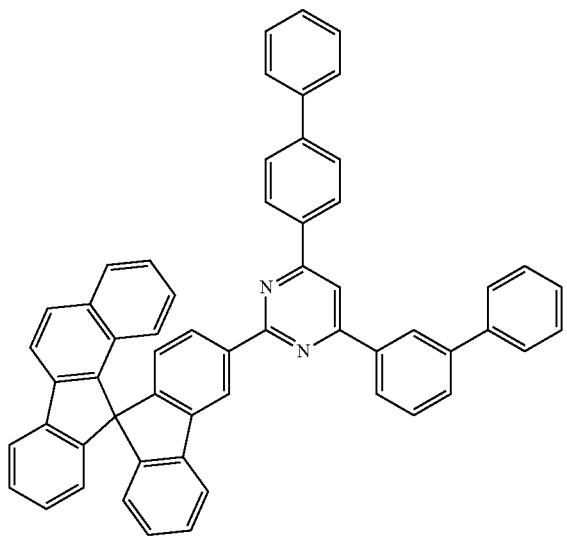
(1-61)
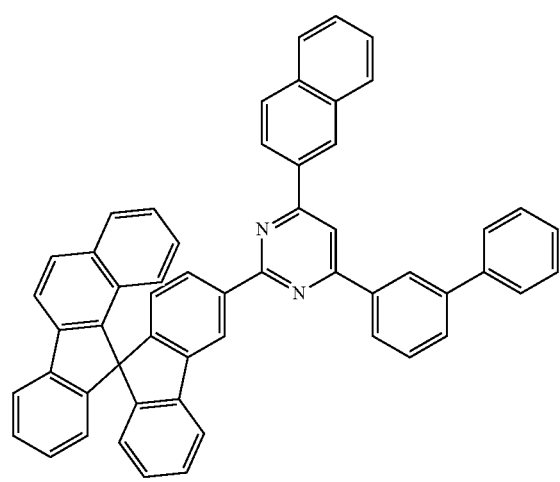
(1-62)
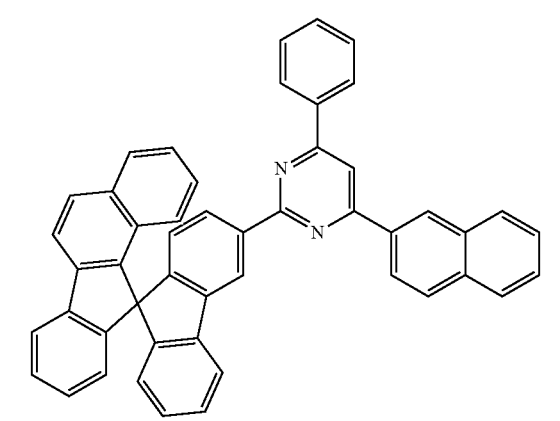

(1-63)
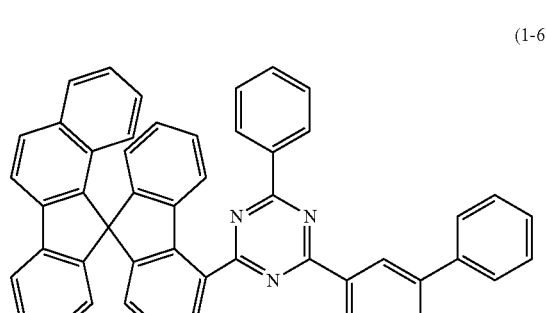
(1-64)
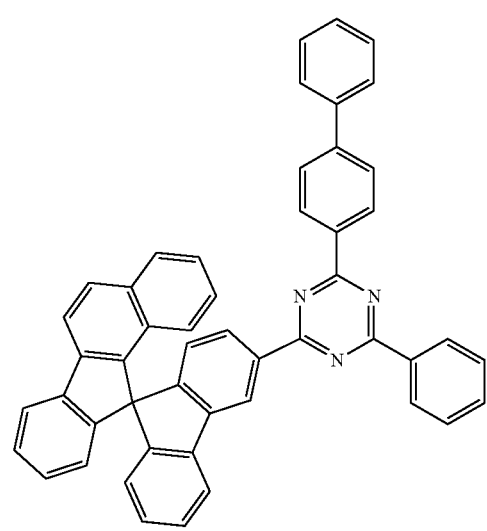
(1-65)
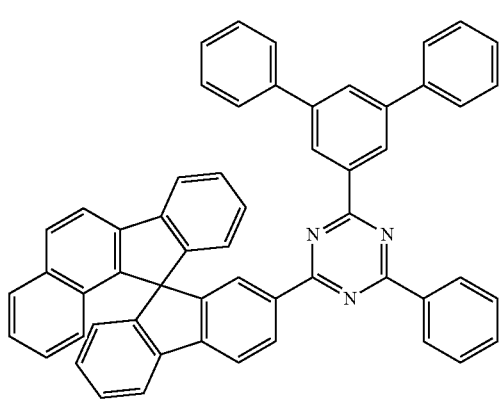
(1-66)
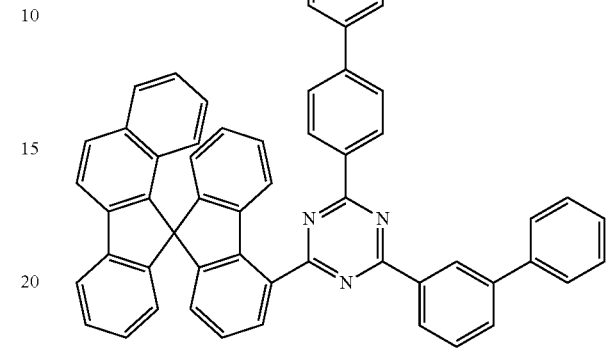
(1-67)
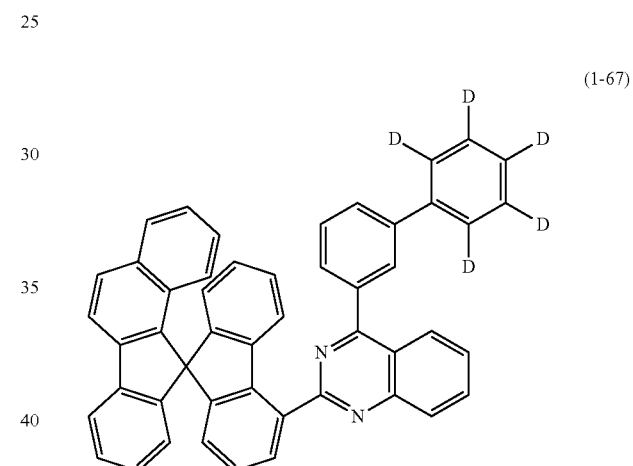
(1-68)
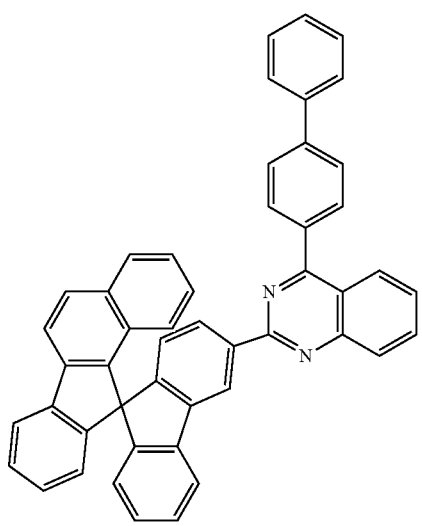

(1-69)
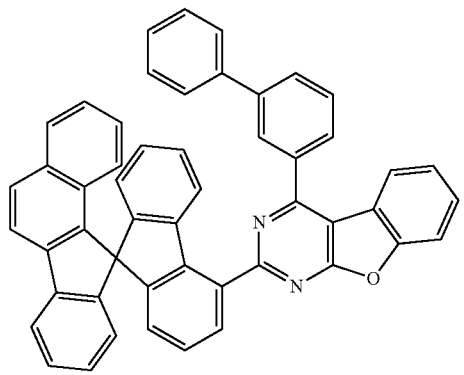
(1-70)
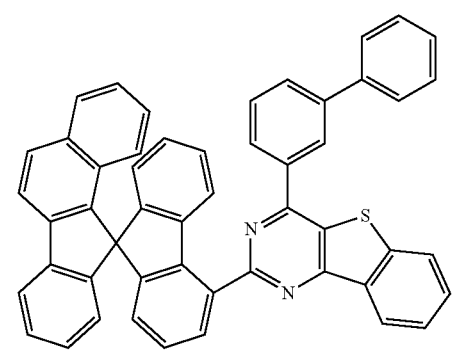
(1-71)
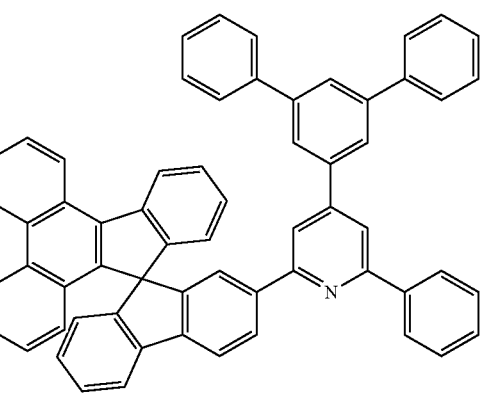
(1-72)
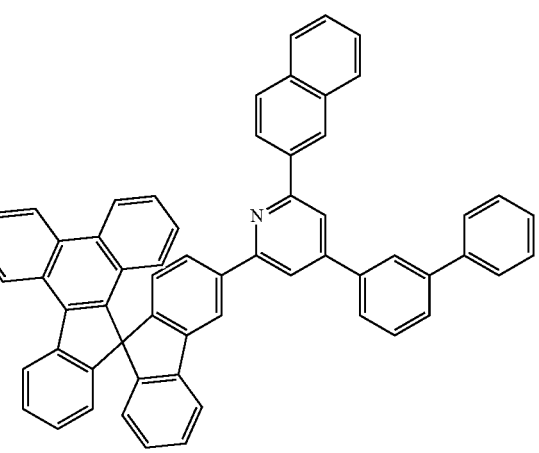
(1-73)
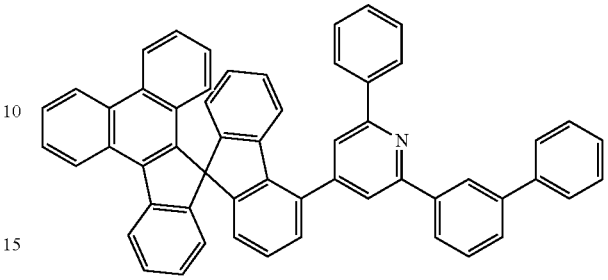
(1-74)
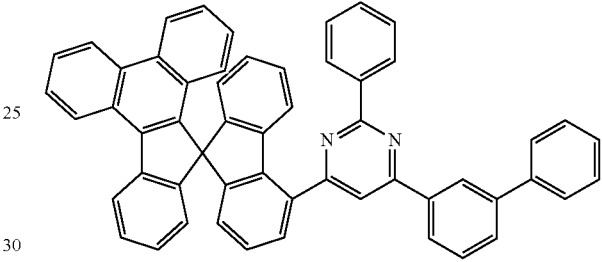
(1-75)
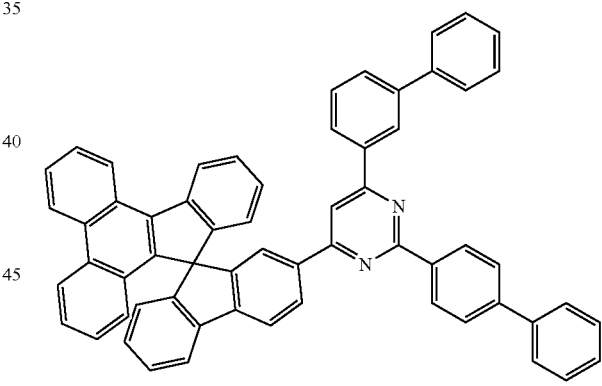
(1-76)
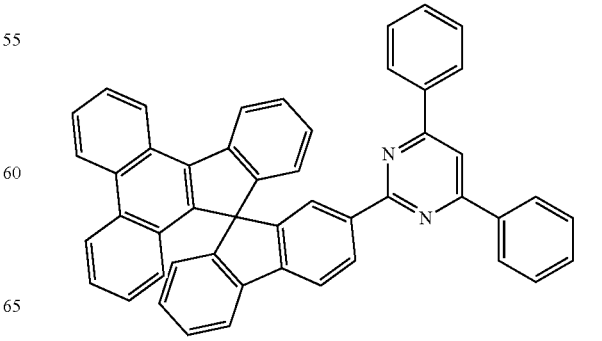

(1-77)
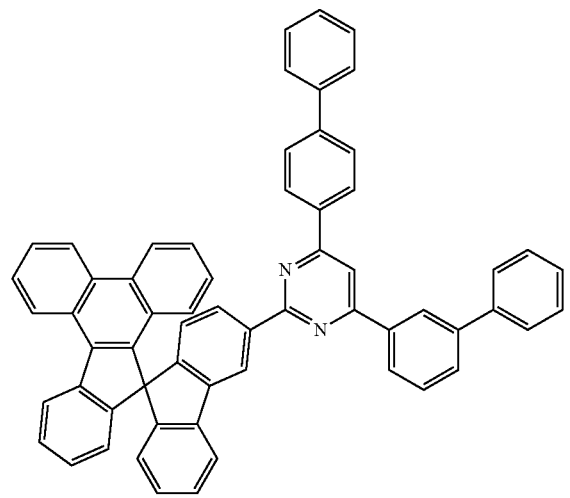
(1-78)
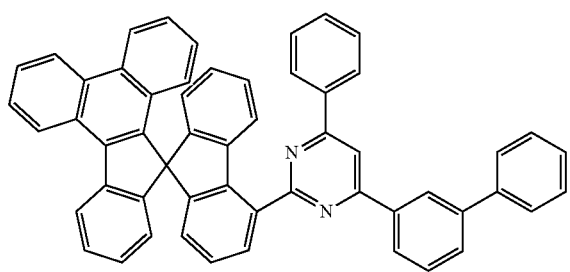
(1-79)
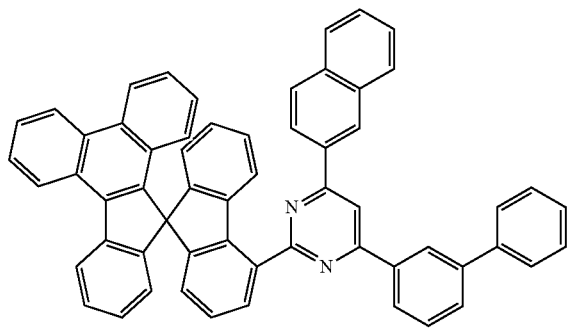
(1-80)
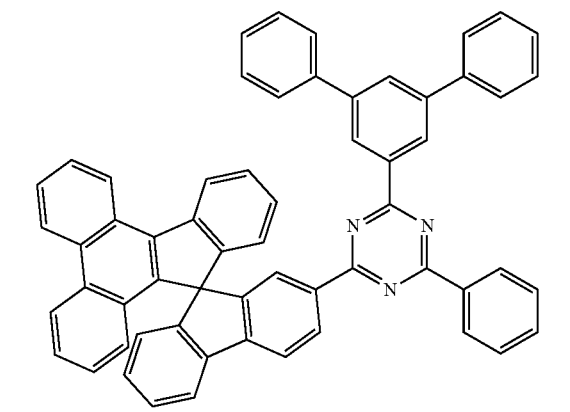
(1-81)
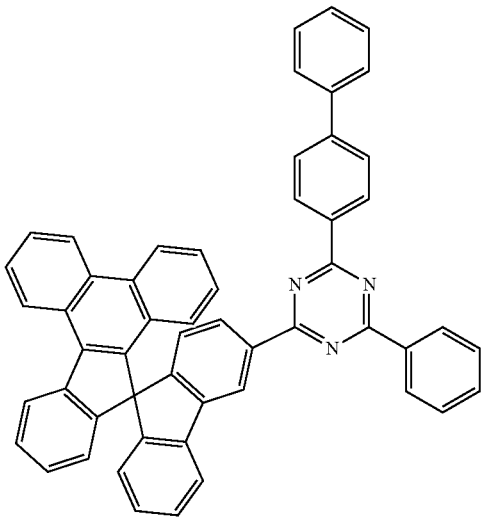
(1-82)
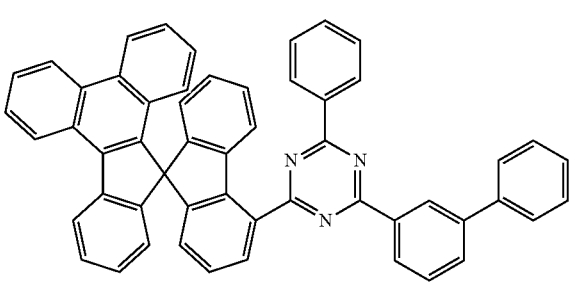
(1-83)
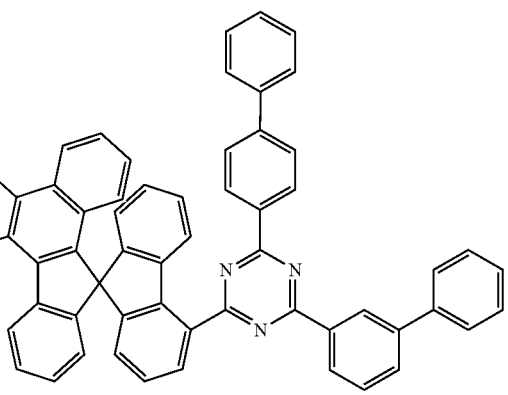
(1-84)
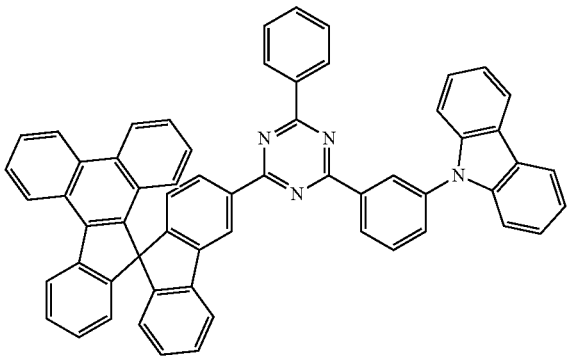

(1-85)
(1-86)
(1-87)
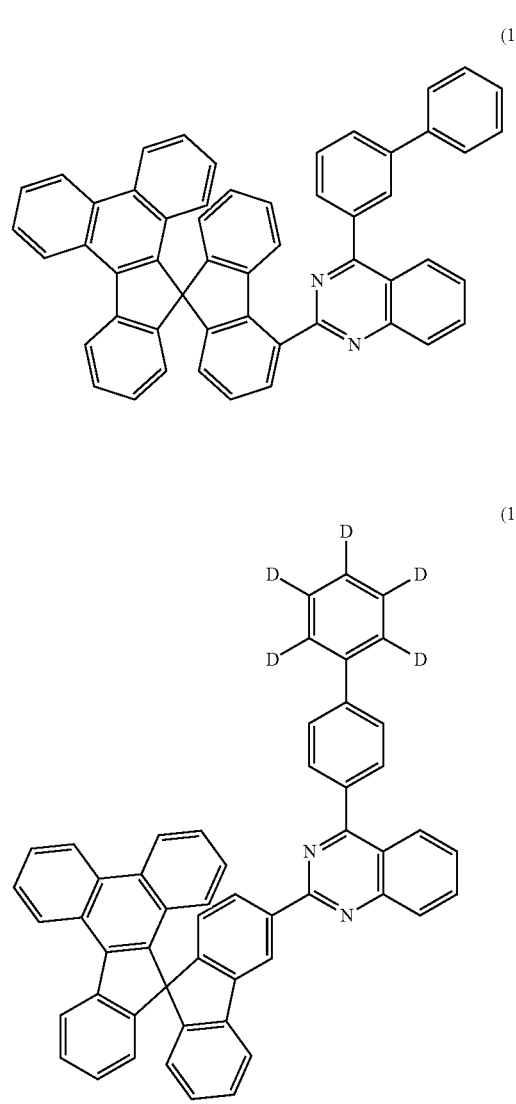
(1-88)
(1-89)
(1-90)
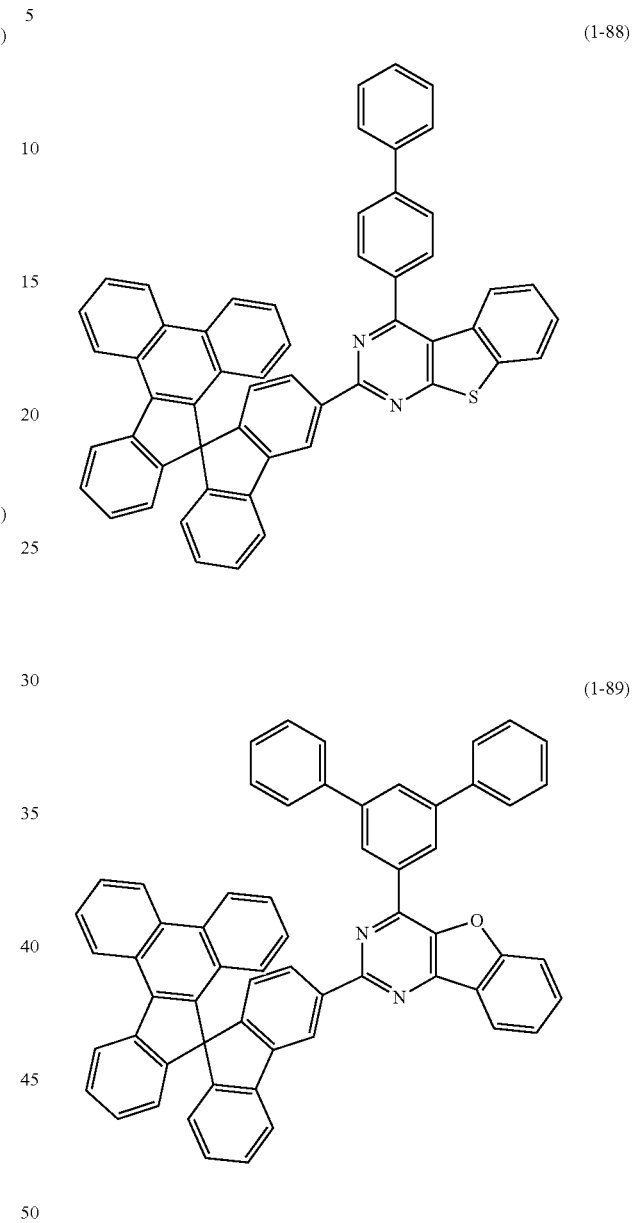
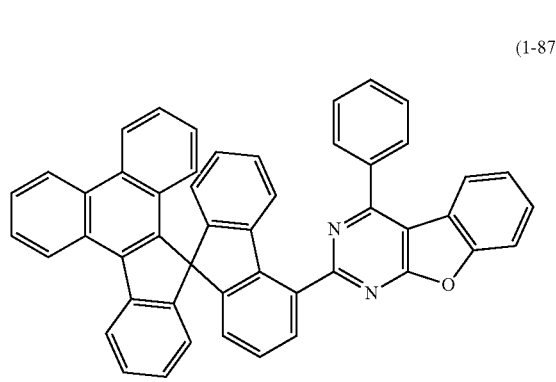
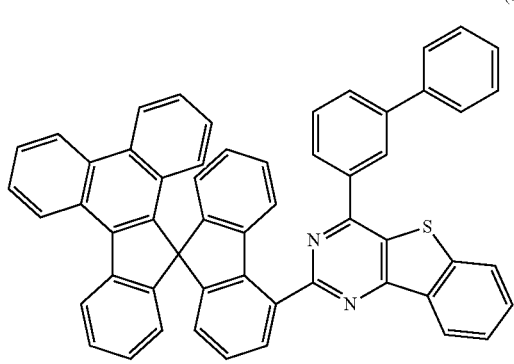

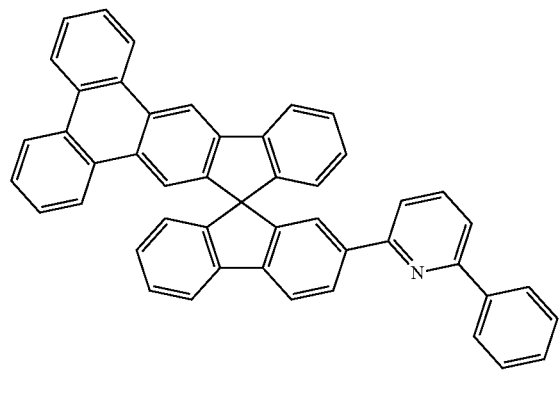
(1-91)
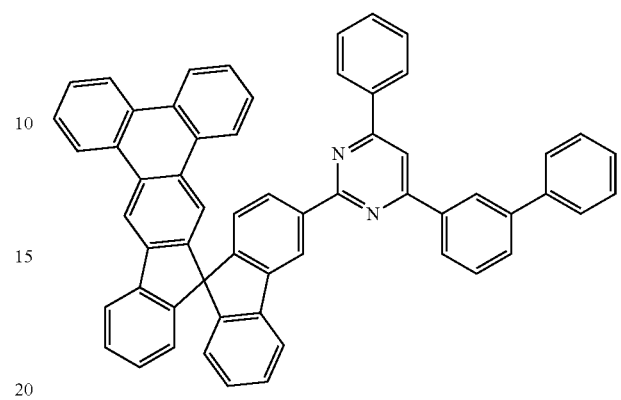
(1-95)
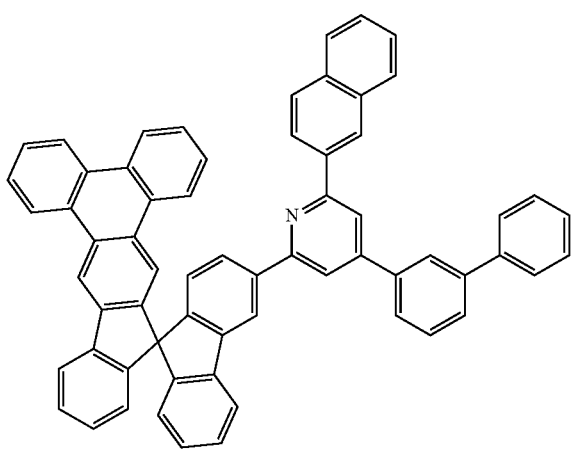
(1-92)
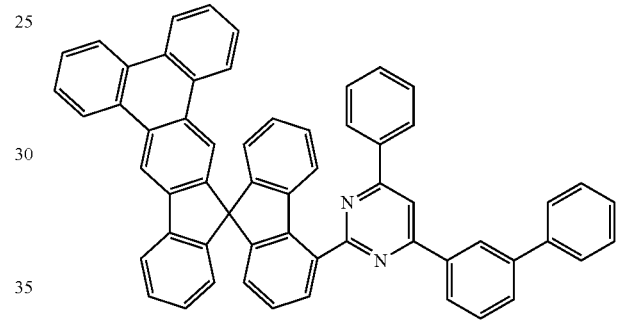
(1-96)
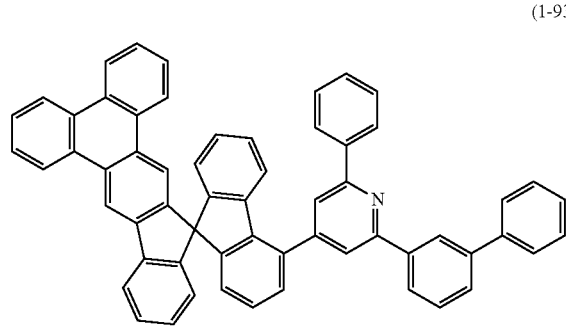
(1-93)
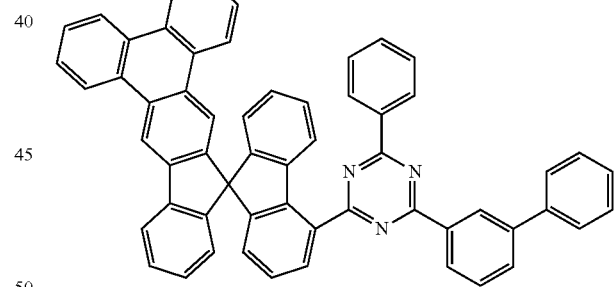
(1-97)
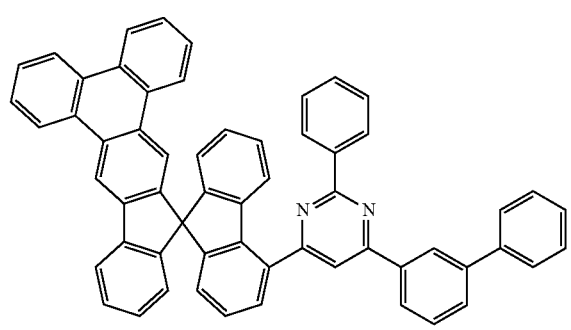
(1-94)
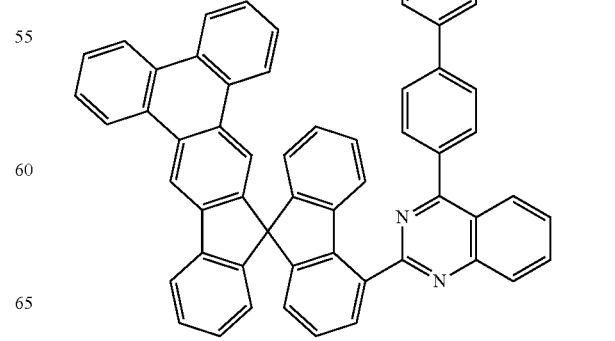
(1-98)

(1-99)
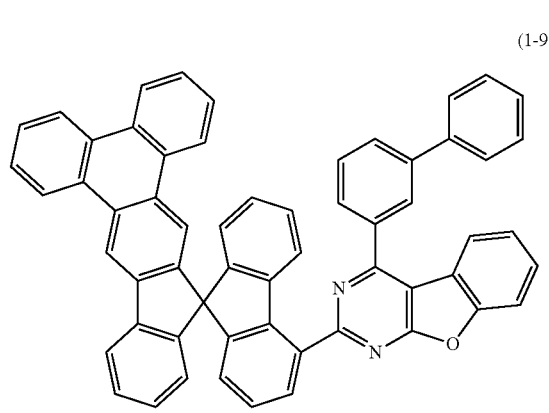
(1-100)
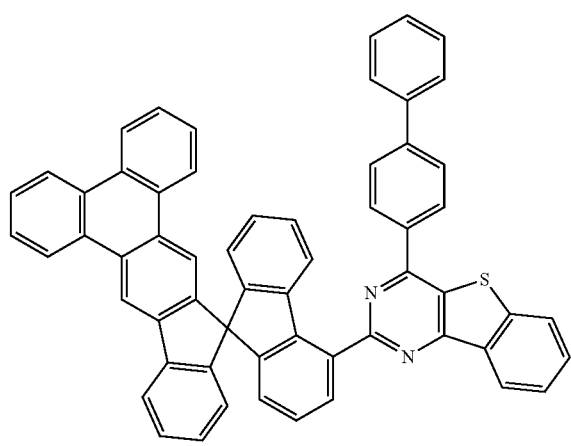
(1-101)
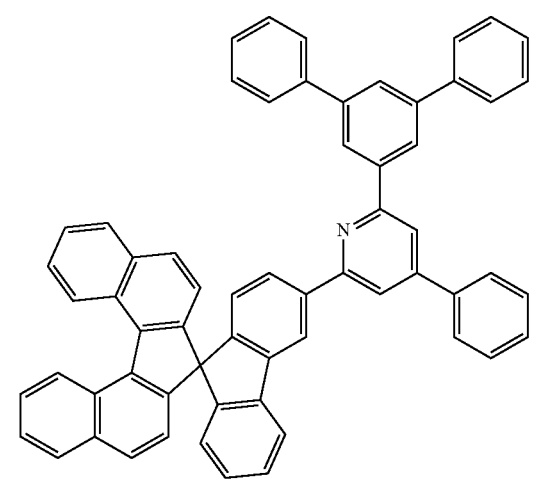
(1-102)
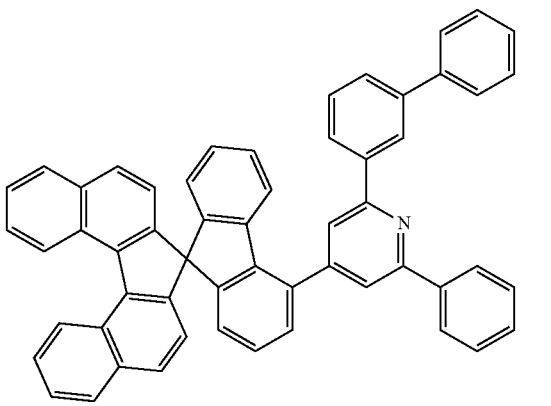
(1-103)
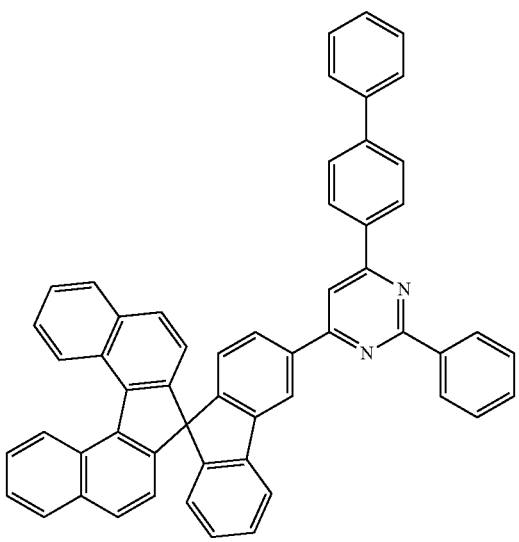
(1-104)
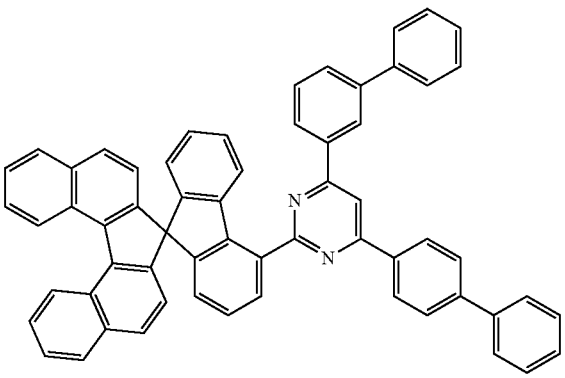

(1-105)
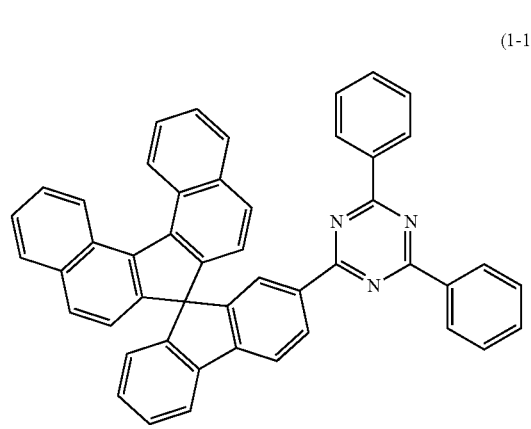
(1-106)
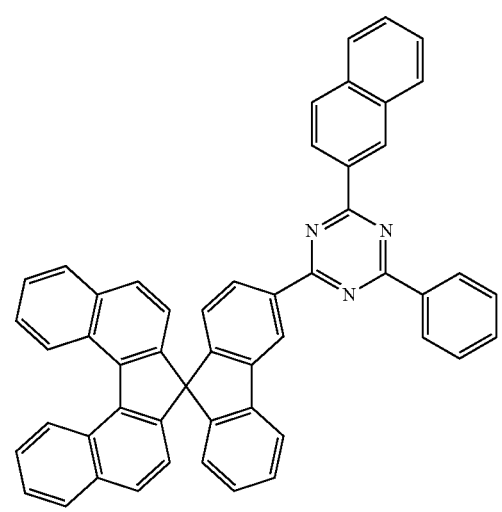
(1-107)
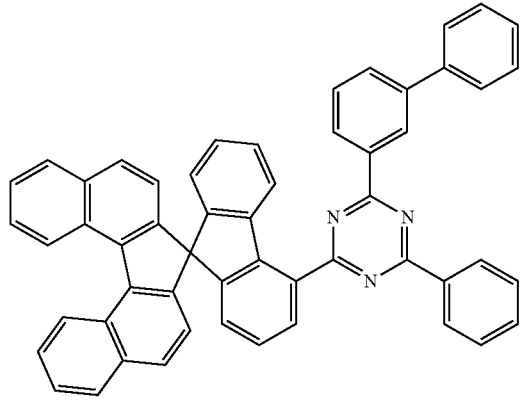
(1-108)
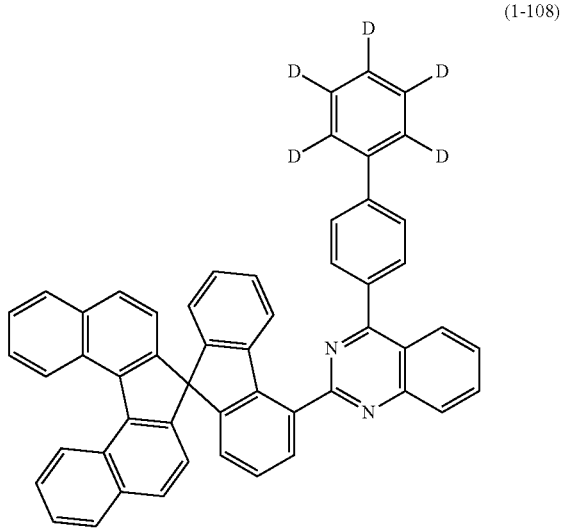
(1-109)
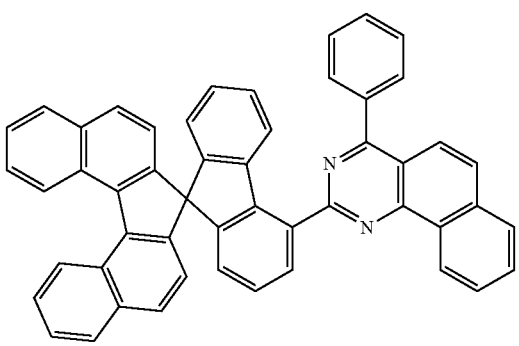
(1-110)
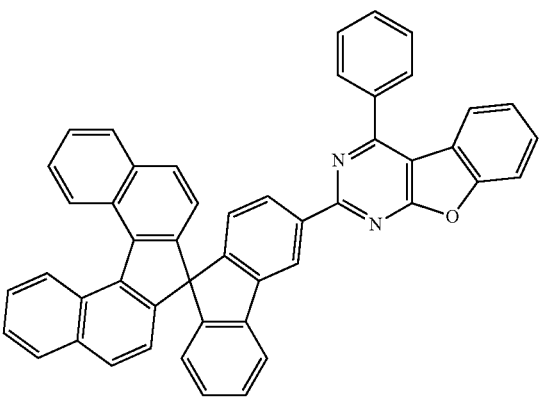

-continued
(1-111)
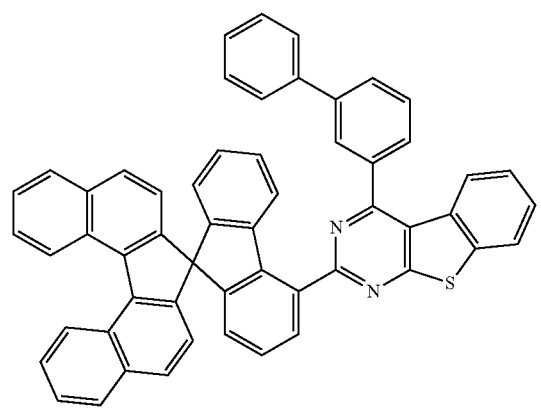
(1-112)
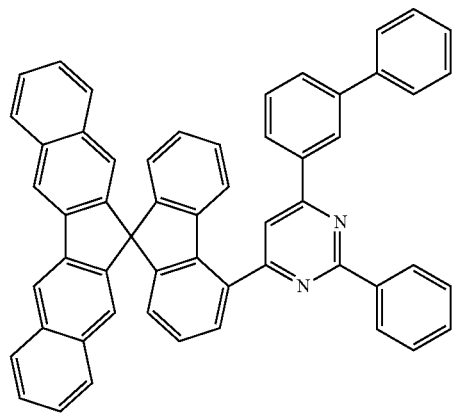
(1-113)
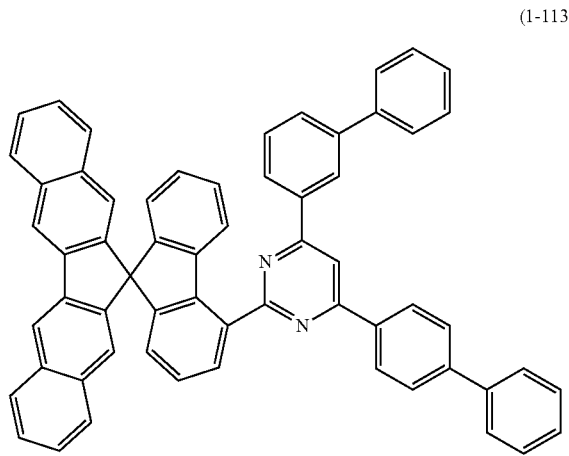
-continued
(1-114)
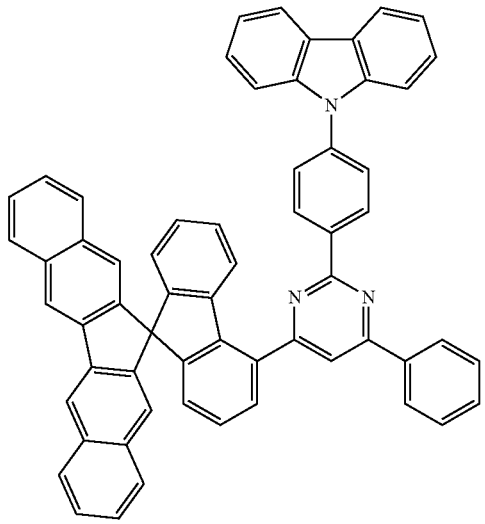
(1-115)
(1-116)
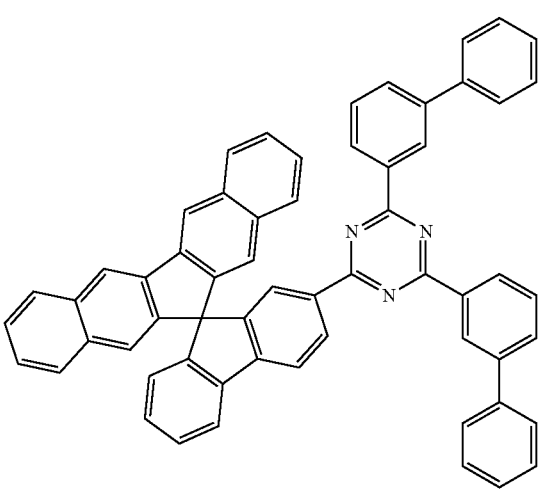

(1-117)
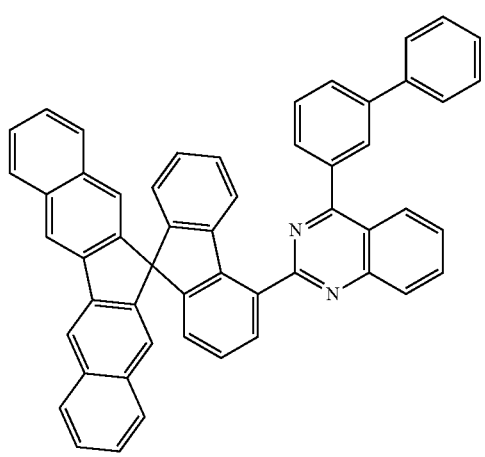
(1-118)
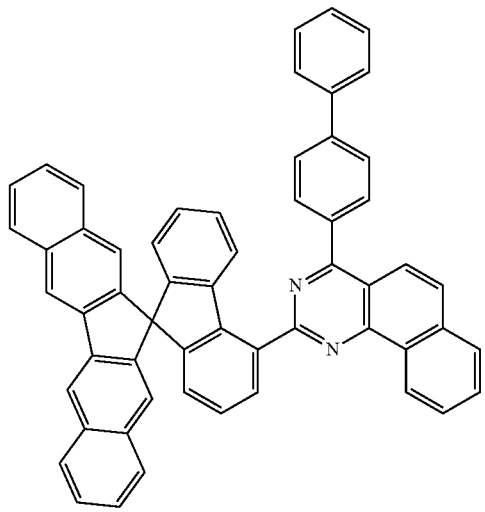
(1-119)
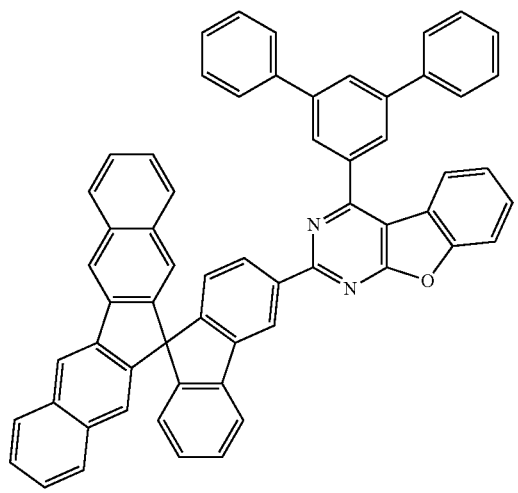
(1-120)
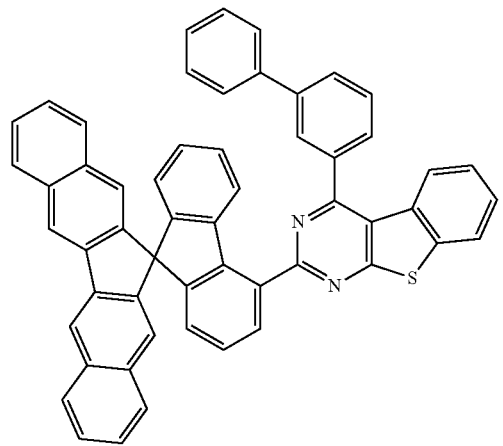
(1-121)
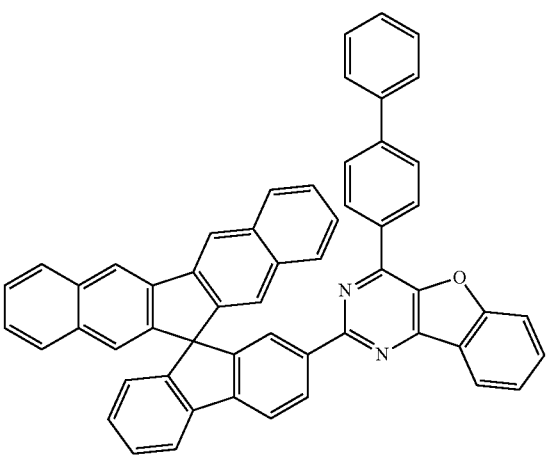
(1-122)
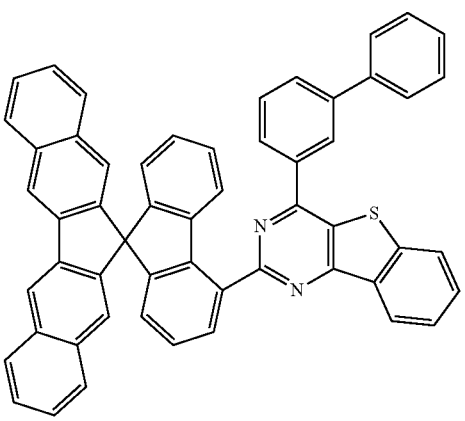

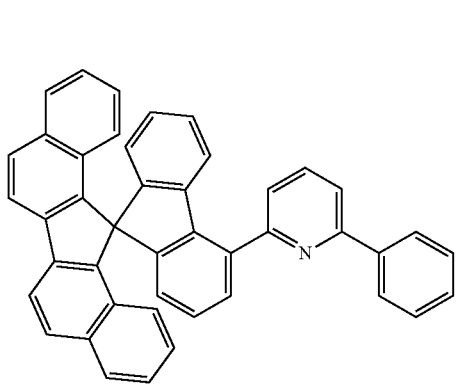 (1-123)
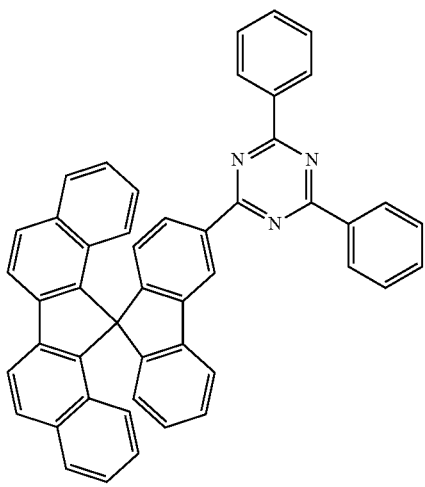 (1-126)
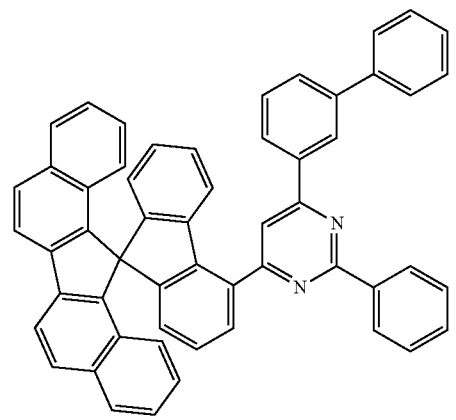 (1-124)
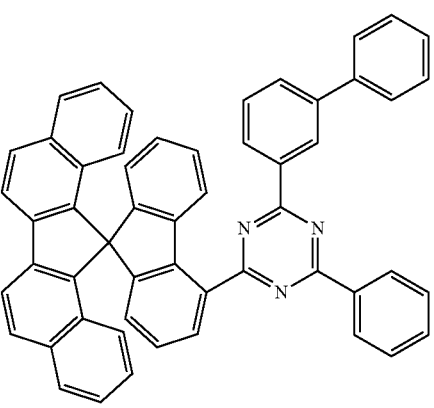 (1-127)
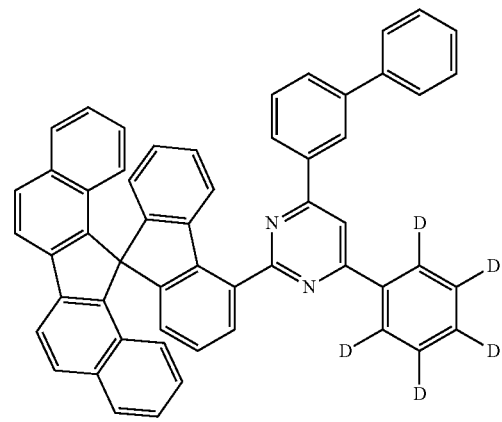 (1-125)
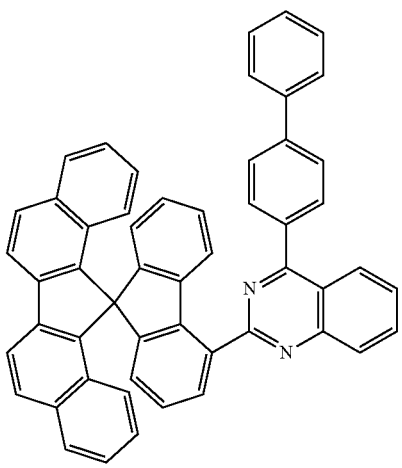 (1-128)

(1-129)
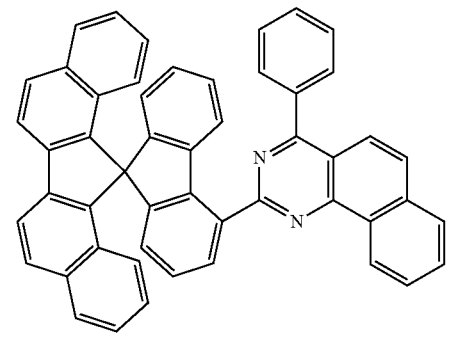
(1-130)
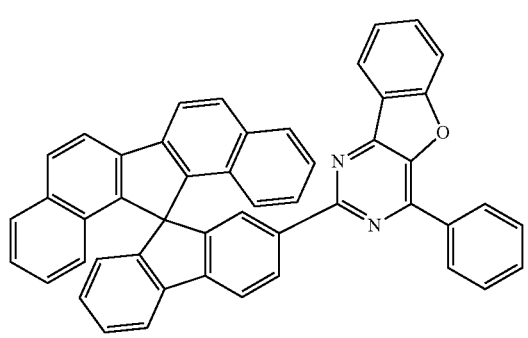
(1-131)
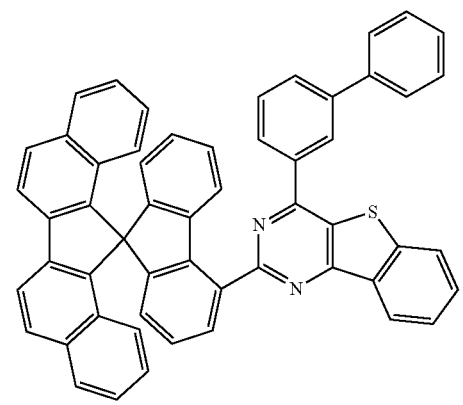
(1-132)
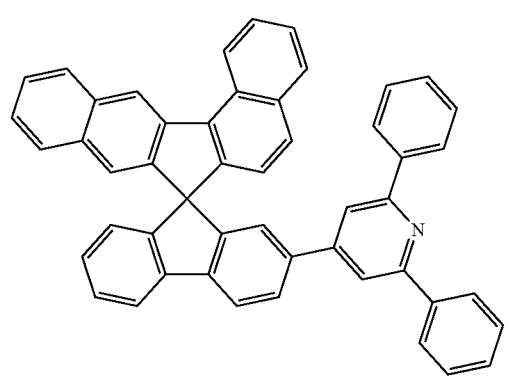
(1-133)
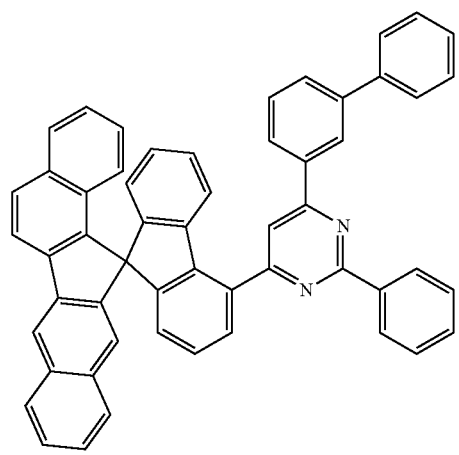
(1-134)
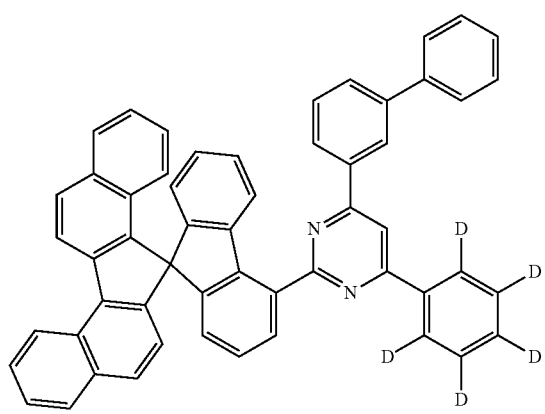
(1-135)
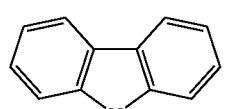
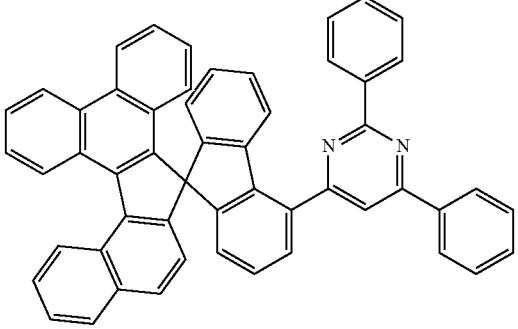

-continued
(1-136)
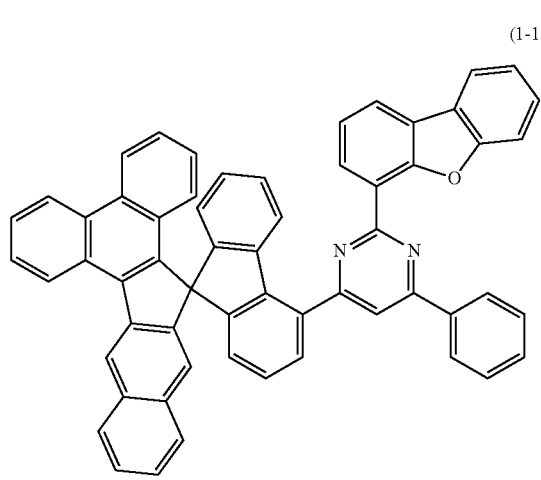
(1-137)
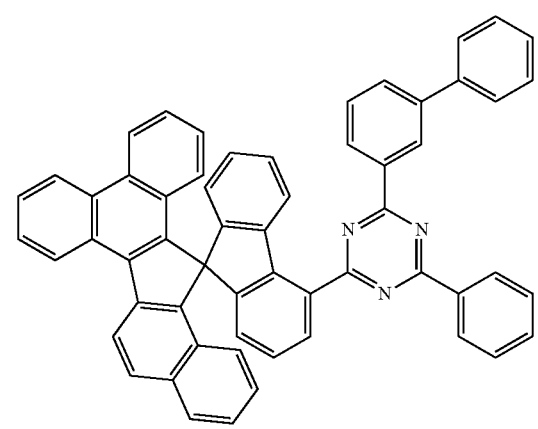
(1-138)
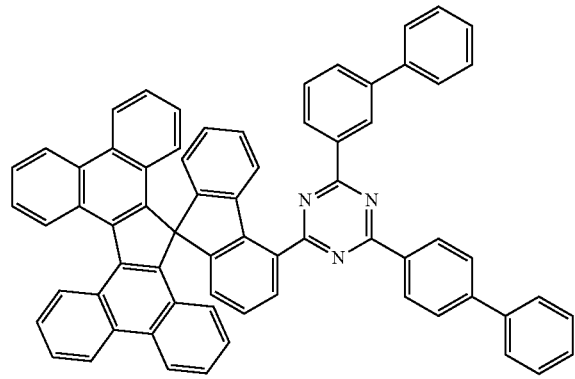
-continued
(1-139)
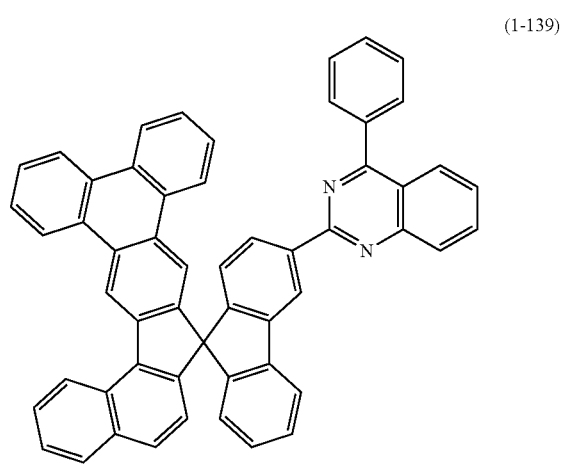
(1-140)
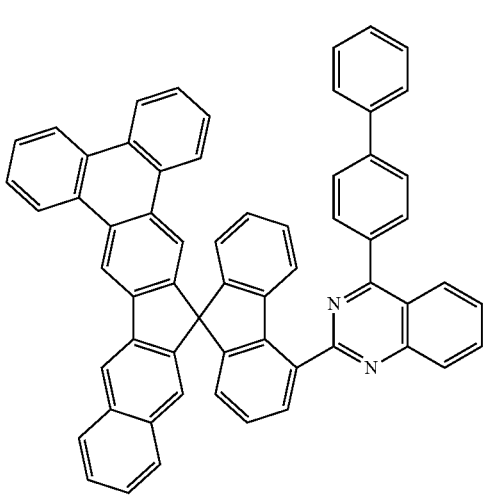
(1-141)
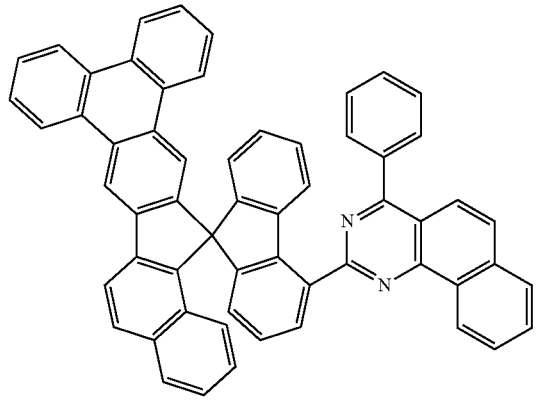

(1-142)
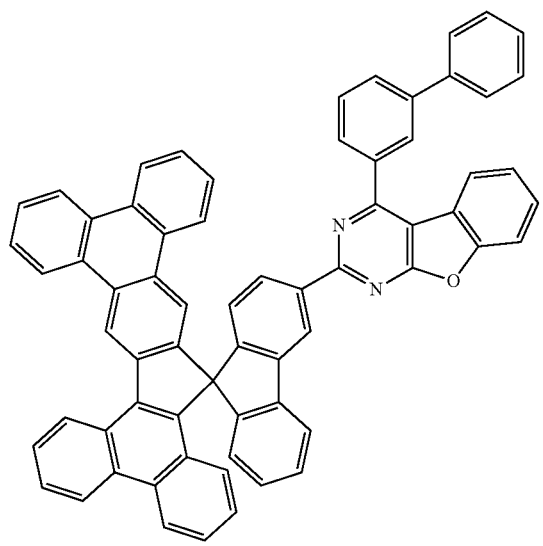
(1-143)
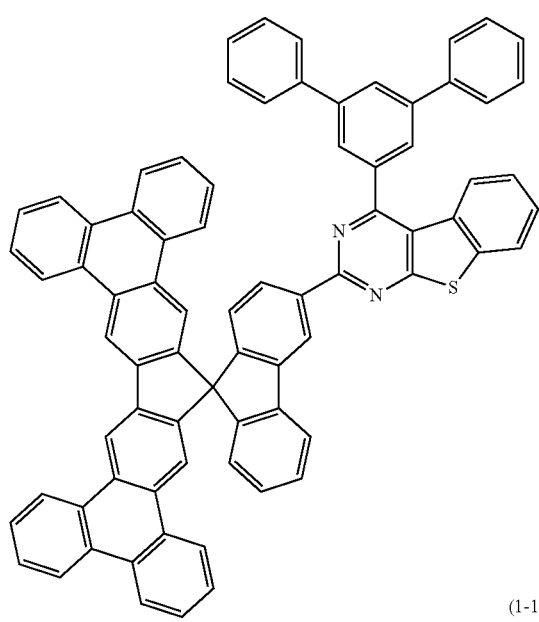
(1-144)
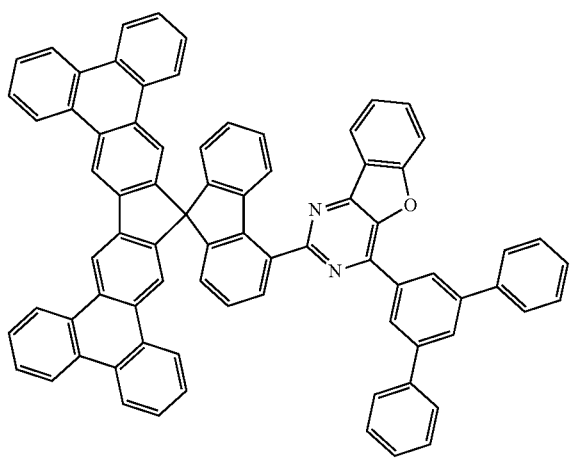
Specific examples of the compound represented by the general formula (2) are exemplified below, but are not limited to:
(2-1)
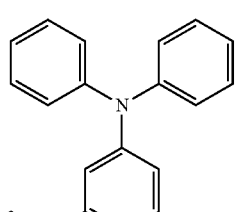
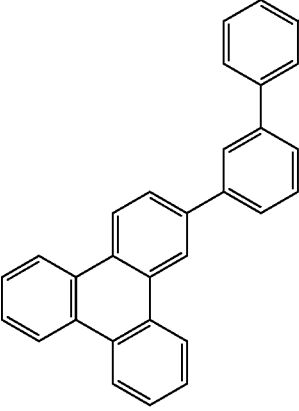
(2-2)
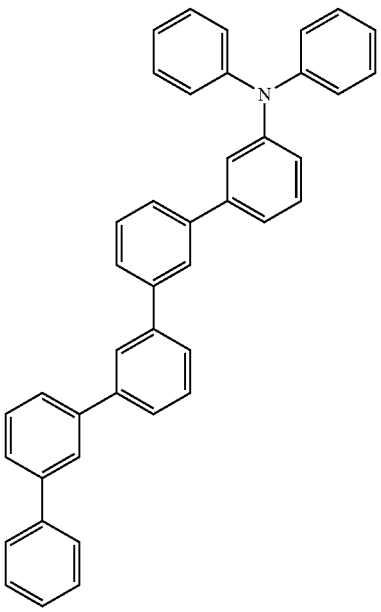

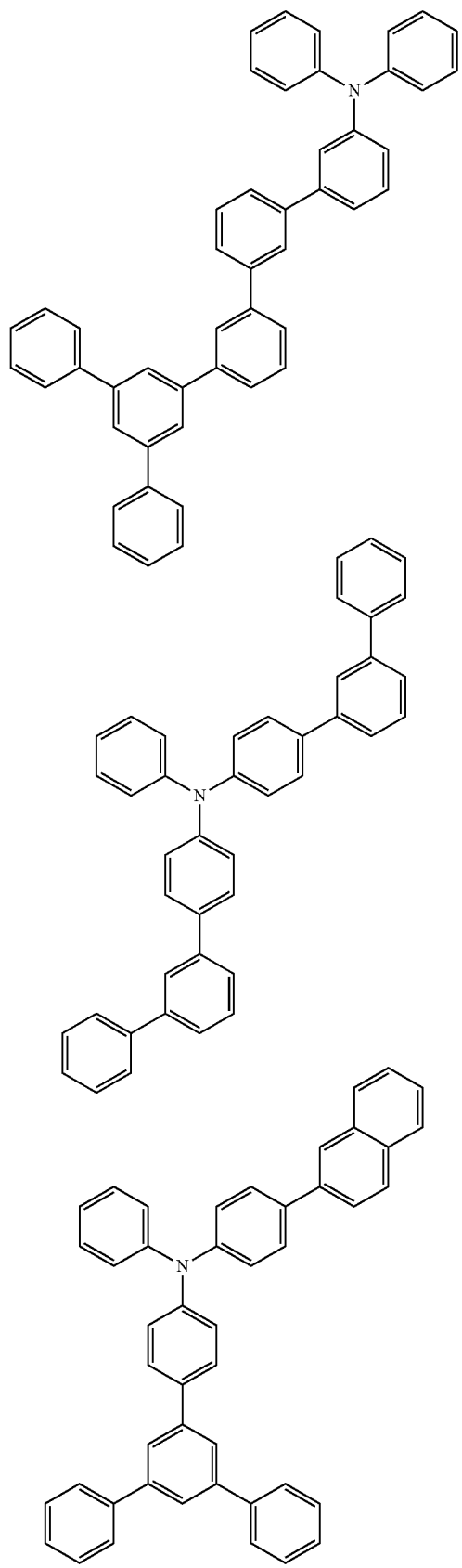
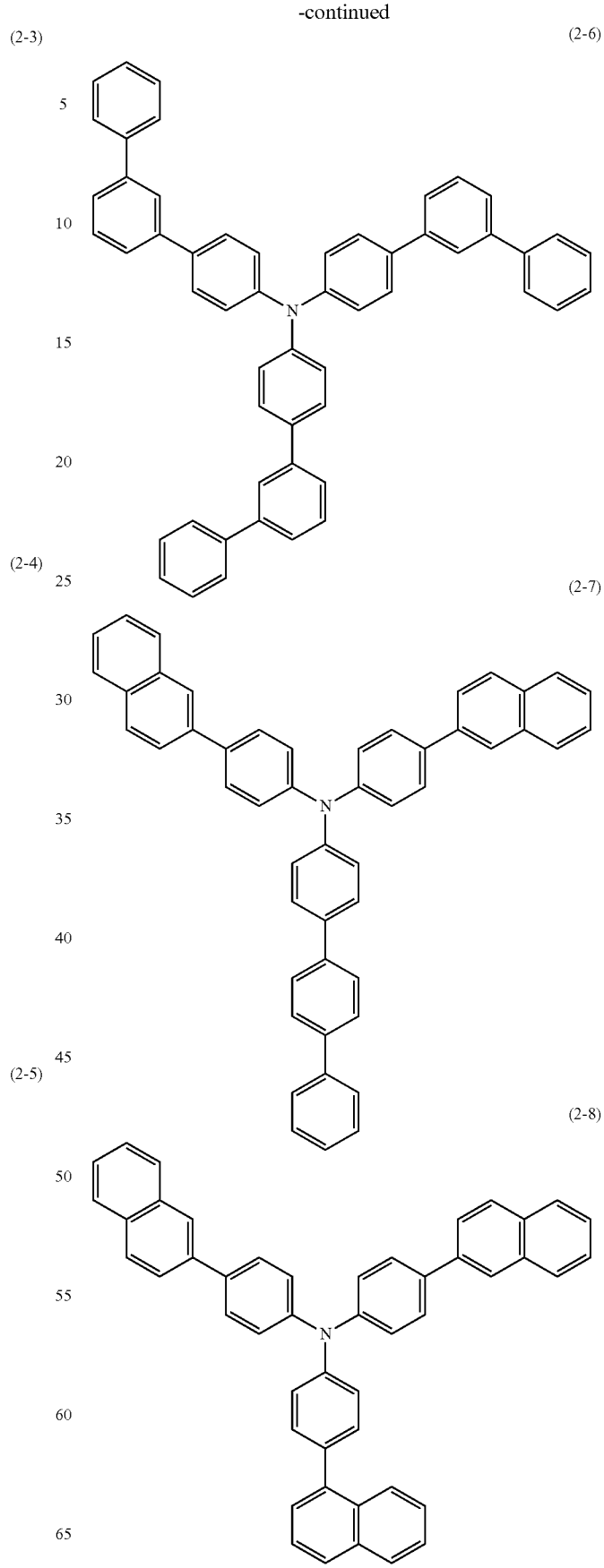

(2-9)
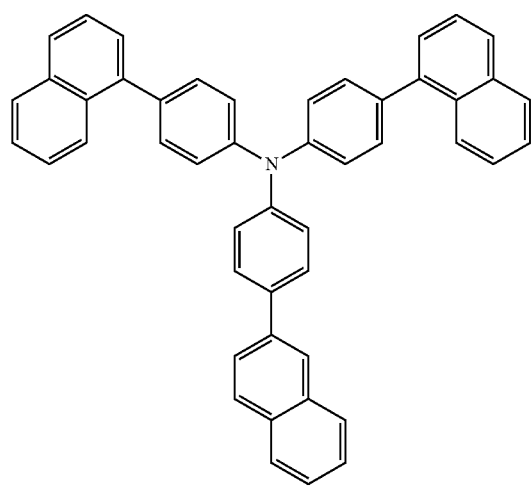
(2-10)
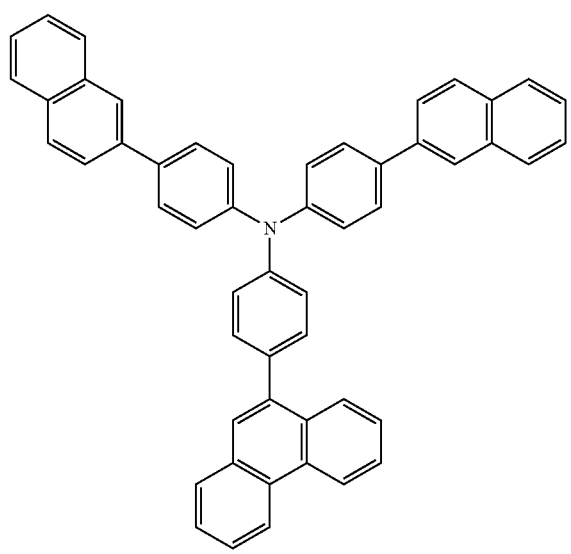
(2-11)
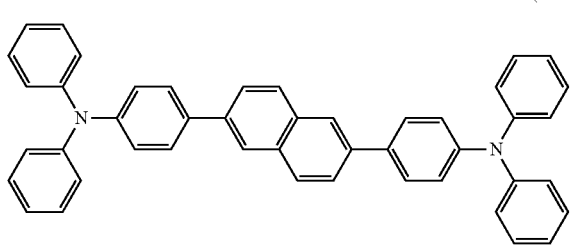
(2-12)
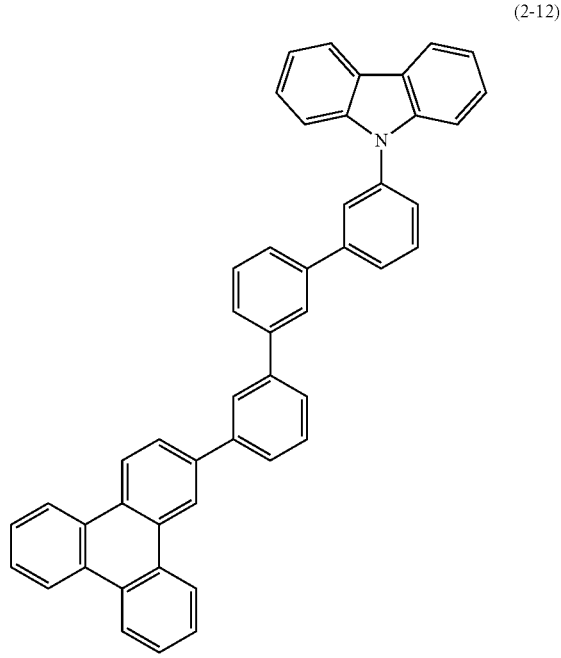
(2-13)
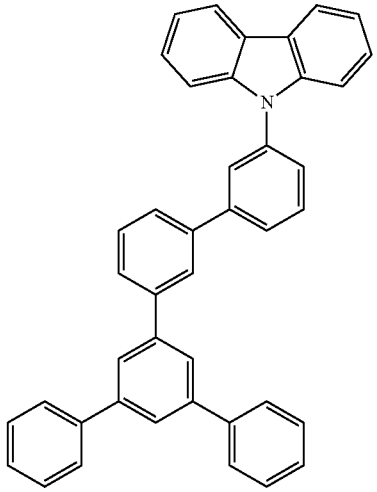
(2-14)
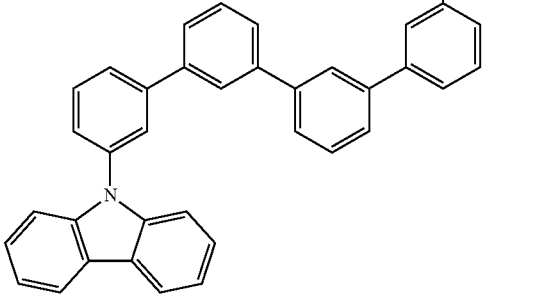

(2-15)
(2-16)
(2-17)
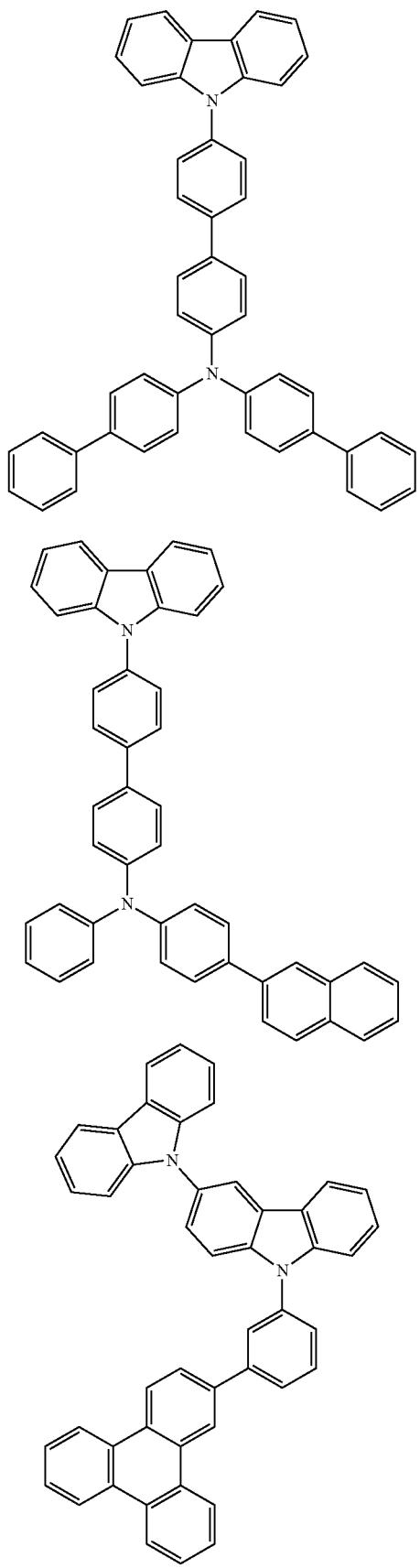
(2-18)
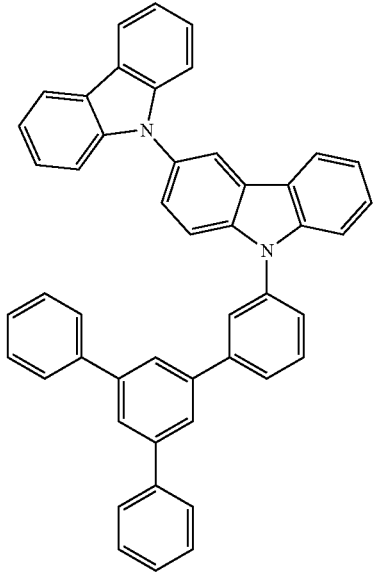
(2-19)
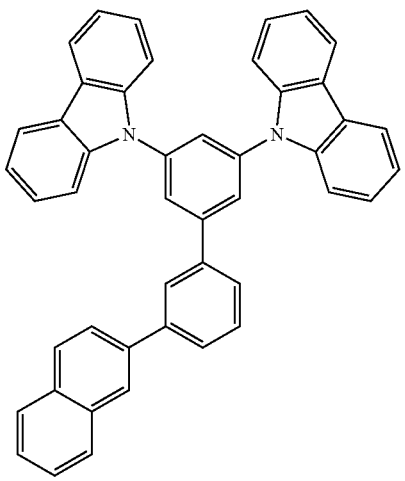
(2-20)
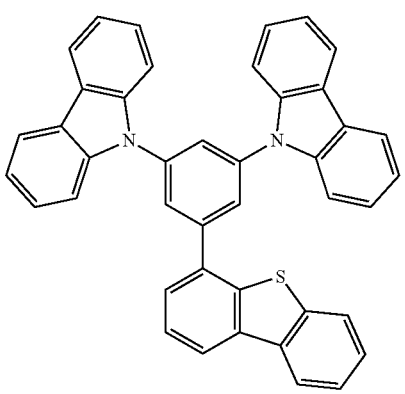

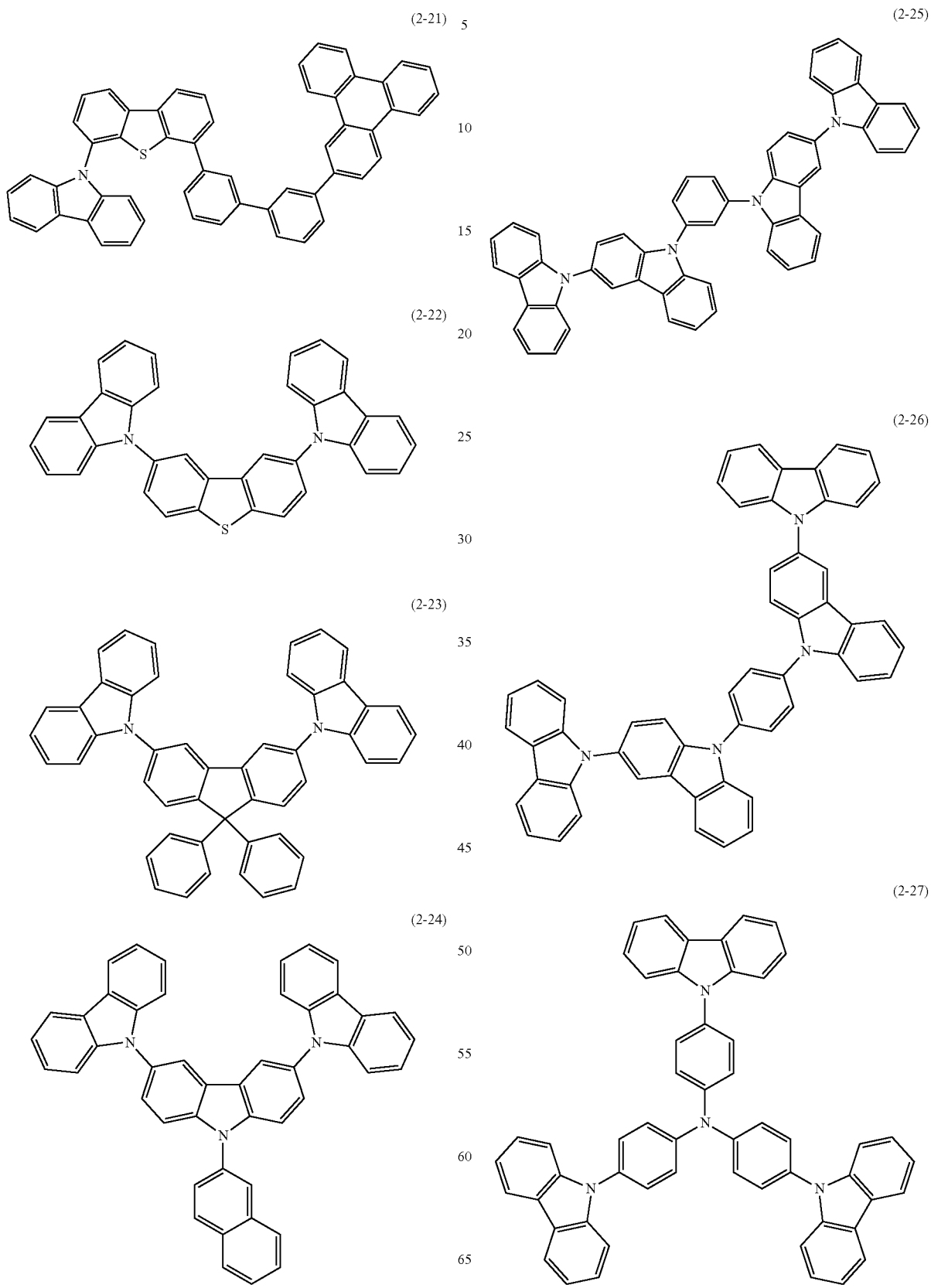

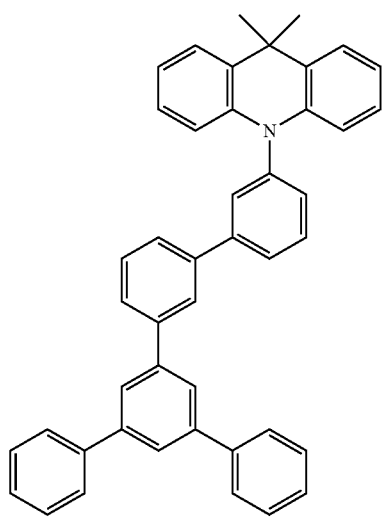
(2-28)
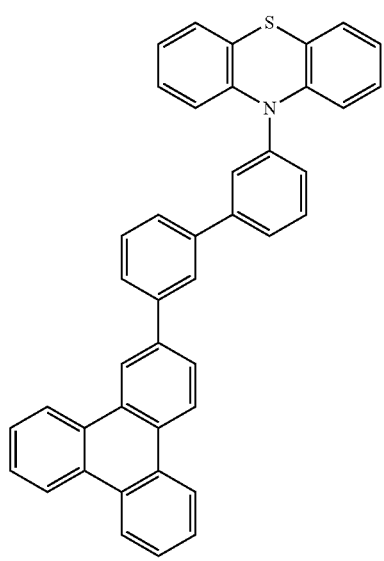
(2-29)
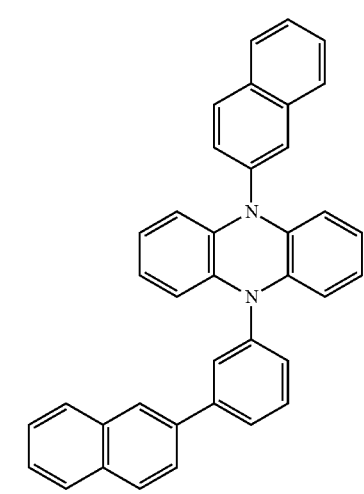
(2-30)
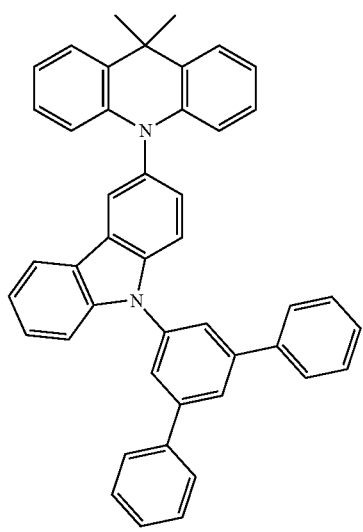
(2-31)
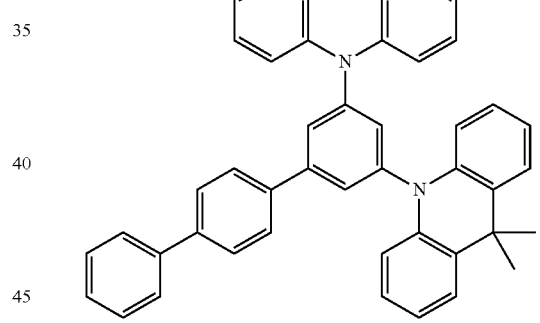
(2-32)
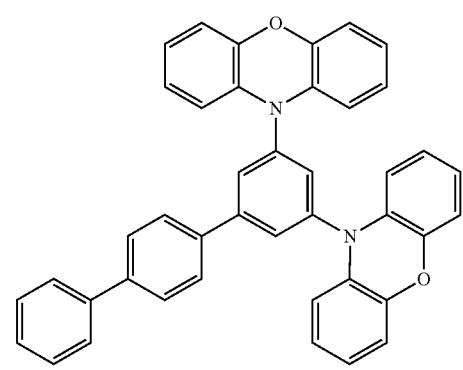
(2-33)

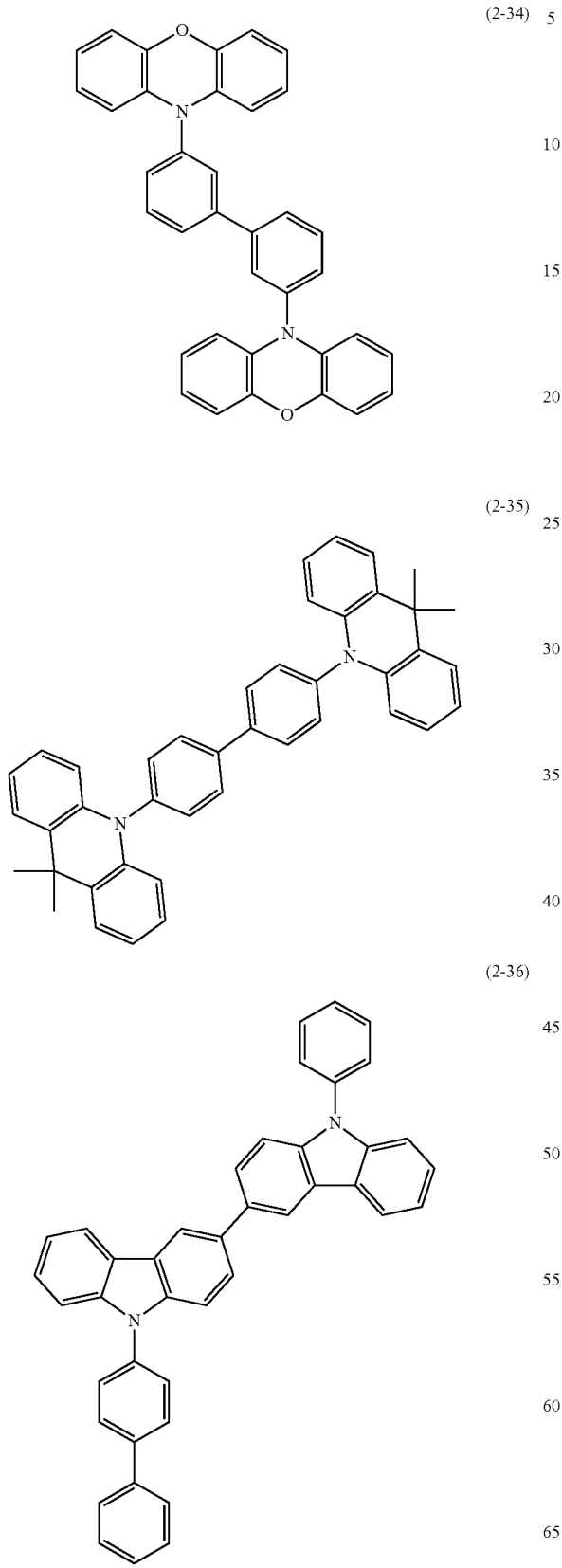
(2-34)
(2-35)
(2-36)
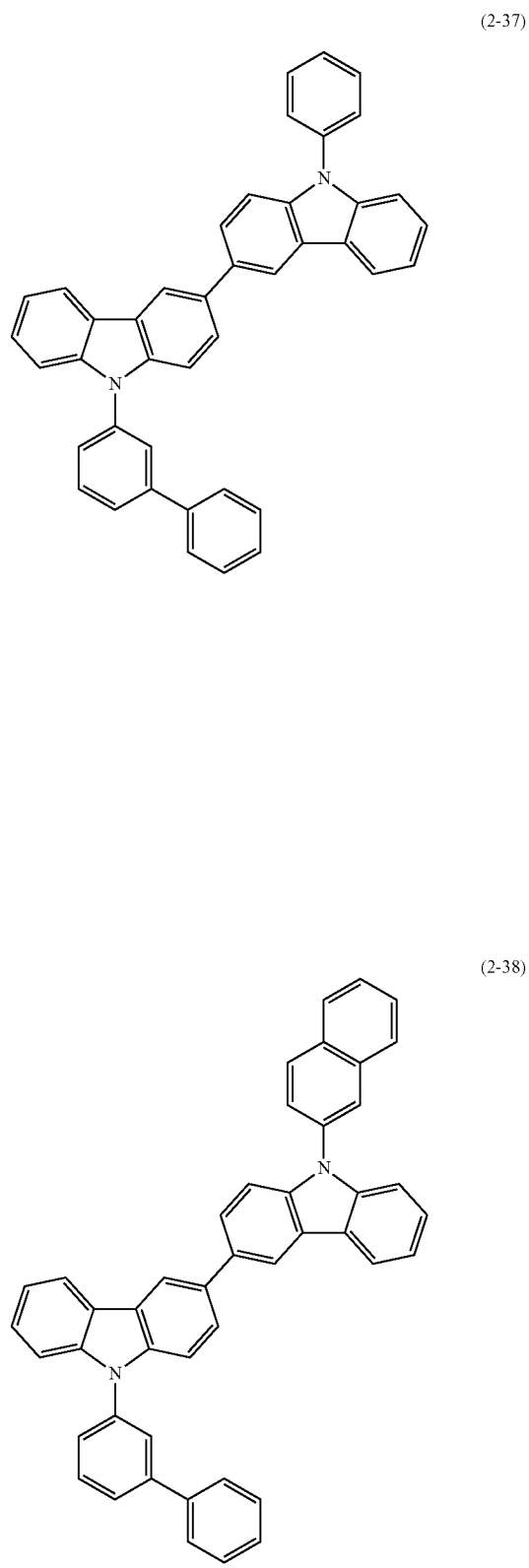
(2-37)
(2-38)

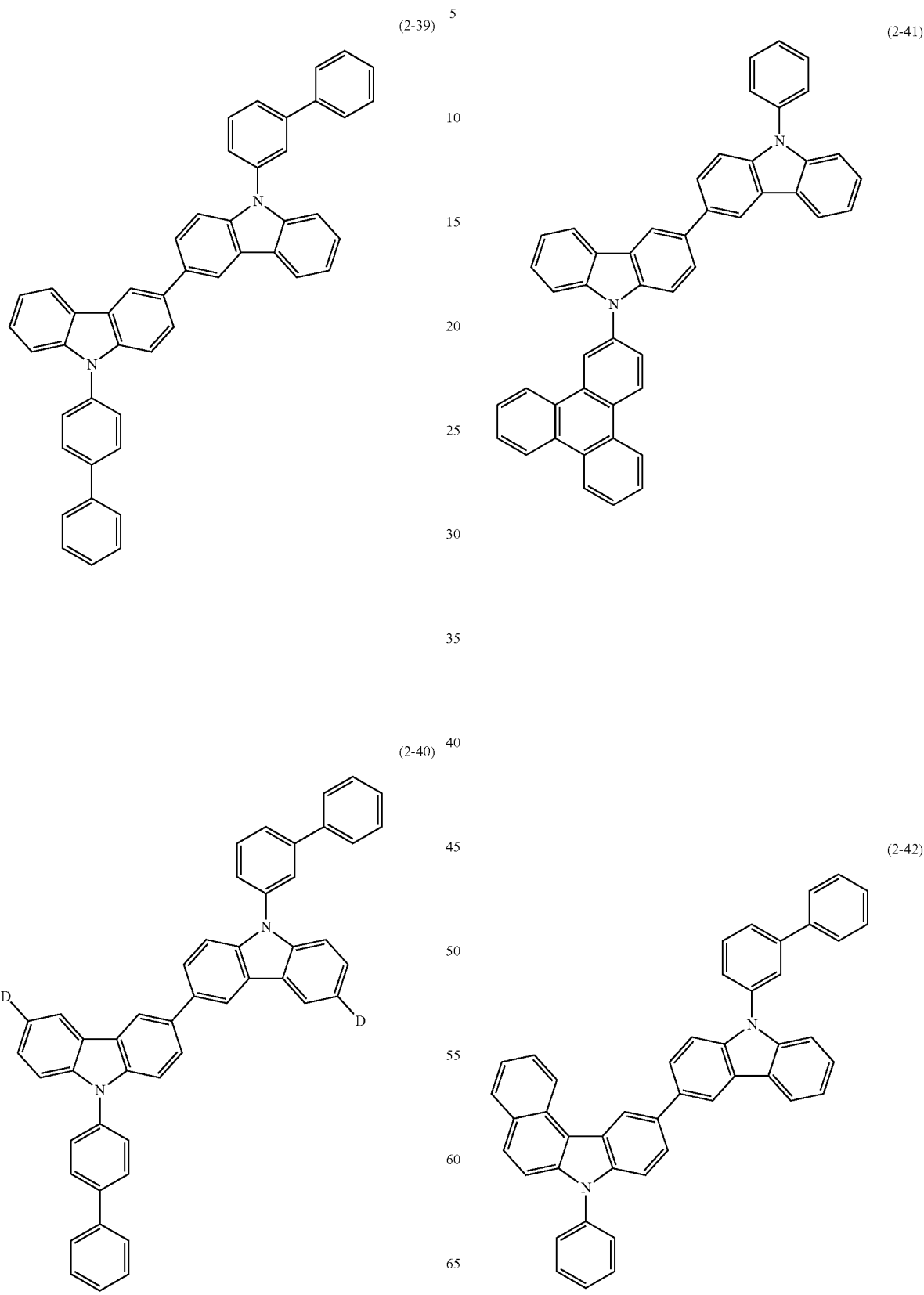

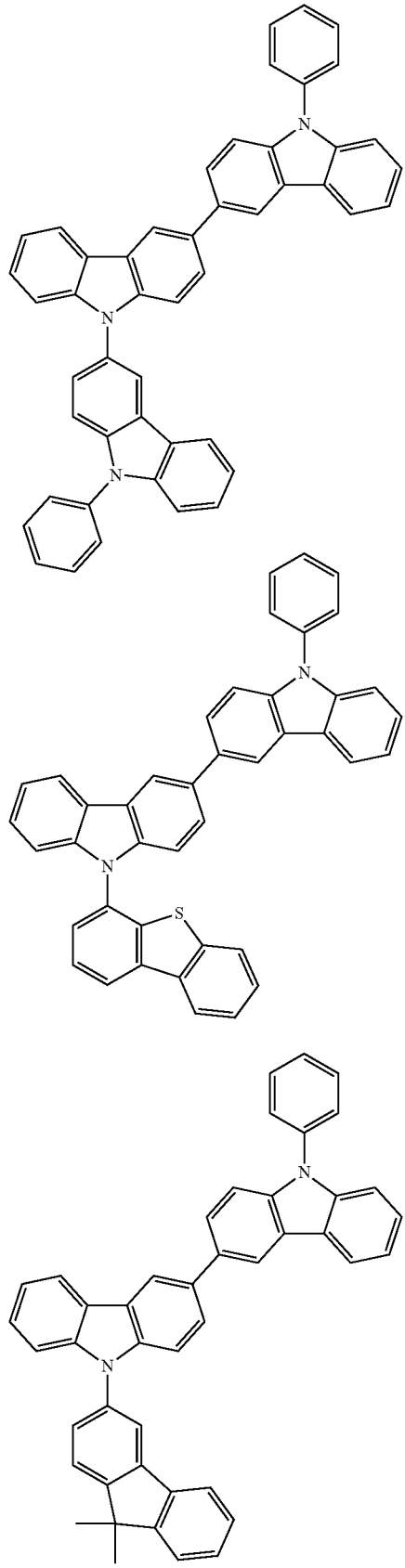
(2-43)
(2-44)
(2-45)
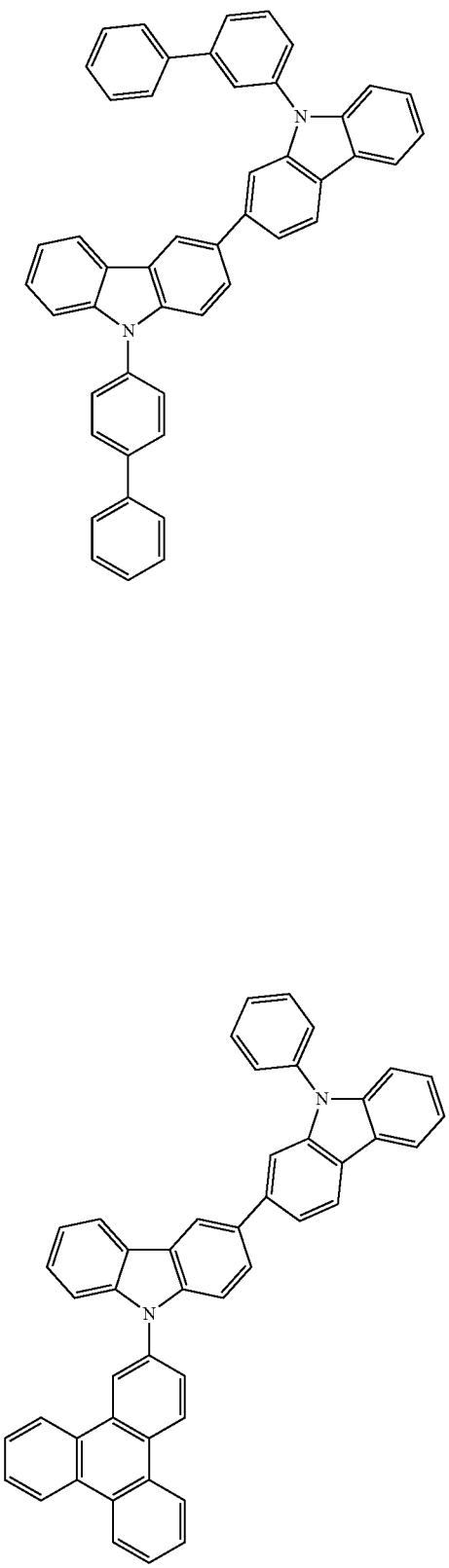
(2-46)
(2-47)

(2-48)
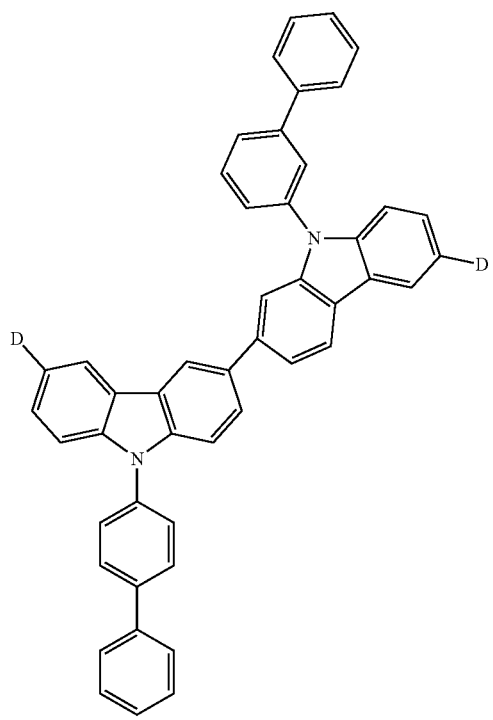
(2-51)
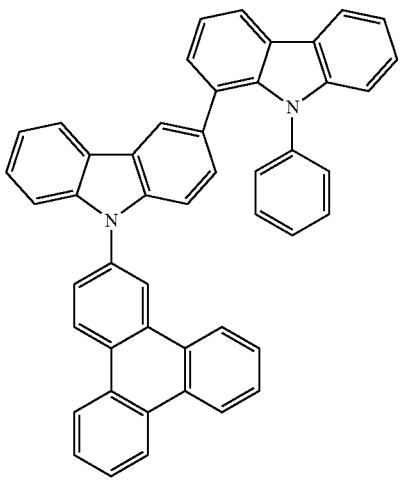
(2-52)
(2-49)
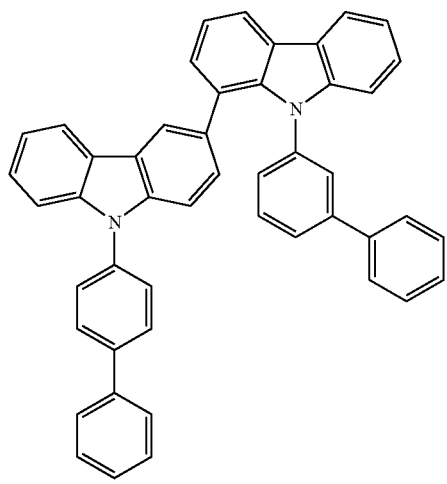
(2-53)
(2-50)
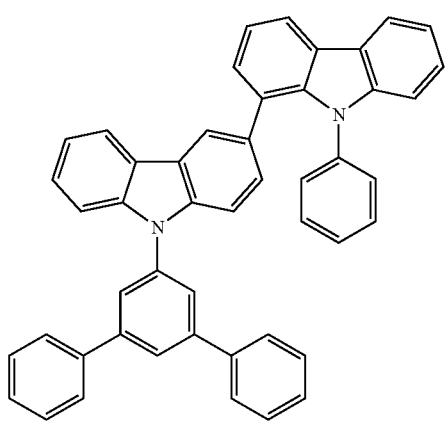

(2-54)
(2-55)
(2-56)
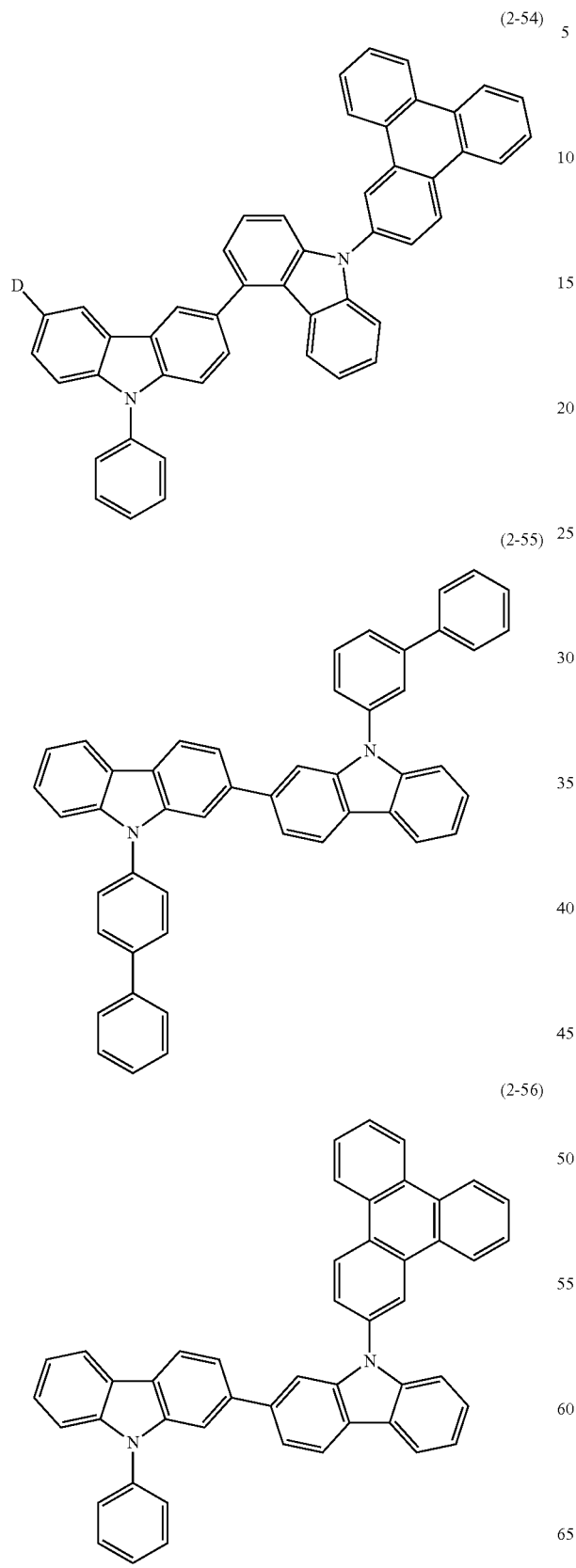
(2-57)
(2-58)
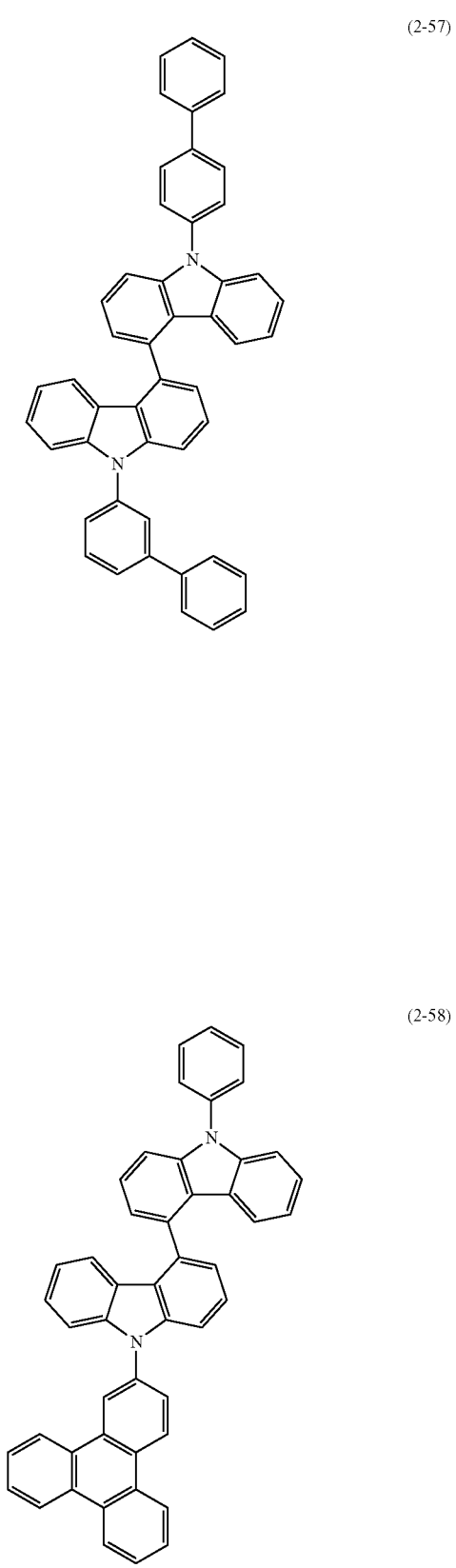

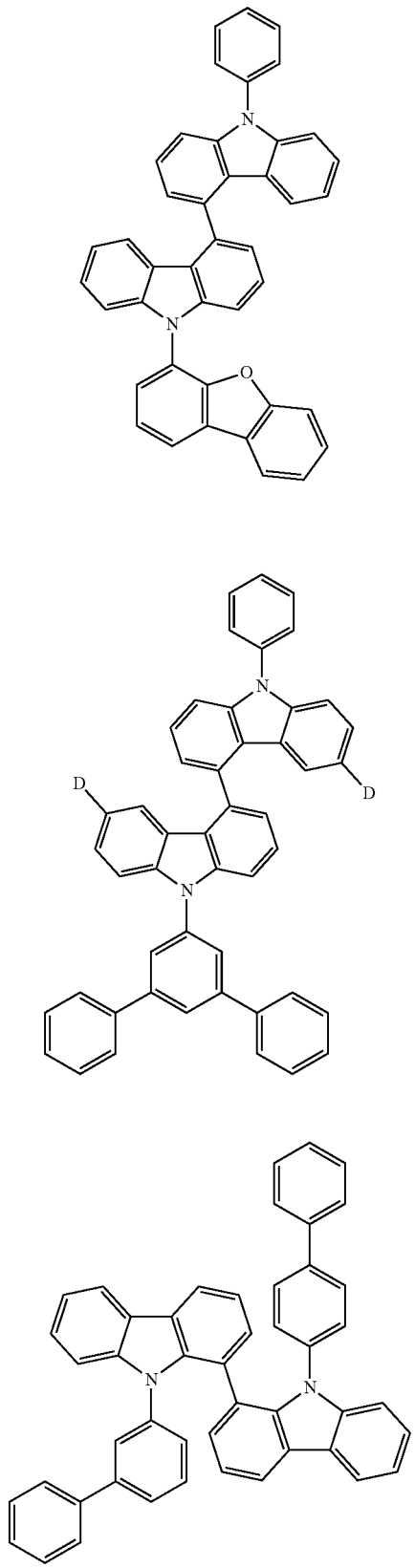
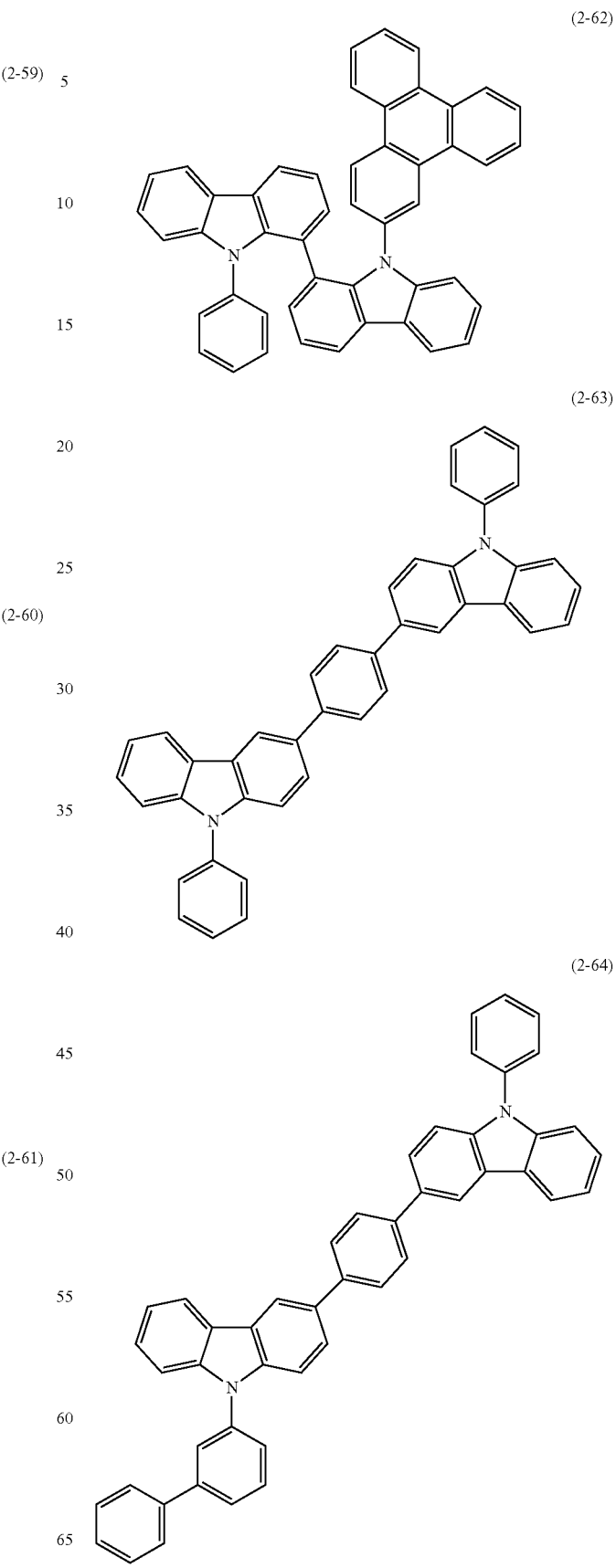

(2-65)
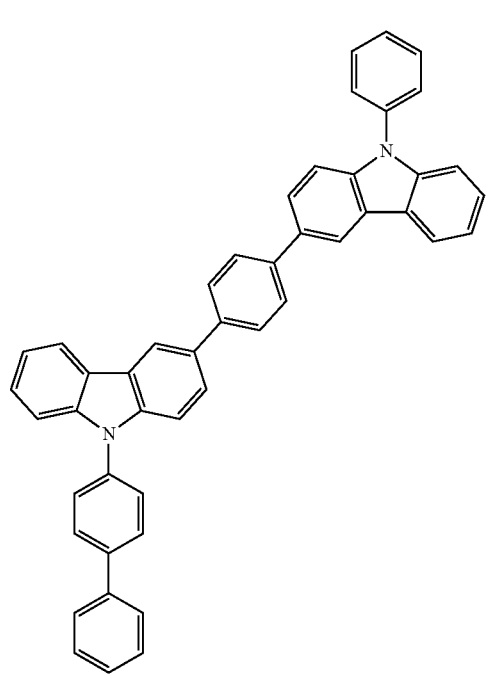
(2-66)
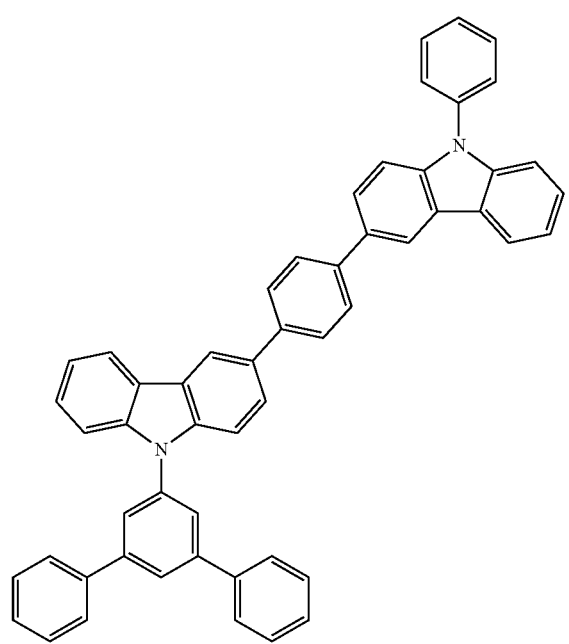
(2-67)
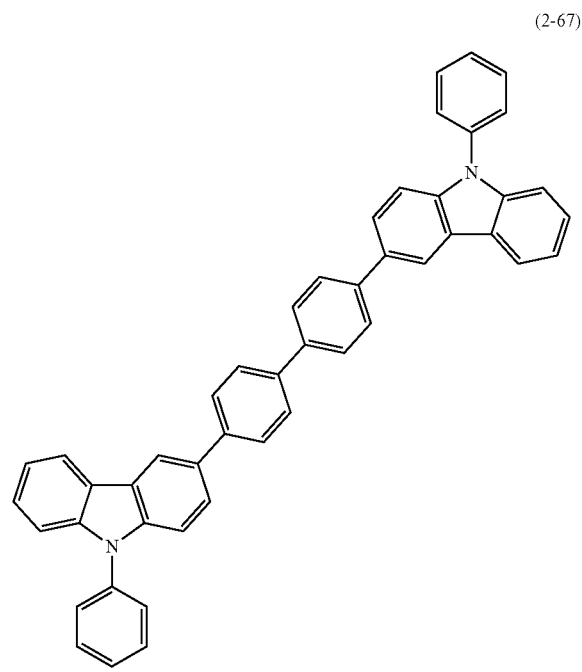
(2-68)
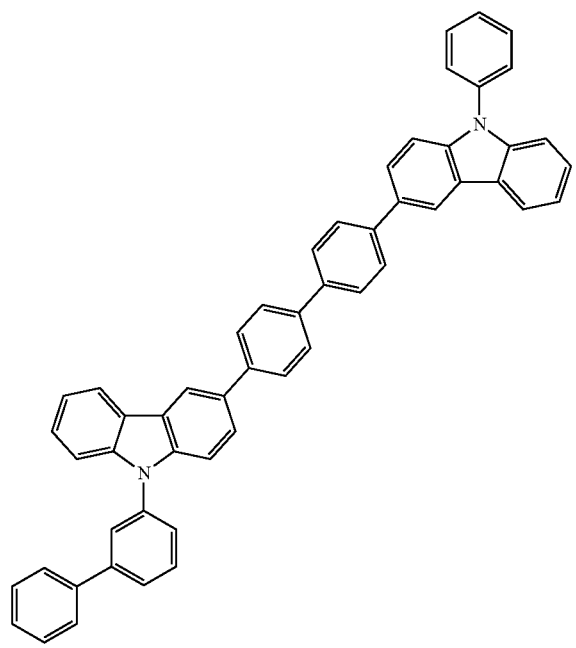

(2-69)
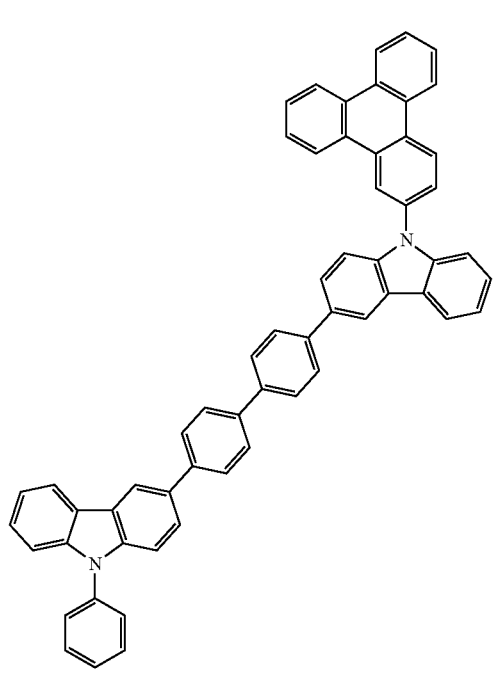
(2-70)
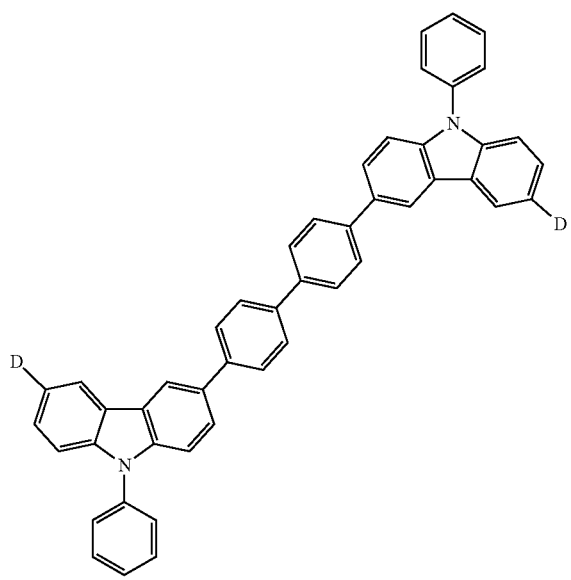
(2-71)
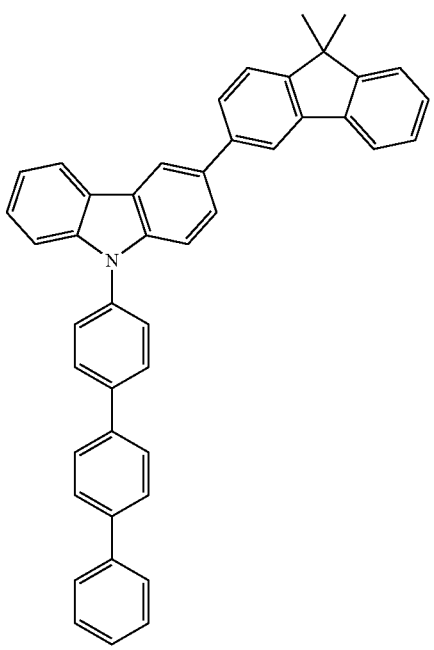
(2-72)
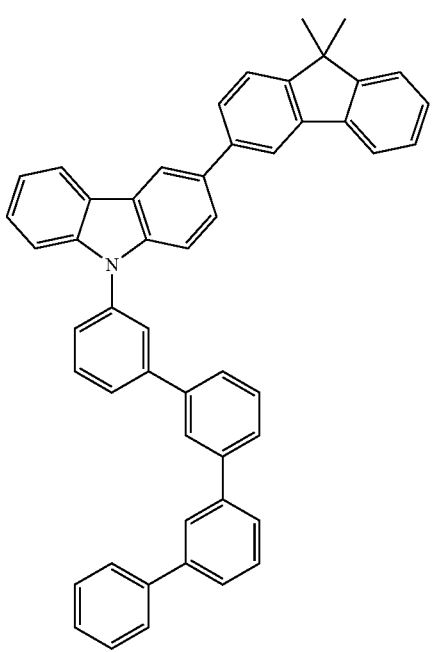

(2-73)
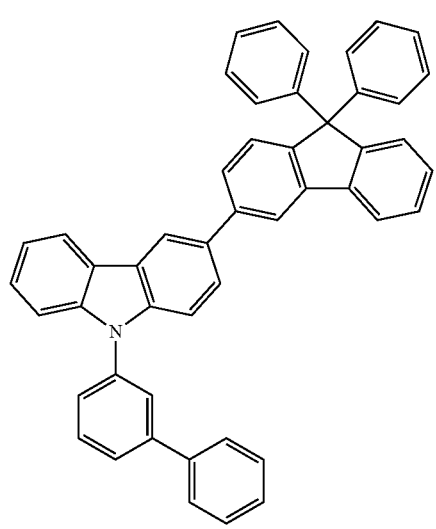
(2-74)
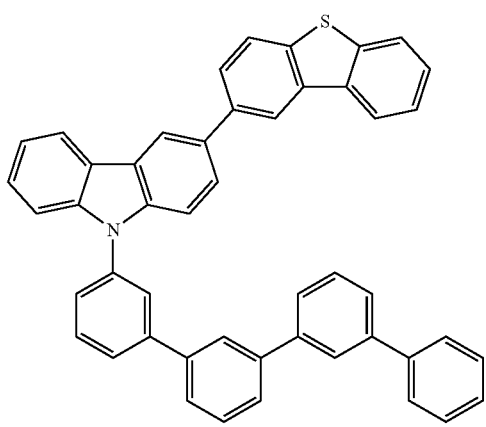
(2-75)
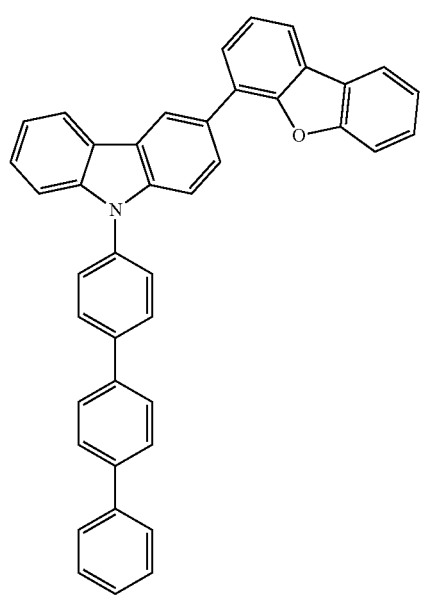
(2-76)
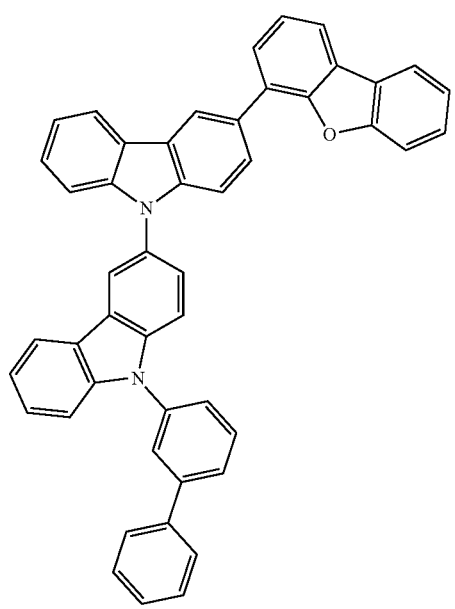
(2-77)
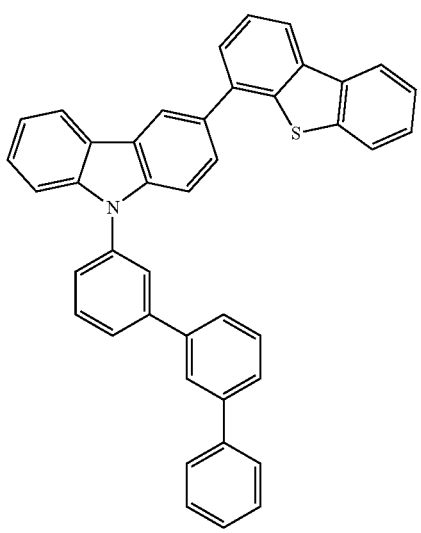
(2-78)
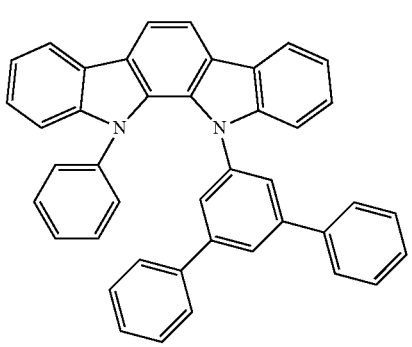

-continued
(2-79)
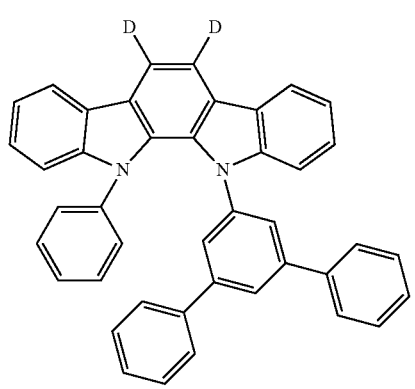
(2-80)
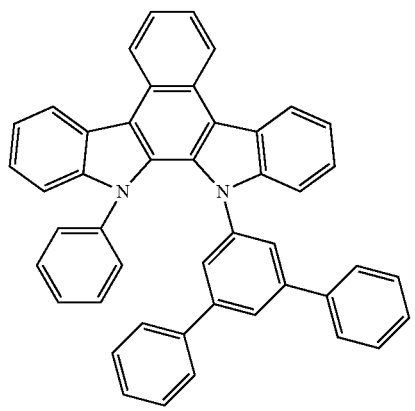
(2-81)
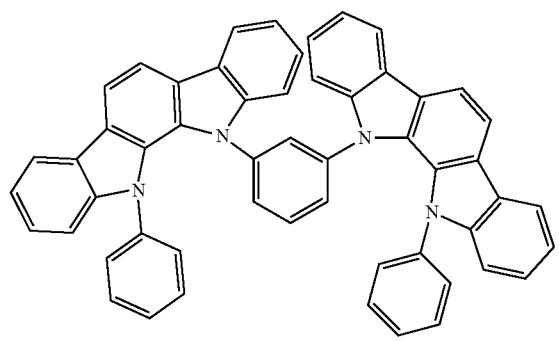
(2-82)
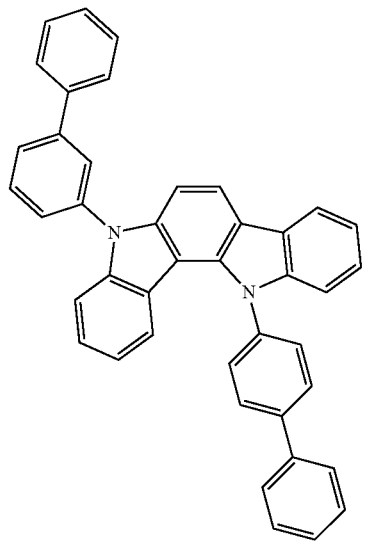
-continued
(2-83)
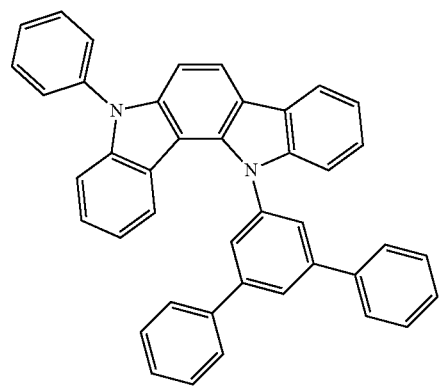
(2-84)
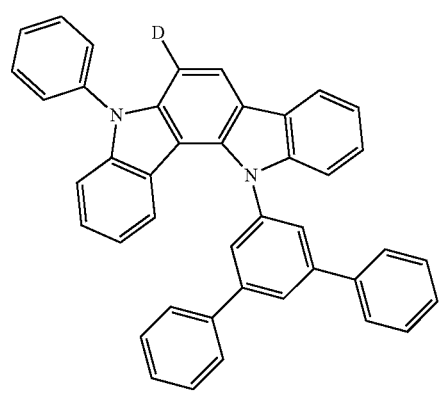
(2-85)
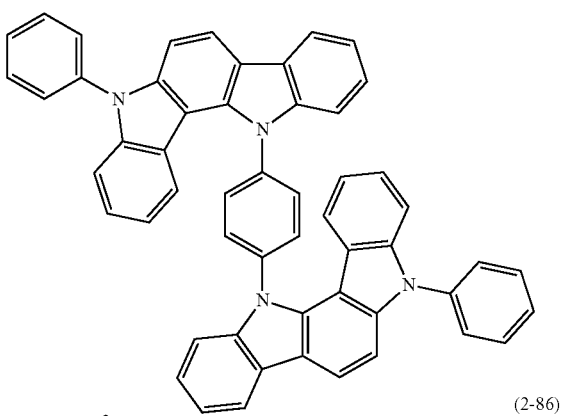
(2-86)
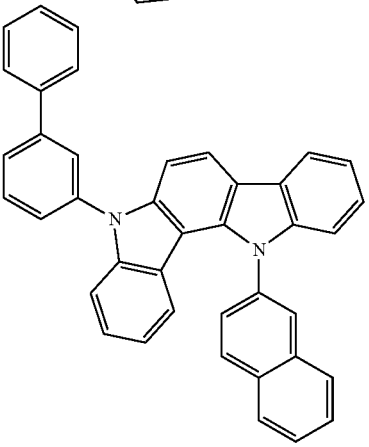

(2-87)
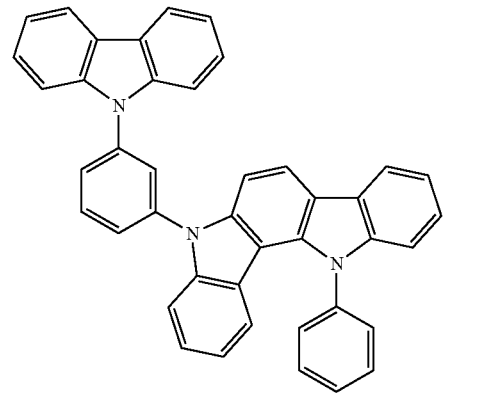
(2-88)
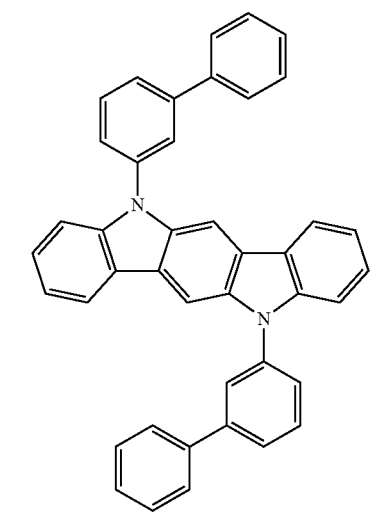
(2-89)
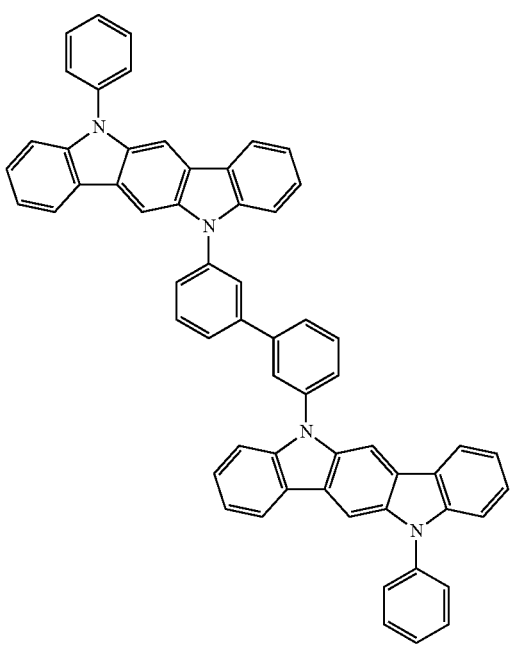
(2-90)
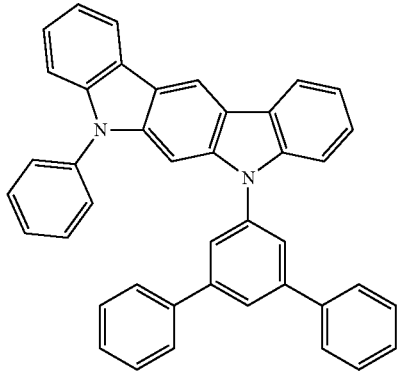
(2-91)
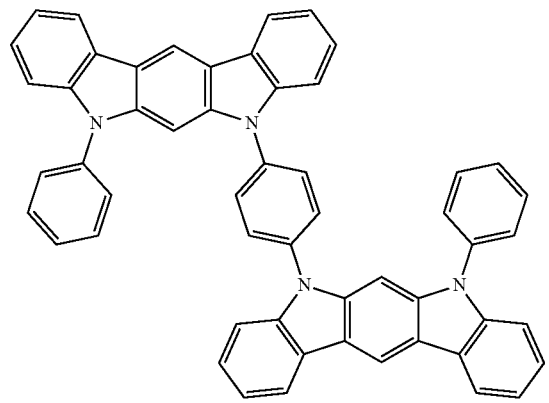
(2-92)
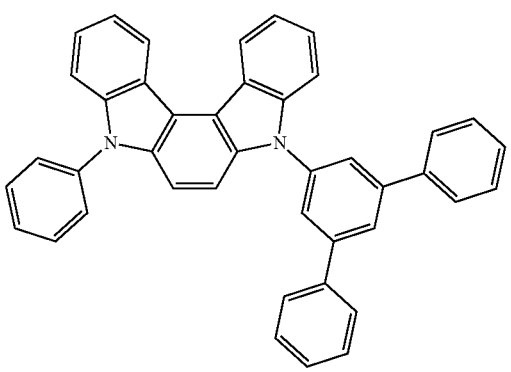
(2-93)
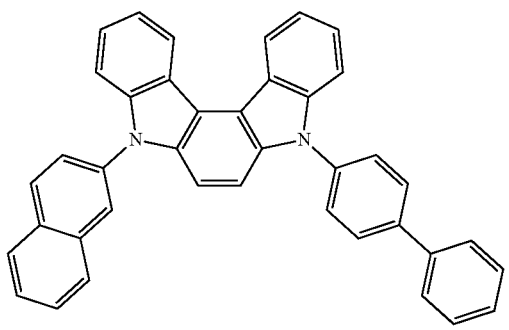

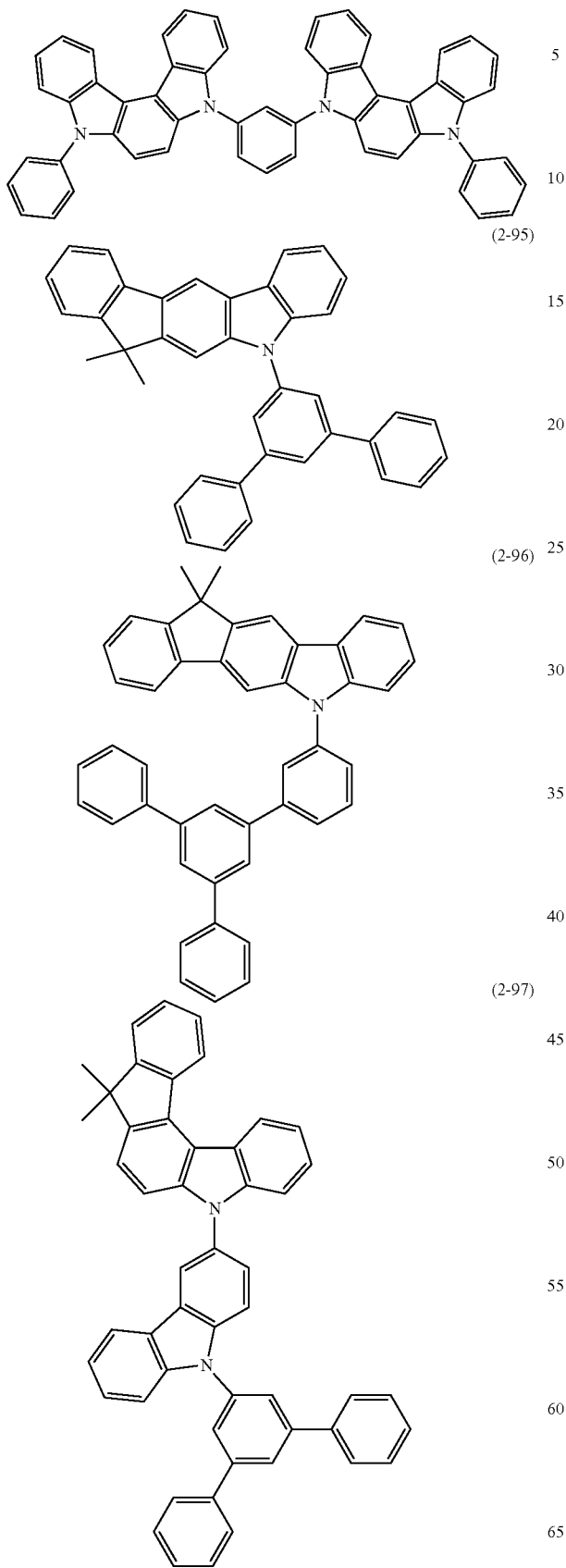
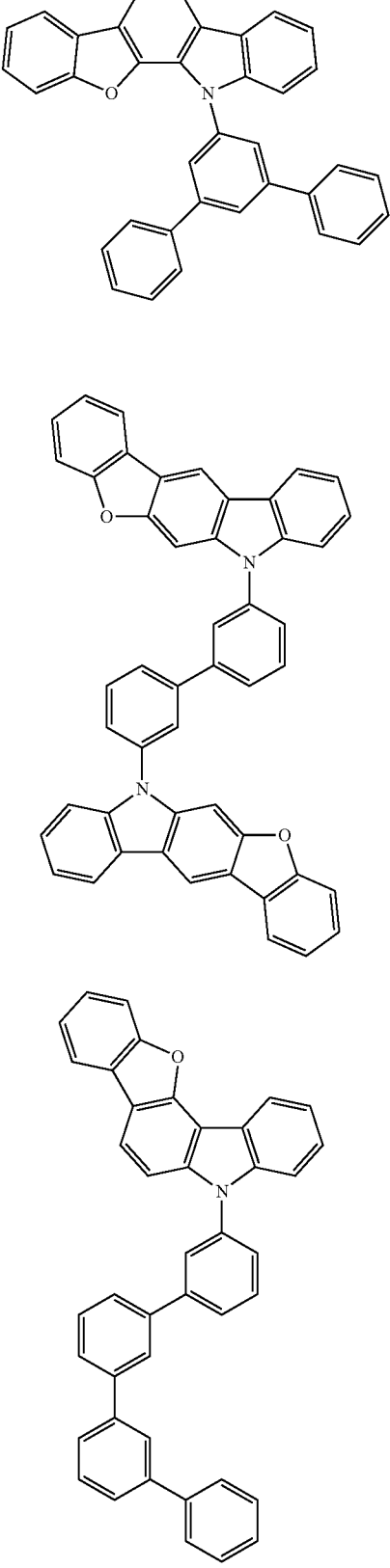

(2-101)
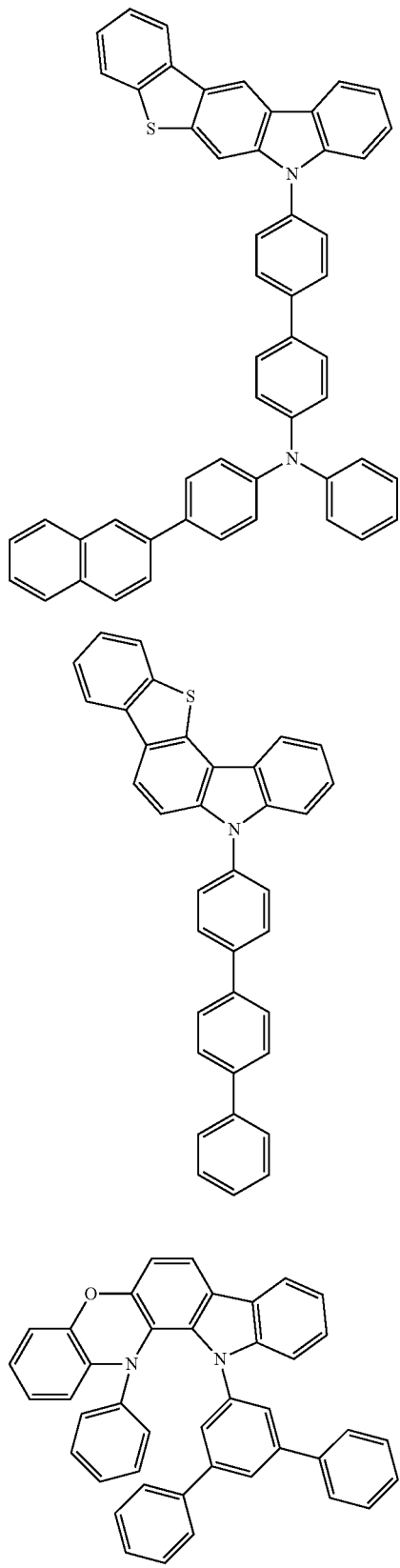
(2-102)
(2-103)
(2-104)
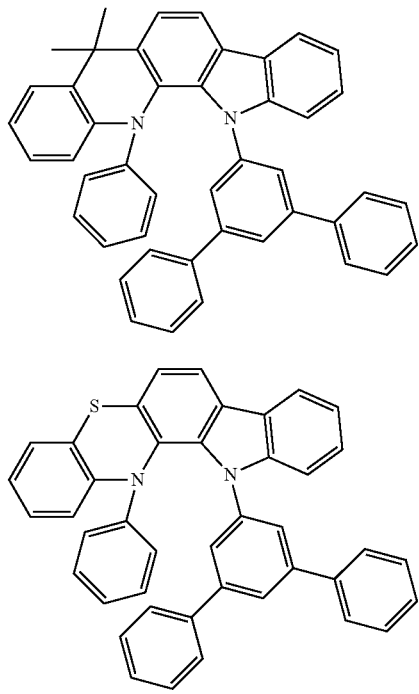
(2-105)
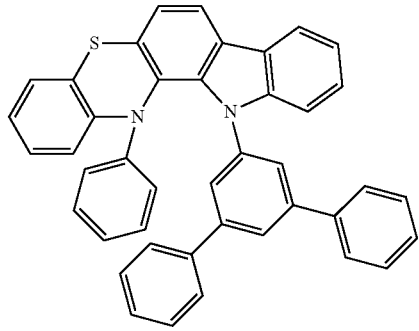
(2-106)
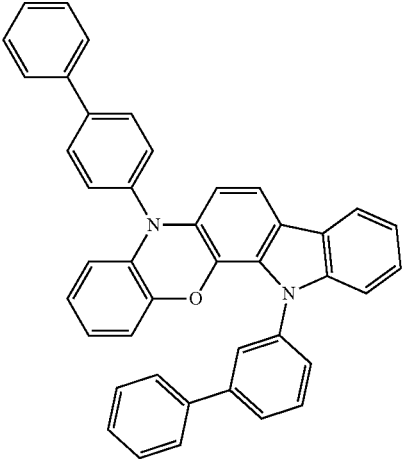
(2-107)
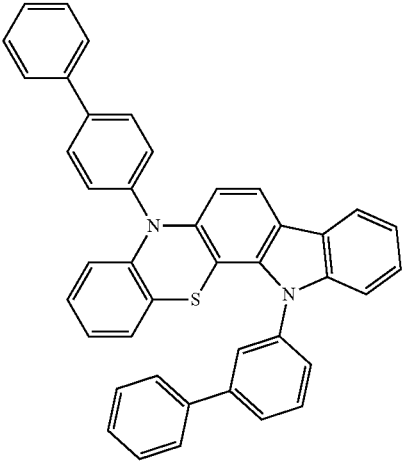

(2-108)
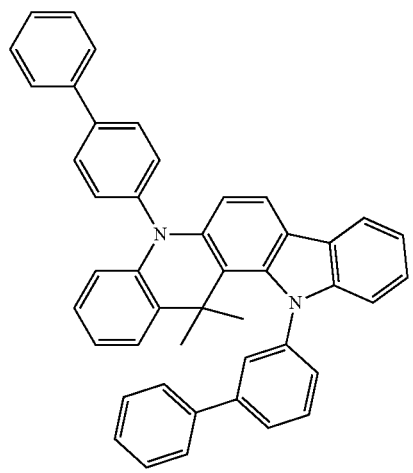
(2-109)
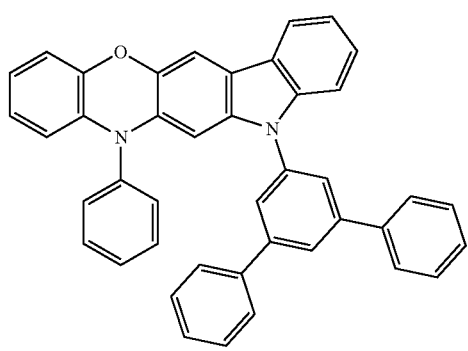
(2-110)
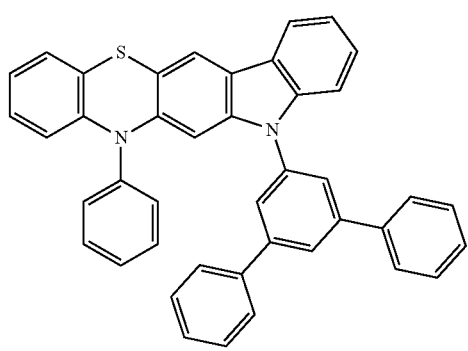
(2-111)
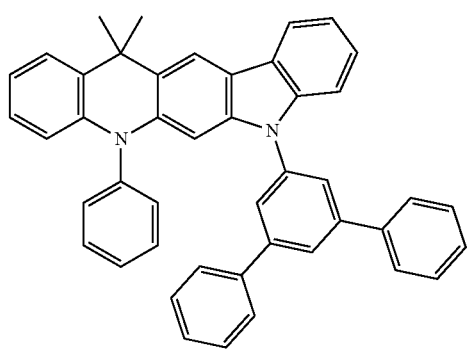
(2-112)
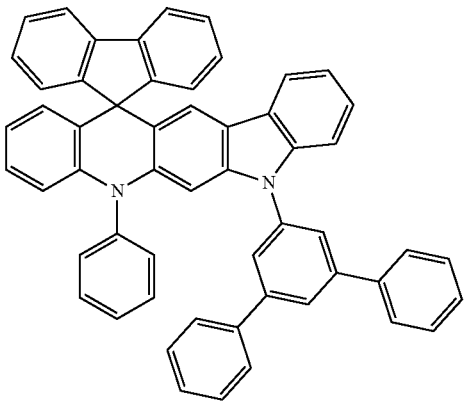
(2-113)
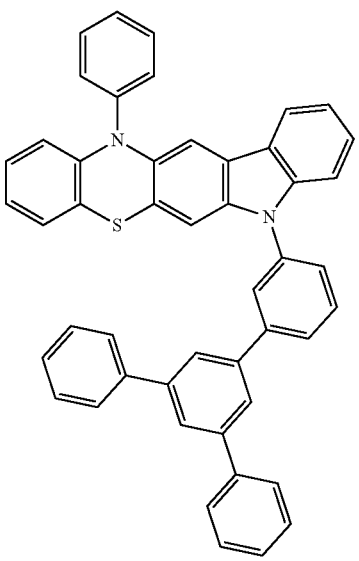
(2-114)
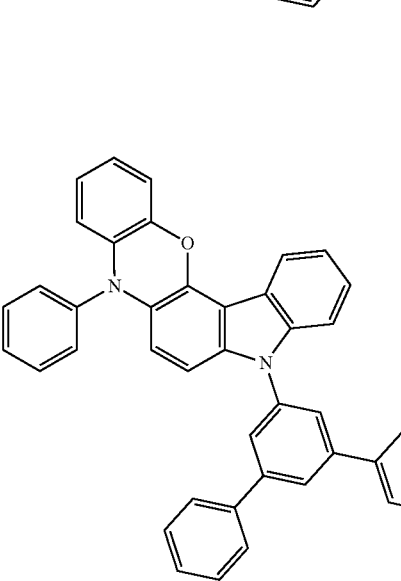

(2-115)

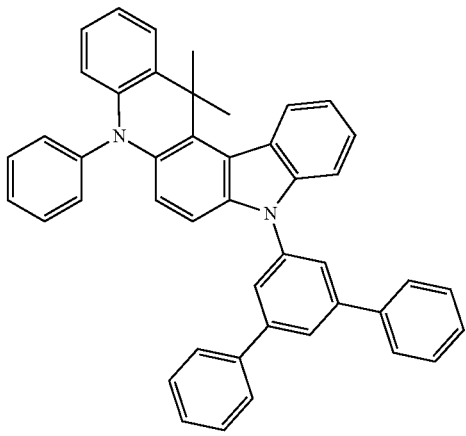

(2-116)

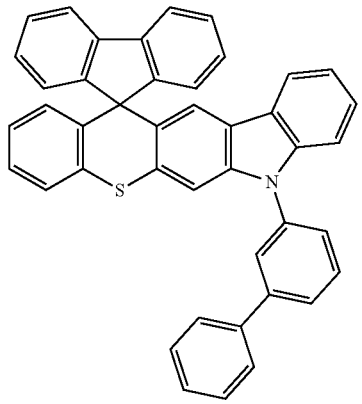

(2-117)

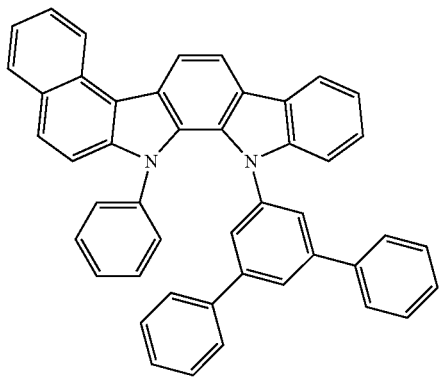

In certain particularly embodiments, the mixture according to the present disclosure also contains another organic functional material. The another organic functional material includes: a hole (also called electron hole) injection or transport material (HIM/HTM), a hole blocking material (HBM), an electron injection or transport material (EIM/ETM), an electron blocking material (EBM), an organic host material (Host), a singlet emitter (fluorescent emitter), a triplet emitter (phosphorescent emitter), a thermally activated delayed fluorescent material (TADF material) and especially a light-emitting organometallic complex. Various organic functional materials are described in detail, for example, in WO2010135519A1, US20090134784A1, and WO2011110277A1, and the entire contents of these three patent documents are hereby incorporated herein by reference. The organic functional material may be a small molecule material and a polymer material.

In certain particularly embodiments, the organic mixture also comprises a light-emitting material selected from the group consisting of fluorescent emitter, phosphorescent emitter, TADF material, and light-emitting quantum dot.

In one embodiment, the mixture comprises the above-mentioned H1 and H2, and a phosphorescent emitter, wherein the phosphorescent emitter has a weight percentage of ≤30 wt %, in a further embodiment, it is ≤25 wt %, in a still further embodiment, it is ≤20 wt %. Especially, the triplet energy level of the phosphorescent emitter ≤min($E_T$(H1), $E_T$(H2), min((LUMO(H1)−HOMO(H2), LUMO(H2)−HOMO(H1))).

In another embodiment, the mixture comprises the above-mentioned H1 and H2, and a fluorescent emitter. Wherein, the fluorescent emitter has a weight percentage of ≤15%, in a further embodiment, it is ≤10%, and in a still further embodiment, it is ≤8%.

In another embodiment, the mixture comprises the above-mentioned H1 and H2, and a TADF light-emitting material. Wherein, the TADF light-emitting material has a weight percentage of ≤15%, in a further embodiment, it is ≤10%, and in a still further embodiment, it is ≤8%. Especially, the triplet energy level of the TADF light-emitting material ≤min($E_T$(H1), $E_T$(H2), min((LUMO(H1) −HOMO(H2), LUMO(H2)−HOMO(H1))).

The fluorescent emitting material or singlet emitter, phosphorescent emitting material or triplet emitter, and TADF material are described in more detail below, but are not limited thereto.

1. Triplet Host Materials:

Examples of triplet host materials are not particularly limited, and any metal complex or organic compound may be used as a host as long as its triplet energy is higher than that of an emitter, particularly a triplet emitter or a phosphorescent emitter. Examples of the metal complexes that can be used as the triplet host include, but are not limited to the following general structure:

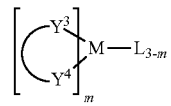

M is a metal; ($Y^3$-$Y^4$) is a bidentate ligand, $Y^3$ and $Y^4$ are independently selected from the group consisting of C, N, O, P and S; L is an auxiliary ligand; m is an integer from 1 to the maximum coordination number of the metal. In one embodiment, the metal complex that may be used as a triplet host has the following forms:

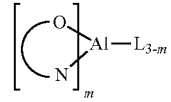 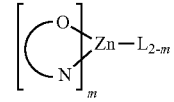

(O—N) is a bidentate ligand, wherein the metal is coordinated with O and N atoms, m is an integer from 1 to the maximum coordination number of the metal.

In a certain embodiment, M may be selected from Ir and Pt.

Examples of organic compounds that may be used as a triplet host are selected from the group consisting of: compounds containing cyclic aromatic hydrocarbon groups, such as benzene, biphenyl, triphenyl benzene, benzofluorene; compounds containing aromatic heterocyclic groups, such as dibenzothiophene, dibenzofuran, dibenzoselenophen, furan, thiophene, benzofuran, benzothiophene, benzoselenophen, carbazole, dibenzocarbazole, indolocarbazole, pyridine indole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, oxazole, dibenzoxazole, benzisoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furopyridine, benzothiophene pyridine, thiophene pyridine, benzoselenophene pyridine and selenophenbenzodipyridine; and groups containing 2 to 10 ring structure, which may be the same or different type of cyclic aromatic hydrocarbon groups or aromatic heterocyclic groups and are connected to each other directly or through at least one of the following groups, such as oxygen atom, nitrogen atom, sulfur atom, silicon atom, phosphorus atom, boron atom, chain structure unit, and aliphatic ring group. Wherein, each Ar may be further substituted, and the substituent may be selected from the group consisting of hydrogen, deuterium, cyano group, halogen, alkyl, alkoxy group, amino group, alkenyl, alkynyl, aralkyl, heteroalkyl, aryl and heteroaryl.

In one embodiment, the triplet host material may be selected from compounds containing at least one of the following groups:

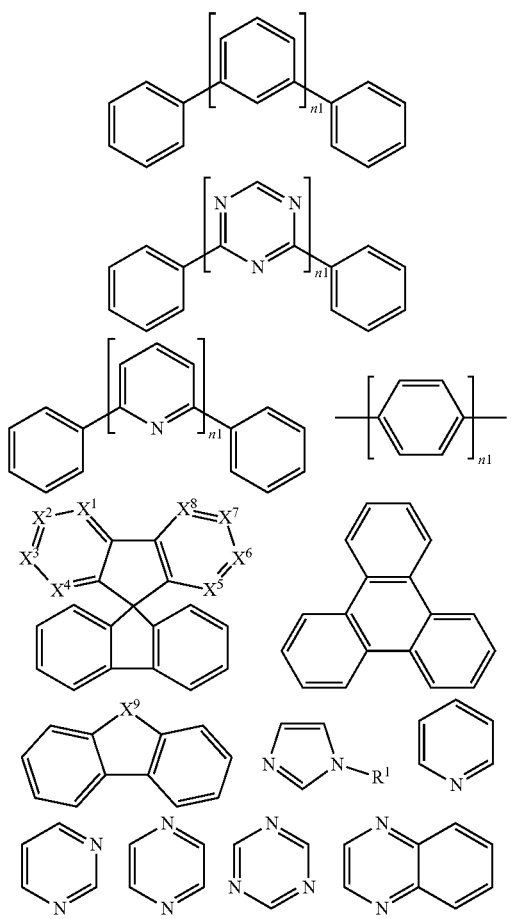

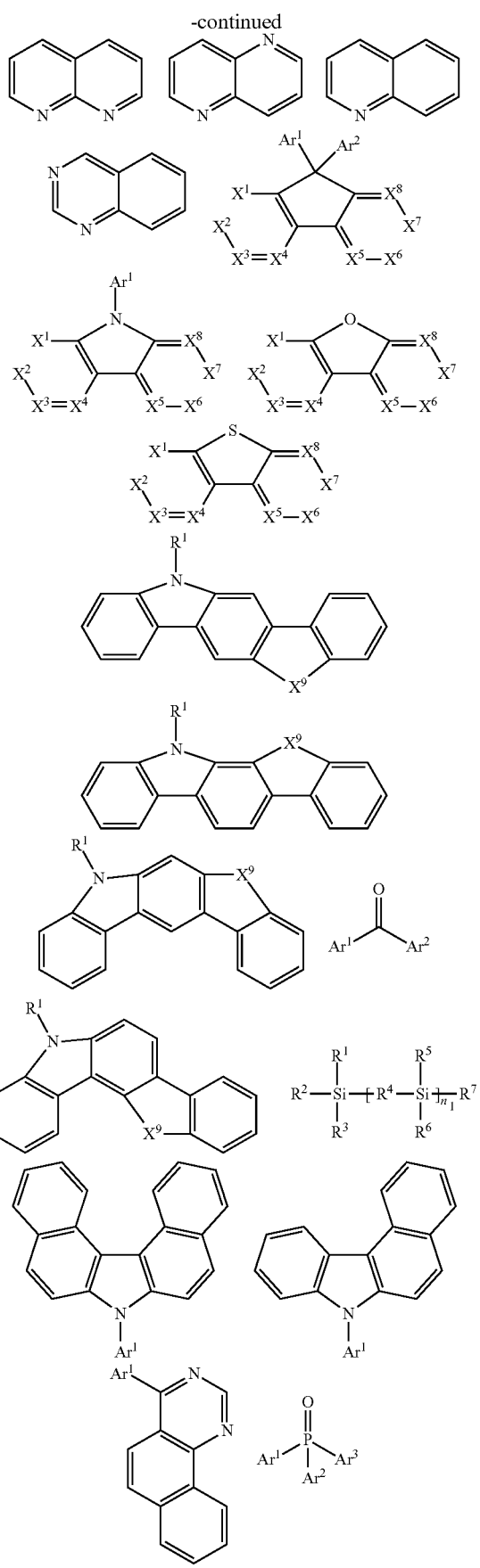

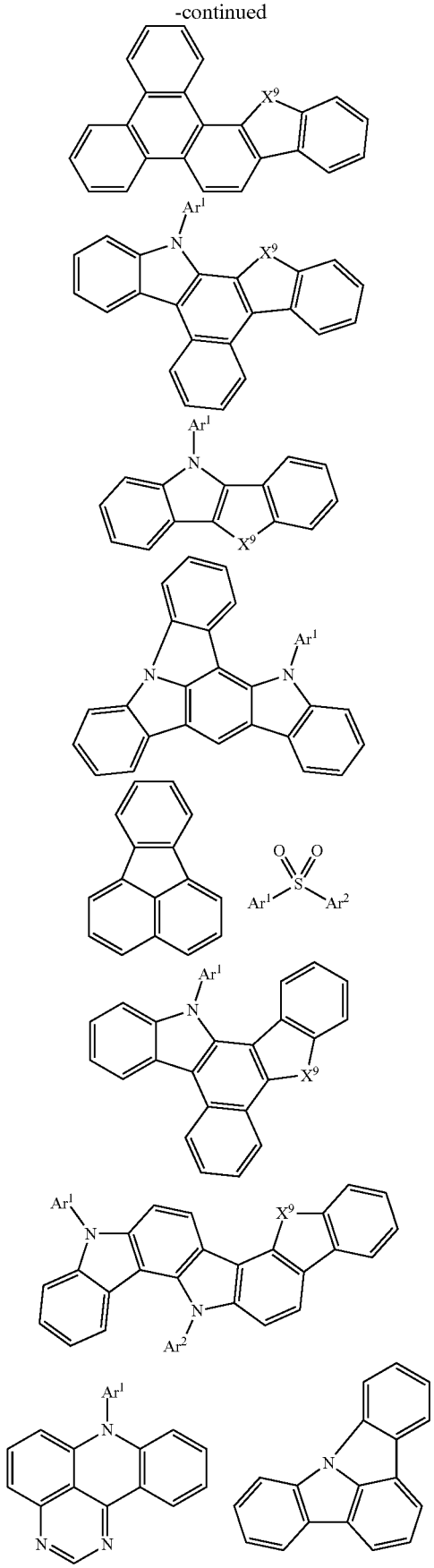
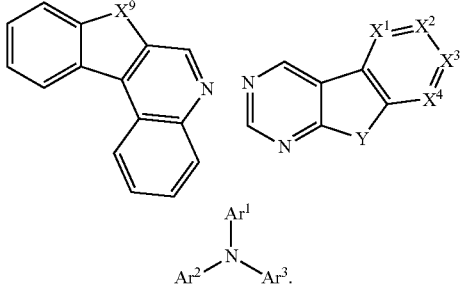
$R^2$-$R^7$ have the same definitions as $R^1$, $X^9$ is selected from $CR^1R^2$ or $NR^1$, and Y is selected from $CR^1R^2$, $NR^1$, O, and S. $R_1$, n, $X^1$-$X^8$, $Ar^1$~$Ar^3$ are defined as above.
Suitable examples of the triplet host materials are listed below, but are not limited to:
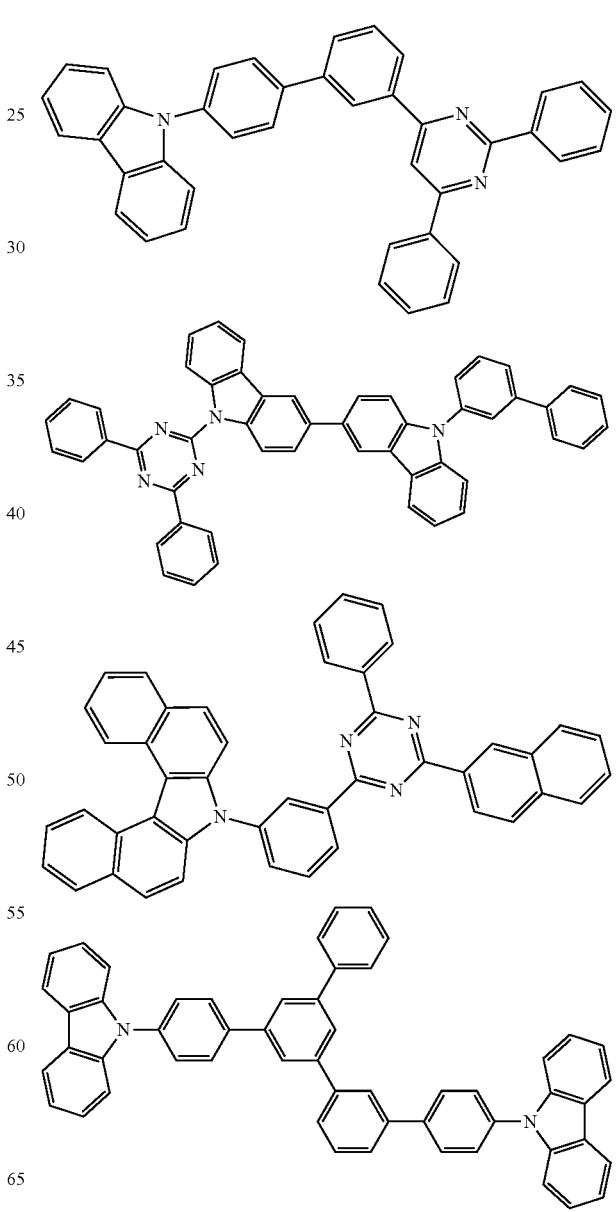

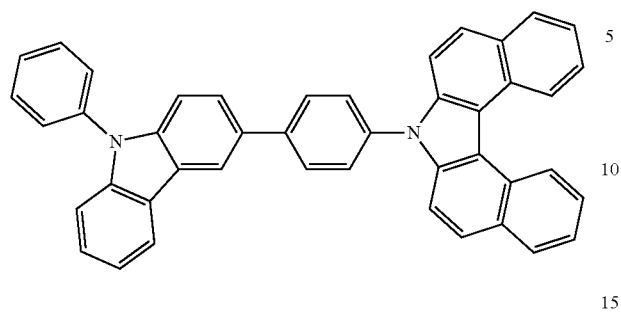
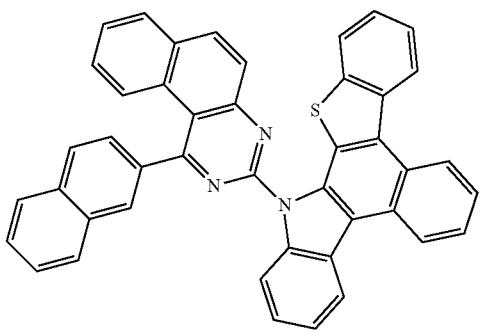
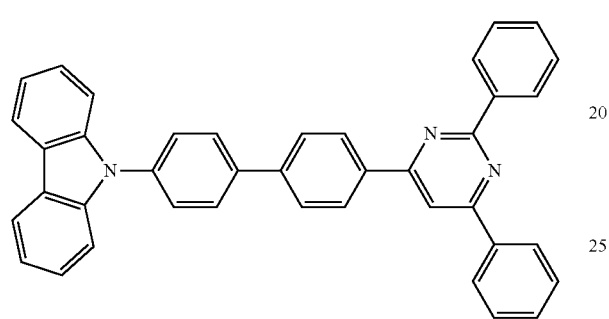
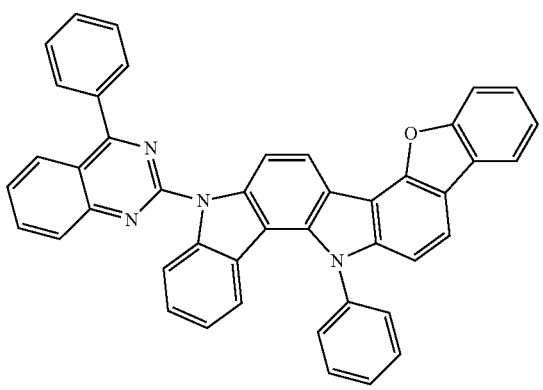
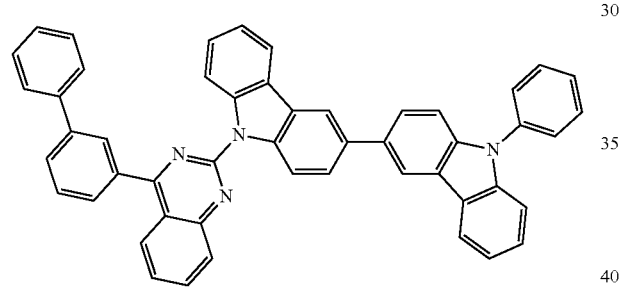
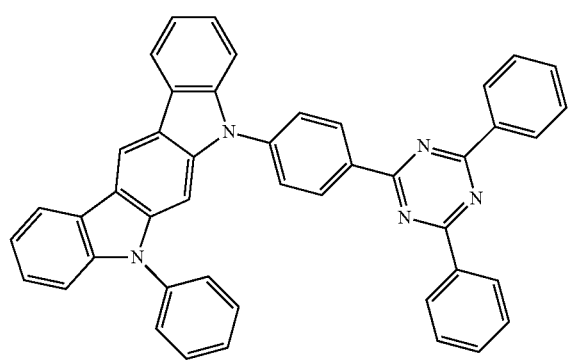
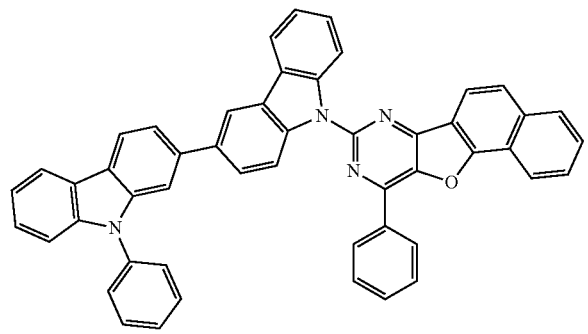
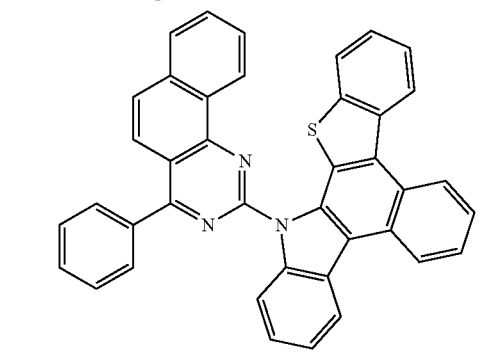
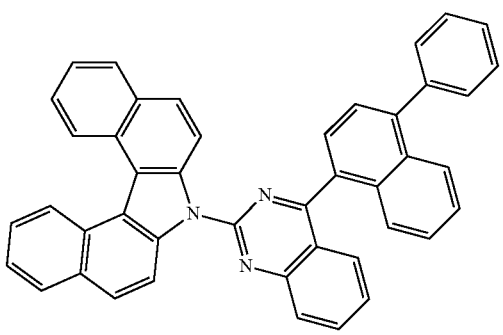

119
-continued
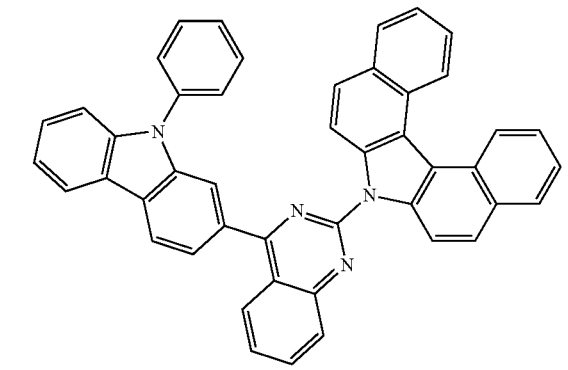
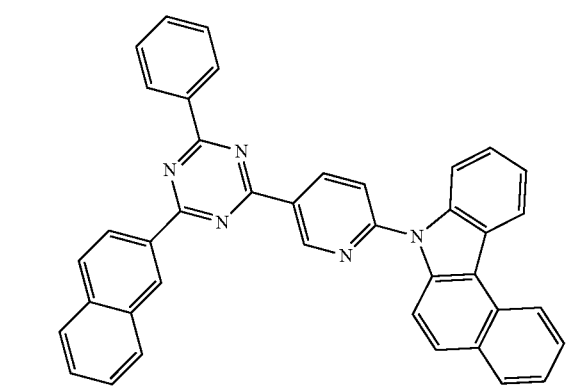
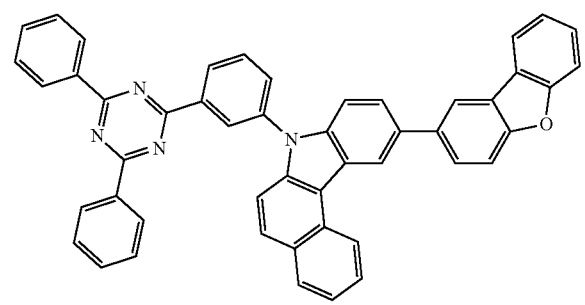
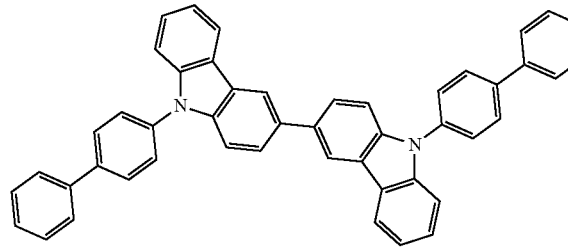
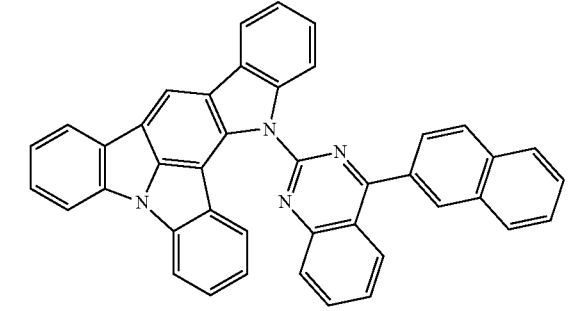
120
-continued
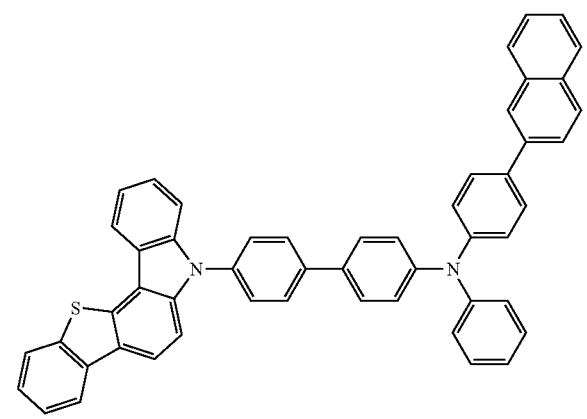
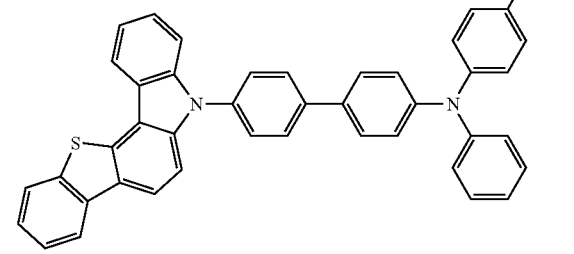
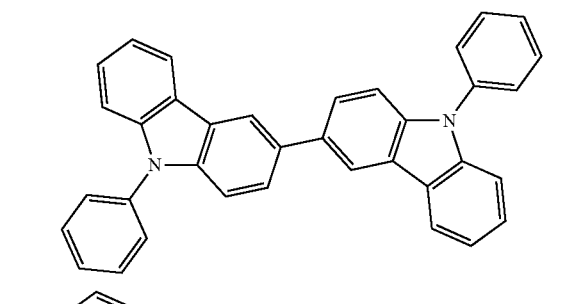
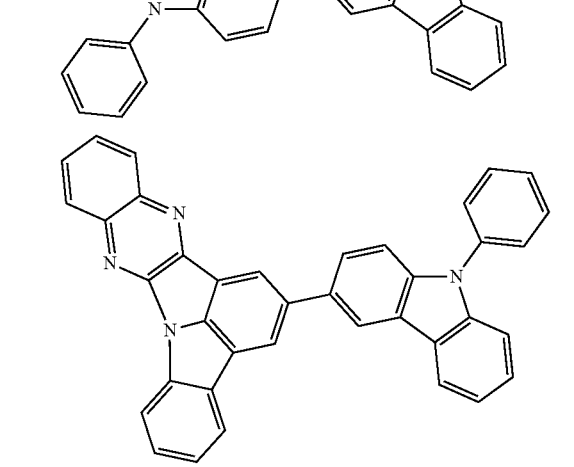
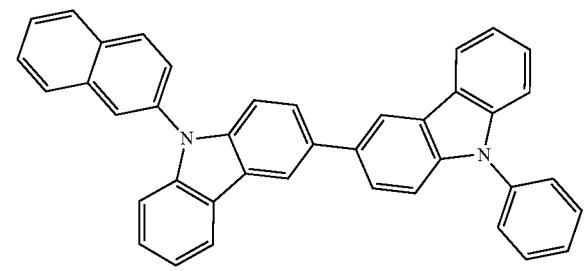
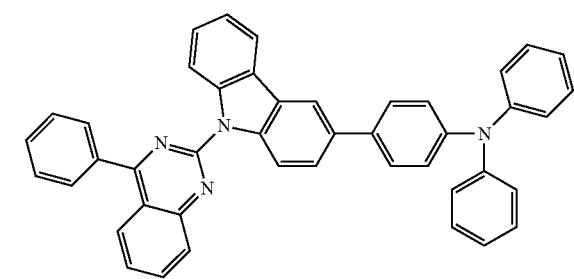

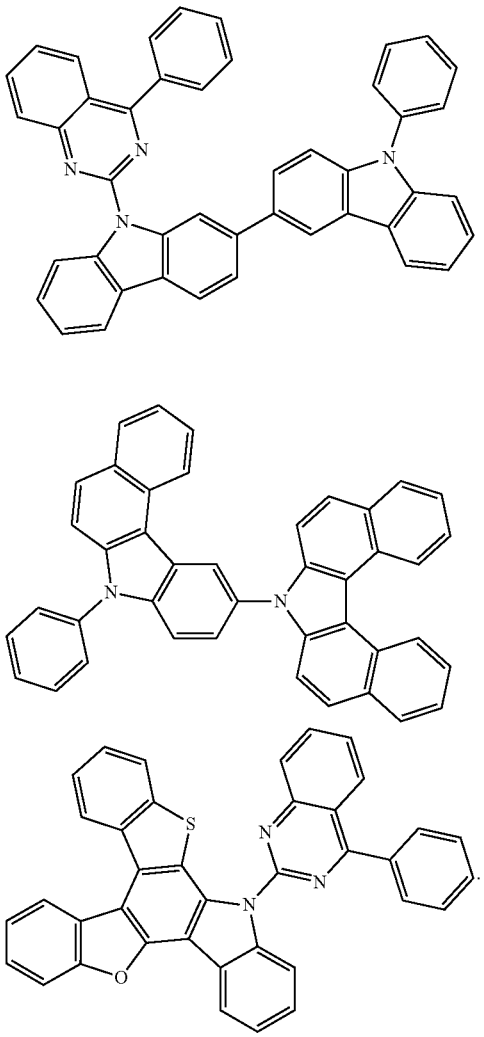

2. Phosphorescent Emitting Materials

Phosphorescent emitters are also called triplet emitters. In one embodiment, the triplet emitters are metal complexes having the general formula M'(L')n, wherein M' is a metal atom, and L' may be the same or different at each occurrence and is an organic ligand which is bonded or coordinated to the metal atom M' through one or more positions, and n is an integer greater than 1, particularly 1, 2, 3, 4, 5 or 6. Optionally, these metal complexes are connected to a polymer through one or more positions, particularly through organic ligands.

In one embodiment, the metal atom M' is selected from the group consisting of transition metal elements, lanthanide elements, and actinide elements. In another embodiment, the metal atom M' is selected from the group consisting of Ir, Pt, Pd, Au, Rh, Ru, Os, Sm, Eu, Gd, Tb, Dy, Re, Cu, and Ag. In a particular embodiment, the metal atom M' is selected from the group consisting of Os, Ir, Ru, Rh, Re, Pd, Au, and Pt.

In one embodiment, the triplet emitters comprise chelating ligands, i.e. ligands, which are coordinated with the metal via at least two bonding sites. In another embodiment, the triplet emitters have two or three identical or different bidentate or multidentate ligands. The chelating ligands are beneficial to improve the stability of the metal complexes.

Examples of the organic ligands may be selected from the group consisting of phenylpyridine derivatives, 7,8-benzoquinoline derivatives, 2 (2-thienyl) pyridine derivatives, 2 (1-naphthyl) pyridine derivatives, and 2-phenylquinoline derivatives. All of these organic ligands may be substituted, for example, substituted with fluoromethyl or trifluoromethyl. Auxiliary ligands may be selected from acetylacetone, and picric acid.

In one embodiment, the metal complexes that can be used as triplet emitters have the following form:

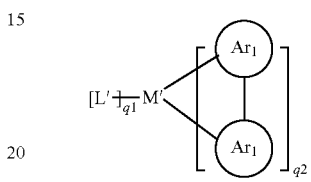

wherein, M' is a metal selected from the group consisting of transition metal elements, lanthanide elements, and actinide elements, particularly from Ir, Pt, and Au;

$Ar_1$ may be the same or different at each occurrence and is a cyclic group, wherein $Ar_1$ contains at least one donor atom, i.e. an atom with a lone pair of electrons, such as nitrogen or phosphorus, through which the cyclic group is coordinated with the metal; $Ar_2$ may be the same or different at each occurrence and is a cyclic group, wherein $Ar_2$ contains at least one C atom, through which the cyclic group is coordinated with the metal; $Ar_1$ and $Ar_2$ are covalently bonded together and may each carry one or more substituents which may also be bonded together by substituents again; L' may be the same or different at each occurrence and is a bidentate chelating auxiliary ligand, particularly a monoanionic bidentate chelating ligand; q1 may be 0, 1, 2 or 3, further 2 or 3; q2 may be 0, 1, 2 or 3, further 1 or 0.

Some examples of triplet emitter materials and applications thereof can be found in the following patent documents and references: WO 200070655, WO 200141512, WO 200202714, WO 200215645, EP 1191613, EP 1191612, EP 1191614, WO 2005033244, WO 2005019373, US 2005/0258742, WO 2009146770, WO 2010015307, WO 2010031485, WO 2010054731, WO 2010054728, WO 2010086089, WO 2010099852, WO 2010102709, US 20070087219 A1, US 20090061681 A1, US 20010053462 A1, Baldo, Thompson et al. Nature 403, (2000), 750-753, US 20090061681 A1, US 20090061681 A1, Adachi et al. *Appl. Phys. Lett.* 78 (2001), 1622-1624, J. Kido et al. *Appl. Phys. Lett.* 65 (1994), 2124, Kido et al. *Chem. Lett.* 657, 1990, US 2007/0252517 A1, Johnson et al., *JACS* 105, 1983, 1795, Wrighton, *JACS* 96, 1974, 998, Ma et al., *Synth. Metals* 94, 1998, 245, U.S. Pat. Nos. 6,824,895, 7,029,766, 6,835,469, 6,830,828, US 20010053462 A1, WO 2007095118 A1, US 2012004407A1, WO 2012007088A1, WO2012007087A1, WO 2012007086A1, US 2008027220A1, WO 2011157339A1, CN 102282150A, WO 2009118087A1, WO 2013107487A1, WO 2013094620A1, WO 2013174471A1, WO 2014031977A1, WO 2014112450A1, WO 2014007565A1, WO 2014038456A1, WO 2014024131A1, WO 2014008982A1, WO2014023377A1. The entire contents of the above listed patent documents and literatures are hereby incorporated herein by reference.

Some suitable examples of triplet emitters are listed in the following table:
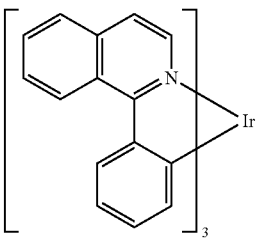
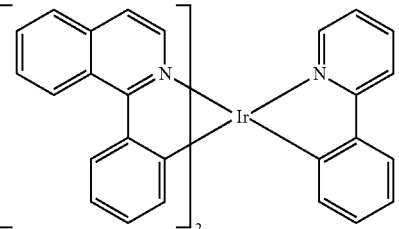
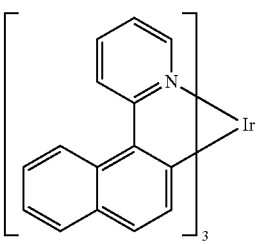
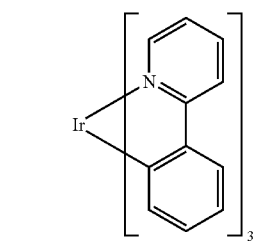
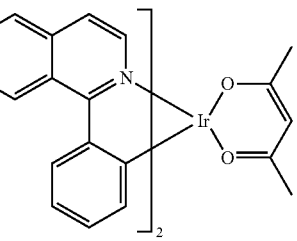
-continued
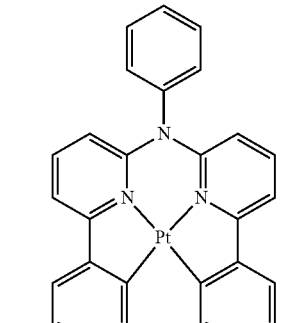
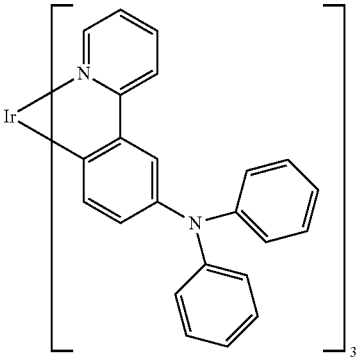
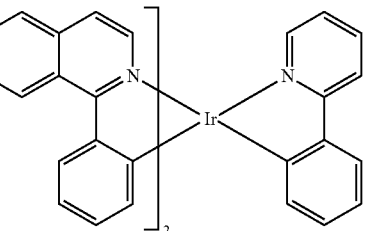
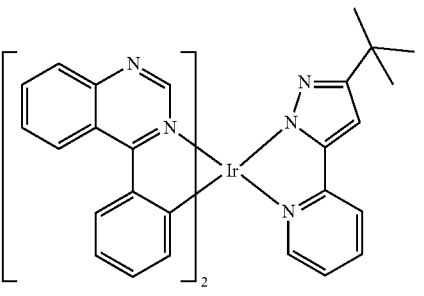
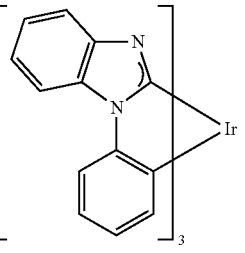

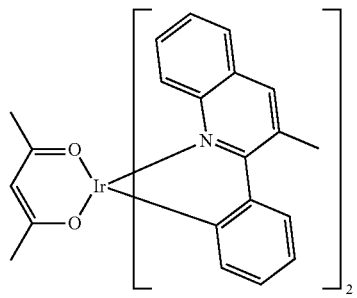
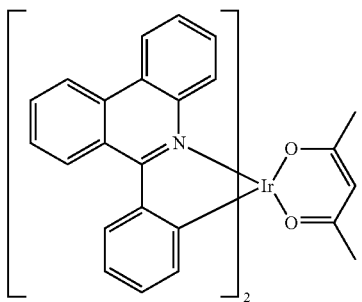
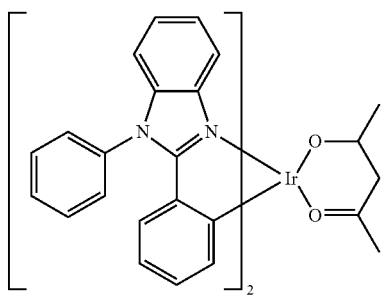
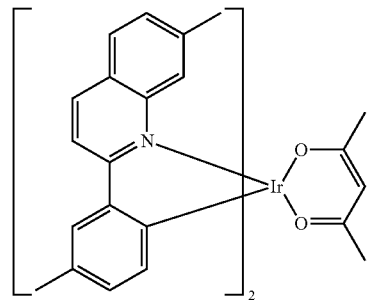
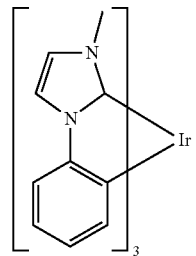
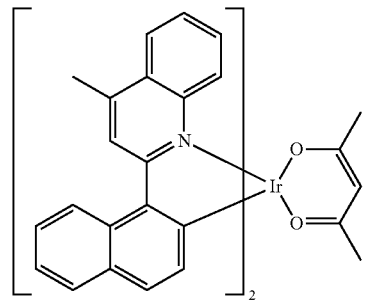
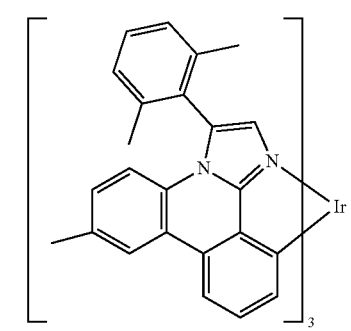
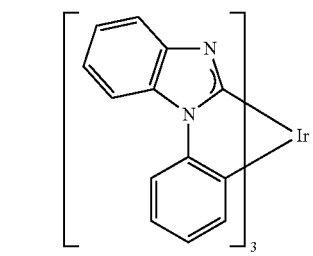
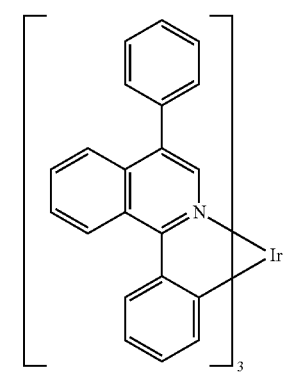
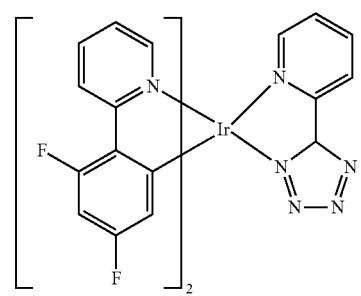

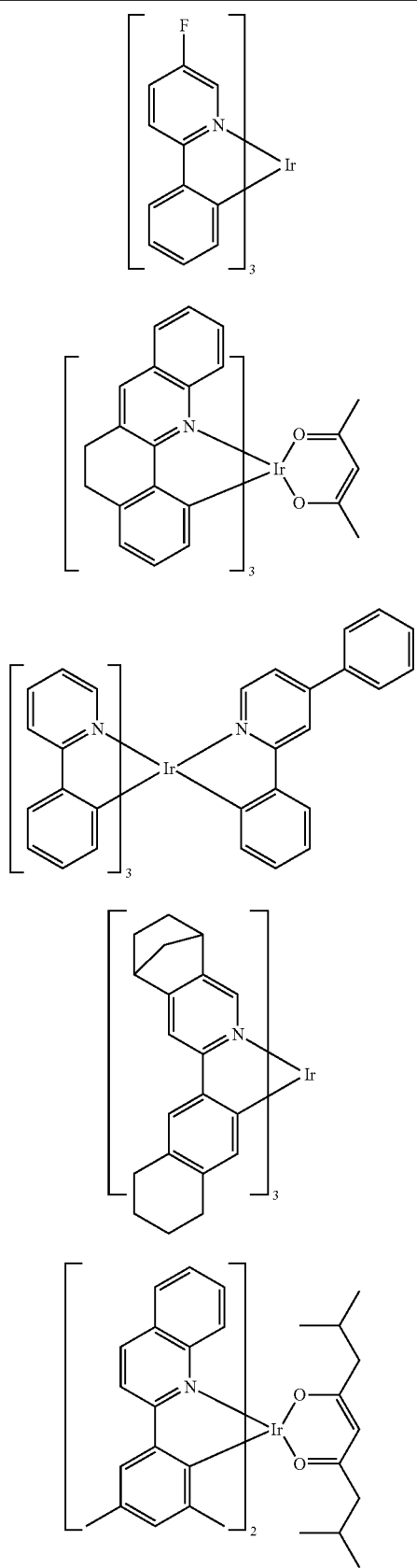
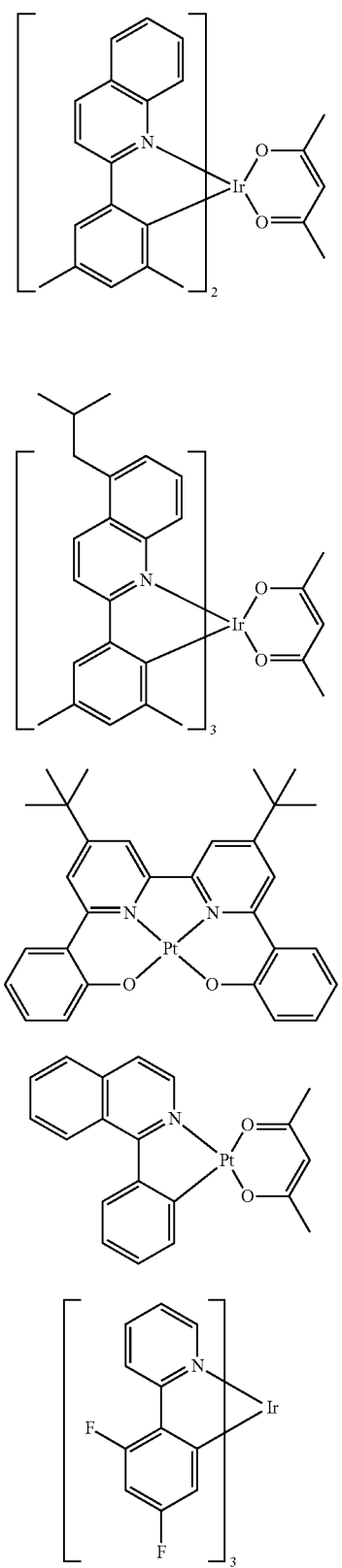

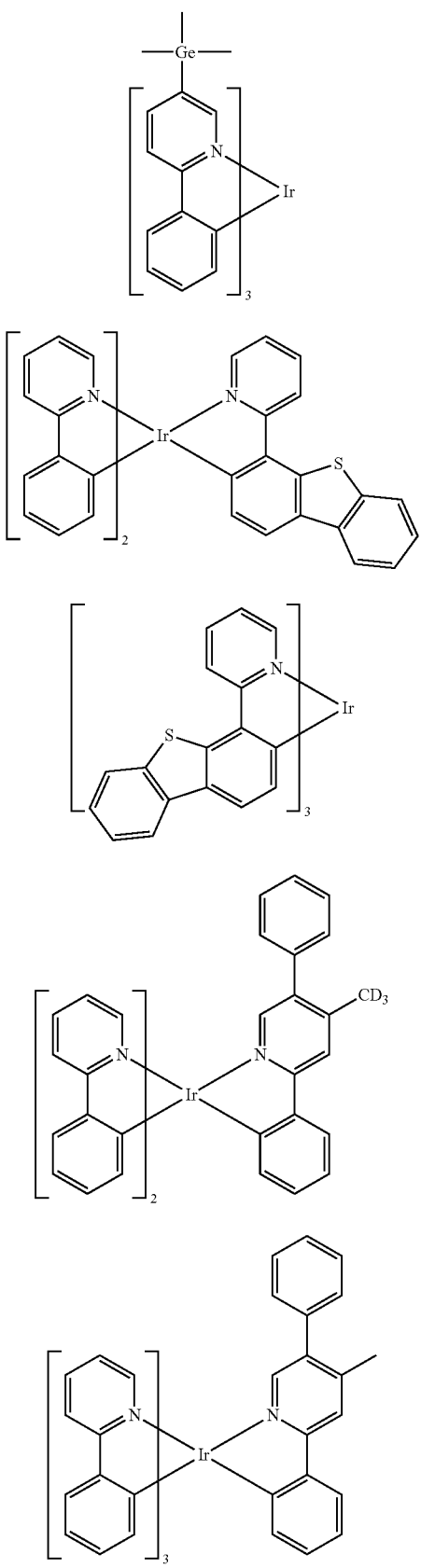

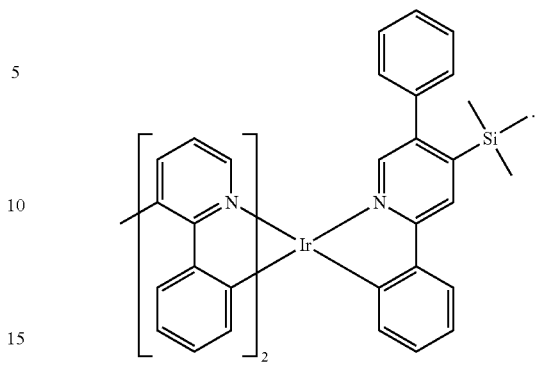

3. TADF Materials

Traditional organic fluorescent materials can only emit light using 25% singlet exciton formed by electric excitation, and the device has a relatively low internal quantum efficiency (up to 25%). Although the intersystem crossing is enhanced due to the strong spin-orbit coupling of the heavy atom center, phosphorescent materials can emit light by using the singlet exciton and triplet exciton formed by the electric excitation effectively, to achieve 100% internal quantum efficiency of the device. However, the use of the phosphorescent materials in OLEDs is limited by problems such as high cost, poor material stability and serious roll-off of the device efficiency. Thermally activated delayed fluorescence light-emitting materials are the third generation of organic light-emitting materials developed after the organic fluorescent materials and organic phosphorescent materials. This type of material generally has a small singlet-triplet energy level difference ($\Delta E_{st}$), and triplet excitons can be converted to singlet excitons by anti-intersystem crossing to emit light. This can make full use of the singlet excitons and triplet excitons formed under electric excitation. The device can achieve 100% internal quantum efficiency. Meanwhile, the materials are controllable in structure, stable in property, have low cost and no need for precious metals, and have a promising application prospect in the OLED field.

TADF materials need to have a smaller singlet-triplet energy level difference, further $\Delta Est<0.3$ eV, still further $\Delta Est<0.2$ eV, particularly $\Delta Est<0.1$ eV In one embodiment, TADF materials have a relatively small $\Delta Est$, and in another embodiment, TADF materials have a better fluorescence quantum efficiency. Some TADF-emitting materials can be found in the following patent documents: CN103483332(A), TW201309696(A), TW201309778(A), TW201343874(A), TW201350558(A), US20120217869(A1), WO2013133359 (A1), WO2013154064(A1), Adachi, et. al. *Adv. Mater.,* 21, 2009, 4802, Adachi, et. al. *Appl. Phys. Lett.,* 98, 2011, 083302, Adachi, et. al. *Appl. Phys. Lett.,* 101, 2012, 093306, Adachi, et. al. *Chem. Commun.,* 48, 2012, 11392, Adachi, et. al. *Nature Photonics,* 6, 2012, 253, Adachi, et. al. *Nature,* 492, 2012, 234, Adachi, et. al. *J. Am. Chem. Soc,* 134, 2012, 14706, Adachi, et. al. *Angew. Chem. Int. Ed,* 51, 2012, 11311, Adachi, et. al. *Chem. Commun.,* 48, 2012, 9580, Adachi, et. al. *Chem. Commun.,* 48, 2013, 10385, Adachi, et. al. *Adv. Mater.,* 25, 2013, 3319, Adachi, et. al. *Adv. Mater.,* 25, 2013, 3707, Adachi, et. al. *Chem. Mater.,* 25, 2013, 3038, Adachi, et. al. *Chem. Mater.,* 25, 2013, 3766, Adachi, et. al. *J. Mater. Chem. C.,* 1, 2013, 4599, Adachi, et. al. *J Phys. Chem. A.,* 117, 2013, 5607, the contents of the above-listed patents or article documents are hereby incorporated by reference in their entirety.

Some suitable examples of TADF light-emitting materials are listed in the table below:
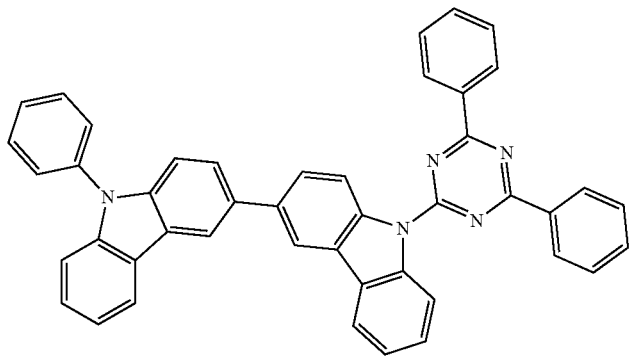 [SMILES: c1ccc(-c2nc(-c3ccccc3)nc(-n3c4ccccc4c4cc(-c5ccc6c(c5)c5ccccc5n6-c5ccccc5)ccc43)n2)cc1]
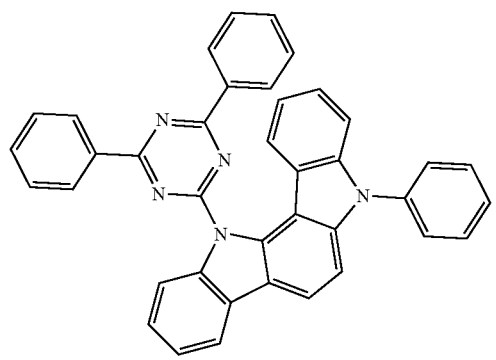 [SMILES: c1ccc(-c2nc(-c3ccccc3)nc(-n3c4ccccc4c4ccc5c(c6ccccc6n5-c5ccccc5)c43)n2)cc1]
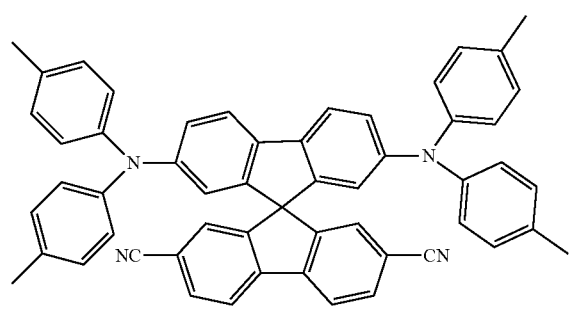
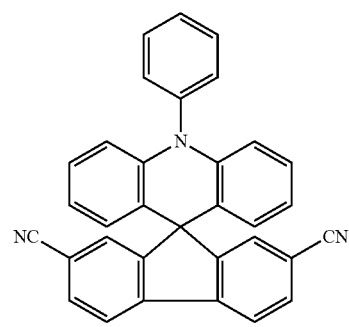 [SMILES: N#Cc1ccc2c(c1)C1(c3cc(C#N)ccc3-2)c2ccccc2N(c2ccccc2)c2ccccc21]

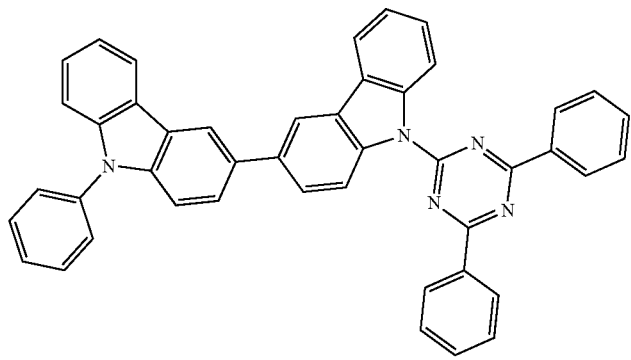 [SMILES: c1ccc(-c2nc(-c3ccccc3)nc(-n3c4ccccc4c4cc(-c5ccc6c(c5)c5ccccc5n6-c5ccccc5)ccc43)n2)cc1]
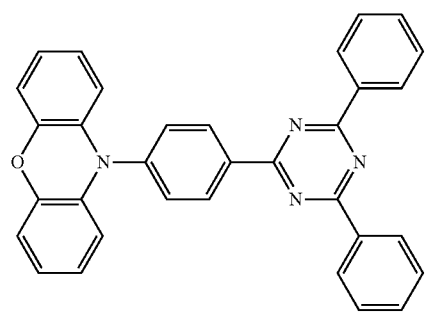 [SMILES: c1ccc(-c2nc(-c3ccccc3)nc(-c3ccc(N4c5ccccc5Oc5ccccc54)cc3)n2)cc1]
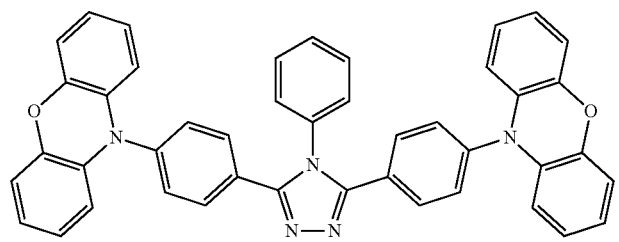 [SMILES: c1ccc(-n2c(-c3ccc(N4c5ccccc5Oc5ccccc54)cc3)nnc2-c2ccc(N3c4ccccc4Oc4ccccc43)cc2)cc1]
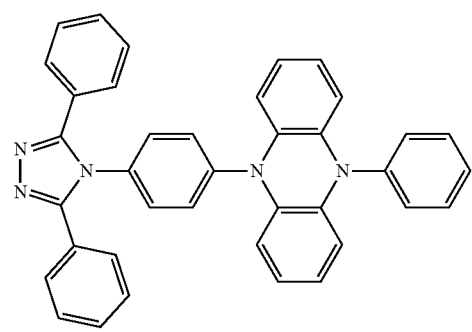 [SMILES: c1ccc(-c2nnc(-c3ccccc3)n2-c2ccc(N3c4ccccc4N(c4ccccc4)c4ccccc43)cc2)cc1]

-continued
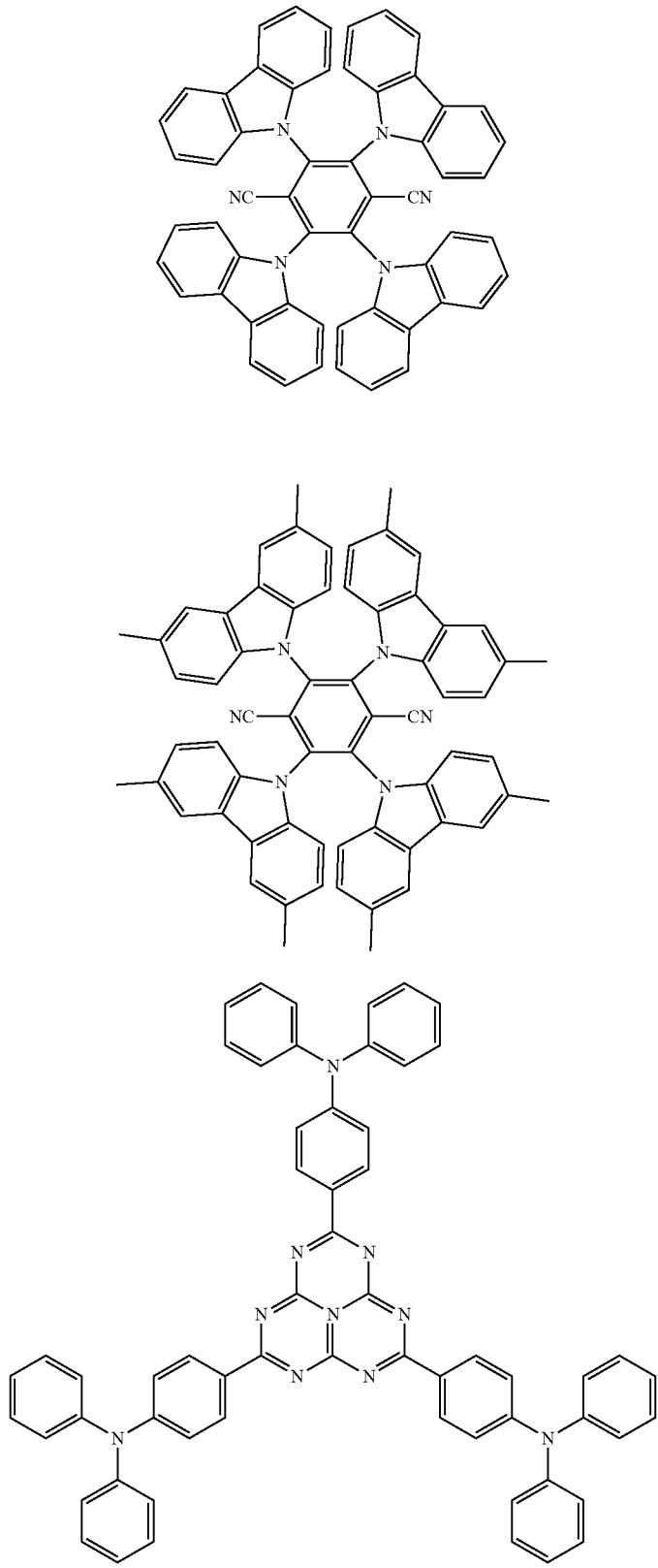

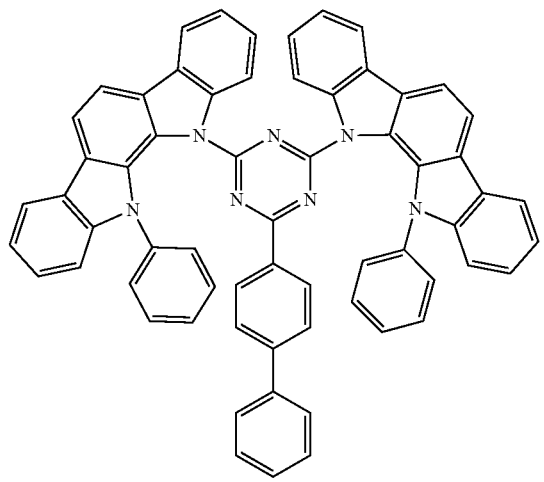 [SMILES: c1ccc(-c2ccc(-c3nc(-n4c5ccccc5c5ccc6c7ccccc7n(-c7ccccc7)c6c54)nc(-n4c5ccccc5c5ccc6c7ccccc7n(-c7ccccc7)c6c54)n3)cc2)cc1]
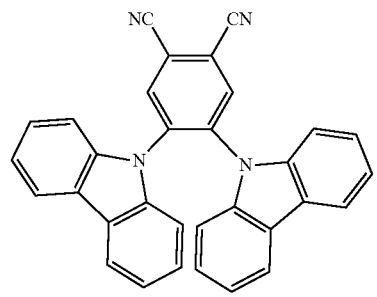 [SMILES: N#Cc1cc(-n2c3ccccc3c3ccccc32)c(-n2c3ccccc3c3ccccc32)cc1C#N]
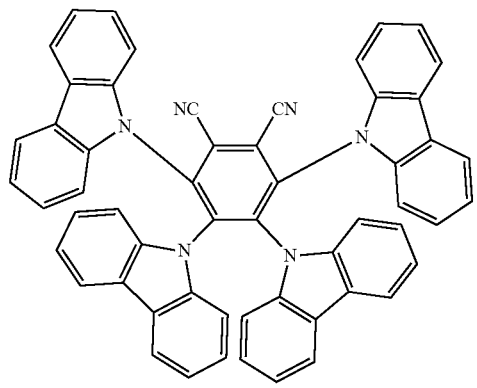 [SMILES: N#Cc1c(C#N)c(-n2c3ccccc3c3ccccc32)c(-n2c3ccccc3c3ccccc32)c(-n2c3ccccc3c3ccccc32)c1-n1c2ccccc2c2ccccc21]
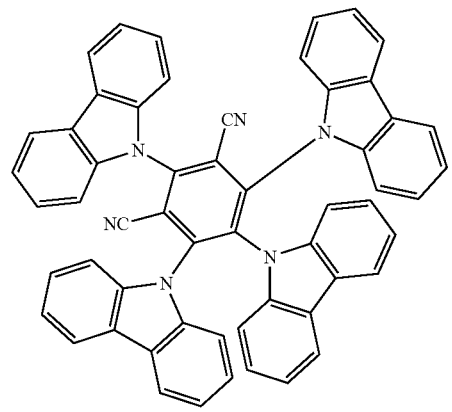 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]

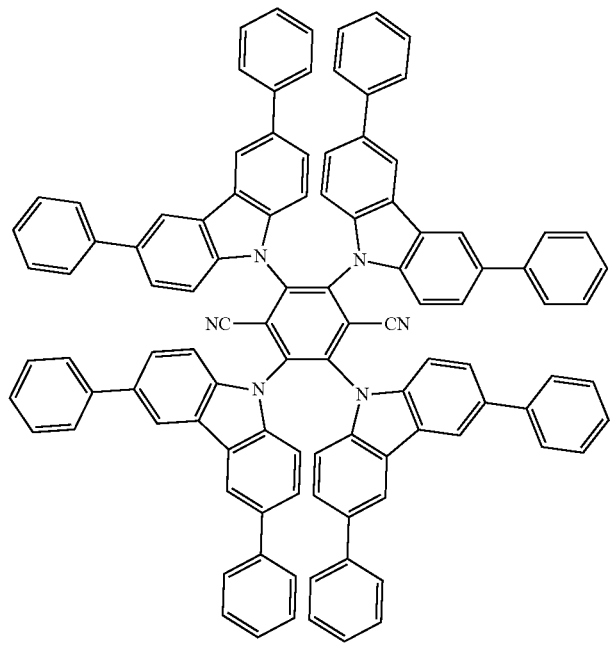 [SMILES: N#Cc1c(-n2c3ccc(-c4ccccc4)cc3c3cc(-c4ccccc4)ccc32)c(-n2c3ccc(-c4ccccc4)cc3c3cc(-c4ccccc4)ccc32)c(C#N)c(-n2c3ccc(-c4ccccc4)cc3c3cc(-c4ccccc4)ccc32)c1-n1c2ccc(-c3ccccc3)cc2c2cc(-c3ccccc3)ccc21]
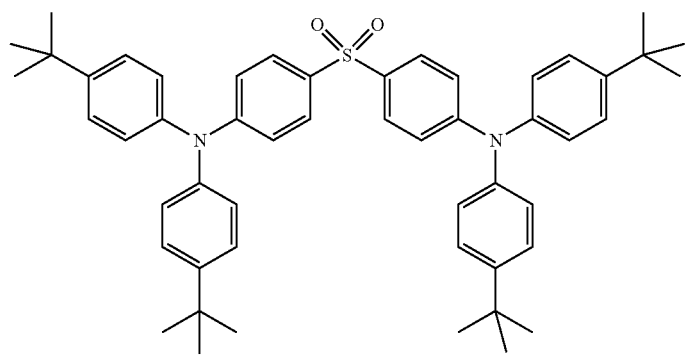 [SMILES: CC(C)(C)c1ccc(N(c2ccc(C(C)(C)C)cc2)c2ccc(S(=O)(=O)c3ccc(N(c4ccc(C(C)(C)C)cc4)c4ccc(C(C)(C)C)cc4)cc3)cc2)cc1]
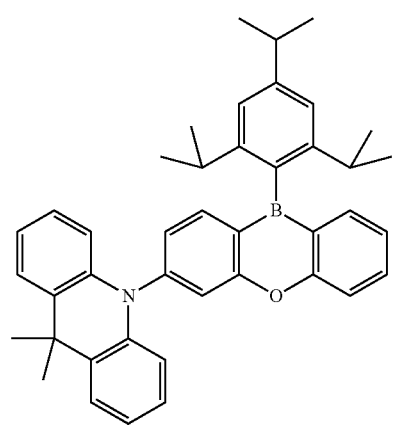 [SMILES: CC(C)c1cc(C(C)C)c(B2c3ccccc3Oc3cc(N4c5ccccc5C(C)(C)c5ccccc54)ccc32)c(C(C)C)c1]

-continued
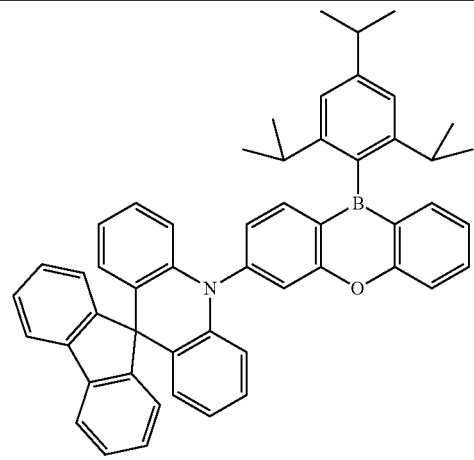
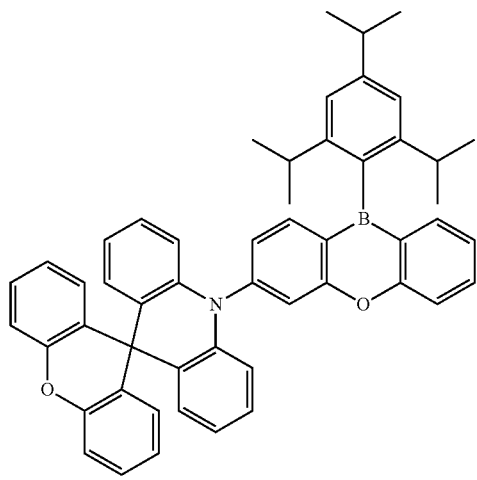 [SMILES: CC(C)c1cc(C(C)C)c(B2c3ccccc3Oc3cc(N4c5ccccc5C5(c6ccccc6Oc6ccccc65)c5ccccc54)ccc32)c(C(C)C)c1]
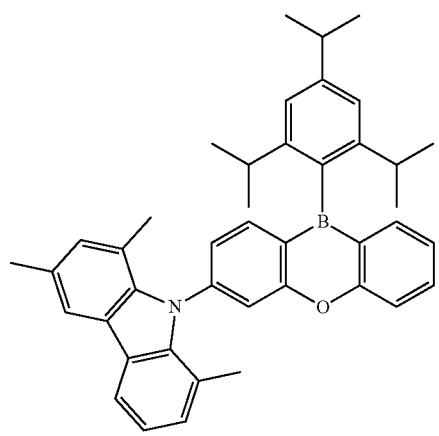 [SMILES: Cc1cc(C)c2c(c1)c1cccc(C)c1n2-c1ccc2c(c1)Oc1ccccc1B2c1c(C(C)C)cc(C(C)C)cc1C(C)C]
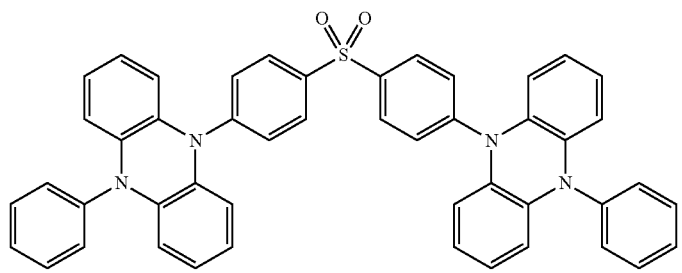 [SMILES: O=S(=O)(c1ccc(N2c3ccccc3N(c3ccccc3)c3ccccc32)cc1)c1ccc(N2c3ccccc3N(c3ccccc3)c3ccccc32)cc1]

-continued
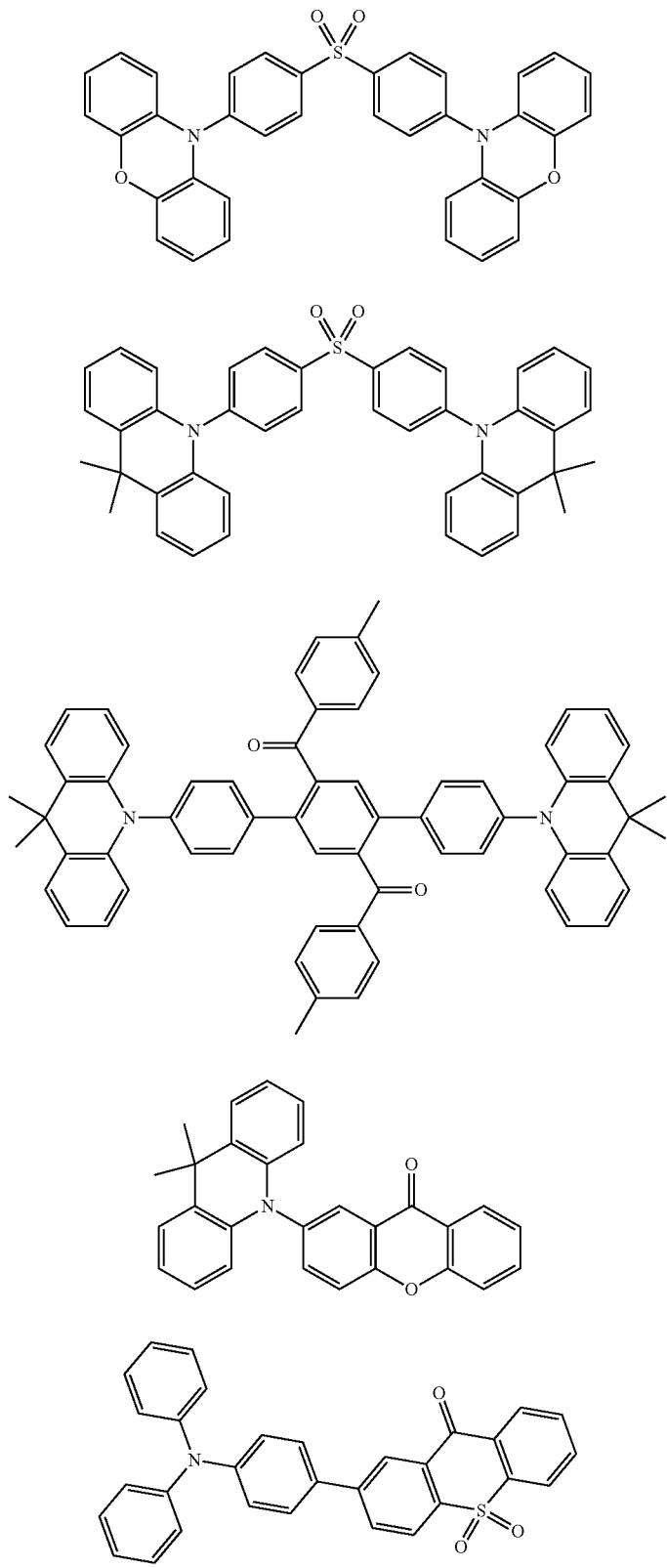

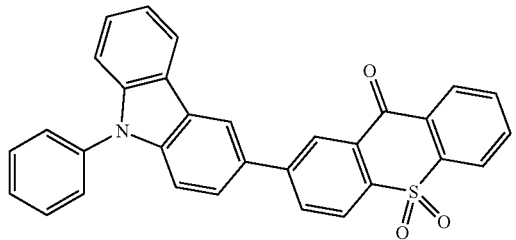 [SMILES: O=C1c2ccccc2S(=O)(=O)c2ccc(-c3ccc4c(c3)c3ccccc3n4-c3ccccc3)cc21]
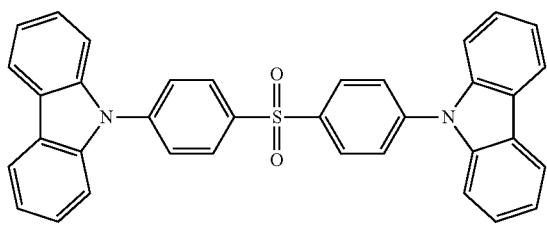 [SMILES: O=S(=O)(c1ccc(-n2c3ccccc3c3ccccc32)cc1)c1ccc(-n2c3ccccc3c3ccccc32)cc1]
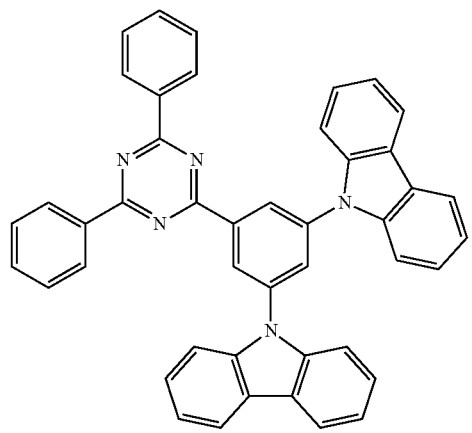 [SMILES: c1ccc(-c2nc(-c3ccccc3)nc(-c3cc(-n4c5ccccc5c5ccccc54)cc(-n4c5ccccc5c5ccccc54)c3)n2)cc1]
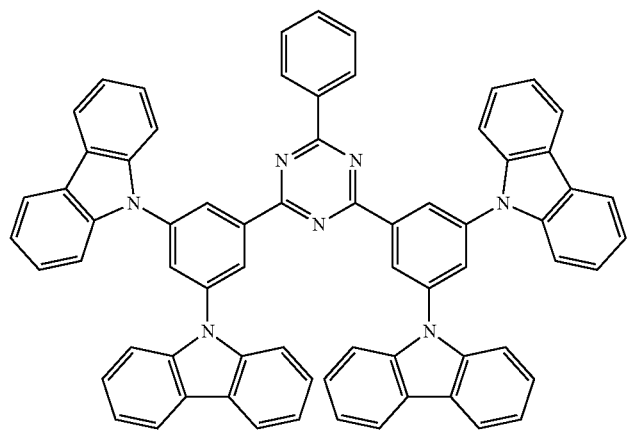 [SMILES: c1ccc(-c2nc(-c3cc(-n4c5ccccc5c5ccccc54)cc(-n4c5ccccc5c5ccccc54)c3)nc(-c3cc(-n4c5ccccc5c5ccccc54)cc(-n4c5ccccc5c5ccccc54)c3)n2)cc1]

-continued
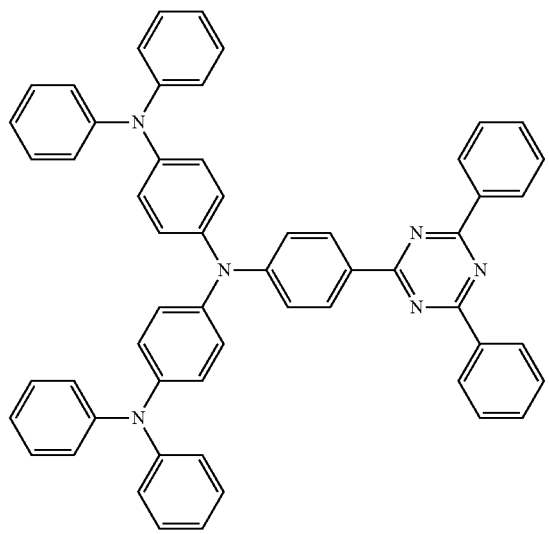 [SMILES: c1ccc(-c2nc(-c3ccccc3)nc(-c3ccc(N(c4ccc(N(c5ccccc5)c5ccccc5)cc4)c4ccc(N(c5ccccc5)c5ccccc5)cc4)cc3)n2)cc1]
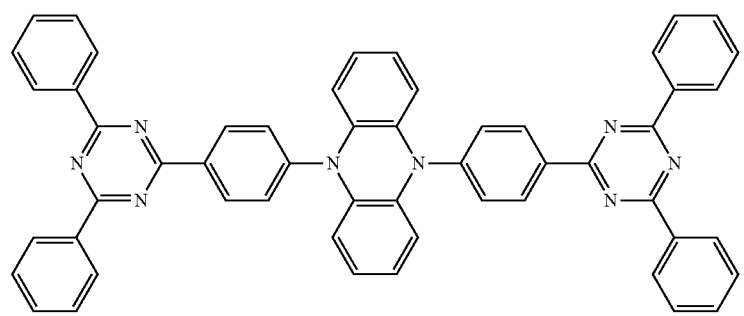 [SMILES: c1ccc(-c2nc(-c3ccccc3)nc(-c3ccc(N4c5ccccc5N(c5ccc(-c6nc(-c7ccccc7)nc(-c7ccccc7)n6)cc5)c5ccccc54)cc3)n2)cc1]
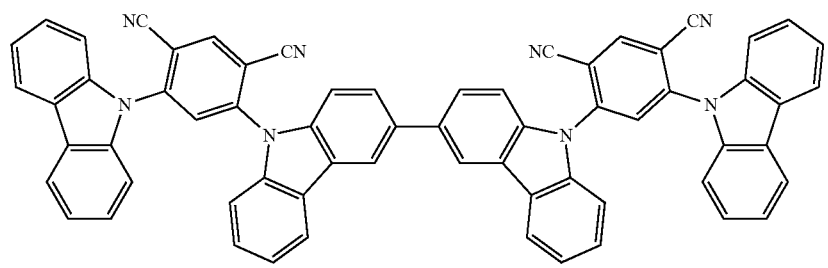 [SMILES: N#Cc1cc(C#N)c(-n2c3ccccc3c3cc(-c4ccc5c(c4)c4ccccc4n5-c4cc(-n5c6ccccc6c6ccccc65)c(C#N)cc4C#N)ccc32)cc1-n1c2ccccc2c2ccccc21]
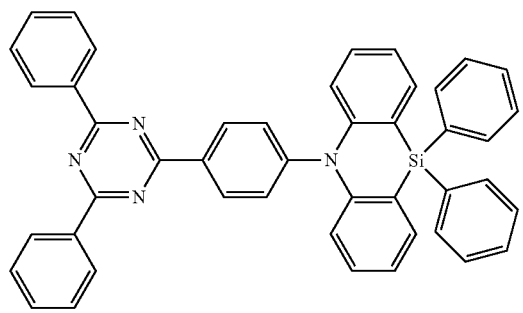 [SMILES: c1ccc(-c2nc(-c3ccccc3)nc(-c3ccc(N4c5ccccc5[Si](c5ccccc5)(c5ccccc5)c5ccccc54)cc3)n2)cc1]

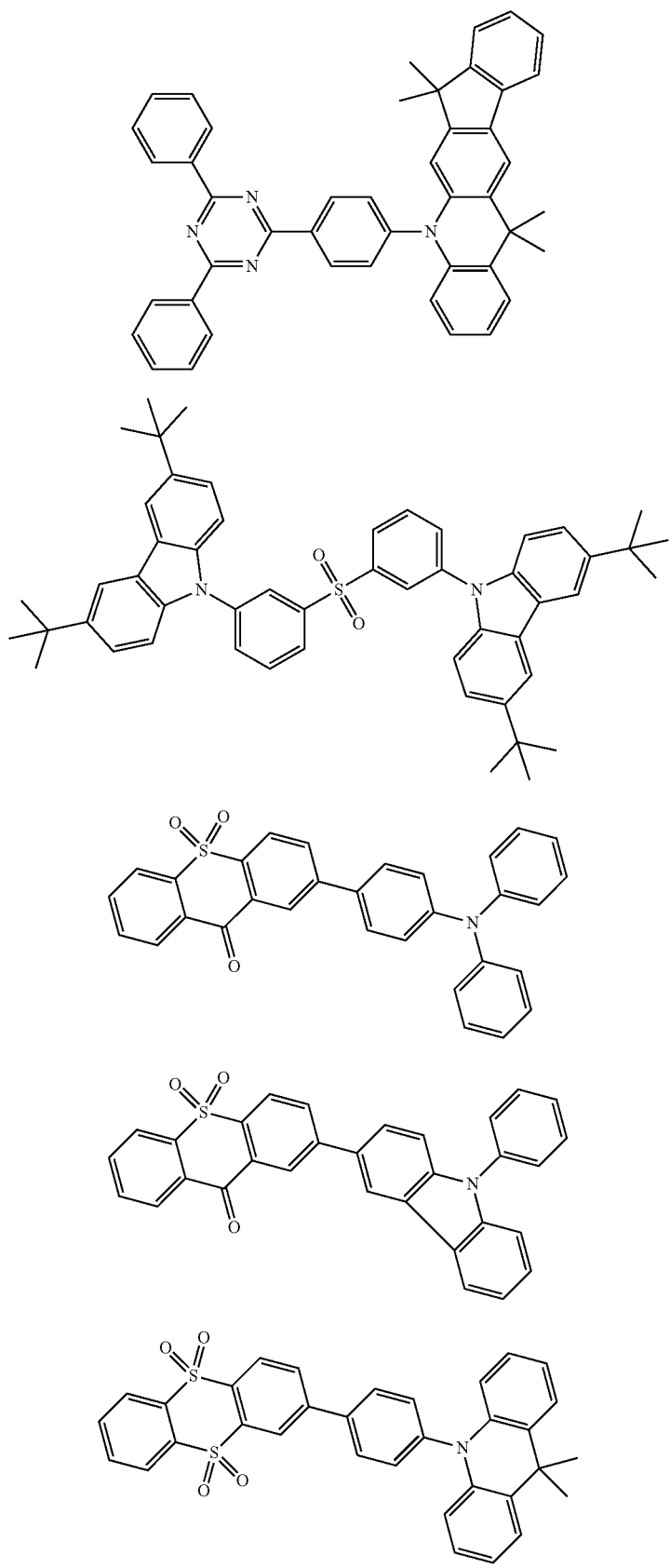

-continued
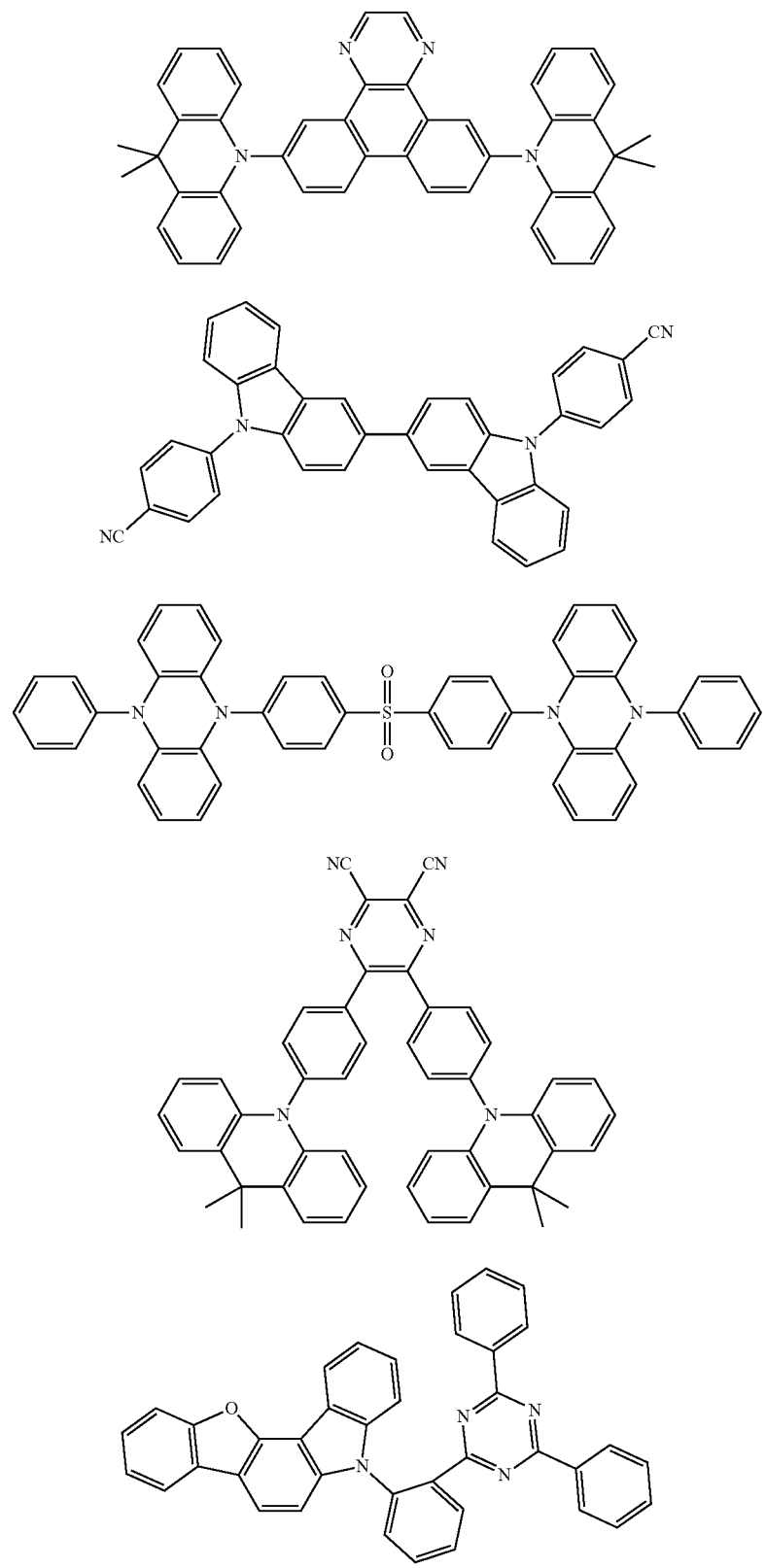

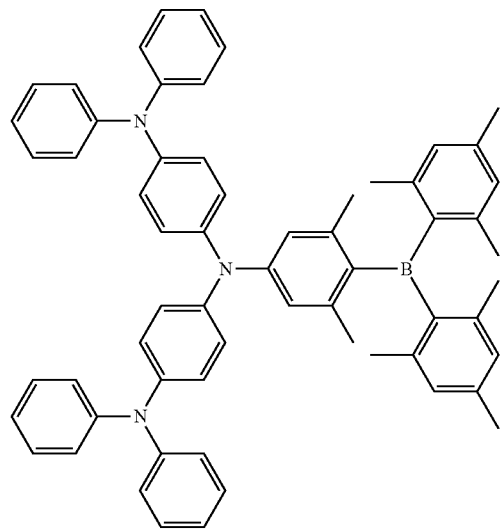 [SMILES: Cc1cc(C)c(B(c2c(C)cc(C)cc2C)c2c(C)cc(N(c3ccc(N(c4ccccc4)c4ccccc4)cc3)c3ccc(N(c4ccccc4)c4ccccc4)cc3)cc2C)c(C)c1]
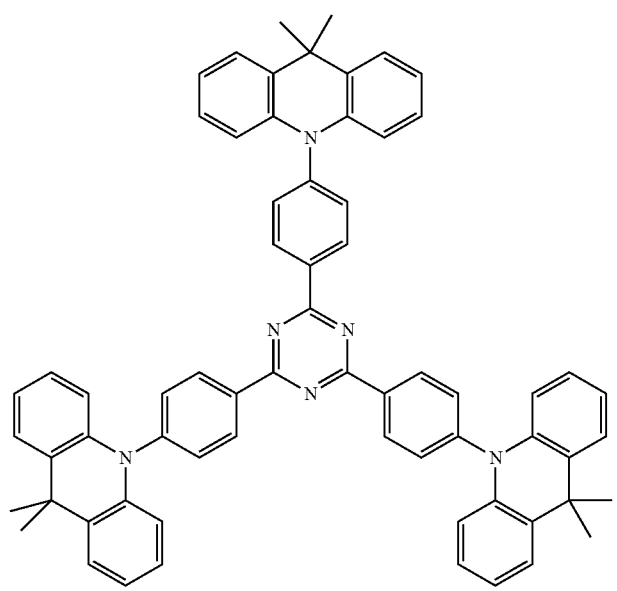

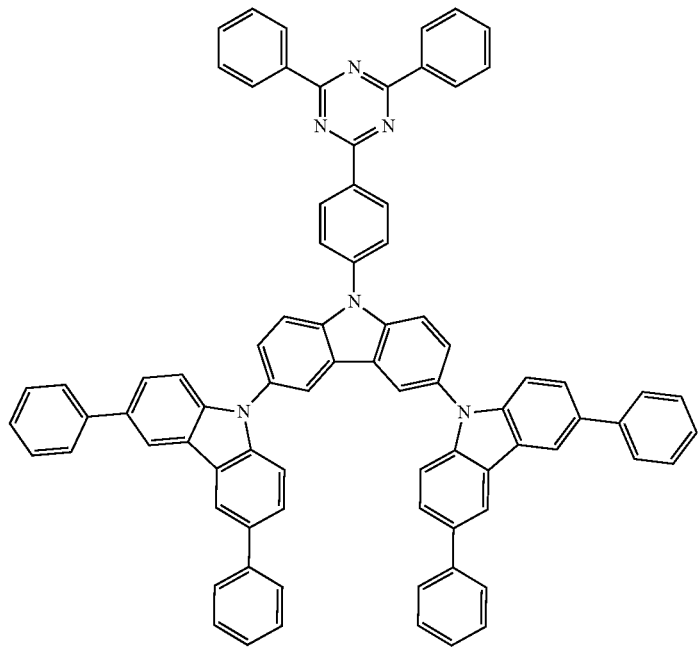 [SMILES: c1ccc(-c2ccc3c(c2)c2cc(-c4ccccc4)ccc2n3-c2ccc3c(c2)c2cc(-n4c5ccc(-c6ccccc6)cc5c5cc(-c6ccccc6)ccc54)ccc2n3-c2ccc(-c3nc(-c4ccccc4)nc(-c4ccccc4)n3)cc2)cc1]
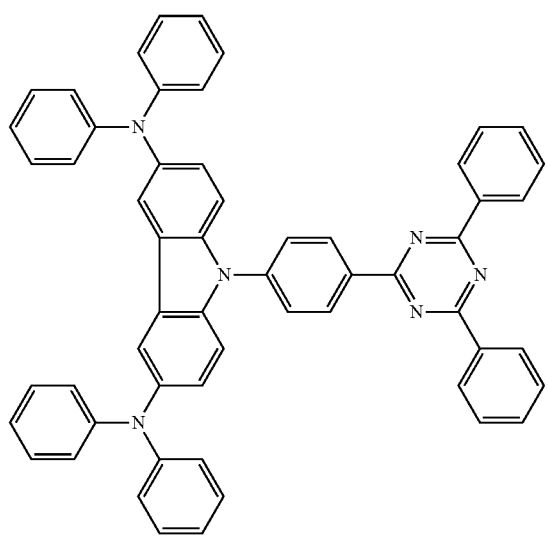 [SMILES: c1ccc(-c2nc(-c3ccccc3)nc(-c3ccc(-n4c5ccc(N(c6ccccc6)c6ccccc6)cc5c5cc(N(c6ccccc6)c6ccccc6)ccc54)cc3)n2)cc1]
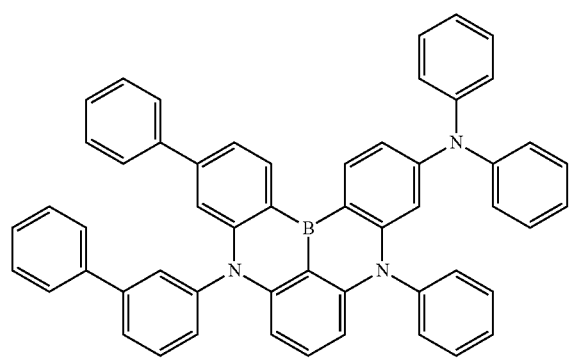 [SMILES: c1ccc(-c2cccc(N3c4cc(-c5ccccc5)ccc4B4c5ccc(N(c6ccccc6)c6ccccc6)cc5N(c5ccccc5)c5cccc3c54)c2)cc1]

-continued
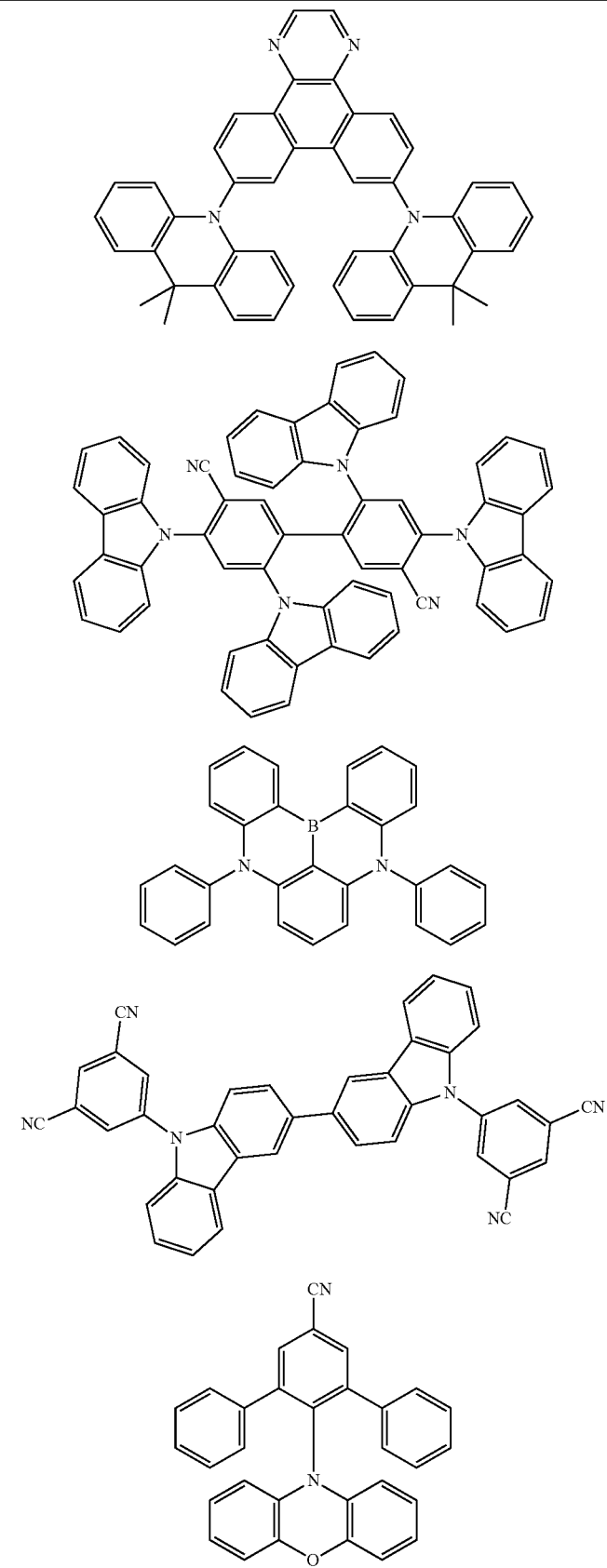

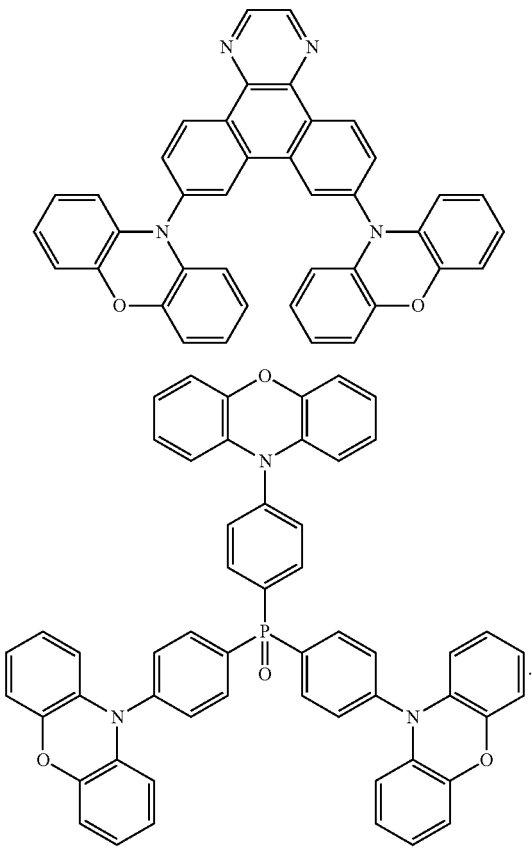

The present disclosure further relates to a formulation or an ink comprising the organic mixture as described above, and at least one organic solvent.

The viscosity and surface tension of inks are important parameters for printing process. Suitable surface tension parameters of ink are suitable for a particular substrate and a particular printing method.

In one embodiment, the surface tension of the ink at working temperature or at 25° C. is in the range of approximately 19 dyne/cm to 50 dyne/cm. In another embodiment, the surface tension of the ink at working temperature or at 25° C. is in the range of 22 dyne/cm to 35 dyne/cm. In another embodiment, the surface tension of the ink at working temperature or at 25° C. is in the range of 25 dyne/cm to 33 dyne/cm.

In one embodiment, the viscosity of the ink at working temperature or at 25° C. is in the range of approximately 1 cps to 100 cps. In another embodiment, the viscosity of the ink at working temperature or at 25° C. is in the range of 1 cps to 50 cps. In another embodiment, the viscosity of the ink at working temperature or at 25° C. is in the range of 1.5 cps to 20 cps. In another embodiment, the viscosity of the ink at working temperature or at 25° C. is in the range of about 4.0 cps to 20 cps. The formulation so formulated will be suitable for inkjet printing.

The viscosity can be adjusted by different methods, such as by selecting appropriate solvents and the concentration of functional materials in the ink. The ink according to the present disclosure comprising the mixture can facilitate the adjustment of the printing ink in an appropriate range according to the used printing method. In general, the weight ratio of the functional material contained in the formulation according to the present disclosure is in the range of 0.3 wt % to 30 wt %. In one embodiment, the weight ratio of the functional material contained in the formulation according to the present disclosure is in the range of 0.5 wt % to 20 wt %. In another embodiment, the weight ratio of the functional material contained in the formulation according to the present disclosure is in the range of 0.5 wt % to 15 wt %. In another embodiment, the weight ratio of the functional material contained in the formulation according to the present disclosure is in the range of 0.5 wt % to 10 wt %. In another embodiment, the weight ratio of the functional material contained in the formulation according to the present disclosure is in the range of 1 wt % to 5 wt %.

In some embodiments, according to the ink of the present disclosure, the at least one organic solvent is selected from solvents based on aromatics or heteroaromatics, particularly aliphatic chain/ring substituted aromatic solvents, or aromatic ketone solvents, or aromatic ether solvents.

Examples suitable for solvents of the present disclosure include, but are not limited to, the solvents based on aromatics or heteroaromatics: p-diisopropylbenzene, pentylbenzene, tetrahydronaphthalene, cyclohexyl benzene, chloronaphthalene, 1,4-dimethylnaphthalene, 3-isopropylbiphenyl, p-cymene, dipentylbenzene, tripentylbenzene, pentyltoluene, o-xylene, m-xylene, p-xylene, o-diethylbenzene, m-diethylbenzene, p-diethylbenzene, 1,2,3,4-tetramethylbenzene, 1,2,3,5-tetramethylbenzene, 1,2,4,5-tetramethylbenzene, butylbenzene, dodecylbenzene, dihexylbenzene, dibutylbenzene, p-diisopropylbenzene, 1-methoxynaphthalene, cyclohexylbenzene, dimethylnaphthalene, 3-isopropylbiphenyl, p-cymene, 1-methylnaphthalene, 1,2,4-trichlorobenzene, 1,3-dipropoxybenzene, 4,4-difluorodiphenylmethane, 1,2-dimethoxy-4-(1-propenyl) benzene, diphenylmethane, 2-phenylpyridine, 3-phenylpyridine, N-methyldiphenylamine, 4-isopropylbiphenyl, α,α-dichlorodiphenylmethane, 4-(3-phenylpropyl) pyridine, benzylbenzoate, 1,1-di(3,4-dimethylphenyl)ethane, 2-isopropylnaphthalene, dibenzylether, and the like; solvents based on ketones: 1-tetralone, 2-tetralone, 2-(phenylepoxy)tetralone, 6-(methoxyl)tetralone, acetophenone, phenylacetone, benzophenone, and derivatives thereof, such as 4-methylacetophenone, 3-methylacetophenone, 2-methylacetophenone, 4-methylphenylacetone, 3-methylphenylacetone, 2-methylphenylacetone, isophorone, 2,6,8-trimethyl-4-nonanone, fenchone, 2-nonanone, 3-nonanone, 5-nonanone, 2-decanone, 2,5-hexanedione, phorone, di-n-amyl ketone; aromatic ether solvents: 3-phenoxytoluene, butoxybenzene, benzylbutylbenzene, p-anisaldehyde dimethyl acetal, tetrahydro-2-phenoxy-2H-pyran, 1,2-dimethoxy-4-(1-propenyl)benzene, 1,4-benzodioxane, 1,3-dipropylbenzene, 2,5-dimethoxytoluene, 4-ethylphenetole, 1,2,4-trimethoxybenzene, 4-(1-propenyl)-1,2-dimethoxybenzene, 1,3-dimethoxybenzene, glycidyl phenyl ether, dibenzyl ether, 4-tert-butylanisole, trans-p-propenylanisole, 1,2-dimethoxybenzene, 1-methoxynaphthalene, diphenyl ether, 2-phenoxymethyl ether, 2-phenoxytetrahydrofuran, ethyl-2-naphthyl ether, amyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether, tetraethylene glycol dimethyl ether; and ester solvents: alkyl octoate, alkyl sebacate, alkyl stearate, alkyl benzoate, alkyl phenylacetate, alkyl cinnamate, alkyl oxalate, alkyl maleate, alkyl lactone, alkyl oleate, and the like.

Further, according to the ink of the present disclosure, the at least one solvent may be selected from the group consisting of: aliphatic ketones, such as 2-nonanone, 3-nonanone, 5-nonanone, 2-decanone, 2,5-hexanedione, 2,6,8-trimethyl-4-nonanone, phorone, di-n-amyl ketone, and the like; and aliphatic ethers, such as amyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether, tetraethylene glycol dimethyl ether, and the like.

In other embodiments, the printing ink further comprises another organic solvent. Examples of another organic solvent comprise, but are not limited to: methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methyl ethyl ketone, 1,2-dichloroethane, 3-phenoxy toluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, decalin, indene, and/or mixtures thereof.

In one embodiment, the formulation according to the present disclosure is a solution.

In another embodiment, the formulation according to the present disclosure is a suspension.

The formulation in the embodiments of the present disclosure may comprise 0.01 wt % to 20 wt % (in a further embodiment, 0.1 wt % to 15 wt %; in a still further embodiment, 0.2 wt % to 10 wt %; and in a particular embodiment, 0.25 wt % to 5 wt %) of the organic mixture according to the disclosure.

The present disclosure further relates to the use of the formulation as a coating or printing ink in the preparation of organic electronic devices, especially by the preparation method of printing or coating.

The appropriate printing technology or coating technology includes, but is not limited to, inkjet printing, nozzle printing, typography, screen printing, dip coating, spin coating, blade coating, roller printing, twist roller printing, lithography, flexography, rotary printing, spray coating, brush coating or transfer printing, slot die coating, and the like. The first preference is gravure printing, nozzle printing and inkjet printing. The solution or the suspension may additionally comprise one or more components, such as a surface-active compound, a lubricant, a wetting agent, a dispersant, a hydrophobic agent, a binder, etc., for adjusting viscosity and film-forming property, and enhancing adhesion property, and the like. For more information about printing technologies and relevant requirements thereof on related solutions, such as solvents and concentration, viscosity, etc., see Handbook of Print Media: Technologies and Production Methods, ISBN 3-540-67326-1, edited by Helmut Kipphan.

Based on the above organic mixture, the present disclosure also provides an application of the above organic mixture, that is, applying the organic mixture in organic electronic devices. The organic electronic devices may be selected from the group consisting of, but not limited to, organic light-emitting diode (OLED), organic photovoltaic cell (OPV), organic light-emitting electrochemical cell (OLEEC), organic field effect transistor (OFET), organic light-emitting field effect transistor, organic laser, organic spintronic device, organic sensor, and organic plasmon emitting diode, and the like, specially OLED. In the embodiments of the present disclosure, the organic mixture materials are especially used in the light-emitting layers of OLED devices.

The present disclosure further provides an organic electronic device comprising at least one mixture as described above.

In some embodiments, the organic electronic device is an organic light-emitting diode (OLED), an organic photovoltaic cell (OPV), an organic light-emitting electrochemical cell (OLEEC), an organic field effect transistor (OFET), an organic light-emitting field effect transistor, an organic sensor or an organic plasmon emitting diode.

In some further embodiments, the organic electronic device is an electroluminescent device, wherein comprising a substrate, an anode, at least one light-emitting layer, a cathode, optionally may also comprise a hole transport layer or a electron transport layer. In certain embodiments, the hole transport layer comprises a compound or a polymer according to the present disclosure. In one embodiment, the light-emitting layer comprises a mixture according to the present disclosure, In another embodiment, the light-emitting layer comprises a mixture according to the present disclosure and at least one light-emitting material which may be especially selected from fluorescent emitter, phosphorescent emitter, TADF material or light-emitting quantum dot.

The device structure of the electroluminescent device is described below, but it is not limited thereto.

The substrate may be opaque or transparent. A transparent substrate may be used to fabricate a transparent lightemitting device. See, for example, Bulovic et al. Nature 1996, 380, p 29 and Gu et al. Appl. Phys. Lett. 1996, 68, p 2606. The substrate may be rigid or elastic. The substrate may be plastic, metal, semiconductor wafer or glass. Particularly, the substrate has a smooth surface. The substrate without surface defect is a particular desirable choice. In one embodiment, the substrate is flexible and may be selected from a polymer thin film or plastic which has a glass transition temperature $T_g$ greater than 150° C., greater than 200° C. in another embodiment, greater than 250° C. in further embodiment, greater than 300° C. in a particular embodiment. Suitable examples of the flexible substrate are polyethylene terephthalate (PET) and polyethylene 2,6-naphthalate (PEN).

The anode may include a conductive metal or a metallic oxide, or a conductive polymer. The anode can inject holes easily into the hole injection layer (HIL), or the hole transport layer (HTL), or the light-emitting layer. In one embodiment, the absolute value of the difference between the work function of the anode and the HOMO energy level or the valence band energy level of the emitter in the light-emitting layer or of the p-type semiconductor material as the HIL or HTL or the electron blocking layer (EBL) is less than 0.5 eV, further less than 0.3 eV, particularly less than 0.2 eV. Examples of the anode materials comprise, but are not limited to, Al, Cu, Au, Ag, Mg, Fe, Co, Ni, Mn, Pd, Pt, ITO, aluminum-doped zinc oxide (AZO), and the like. Other suitable anode materials are known and may be easily selected by one of ordinary skilled in the art. The anode material may be deposited by any suitable technologies, such as a suitable physical vapor deposition method, which includes radio frequency magnetron sputtering, vacuum thermal evaporation, e-beam, and the like. In some embodiments, the anode is patterned and structured. Patterned ITO conductive substrates are commercially available and can be used to prepare the device according to the present disclosure.

The cathode may comprise a conductive metal or a metallic oxide. The cathode can inject electrons easily into the EIL or ETL, or directly into the light-emitting layer. In one embodiment, the absolute value of the difference between the work function of the cathode and the LUMO energy level or the valence band energy level of the emitter in the light-emitting layer or of the n-type semiconductor material as the electron injection layer (EIL) or the electron transport layer (ETL) or the hole blocking layer (HBL) is less than 0.5 eV, further less than 0.3 eV, particularly less than 0.2 eV. In principle, all materials that can be used as the cathode of the OLED may be used as the cathode materials of the devices of the present disclosure. Examples of the cathode materials include, but are not limited to: Al, Au, Ag, Ca, Ba, Mg, LiF/Al, MgAg alloy, BaF$_2$/Al, Cu, Fe, Co, Ni, Mn, Pd, Pt, ITO, and the like. The cathode material may be deposited by any suitable technologies, such as a suitable physical vapor deposition method, which includes radio frequency magnetron sputtering, vacuum thermal evaporation, e-beam, and the like.

The OLED may also comprise other functional layers such as hole injection layer (HIL), hole transport layer (HTL), electron blocking layer (EBL), electron injection layer (EIL), electron transport layer (ETL), and hole blocking layer (HBL). Materials suitable for use in such functional layers have been described in detail above and in WO2010135519A1, US20090134784A1 and WO2011110277A1, the entire contents of which are hereby incorporated herein by reference.

In one embodiment, in the light-emitting device according to the present disclosure, the light-emitting layer thereof comprises the mixture materials of the present disclosure.

In another embodiment, the light-emitting layer of the electroluminescent device may be prepared by one of the following methods:

(1) vacuum evaporating a source being the mixture comprising the organic compound H1 and the organic compound H2 to deposit the light-emitting layer;

(2) vacuum evaporating two separate sources being the organic compound H1 and the organic compound H2 respectively, to deposit the light-emitting layer; and;

(3) solution processing a raw material being the above-mentioned formulation to deposit the light-emitting layer.

The light-emitting wavelength of the light-emitting device according to the present disclosure is between 300 nm and 1000 nm. In a further embodiment, the light-emitting wavelength of the light-emitting device according to the present disclosure is between 350 nm and 900 nm. In a particular embodiment, the light-emitting wavelength of the light-emitting device according to the present disclosure is between 400 nm and 800 nm.

The present disclosure also relates to the application of the electroluminescent device according to the present disclosure in various electronic equipments, which includes, but are not limited to, display equipment, lighting equipment, light source, and sensor, and the like.

The present disclosure will be described below with reference to the preferred embodiments, but the present disclosure is not limited to the following embodiments. It should be understood that the appended claims summarized the scope of the present disclosure. Those skilled in the art should realize that certain changes to the embodiments of the present disclosure that are made under the guidance of the concept of the present disclosure will be covered by the spirit and scope of the claims of the present disclosure.

1. Detailed Examples (1) Synthesis of Compound (1-18):

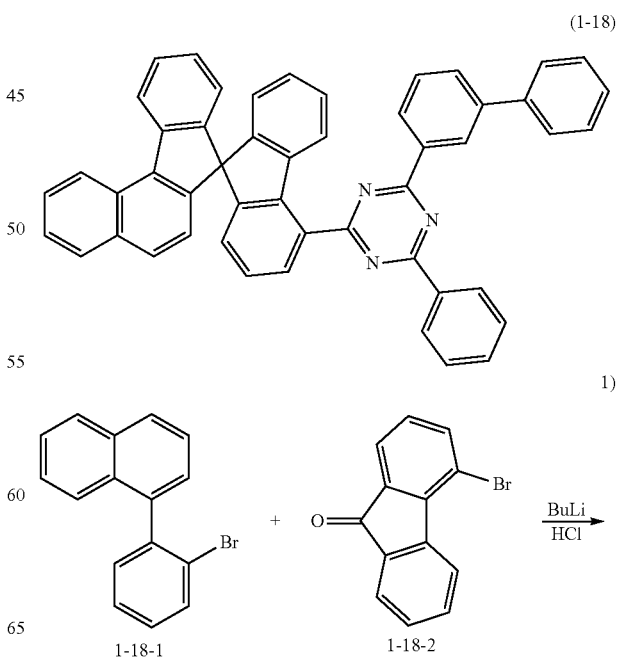

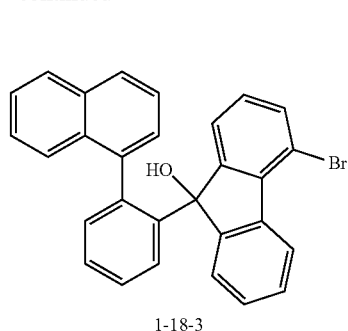

1-18-3

Compound 1-18-1 (28.3 g, 100 mmol) and 400 mL of anhydrous tetrahydrofuran were added to a 1000 mL three-necked flask under nitrogen atmosphere, cooled to −78° C., and 100 mmol of n-butyllithium was slowly added dropwise, the solution was reacted for 2 hours, then compound 1-18-2 (25.9 g, 100 mmol) was added one time, and the reaction temperature was raised to room temperature naturally. The reaction was further performed for 12 hours, then dilute hydrochloric acid was added one time to the reaction solution, and then the reaction was further performed for 0.5 hour. The reaction solution was rotary evaporated to remove most of the solvent, and then extracted with dichloromethane and washed with water for 3 times. The organic phase was collected, rotary evaporated dried, and then directly used as a raw material for the next reaction without further purification.

2)

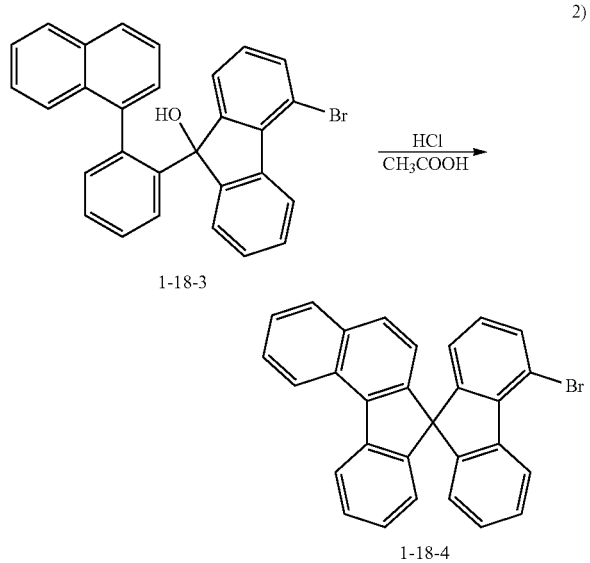

The reaction product 1-18-3 of the previous step, acetic acid (60 mL) and hydrochloric acid (10 mL) were added to a 250 mL three-necked flask, and the solution was heated to 110° C. and reacted under stirring for 4 hours, and then the reaction was ended. The reaction solution was poured into 500 mL of pure water, stirred and precipitated, and then filtered with suction. The filter residue was washed with water and ethanol successively, then collected and recrystallized, with a two-step yield of 65%.

3)

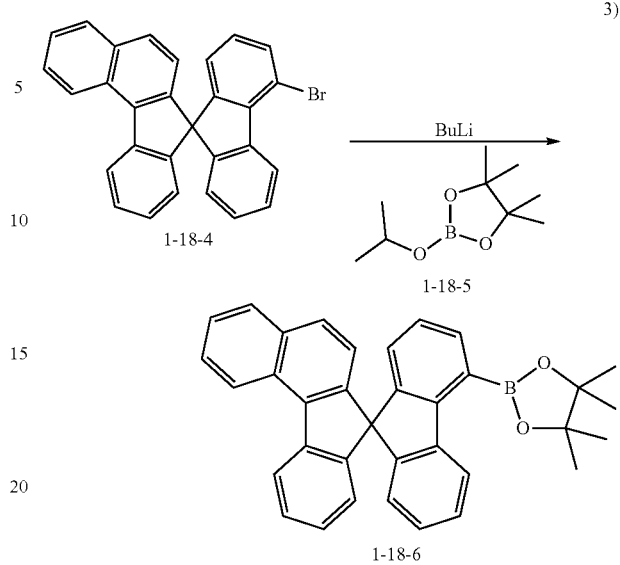

Compound 1-18-4 (22.3 g, 50 mmol) and 200 mL of anhydrous tetrahydrofuran were added to a 500 mL three-necked flask under nitrogen atmosphere, cooled to −78° C., and 50 mmol of n-butyllithium was slowly added dropwise, the solution was reacted for 2 hours, then compound 1-18-5 (9.3 g, 50 mmol) was added one time, and the reaction temperature was raised to room temperature naturally. The reaction was further performed for 12 hours, then the reaction solution was rotary evaporated to remove most of the solvent, and then extracted with dichloromethane and washed with water for 3 times. The organic phase was collected, rotary evaporated dried, and then purified by recrystallization, with a yield of 80%.

4)

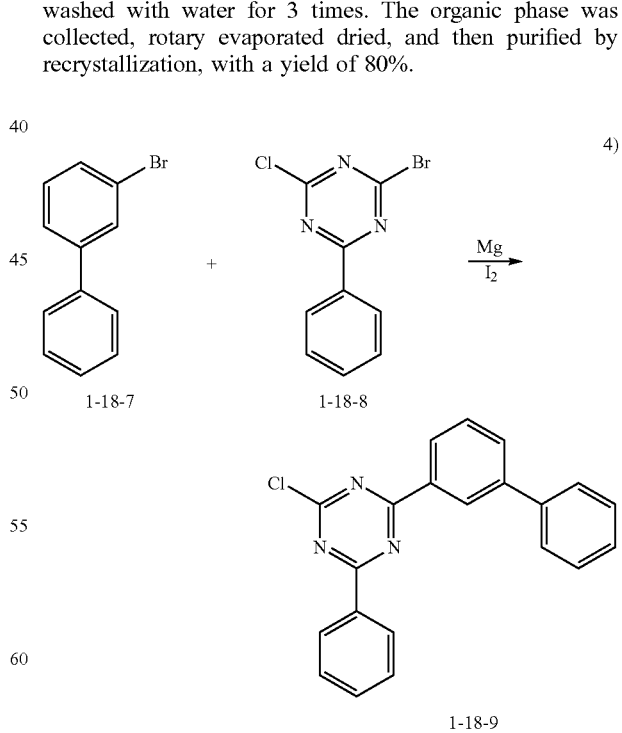

Compound 1-18-7 (2.33 g, 10 mmol), magnesium turnings (2.4 g, 100 mmol), 0.1 g of iodine, and 15 mL of anhydrous tetrahydrofuran were added to a 250 mL three-necked flask under nitrogen atmosphere, heated to 60° C., then the grignard reaction was initiated, and then a solution of 90 mmol of compound 1-18-7 in 100 mL of anhydrous tetrahydrofuran was slowly added dropwise. The solution was reacted for 2 hours at room temperature, then transferred to a 500 mL three-necked bottle containing compound 1-18-8 (22.6 g, 100 mmol) and 100 mL of anhydrous tetrahydrofuran solution. The reaction was further performed for 4 hours and then quenched by addition of pure water. The reaction solution was rotary evaporated to remove most of the solvent, and then extracted with dichloromethane and washed with water for 3 times. The organic phase was collected, rotary evaporated dried, and then recrystallized, with a yield of 80%.

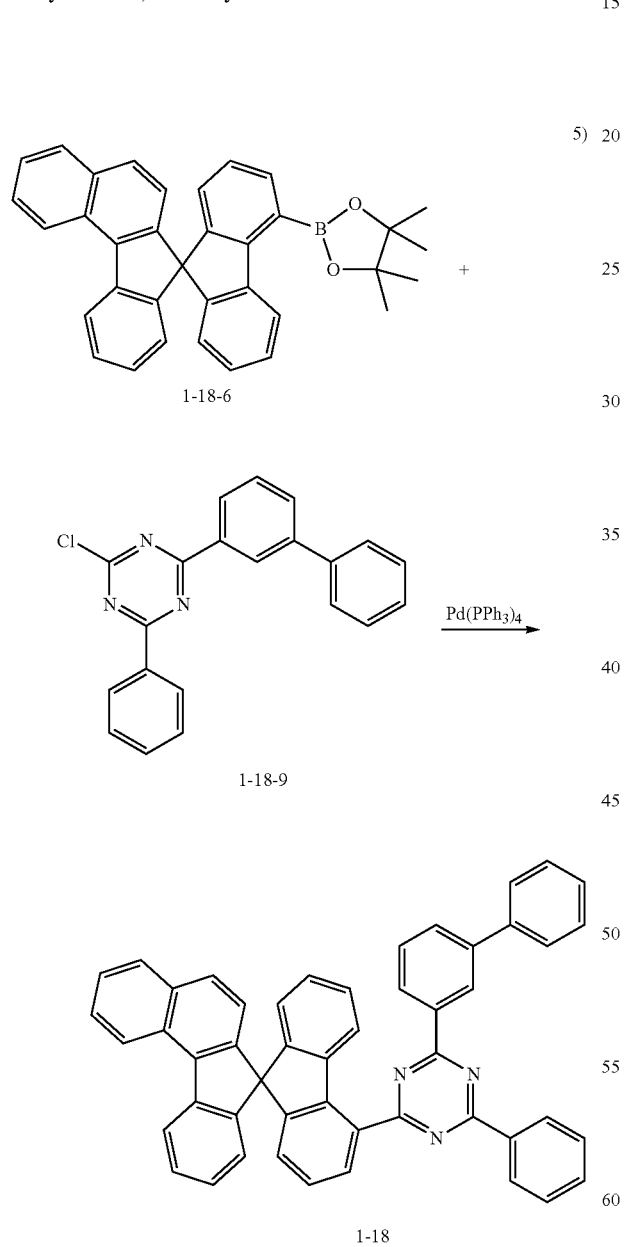

(10 mL), and toluene (80 mL) were added to a 250 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 70%.

(2) Synthesis of Compound (1-23):

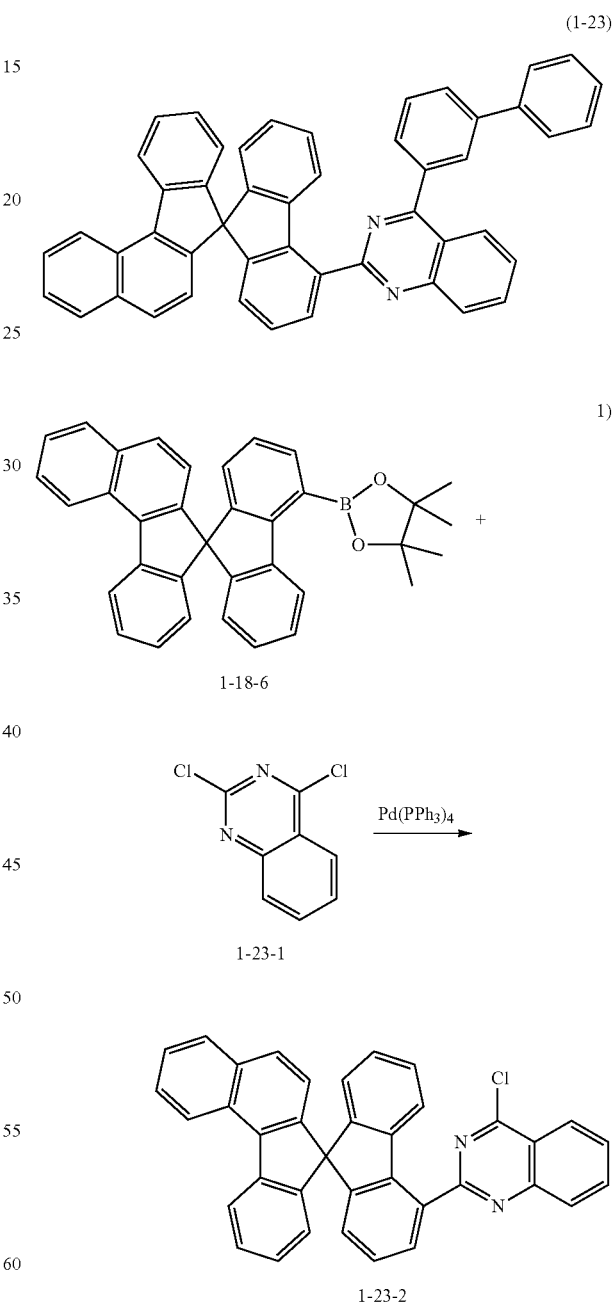

Compound 1-18-6 (14.8 g, 30 mmol) and compound 1-18-9 (10.3 g, 30 mmol), tetrakis(triphenylphosphine)palladium (1.23 g, 1.5 mmol), tetrabutylammonium bromide (1.3 g, 4 mmol), sodium hydroxide (1.6 g, 40 mmol), water Compound 1-18-6 (14.8 g, 30 mmol) and compound 1-23-1 (5.9 g, 30 mmol), tetrakis(triphenylphosphine)palladium (1.23 g, 1.5 mmol), tetrabutylammonium bromide (1.3 g, 4 mmol), sodium hydroxide (1.6 g, 40 mmol), water (10 mL), and toluene (80 mL) were added to a 250 mL three-necked flask under nitrogen atmosphere, and the solution was heated to 60° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 70%.

(3) Synthesis of Compound (1-41):

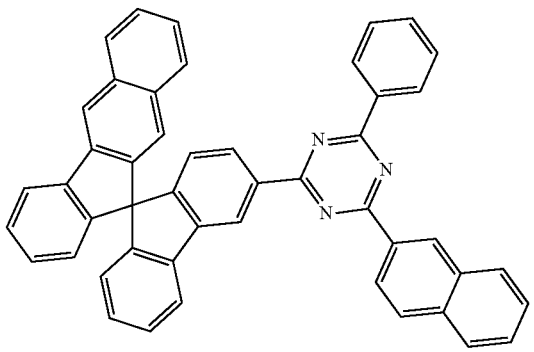

(1-41)

2)

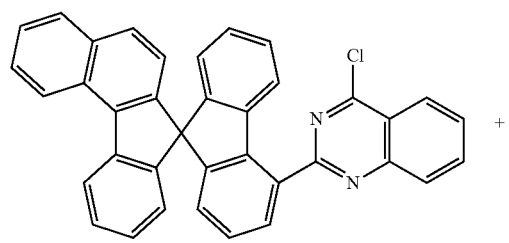

1-23-2

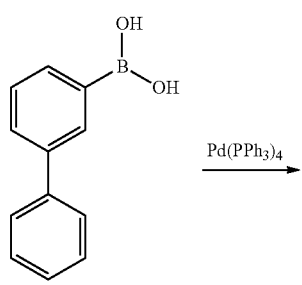

1-23-3

Pd(PPh₃)₄ →

1)

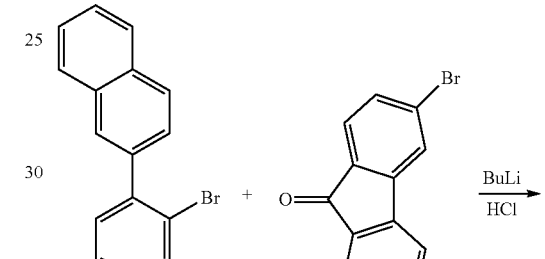

1-41-1   1-41-2

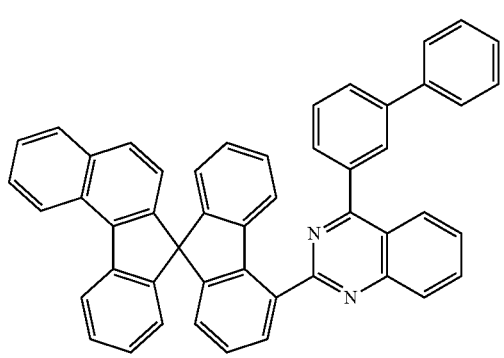

1-23

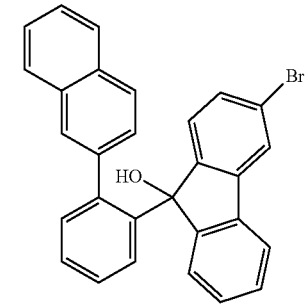

1-41-3

Compound 1-23-2 (5.3 g, 10 mmol) and compound 1-23-3 (2.0 g, 10 mmol), tetrakis(triphenylphosphine)palladium (0.41 g, 0.5 mmol), tetrabutylammonium bromide (0.4 g, 1 mmol), sodium hydroxide (0.6 g, 15 mmol), water (5 mL), and toluene (50 mL) were added to a 150 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 65%.

Compound 1-41-1 (28.3 g, 100 mmol) and 400 mL of anhydrous tetrahydrofuran were added to a 1000 mL three-necked flask under nitrogen atmosphere, cooled to −78° C., and 100 mmol of n-butyllithium was slowly added dropwise, the solution was reacted for 2 hours, then compound 1-41-2 (25.9 g, 100 mmol) was added one time, and the reaction temperature was raised to room temperature naturally. The reaction was further performed for 12 hours, then dilute hydrochloric acid was added one time to the reaction solution, and then the reaction was further performed for 0.5 hour. The reaction solution was rotary evaporated to remove most of the solvent, and then extracted with dichloromethane and washed with water for 3 times. The organic phase was collected, rotary evaporated dried, and then directly used as a raw material for the next reaction without further purification.

2)

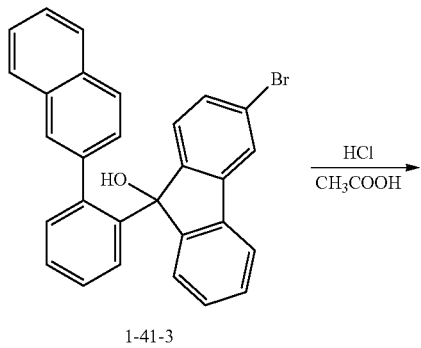

1-41-3

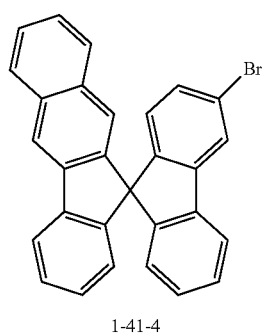

1-41-4

The reaction product 1-41-3 of the previous step, acetic acid (60 mL) and hydrochloric acid (10 mL) were added to a 250 mL three-necked flask, and the solution was heated to 110° C. and reacted under stirring for 4 hours, and then the reaction was ended. The reaction solution was poured into 500 mL of pure water, stirred and precipitated, and then filtered with suction. The filter residue was washed with water and ethanol successively, then collected and recrystallized, with a two-step yield of 60%.

3)

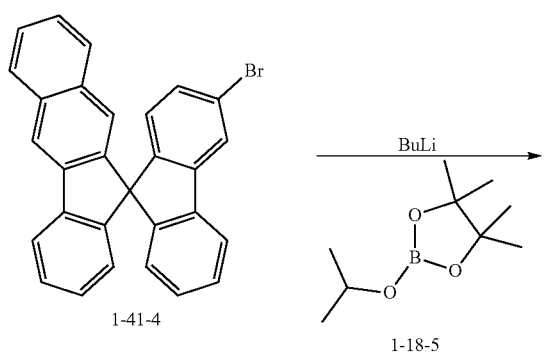

-continued

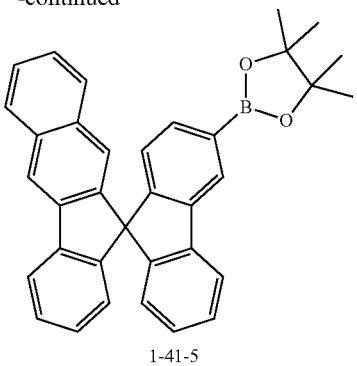

1-41-5

Compound 1-41-4 (22.3 g, 50 mmol) and 200 mL of anhydrous tetrahydrofuran were added to a 500 mL three-necked flask under nitrogen atmosphere, cooled to −78° C., and 50 mmol of n-butyllithium was slowly added dropwise, the solution was reacted for 2 hours, then compound 1-18-5 (9.3 g, 50 mmol) was added one time, and the reaction temperature was raised to room temperature naturally. The reaction was further performed for 12 hours, then the reaction solution was rotary evaporated to remove most of the solvent, and then extracted with dichloromethane and washed with water for 3 times. The organic phase was collected, rotary evaporated dried, and then purified by recrystallization, with a yield of 85%.

4)

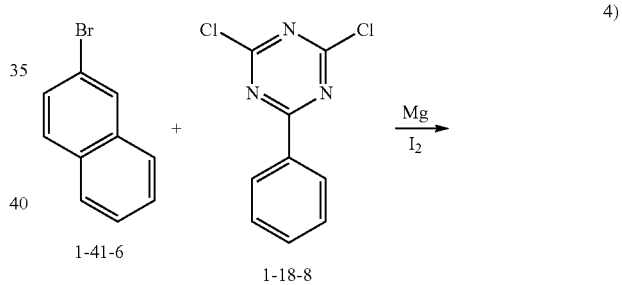

1-41-7

Compound 1-41-6 (2.07 g, 10 mmol), magnesium turnings (2.4 g, 100 mmol), 0.1 g of iodine, and 15 mL of anhydrous tetrahydrofuran were added to a 250 mL three-necked flask under nitrogen atmosphere, heated to 60° C., then the grignard reaction was initiated, and then a solution of 90 mmol of compound 1-41-6 in 100 mL of anhydrous tetrahydrofuran was slowly added dropwise. The solution was reacted for 2 hours at room temperature, then transferred to a 500 mL three-necked bottle containing compound 1-18-8 (22.6 g, 100 mmol) and 100 mL of anhydrous tetrahydrofuran solution. The reaction was further performed for 4 hours and then quenched by addition of pure water. The reaction solution was rotary evaporated to remove most of the solvent, and then extracted with dichloromethane and washed with water for 3 times. The organic phase was collected, rotary evaporated dried, and then recrystallized, with a yield of 75%.

5)

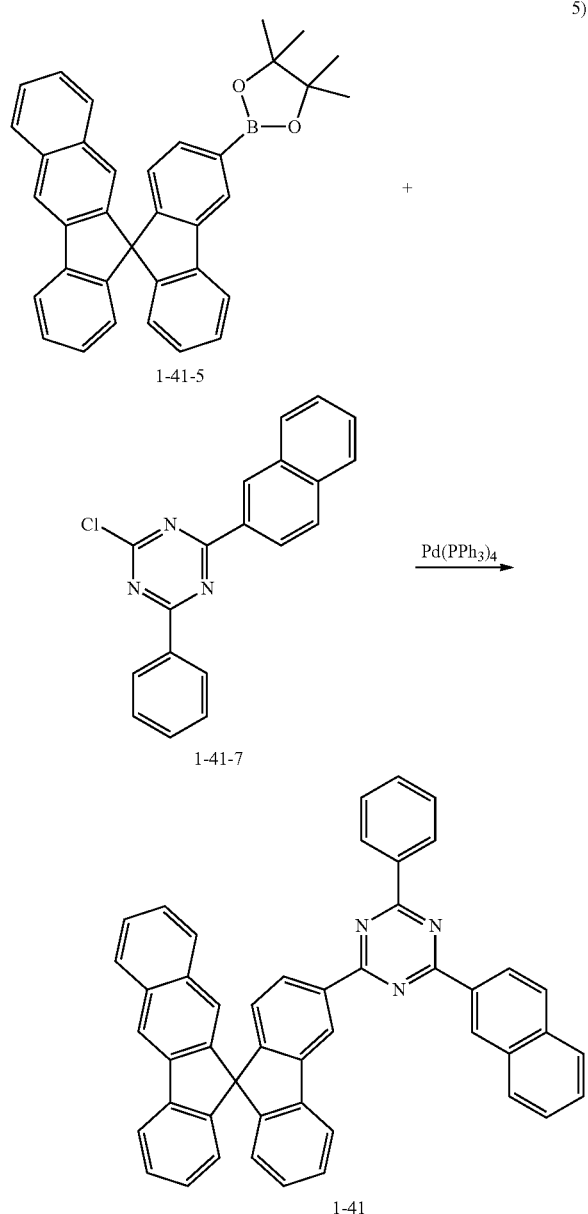

Compound 1-41-5 (14.8 g, 30 mmol) and compound 1-41-7 (10.3 g, 30 mmol), tetrakis(triphenylphosphine)palladium (1.23 g, 1.5 mmol), tetrabutylammonium bromide (1.3 g, 4 mmol), sodium hydroxide (1.6 g, 40 mmol), water (10 mL), and toluene (80 mL) were added to a 250 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 75%.

(4) Synthesis of Compound (1-63):

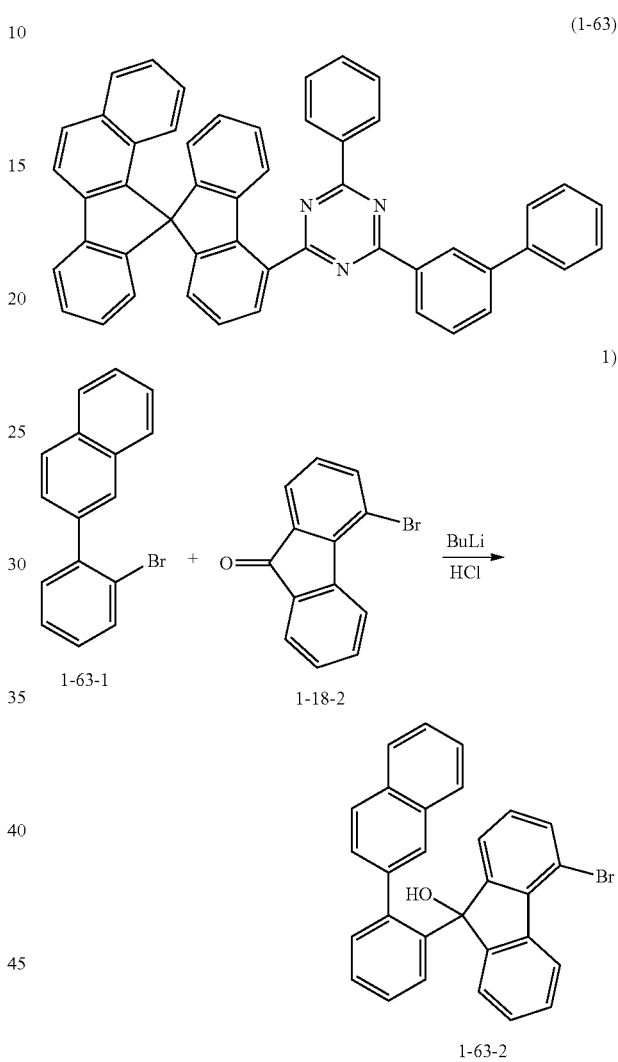

Compound 1-63-1 (28.3 g, 100 mmol) and 400 mL of anhydrous tetrahydrofuran were added to a 1000 mL three-necked flask under nitrogen atmosphere, cooled to −78° C., and 100 mmol of n-butyllithium was slowly added dropwise, the solution was reacted for 2 hours, then compound 1-18-2 (25.9 g, 100 mmol) was added one time, and the reaction temperature was raised to room temperature naturally. The reaction was further performed for 12 hours, then dilute hydrochloric acid was added one time to the reaction solution, and then the reaction was further performed for 0.5 hour. The reaction solution was rotary evaporated to remove most of the solvent, and then extracted with dichloromethane and washed with water for 3 times. The organic phase was collected, rotary evaporated dried, and then directly used as a raw material for the next reaction without further purification.

2)

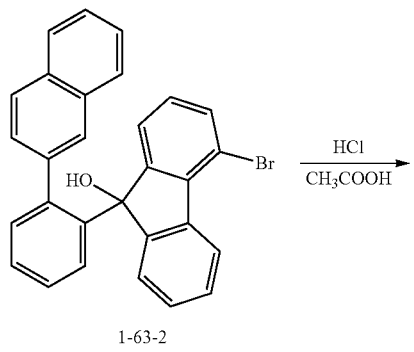

1-63-2

The reaction product 1-63-2 of the previous step, acetic acid (60 mL) and hydrochloric acid (10 mL) were added to a 250 mL three-necked flask, and the solution was heated to 110° C. and reacted under stirring for 4 hours, and then the reaction was ended. The reaction solution was poured into 500 mL of pure water, stirred and precipitated, and then filtered with suction. The filter residue was washed with water and ethanol successively, then collected and recrystallized, with a two-step yield of 60%.

3)

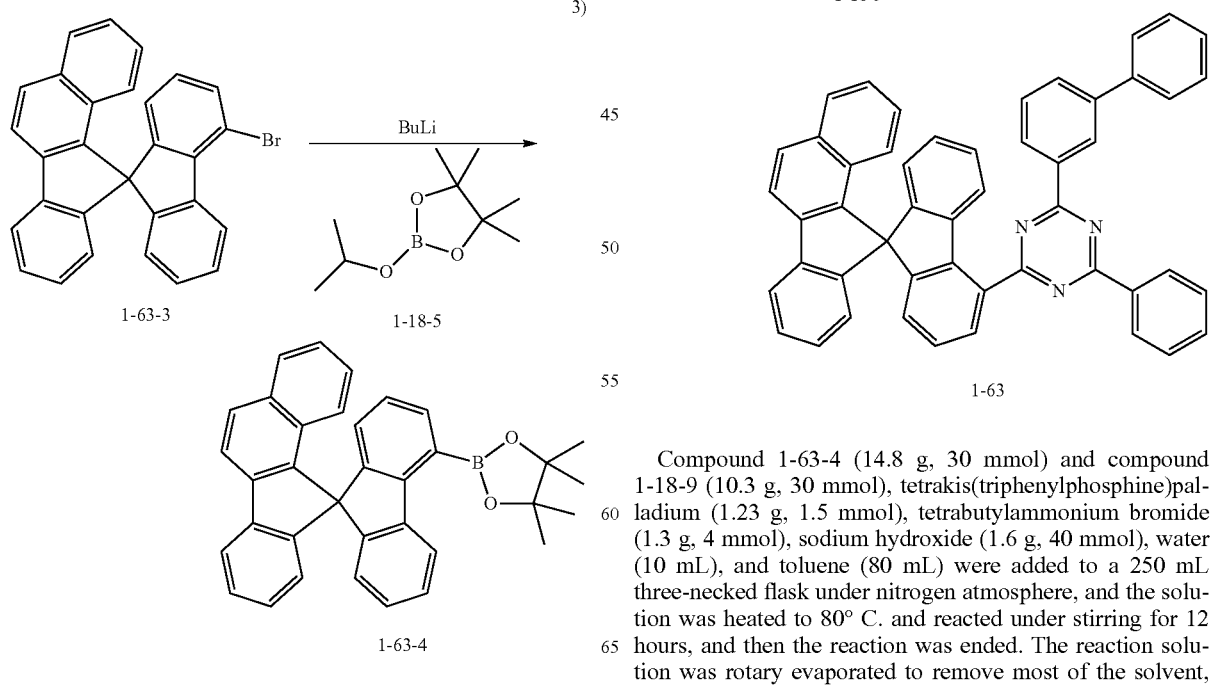

Compound 1-63-3 (22.3 g, 50 mmol) and 200 mL of anhydrous tetrahydrofuran were added to a 500 mL three-necked flask under nitrogen atmosphere, cooled to −78° C., and 50 mmol of n-butyllithium was slowly added dropwise, the solution was reacted for 2 hours, then compound 1-18-5 (9.3 g, 50 mmol) was added one time, and the reaction temperature was raised to room temperature naturally. The reaction was further performed for 12 hours, then the reaction solution was rotary evaporated to remove most of the solvent, and then extracted with dichloromethane and washed with water for 3 times. The organic phase was collected, rotary evaporated dried, and then purified by recrystallization, with a yield of 80%.

4)

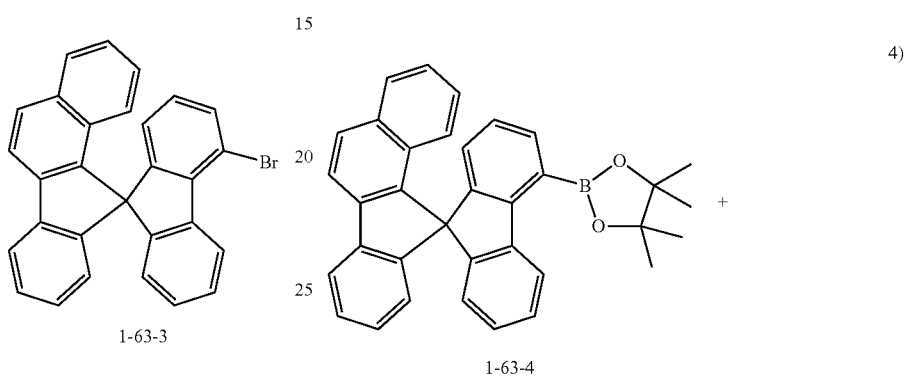

Compound 1-63-4 (14.8 g, 30 mmol) and compound 1-18-9 (10.3 g, 30 mmol), tetrakis(triphenylphosphine)palladium (1.23 g, 1.5 mmol), tetrabutylammonium bromide (1.3 g, 4 mmol), sodium hydroxide (1.6 g, 40 mmol), water (10 mL), and toluene (80 mL) were added to a 250 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 70%.

(5) Synthesis of Compound (1-83):

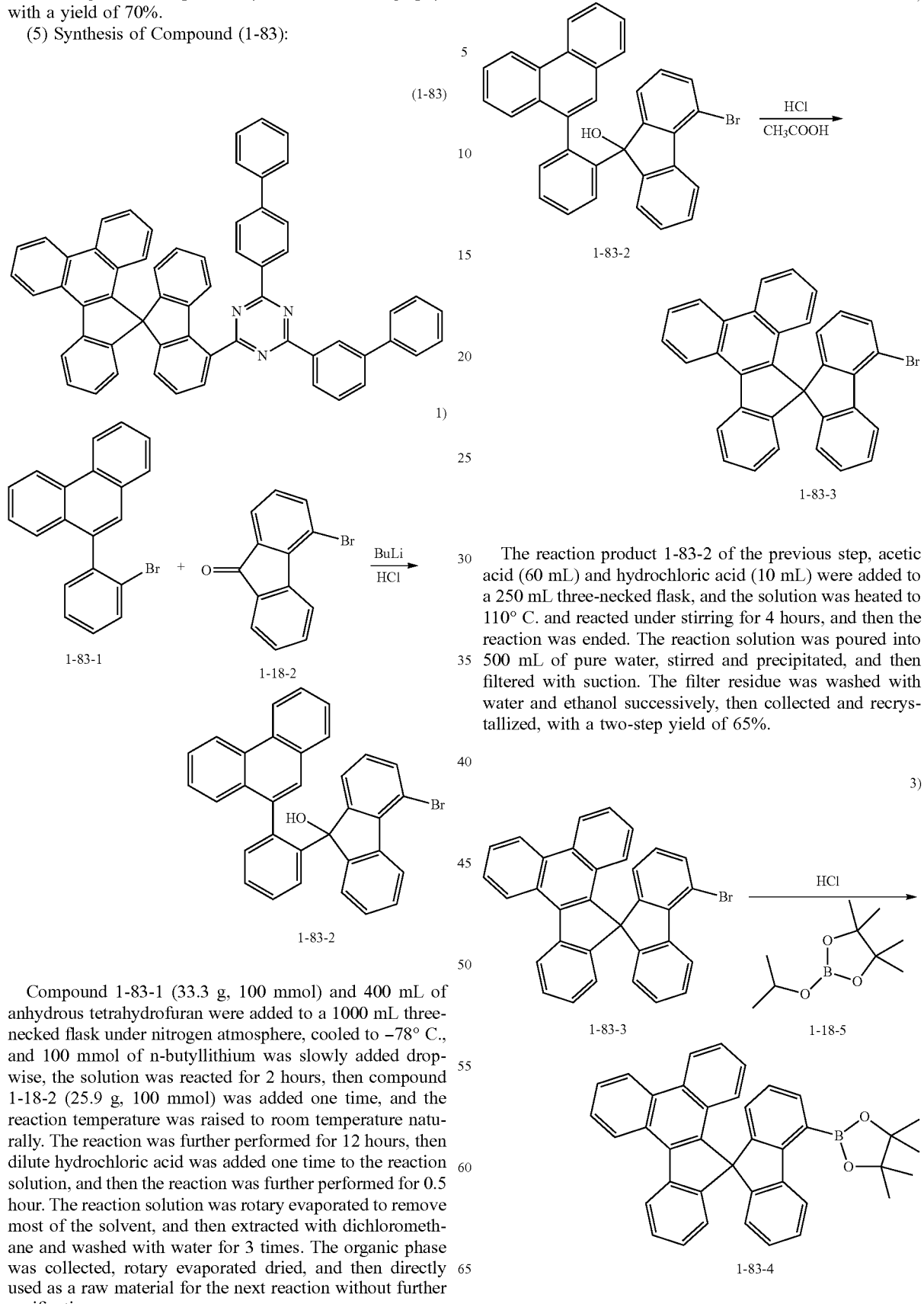

Compound 1-83-1 (33.3 g, 100 mmol) and 400 mL of anhydrous tetrahydrofuran were added to a 1000 mL three-necked flask under nitrogen atmosphere, cooled to −78° C., and 100 mmol of n-butyllithium was slowly added dropwise, the solution was reacted for 2 hours, then compound 1-18-2 (25.9 g, 100 mmol) was added one time, and the reaction temperature was raised to room temperature naturally. The reaction was further performed for 12 hours, then dilute hydrochloric acid was added one time to the reaction solution, and then the reaction was further performed for 0.5 hour. The reaction solution was rotary evaporated to remove most of the solvent, and then extracted with dichloromethane and washed with water for 3 times. The organic phase was collected, rotary evaporated dried, and then directly used as a raw material for the next reaction without further purification.

The reaction product 1-83-2 of the previous step, acetic acid (60 mL) and hydrochloric acid (10 mL) were added to a 250 mL three-necked flask, and the solution was heated to 110° C. and reacted under stirring for 4 hours, and then the reaction was ended. The reaction solution was poured into 500 mL of pure water, stirred and precipitated, and then filtered with suction. The filter residue was washed with water and ethanol successively, then collected and recrystallized, with a two-step yield of 65%.

Compound 1-83-3 (22.3 g, 50 mmol) and 200 mL of anhydrous tetrahydrofuran were added to a 500 mL three-necked flask under nitrogen atmosphere, cooled to −78° C., and 50 mmol of n-butyllithium was slowly added dropwise, the solution was reacted for 2 hours, then compound 1-18-5 (9.3 g, 50 mmol) was added one time, and the reaction temperature was raised to room temperature naturally. The reaction was further performed for 12 hours, then the reaction solution was rotary evaporated to remove most of the solvent, and then extracted with dichloromethane and washed with water for 3 times. The organic phase was collected, rotary evaporated dried, and then purified by recrystallization, with a yield of 80%.

4)

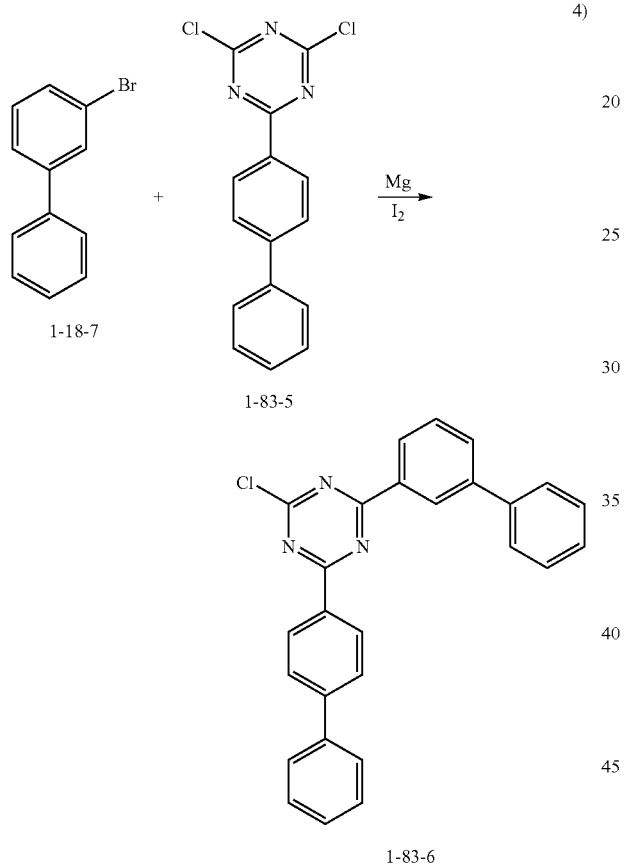

Compound 1-18-7 (2.33 g, 10 mmol), magnesium turnings (2.4 g, 100 mmol), 0.1 g of iodine, and 15 mL of anhydrous tetrahydrofuran were added to a 250 mL three-necked flask under nitrogen atmosphere, heated to 60° C., then the grignard reaction was initiated, and then a solution of 90 mmol of compound 1-18-7 in 100 mL of anhydrous tetrahydrofuran was slowly added dropwise. The solution was reacted for 2 hours at room temperature, then transferred to a 500 mL three-necked bottle containing compound 1-83-5 (22.6 g, 100 mmol) and 100 mL of anhydrous tetrahydrofuran solution. The reaction was further performed for 4 hours and then quenched by addition of pure water. The reaction solution was rotary evaporated to remove most of the solvent, and then extracted with dichloromethane and washed with water for 3 times. The organic phase was collected, rotary evaporated dried, and then recrystallized, with a yield of 80%.

5)

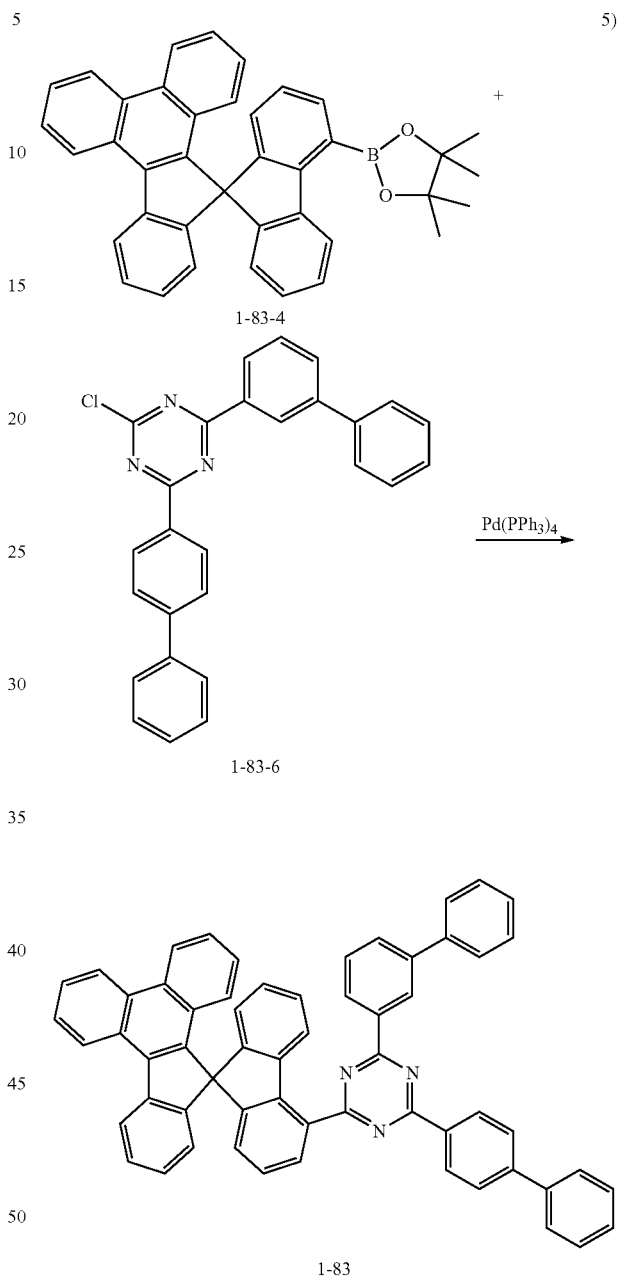

Compound 1-83-4 (14.8 g, 30 mmol) and compound 1-83-6 (10.3 g, 30 mmol), tetrakis(triphenylphosphine)palladium (1.23 g, 1.5 mmol), tetrabutylammonium bromide (1.3 g, 4 mmol), sodium hydroxide (1.6 g, 40 mmol), water (10 mL), and toluene (80 mL) were added to a 250 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 70%.

(6) Synthesis of Compound (2-8):

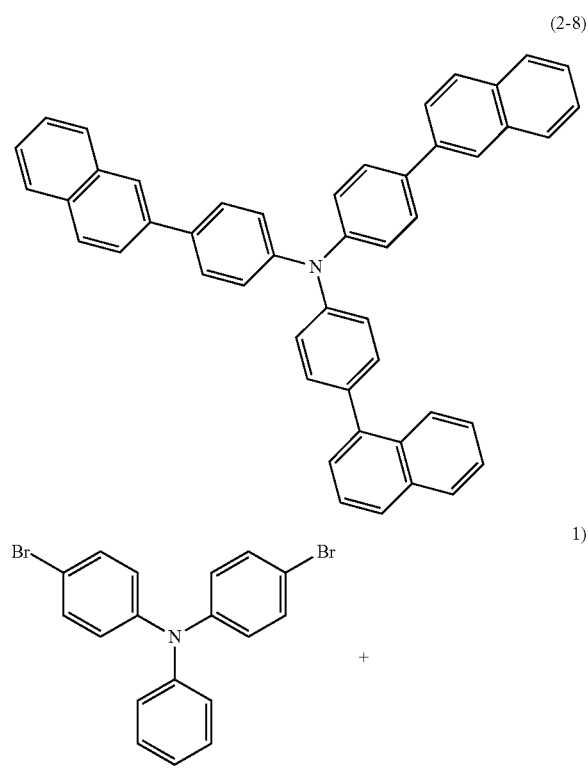

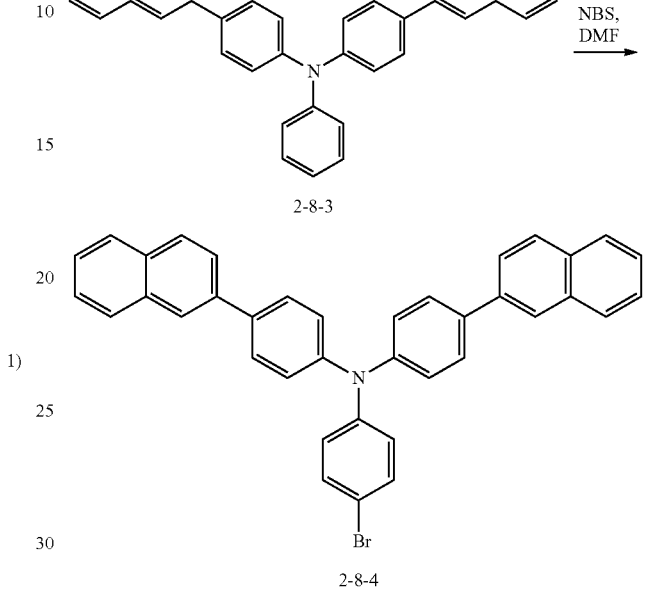

Compound 2-8-1 (20.2 g, 50 mmol) and compound 2-8-2 (17.2 g, 100 mmol), tetrakis(triphenylphosphine)palladium (3.5 g, 3 mmol), tetrabutylammonium bromide (8.1 g, 25 mmol), sodium hydroxide (4 g, 100 mmol), water (20 mL), and toluene (150 mL) were added to a 300 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 75%.

Compound 2-8-3 (14.9 g, 30 mmol) and 100 mL of N,N-dimethylformamide were added into a 250 mL single-necked flask, and a solution of 30 mmol NBS in N,N-dimethylformamide was added dropwise in an ice bath. The solution was reacted under stirring for 12 hours in the dark, and then the reaction was ended. The reaction solution was poured into 300 mL of water, filtered with suction, and the filter residue was recrystallized, with a yield 90%.

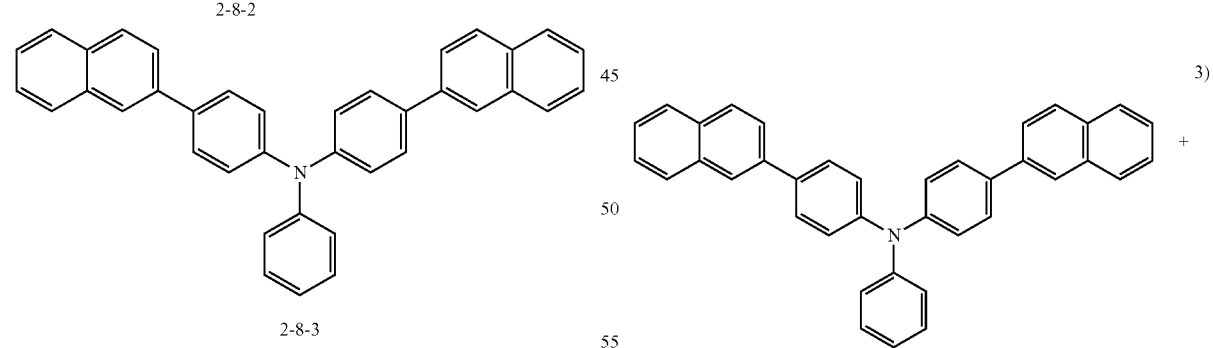

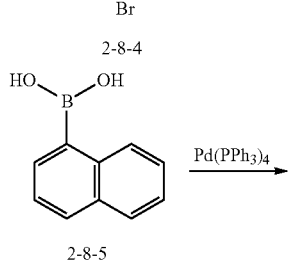

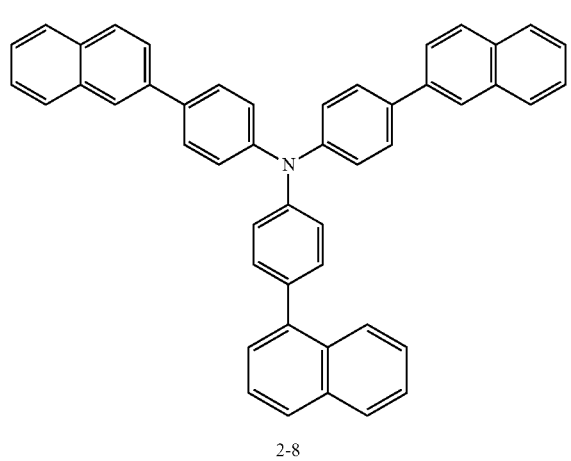

2-8

Compound 2-8-4 (11.5 g, 20 mmol) and compound 2-8-5 (34.4 g, 20 mmol), tetrakis(triphenylphosphine)palladium (0.7 g, 0.6 mmol), tetrabutylammonium bromide (3.2 g, 10 mmol), sodium hydroxide (1.6 g, 40 mmol), water (10 mL), and toluene (80 mL) were added to a 250 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 85%.

(7) Synthesis of Compound (2-10):

(2-10)

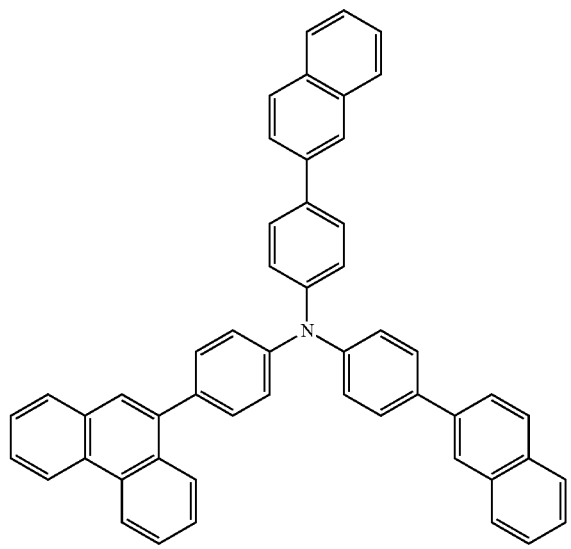

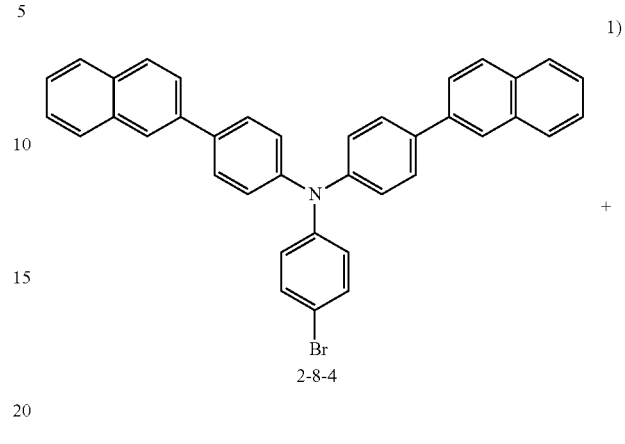

2-8-4

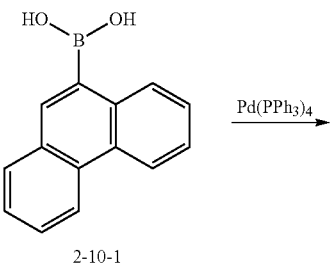

2-10-1

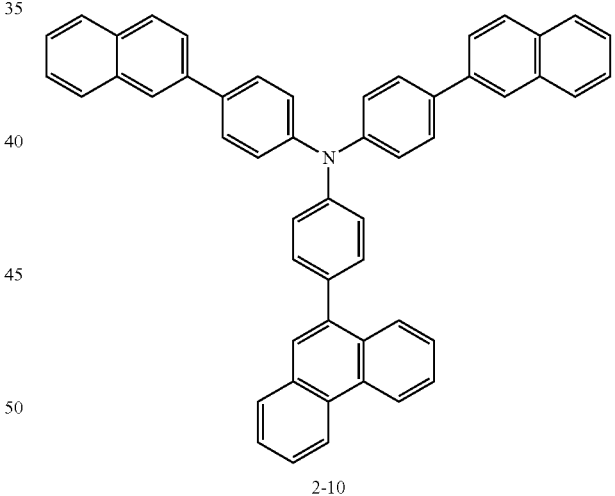

2-10

Compound 2-8-4 (11.5 g, 20 mmol) and compound 2-10-1 (44.4 g, 20 mmol), tetrakis(triphenylphosphine)palladium (0.7 g, 0.6 mmol), tetrabutylammonium bromide (3.2 g, 10 mmol), sodium hydroxide (1.6 g, 40 mmol), water (10 mL), and toluene (80 mL) were added to a 250 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 85%.

(8) Synthesis of Compound (2-24):

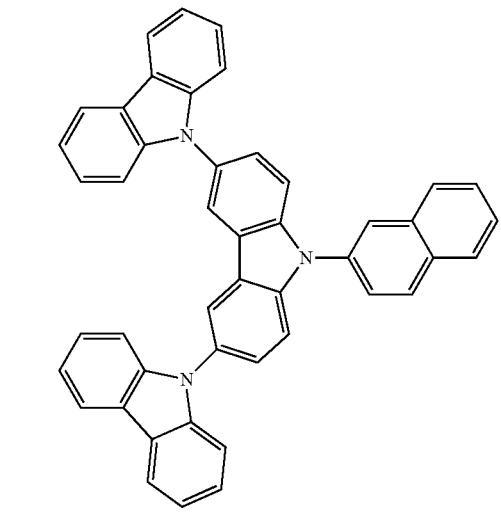

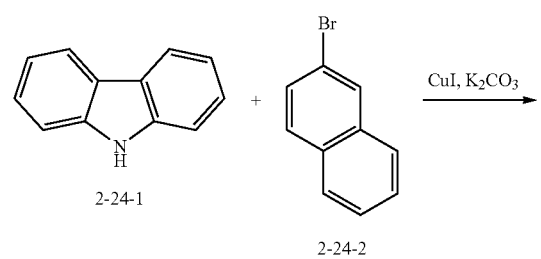

Compound 2-24-1 (16.7 g, 100 mmol), compound 2-24-2 (20.7 g, 100 mmol), cuprous iodide (1.9 g, 10 mmol), potassium carbonate (13.8 g, 100 mmol) and 18-crown-6 (2.65 g, 5 mmol) and o-dichlorobenzene (200 mL) were added to a 500 mL two-necked flask under nitrogen atmosphere, and the solution was heated to 150° C. and reacted under stirring for 24 hours, and then the reaction was end. The reaction solution was distilled under reduced pressure to remove most of the solvent, and then dissolved with dichloromethane and washed with water for 3 times. The organic solution was collected, mixed with silica gel, and purified by column chromatography, with a yield of 85%.

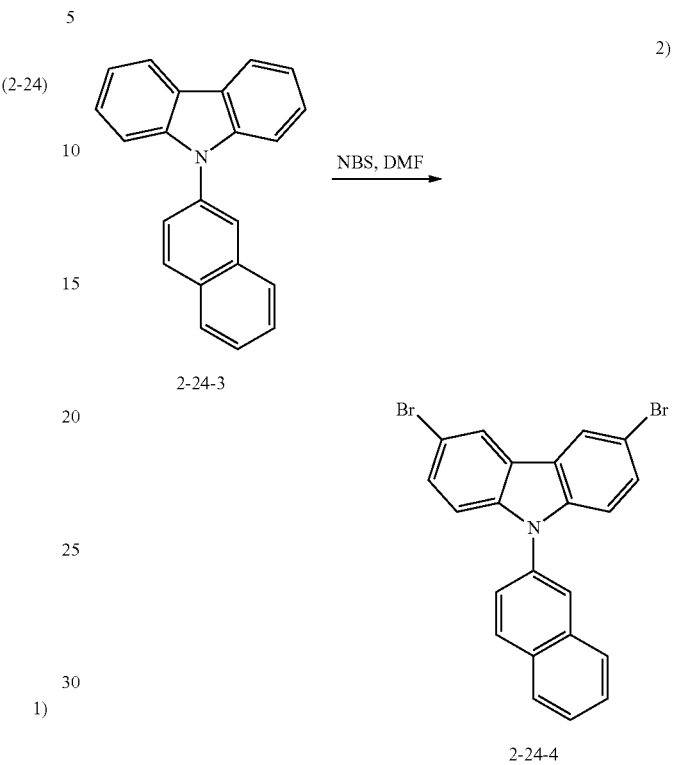

Compound 2-24-3 (17.6 g, 60 mmol) and 100 mL of N,N-dimethylformamide were added into a 250 mL single-necked flask, and a solution of 120 mmol NBS in N,N-dimethylformamide was added dropwise in an ice bath. The solution was reacted under stirring for 12 hours in the dark, and then the reaction was ended. The reaction solution was poured into 500 mL of water, filtered with suction, and the filter residue was recrystallized, with a yield 85%.

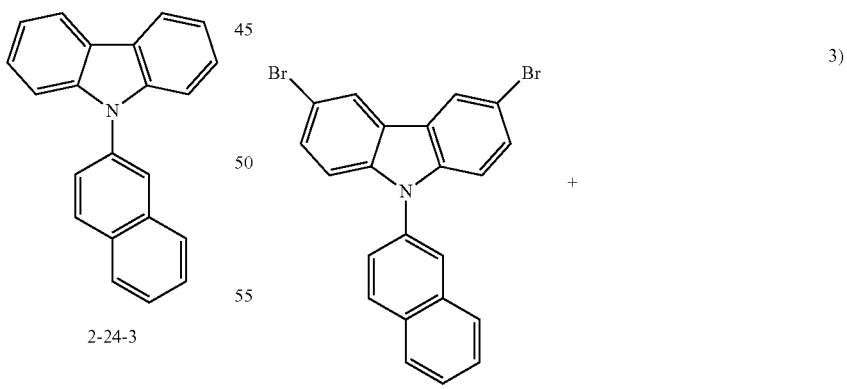

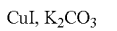

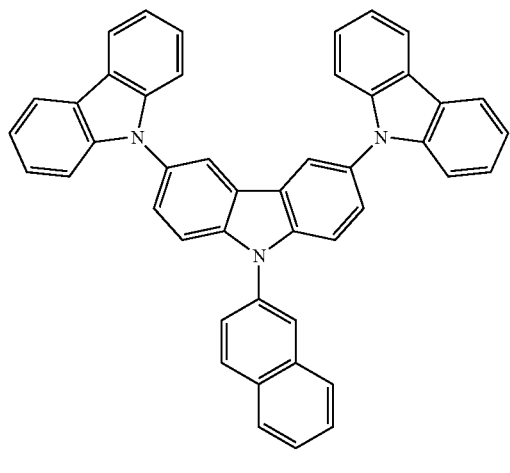

2-24

Compound 2-24-4 (13.5 g, 30 mmol), compound 2-24-1 (10.0 g, 60 mmol), cuprous iodide (0.9 g, 5 mmol), potassium carbonate (4.1 g, 30 mmol) and 18-crown-6 (1.6 g, 3 mmol) and o-dichlorobenzene (150 mL) were added to a 500 mL two-necked flask under nitrogen atmosphere, and the solution was heated to 150° C. and reacted under stirring for 24 hours, and then the reaction was end. The reaction solution was distilled under reduced pressure to remove most of the solvent, and then dissolved with dichloromethane and washed with water for 3 times. The organic solution was collected, mixed with silica gel, and purified by column chromatography, with a yield of 80%.

(9) Synthesis of Compound (2-39):

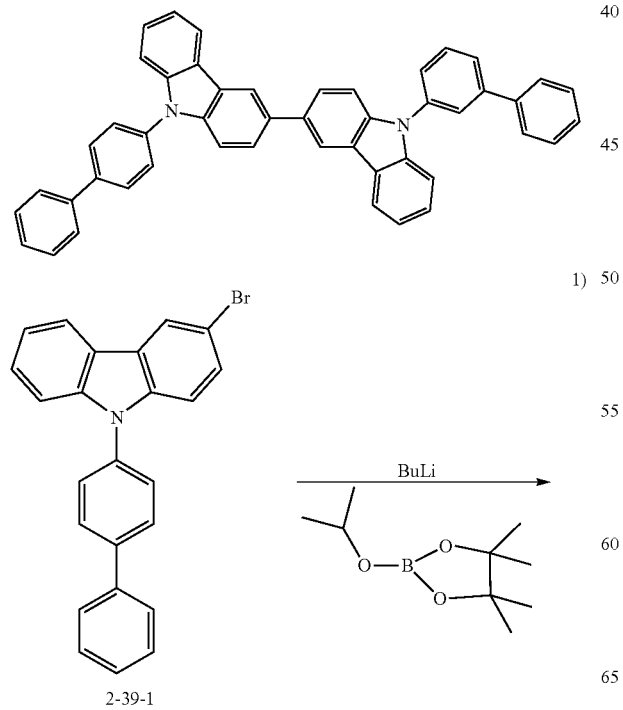

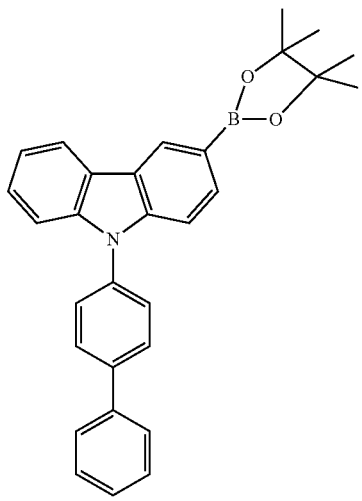

2-39-2

Compound 2-39-1 (15.9 g, 40 mmol) and 300 mL of anhydrous tetrahydrofuran were added to a 500 mL three-necked flask under nitrogen atmosphere, cooled to −78° C., and 50 mmol of n-butyllithium was slowly added dropwise, the solution was reacted for 2 hours, then 55 mmol of isopropoxyboronic acid pinacol ester was added one time, and the reaction temperature was raised to room temperature naturally. The reaction was further performed for 12 hours and then quenched by addition of pure water. The reaction solution was rotary evaporated to remove most of the solvent, and then extracted with dichloromethane and washed with water for 3 times. The organic phase was collected, rotary evaporated dried, and then recrystallized, with a yield of 80%.

-continued

(10) Synthesis of Compound (2-42):

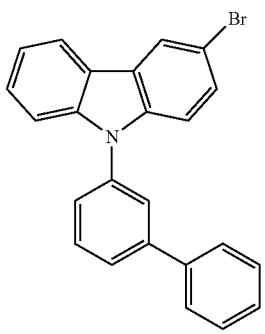

2-39-3

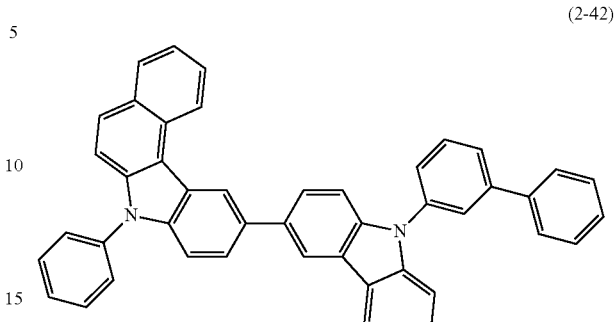

(2-42)

1)

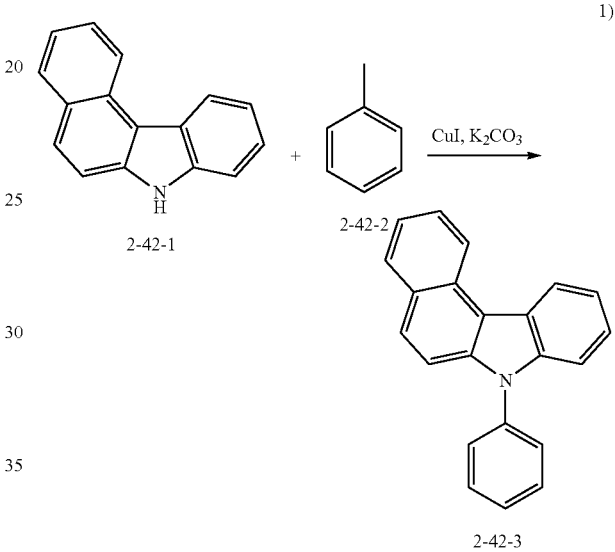

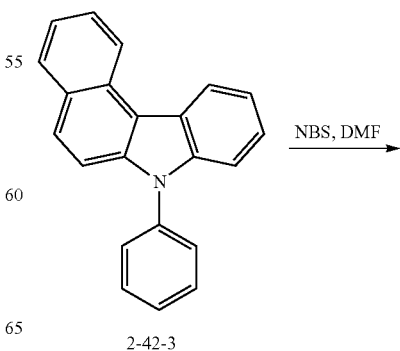

2-39

Compound 2-39-2 (4.45 g, 20 mmol) and compound 2-39-3 (3.98 g, 20 mmol), tetrakis(triphenylphosphine)palladium (1.15 g, 1 mmol), tetrabutylammonium bromide (2.6 g, 8 mmol), sodium hydroxide (3.2 g, 80 mmol), water (10 mL), and toluene (100 mL) were added to a 250 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 80%.

Compound 2-42-1 (21.7 g, 100 mmol), compound 2-42-2 (20.4 g, 100 mmol), cuprous iodide (1.9 g, 10 mmol), potassium carbonate (13.8 g, 100 mmol) and 18-crown-6 (2.65 g, 5 mmol) and o-dichlorobenzene (200 mL) were added to a 500 mL two-necked flask under nitrogen atmosphere, and the solution was heated to 150° C. and reacted under stirring for 24 hours, and then the reaction was end. The reaction solution was distilled under reduced pressure to remove most of the solvent, and then dissolved with dichloromethane and washed with water for 3 times. The organic solution was collected, mixed with silica gel, and purified by column chromatography, with a yield of 90%.

2)

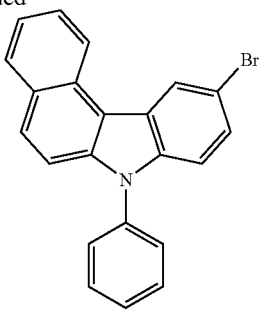

2-42-4

Compound 2-42-3 (17.6 g, 60 mmol) and 100 mL of N,N-dimethylformamide were added into a 250 mL single-necked flask, and a solution of 60 mmol NBS in N,N-dimethylformamide was added dropwise in an ice bath. The solution was reacted under stirring for 12 hours in the dark, and then the reaction was ended. The reaction solution was poured into 500 mL of water, filtered with suction, and the filter residue was recrystallized, with a yield 90%.

naturally. The reaction was further performed for 12 hours and then quenched by addition of pure water. The reaction solution was rotary evaporated to remove most of the solvent, and then extracted with dichloromethane and washed with water for 3 times. The organic phase was collected, rotary evaporated dried, and then recrystallized, with a yield of 90%.

3)

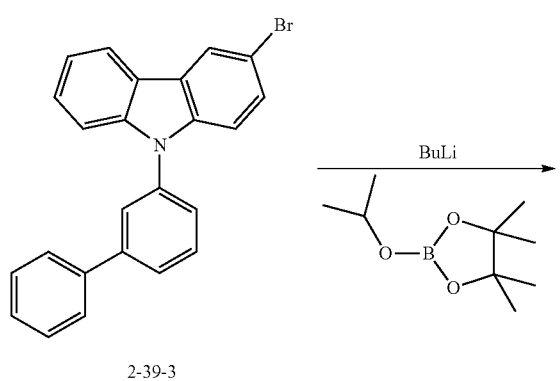

2-39-3

2-42-5

4)

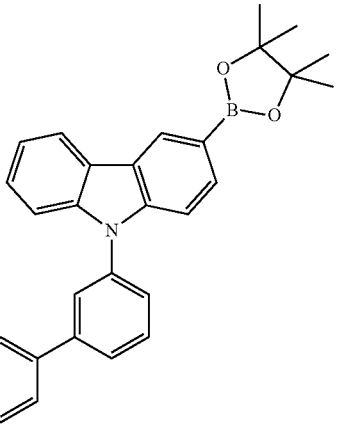

2-42-5

+

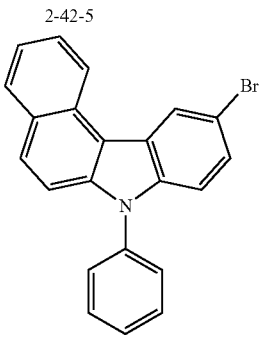

2-42-4

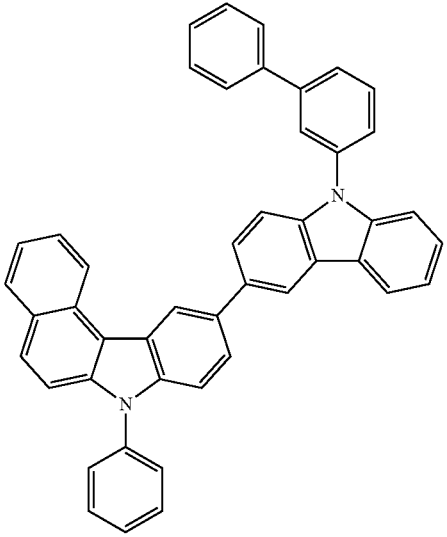

2-42

Compound 2-39-3 (31.5 g, 80 mmol) and 300 mL of anhydrous tetrahydrofuran were added to a 500 mL three-necked flask under nitrogen atmosphere, cooled to −78° C., and 85 mmol of n-butyllithium was slowly added dropwise, the solution was reacted for 2 hours, then 90 mmol of isopropoxyboronic acid pinacol ester was added one time, and the reaction temperature was raised to room temperature Compound 2-42-5 (8.9 g, 20 mmol) and compound 2-42-4 (7.4 g, 20 mmol), tetrakis(triphenylphosphine)palladium (1.15 g, 1 mmol), tetrabutylammonium bromide (2.6 g, 8 mmol), sodium hydroxide (3.2 g, 80 mmol), water (10 mL), and toluene (100 mL) were added to a 250 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 80%.

(11) Synthesis of Compound (2-86):

Compound 2-42-5 (26.7 g, 60 mmol) and compound 2-86-1 (12.1 g, 60 mmol), tetrakis(triphenylphosphine)palladium (3.45 g, 3 mmol), tetrabutylammonium bromide (7.8 g, 24 mmol), sodium hydroxide (4.8 g, 120 mmol), water (15 mL), and toluene (120 mL) were added to a 250 mL three-necked flask under nitrogen atmosphere, and the solution was heated to 80° C. and reacted under stirring for 12 hours, and then the reaction was ended. The reaction solution was rotary evaporated to remove most of the solvent, and then dissolved with dichloromethane and washed with water for 3 times. The organic solution was collected, mixed with silica gel, and then purified by column chromatography, with a yield of 80%.

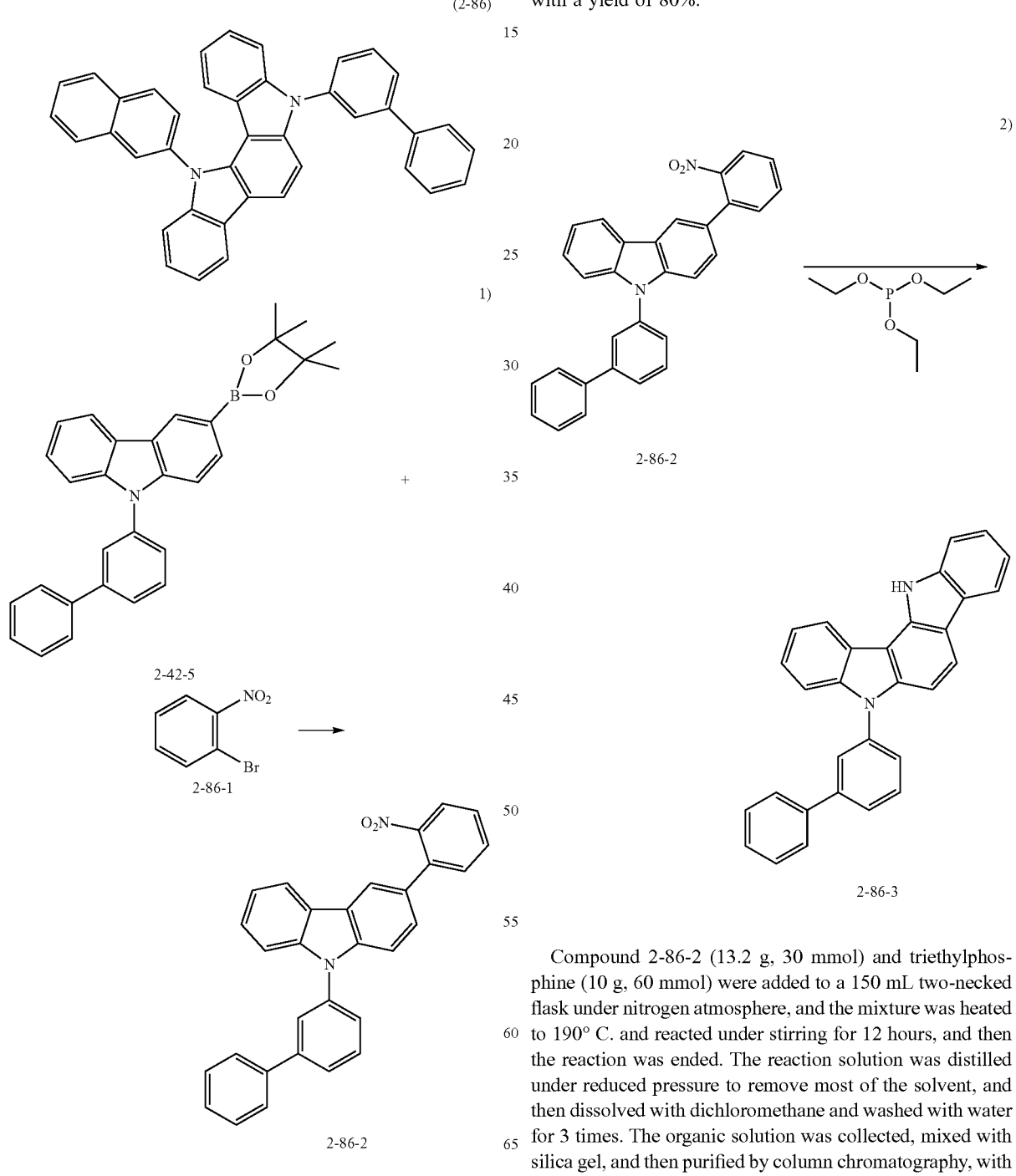

Compound 2-86-2 (13.2 g, 30 mmol) and triethylphosphine (10 g, 60 mmol) were added to a 150 mL two-necked flask under nitrogen atmosphere, and the mixture was heated to 190° C. and reacted under stirring for 12 hours, and then the reaction was ended. The reaction solution was distilled under reduced pressure to remove most of the solvent, and then dissolved with dichloromethane and washed with water for 3 times. The organic solution was collected, mixed with silica gel, and then purified by column chromatography, with a yield of 85%.

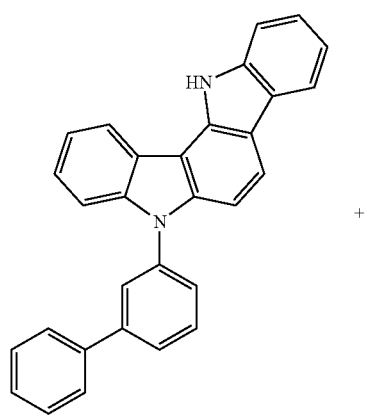

2-86-3

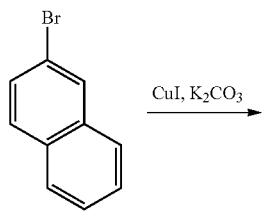

2-24-2

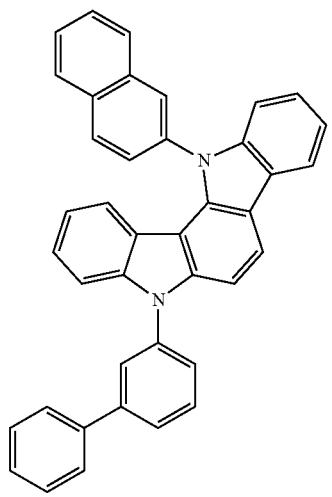

2-86

Compound 2-86-3 (8.16 g, 20 mmol), compound 3-24-2 (4.66 g, 20 mmol), cuprous iodide (0.76 g, 4 mmol), potassium carbonate (5.5 g, 40 mmol) and 18-crown-6 (2.12 g, 4 mmol) and o-dichlorobenzene (100 mL) were added to a 250 mL two-necked flask under nitrogen atmosphere, and the solution was heated to 150° C. and reacted under stirring for 24 hours, and then the reaction was end. The reaction solution was distilled under reduced pressure to remove most of the solvent, and then dissolved with dichloromethane and washed with water for 3 times. The organic solution was collected, mixed with silica gel, and purified by column chromatography, with a yield of 85%.

2. Energy Structure of Organic Compounds

The energy levels of organic materials can be obtained by quantum calculations, such as using TD-DFT (Time Dependent-Density Functional Theory) by Gaussian03W (Gaussian Inc.), and the specific simulation methods can be found in WO2011141110. Firstly, the molecular geometry is optimized by semi-empirical method "Ground State/DFT/Default Spin/B3LYP" and the basis set "6-31G (d)" (Charge 0/Spin Singlet), and then the energy structure of organic molecules is calculated by TD-DFT (Time-Density Functional Theory) method "TD-SCF/DFT/Default Spin/B3PW91" and the basis set "6-31G (d)" (Charge 0/Spin Singlet). The HOMO and LUMO energy levels are calculated according to the following calibration formulas, S and T1 are used directly.

$$HOMO(eV) = ((HOMO(G) \times 27.212) - 0.9899)/1.1206$$

$$LUMO(eV) = ((LUMO(G) \times 27.212) - 2.0041)/1.385$$

wherein, HOMO(G) and LUMO(G) in the unit of Hartree are the direct calculation results of Gaussian 09W. The results are shown in Table 1, wherein, $\Delta HOMO = HOMO - (HOMO-1)$, $\Delta LUMO = (LUMO+1) - LUMO$:

TABLE 1

| Materials | HOMO [eV] | ΔHOMO [eV] | LUMO [eV] | ΔLUMO [eV] | T1 [eV] | S1 [eV] |
|---|---|---|---|---|---|---|
| HATCN | −9.04 | | −5.08 | | 2.32 | 3.17 |
| SFNFB | −5.26 | | −2.19 | | 2.59 | 3.22 |
| (1-18) | −5.70 | 0.41 | −2.78 | 0.02 | 2.42 | 2.82 |
| (1-23) | −5.73 | 0.35 | −2.94 | 0.53 | 2.36 | 3.01 |
| (1-63) | −5.85 | 0.41 | −2.88 | 0.03 | 2.43 | 3.14 |
| (1-83) | −5.78 | 0.46 | −2.93 | 0.06 | 2.34 | 3.03 |
| (2-8) | −5.34 | 0.72 | −2.42 | 0.04 | 2.43 | 2.91 |
| (2-10) | −5.35 | 0.69 | −2.42 | 0.03 | 2.46 | 2.91 |
| (2-42) | −5.45 | 0.21 | −2.28 | 0.07 | 2.55 | 3.19 |
| Ref1 | −6.01 | 0.28 | −2.84 | 0.19 | 2.95 | 3.26 |
| Ir(mphq)$_2$acac | −5.13 | | −2.71 | | 2.14 | 2.35 |
| NaTzF$_2$ | −6.19 | | −2.82 | | 2.55 | 3.52 |

3. Preparation and Characterization of OLED Devices

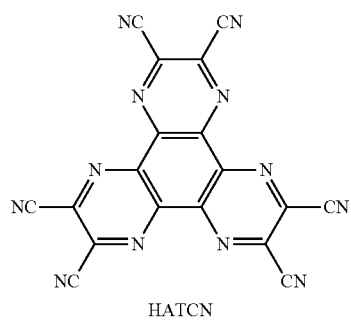

HATCN

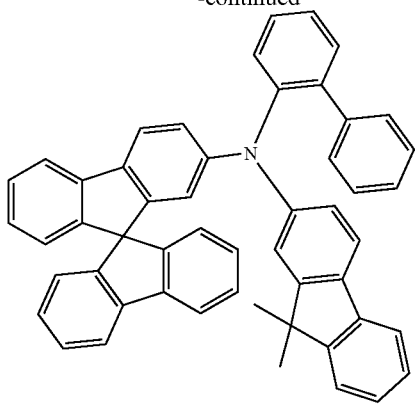

SFNFB

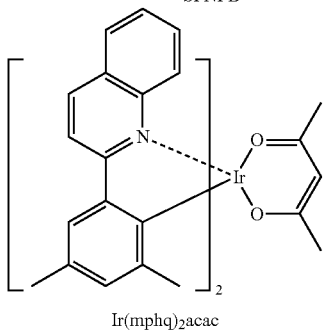

Ir(mphq)₂acac

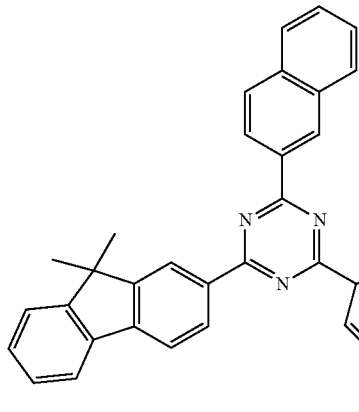

NaTzF2

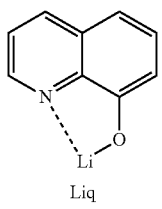

Liq

In the present embodiment, compounds (1-18), (1-23), (1-63), and (1-83) were premixed with compounds (2-8), (2-10), and (2-42) as co-host materials, respectively. As shown in the following figure, Ir(mphq)₂acac was used as the light-emitting material, HATCN as the hole injection material, SFNFB as the hole transport material, NaTzF2 as the electron transport material, and Liq as the electron injection material, to make an electroluminescent device has a device structure of ITO/HATCN/SFNFB/co-host material: Ir(mphq)₂acac (3%)/NaTzF₂: Liq/Liq/Al.

The above materials HATCN, SFNFB, Ir(mphq)₂acac (3%), NaTzF2, and Liq are all commercially available, such as from Jilin OLED Material Tech Co., Ltd (www.jl-oled.com), and the like, or all the synthesis methods thereof are all known which can be found in the references of the prior art and will not be described here.

The preparation process of the above OLED device was described in detail through a specific embodiment. The structure of the OLED device (as shown in Table 2) is: ITO/HATCN/NPB/TCTA/co-host material: Ir(mphq)₂acac (3%)/NaTzF₂: Liq/Liq/Al, and the preparation steps are as follows:

a. Cleaning of ITO (Indium Tin Oxide) conductive glass substrate: the substrate was cleaned with a variety of solvents (such as one or more of chloroform, acetone or isopropanol), and then treated with ultraviolet and ozone;

b. HATCN (30 nm), SFNFB (50 nm), co-host material: Ir(mphq)₂acac (3%) (40 nm), NaTzF2: Liq (30 nm), Liq (1 nm), Al (100 nm) was formed by thermal evaporation in high vacuum ($1\times10^{-6}$ mbar);

c. Encapsulating: the device was encapsulated with UV-curable resin in a glove box filled with nitrogen gas.

TABLE 2

| OLED devices | Host materials | T90@1000 nits |
|---|---|---|
| OLED1 | (1-18): (2-8) = 5:5 | 256 |
| OLED2 | (1-18): (2-10) = 5:5 | 232 |
| OLED3 | (1-23): (2-8) = 5:5 | 215 |
| OLED4 | (1-63): (2-8) = 5:5 | 208 |
| OLED5 | (1-63): (2-42) = 5:5 | 178 |
| OLED6 | (1-83): (2-10) = 5:5 | 202 |
| RefOLED1 | Ref1: (2-8) = 5:5 | 102 |
| RefOLED2 | (1-18) | 40 |
| RefOLED3 | (2-8) | 1 |

(Ref1)

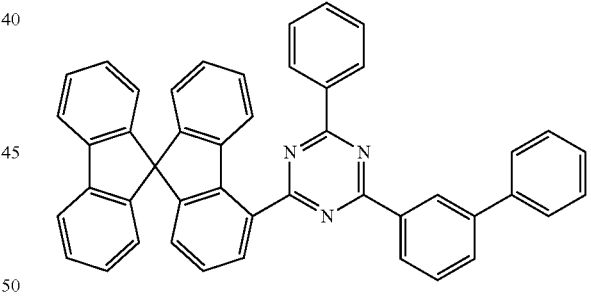

Wherein, refers to patent WO2018095393 for Ref1.

The current-voltage (J-V) characteristics of each OLED device were characterized by characterization equipment while important parameters such as efficiency, lifetime and external quantum efficiency were recorded. The lifetimes of each OLED device are shown in Table 2, wherein, T90@1000nits are values relative to RefOLED3. The OLED3 comprising the co-host material (1-18): (2-8) has a highest lifetime in the same type of devices after tested, which are more than 4 times higher than that of RefOLED2 and RefOLED3 comprising a single host, while is about 2 times higher than that of RefOLED1. The main reason may be that the mixture device is more balanced in electron and hole transport compared to the single-host device, and compared to the RefOLED1 device, the electron-transporting molecule described in the present disclosure has a better matched triplet energy level in the red-light device after the fused ring has been introduced thereto, which is more beneficial to the transport of energy. This proves that the mixed hosts collocated as a co-host of the present disclosure has a relatively better device performance.

The invention claimed is:

1. An organic mixture comprising an organic compound H1 and an organic compound H2, wherein the organic compound H1 is a compound represented by general formula (1):

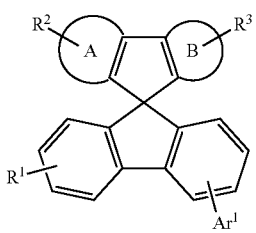

(1)

wherein,

A and B each independently represent an aromatic hydrocarbon group with 6 to 30 ring atoms or an aromatic heterocyclic group with 6 to 30 ring atoms, and at least one of A and B has more than 6 ring atoms;

$R^1$, $R^2$ and $R^3$ are substituents, each independently selected from the group consisting of H, deuterium, F, CN, alkenyl, alkynyl, nitrile group, amino group, nitro group, acyl, alkoxy group, carbonyl, sulfonyl, substituted or unsubstituted alkyl with 1 to 30 carbon atoms, substituted or unsubstituted cycloalkyl with 3 to 30 carbon atoms, and substituted or unsubstituted aromatic hydrocarbon group with 5 to 60 ring atoms or substituted or unsubstituted aromatic heterocyclic group with 5 to 60 ring atoms;

$Ar^1$ represents a substituted or unsubstituted aromatic hydrocarbon group with 5 to 100 ring atoms or substituted or unsubstituted aromatic heterocyclic group with 5 to 100 ring atoms, and contains at least one electron-accepting group;

the organic compound H2 is a compound represented by general formula (2):

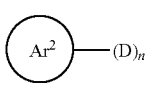

(2)

wherein, $Ar^2$ represents a substituted or unsubstituted alkyl with 1 to 30 carbon atoms, a substituted or unsubstituted cycloalkyl with 3 to 30 carbon atoms, a substituted or unsubstituted aromatic hydrocarbon group with 5 to 100 ring atoms or substituted or unsubstituted aromatic heterocyclic group with 5 to 100 ring atoms;

D is an electron-donating group; and n is an integer of 1-6;

wherein the difference between sublimation temperature of the organic compound H1 and that of the organic compound H2 does not exceed 30 K.

2. The organic mixture according to claim 1, wherein A and B are the same or different, and each are selected from the group consisting of:

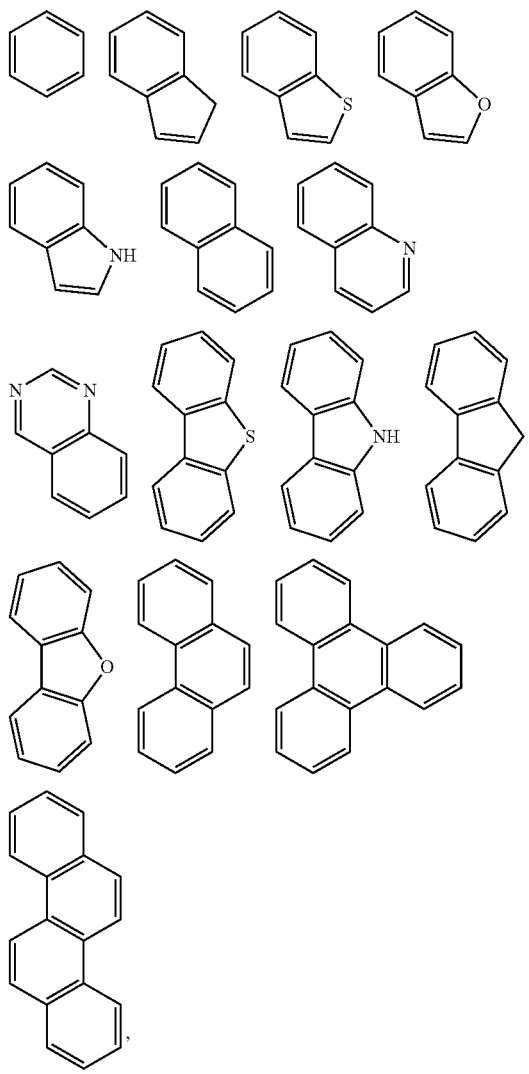

wherein hydrogen(s) on rings of the above groups can be arbitrarily substituted.

3. The organic mixture according to claim 1, wherein $Ar^1$ and $Ar^2$ each comprise one or more of the following structural groups:

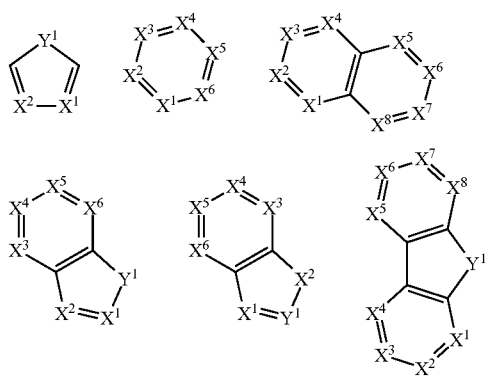

-continued

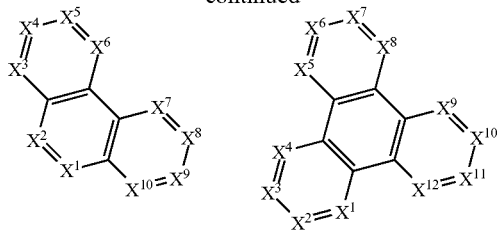

wherein, $X^1$-$X^{12}$ each independently represent $CR^4$ or N;

Y is selected from the group consisting of $N(R^4)$, $C(R^4R^5)$, $Si(R^4R^5)$, $C(=O)$, S and O;

$R^4$ and $R^5$ each independently represent H, substituted or unsubstituted alkyl with 1 to 30 carbon atoms, a substituted or unsubstituted cycloalkyl with 3 to 30 carbon atoms, or, a substituted or unsubstituted aromatic hydrocarbon group or aromatic heterocyclic group with 5 to 60 ring atoms.

4. The organic mixture according to claim 1, wherein, $Ar^1$ and $Ar^2$ each comprise one or more of the following structural groups:

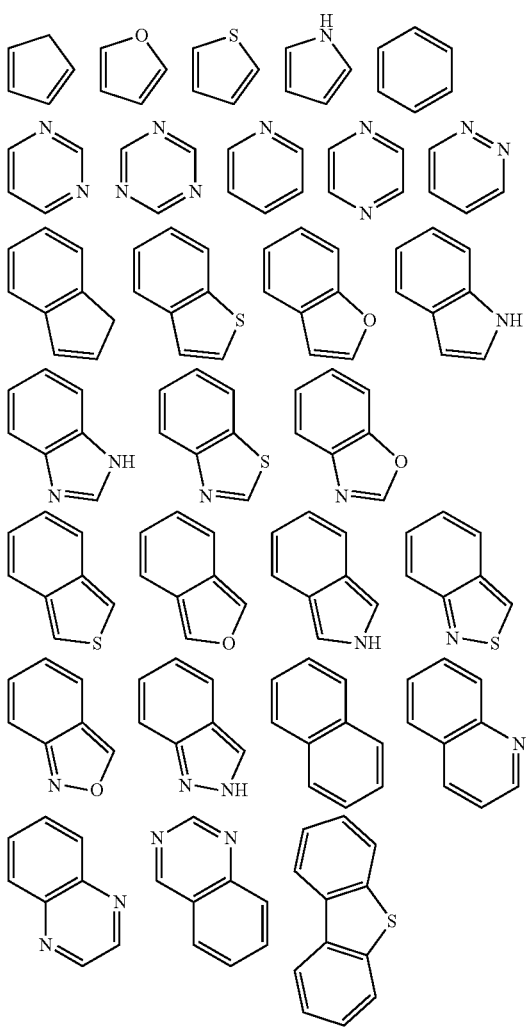

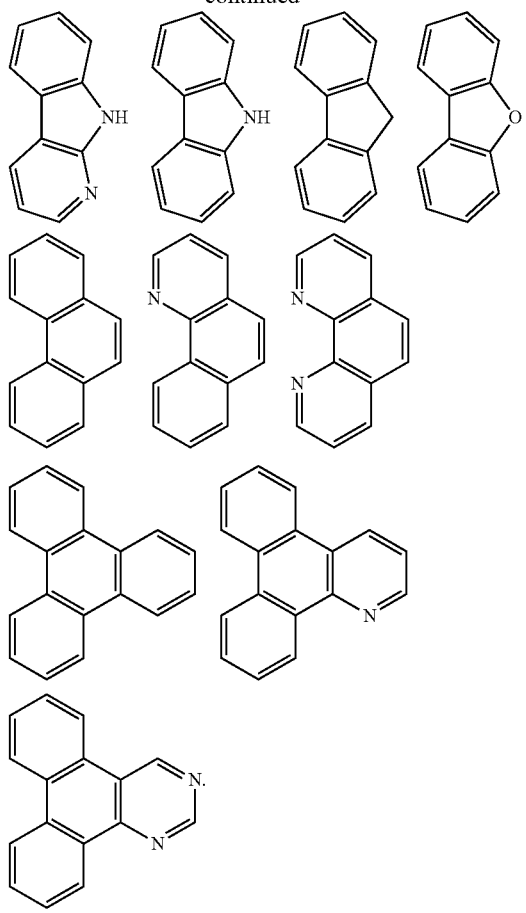

5. The organic mixture according to claim 1, wherein to electron-accepting group comprised in $Ar^1$ is selected from the group consisting o F, cyano group, and the following groups:

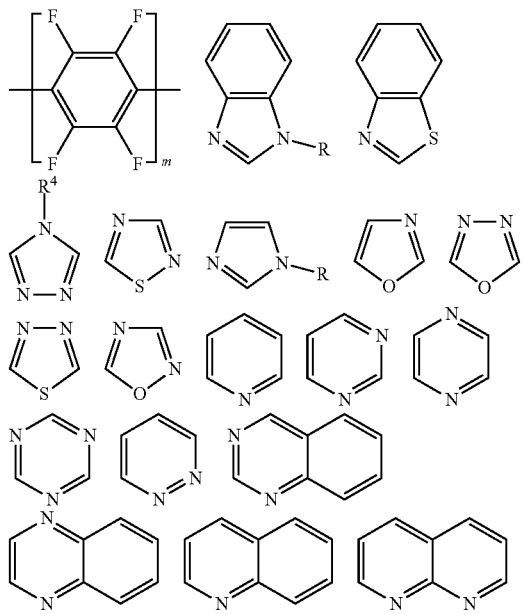

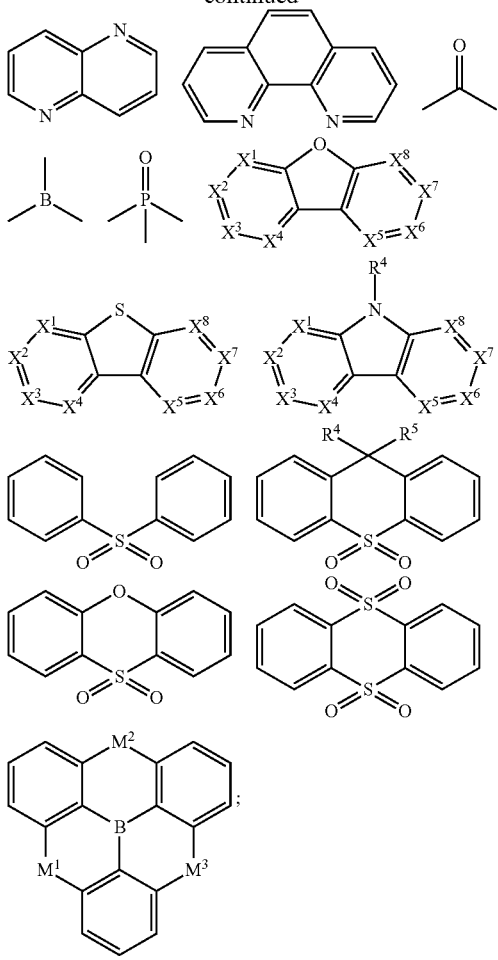

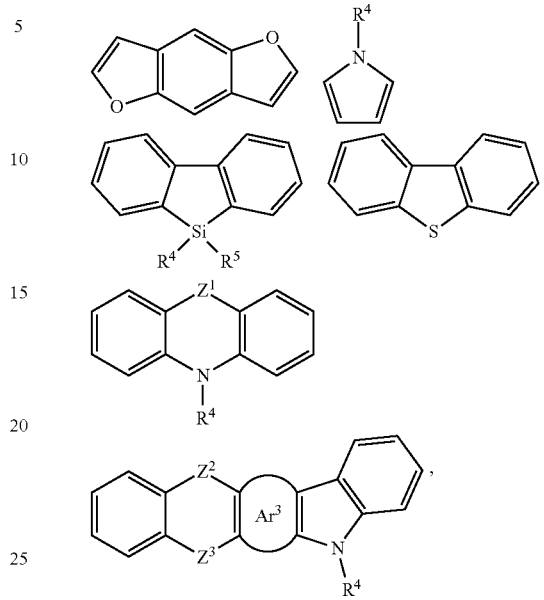

wherein,

Ar³ represents an aromatic hydrocarbon group with 5 to 40 ring atoms or an aromatic heterocyclic group with 5 to 40 ring atoms;

$Z^1$, $Z^2$ and $Z^3$ each independently represent a single bond, $N(R^4)$, $C(R^4R^5)$, $Si(R^4R^5)$, O, $C=N(R^4)$, $C=C(R^4R^5)$, $P(R^4)$, $P(=O)R^4$, S, S=O or SO2, wherein $Z^2$ and $Z^3$ are not single bonds simultaneously; $R^4$ and $R^5$ each independently represent H, a substituted or unsubstituted alkyl with 1 to 30 carbon atoms, a substituted or unsubstituted cycloalkyl with 3 to 30 carbon atoms, or a substituted or unsubstituted aromatic hydrocarbon group or aromatic heterocyclic group with 5 to 60 ring atoms.

wherein, m is 1, 2 or 3; $X^1$-$X^8$ are each selected from $CR^4$ or N, and at least one of $X^1$-$X^8$ is N; $M^1$, $M^2$ and $M^3$ each independently represent $N(R^4)$, $C(R^4R^5)$, $Si(R^4R^5)$, O, $C=N(R^4)$, $C=C(R^4R^5)$, $P(R^4)$, $P(=O)R^4$, S, S=O, SO2 or none; R, $R^4$ and $R^5$ each independently represent H, a substituted or unsubstituted alkyl with 1 to 30 carbon atoms, a substituted or unsubstituted cycloalkyl with 3 to 30 carbon atoms, or, a substituted or unsubstituted aromatic hydrocarbon group or aromatic heterocyclic group with 5 to 60 ring atoms.

6. The organic mixture according to claim 1, wherein the electron-donating group D comprises any one of the following groups:

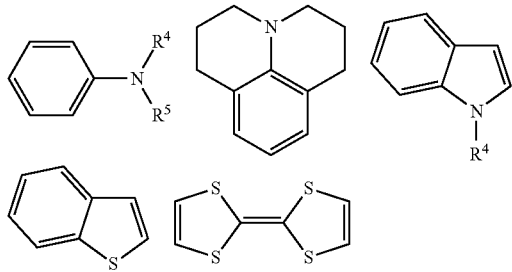

7. The organic mixture according to claim 1, wherein molar ratio of the organic compound H1 to the organic compound H2 is between 1:9 and 9:1.

8. The organic mixture according to claim 1, wherein the difference between molecular weight of the organic compound H1 and that of the organic compound H2 does not exceed 100 Dalton.

9. The organic mixture according to claim 1, wherein the organic mixture further comprises a light-emitting material selected from the group consisting of a fluorescent emitter, a phosphorescent emitter and a TADF material.

10. A formulation comprising the organic mixture of claim 1, and at least one organic solvent.

11. An organic electronic device comprising the organic mixture of claim 1.

12. An organic electronic device comprising the organic mixture of claim 1, wherein the organic electronic device is an electroluminescent device comprising at least one light-emitting layer, and the light-emitting layer includes the organic mixture of claim 1.

13. The organic mixture according to claim 1, wherein at least one of A and B is

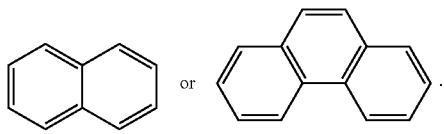

14. The organic mixture according to claim 13, wherein H1 is a compound represented by following formulas:

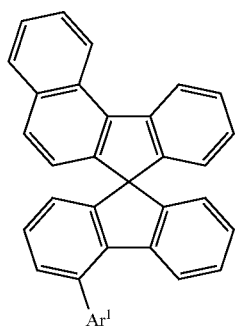

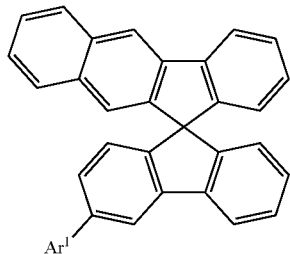

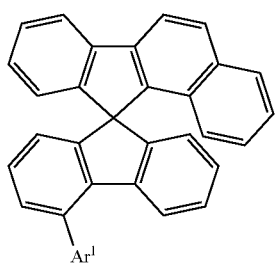

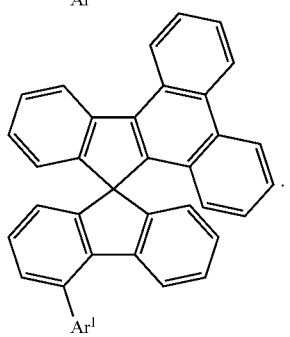

15. The organic mixture according to claim 1, Ar¹ of general formula (1) is selected from the following groups:

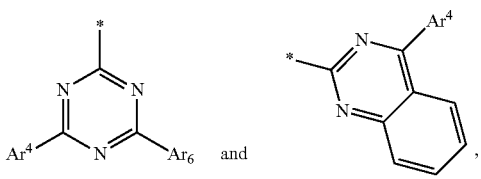

wherein, $Ar^4$ and $Ar^6$ each independently represent a substituted or unsubstituted aromatic hydrocarbon group with 5 to 30 ring atoms or substituted or unsubstituted aromatic heterocyclic group with 5 to 30 ring atoms, or is absent.

16. The organic mixture according to claim 1, wherein the organic compound H2 is a compound represented by following formulas:

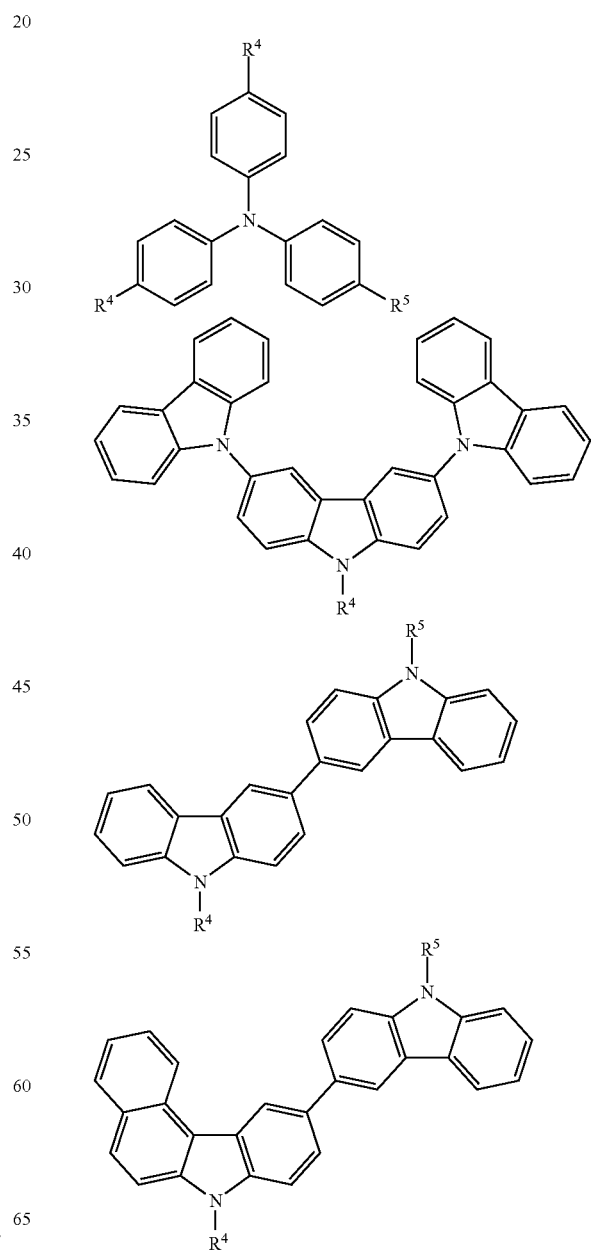

-continued

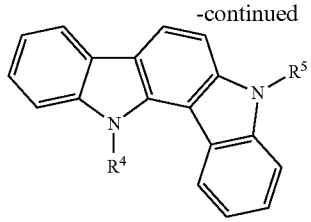

wherein, $R^4$ and $R^5$ each independently represent a substituted or unsubstituted alkyl with 1 to 30 carbon atoms, a substituted or unsubstituted cycloalkyl with 3 to 30 carbon atoms, or a substituted or unsubstituted aromatic hydrocarbon group or aromatic heterocyclic group with 5 to 60 ring atoms.

17. The organic mixture according to claim 1, wherein H1 is selected from the following structures:

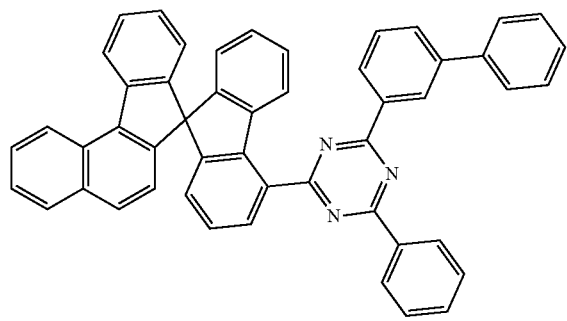

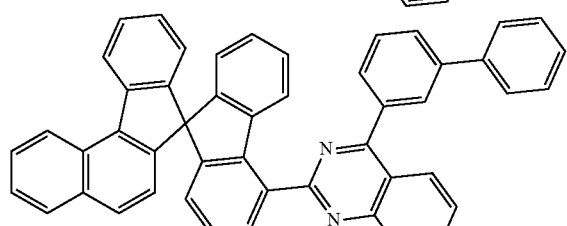

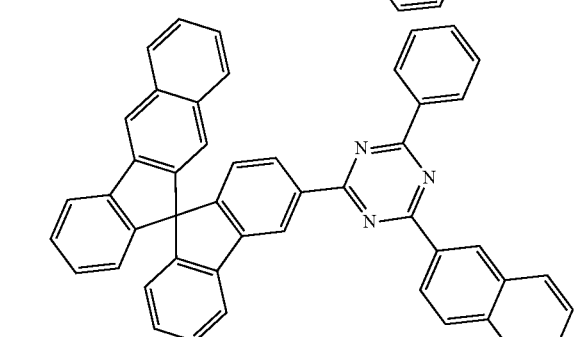

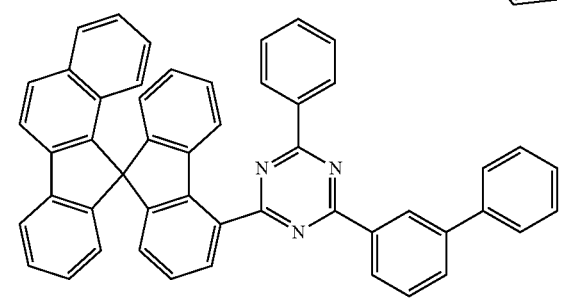

-continued

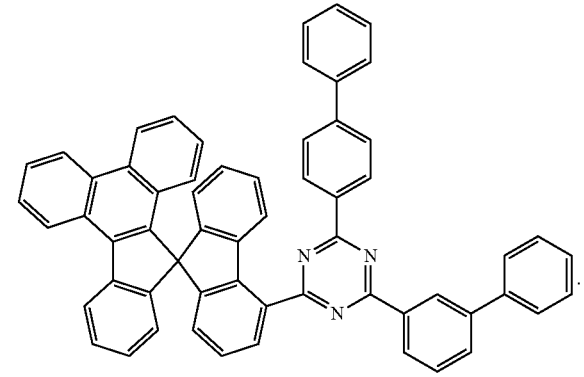

18. The organic mixture according to claim 1, wherein H2 is selected from the following structures:

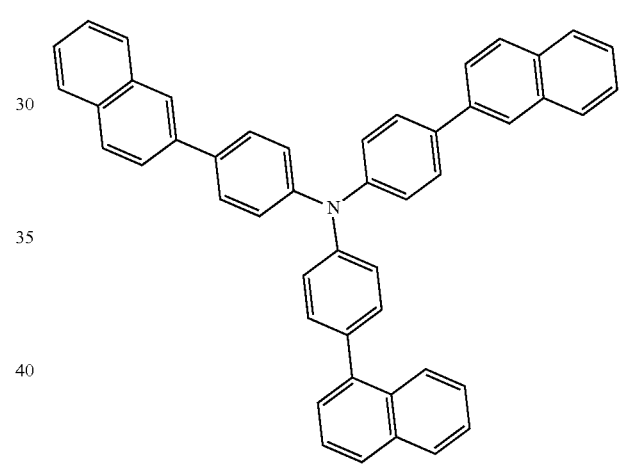

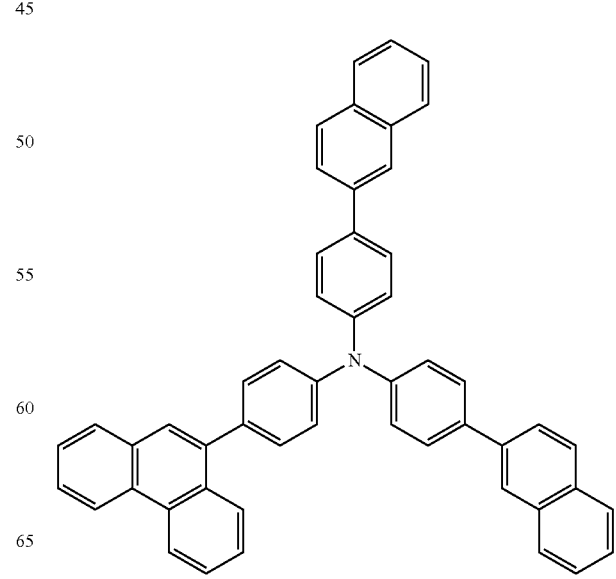

-continued

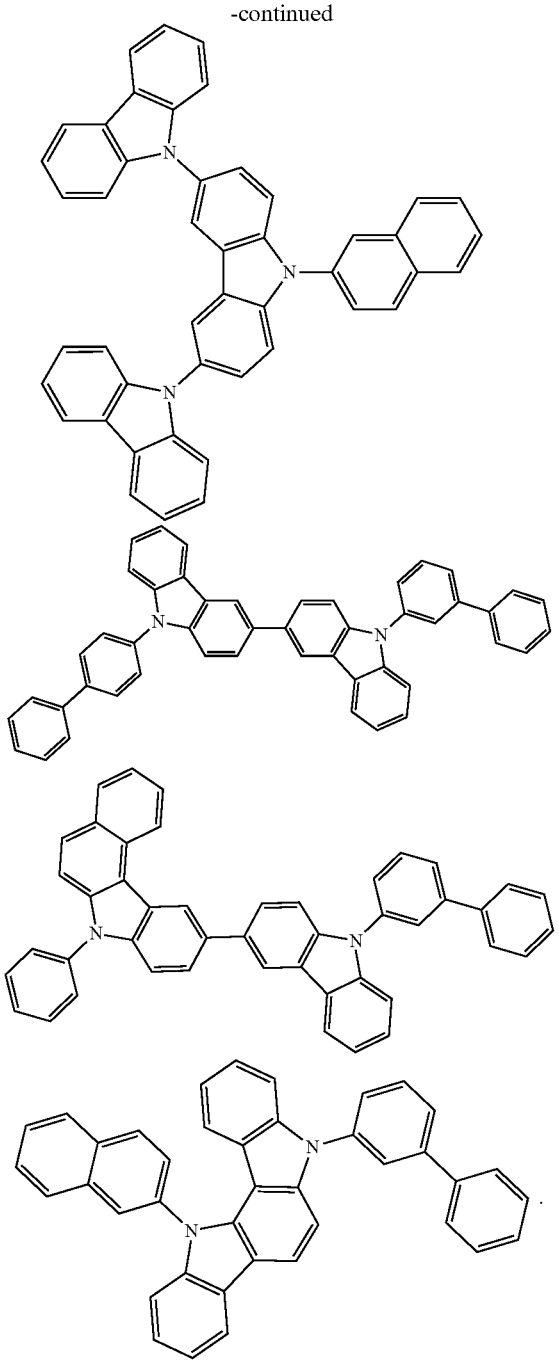

19. The organic mixture according to claim 1, wherein min((LUMO(H1)−HOMO(H2), LUMO(H2)−HOMO(H1)) ≤min(ET(H1), ET(H2))+0.1 eV, wherein, LUMO(H1) is the lowest unoccupied molecular orbital energy level of H1,HOMO(H1) is the highest occupied molecular orbital energy level of H1,ET(H1) is the triplet energy levels of H1,LUMO(H2) is the lowest unoccupied molecular orbital energy level of H2, HOMO(H2) is the highest occupied molecular orbital energy level of H2, ET(H2) is the triplet energy levels of H2.

20. An organic mixture comprising an organic compound H1 and an organic compound H2, wherein the organic compound H1 is a compound represented by general formula (1):

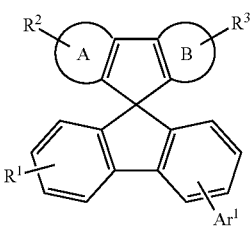

(1)

wherein,

A and B each independently represent an aromatic hydrocarbon group with 6 to 30 ring atoms or an aromatic heterocyclic group with 6 to 30 ring atoms, at least one of A and B has more than 6 ring atoms, and at least one of A and B is

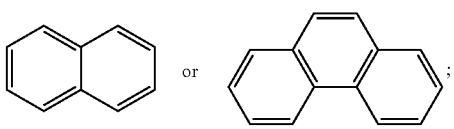

$R^1$, $R^2$ and $R^3$ are substituents, each independently selected from the group consisting of H, deuterium, F, CN, alkenyl, alkynyl, nitrile group, amino group, nitro group, acyl, alkoxy group, carbonyl, sulfonyl, substituted or unsubstituted alkyl with 1 to 30 carbon atoms, substituted or unsubstituted cycloalkyl with 3 to 30 carbon atoms, and substituted or unsubstituted aromatic hydrocarbon group with 5 to 60 ring atoms or substituted or unsubstituted aromatic heterocyclic group with 5 to 60 ring atoms;

$Ar^1$ represents a substituted or unsubstituted aromatic hydrocarbon group with 5 to 100 ring atoms or substituted or unsubstituted aromatic heterocyclic group with 5 to 100 ring atoms, and contains at least one electron-accepting group;

the organic compound H2 is a compound represented by general formula (2):

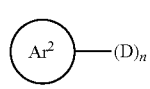

(2)

wherein, $Ar^2$ represents a substituted or unsubstituted alkyl with 1 to 30 carbon atoms, a substituted or unsubstituted cycloalkyl with 3 to 30 carbon atoms, a substituted or unsubstituted aromatic hydrocarbon group with 5 to 100 ring atoms or substituted or unsubstituted aromatic heterocyclic group with 5 to 100 ring atoms;

D is an electron-donating group; and n is an integer of 1-6.

* * * * *